United States Patent [19]
Blit et al.

[11] Patent Number: 5,526,119
[45] Date of Patent: Jun. 11, 1996

[54] APPARATUS & METHOD FOR INSPECTING ARTICLES SUCH AS AGRICULTURAL PRODUCE

[75] Inventors: Shmuel Blit, Rehovot; Eyal Bartfeld, Mazkeret Batya; Idan Pais, Tel Aviv; Yair Eilam, Kfar Saba; Efraim Vallach, Jerusalem; Haim Bezdin, Bat Yam; Israel Laron, Rehovot; Doron Katzin, Hod Hasharon; Abraham Reichart; Jacob Samekh, both of Rehovot, all of Israel

[73] Assignee: ELOP Electro-Optics Industries, Ltd., Rehovot, Israel

[21] Appl. No.: 49,713

[22] Filed: Apr. 16, 1993

[30] Foreign Application Priority Data

Apr. 16, 1992 [IL] Israel ............................ 101612

[51] Int. Cl.⁶ .................... G01N 21/88; G01J 3/50
[52] U.S. Cl. .................. 356/402; 356/237; 209/577; 209/580
[58] Field of Search .................... 356/346, 237, 356/402, 425; 209/580, 583, 587, 577

[56] References Cited

U.S. PATENT DOCUMENTS

| | | |
|---|---|---|
| 2,933,613 | 4/1960 | Powers. |
| 3,225,892 | 12/1965 | Keesling. |
| 3,867,041 | 2/1975 | Brown et al.. |
| 3,961,701 | 6/1976 | Paddock et al.. |
| 4,146,135 | 3/1979 | Sarkar et al.. |
| 4,204,950 | 5/1980 | Burford, Jr.. |
| 4,246,098 | 1/1981 | Conway et al. ............ 209/587 |
| 4,515,275 | 5/1985 | Mills et al.. |
| 4,534,470 | 8/1985 | Mills ........................... 209/587 |
| 4,645,080 | 2/1987 | Scopatz. |
| 4,741,042 | 4/1988 | Throop et al.. |
| 4,799,596 | 1/1989 | Mallant ....................... 209/580 |
| 4,863,041 | 9/1989 | Bailey. |
| 4,878,582 | 11/1989 | Codding. |
| 4,940,850 | 7/1990 | Satake. |
| 5,010,247 | 4/1991 | Smith et al.. |
| 5,012,116 | 4/1991 | Russell. |
| 5,024,530 | 6/1991 | Mende ......................... 356/419 |
| 5,078,258 | 1/1992 | van der Schoot. |
| 5,085,325 | 2/1992 | Jones et al.. |
| 5,315,384 | 5/1994 | Heffington et al. ............ 348/93 |
| 5,339,963 | 8/1994 | Tao ............................... 209/587 |

FOREIGN PATENT DOCUMENTS

| | | |
|---|---|---|
| 2327355 | 1/1975 | Germany. |
| WO9104803 | 4/1991 | WIPO. |

OTHER PUBLICATIONS

Wolfe, R. R. and Sandler, W. E., "An Algorithm for Star Detection Using Digital Image Processing", Trans. ASAW, 28, pp. 641–644, 1984.

Upchurch, B. L., et al, "Spectrophotometric Study of Bruises on Whole, Red Delicious Apples", Trans ASAE, 33(2), Mar.–Apr. 1990.

Bezdek, James C. and Pal, Sankar K., "Fuzzy Models for Pattern Recognition", IEEE Press 1992, ISBN 0-7803-0422-5.

(List continued on next page.)

*Primary Examiner*—F. L. Evans
*Attorney, Agent, or Firm*—Weiser & Associates

[57] ABSTRACT

A complete sorting system is provided herein including a sequence of interlacing cable conveyors for conveying objects to be sorted, such as apples or other agricultural produce, from bulk storage at the input to the system, through the system, and along to drops at the output of the system. The cable conveyors are configured and arranged to handle even delicate agricultural produce without damage and at high speed. The produce or objects which are conveyed typically do not roll along the conveyors. Preferably, objects of substantially any shape can be conveyed along the system.

35 Claims, 31 Drawing Sheets

OTHER PUBLICATIONS

Ballard, D. H. and Brown, C. M., "Computer Vision", pp. 72–73, Prentice–Hall, Englewood Cliffs, New Jersey, 1982.

Barnard, S. T. and Fischler, M. A., "Computational stereo", Computing Surveys, 14(4), 553–572, 1982.

Davenel et al. "Automatic detection of surface defects on fruit by using a vision system", J. Agricultural and Engineering Research, 41, 1–9, 1988.

G. L. Graf "Automatic detection of surface blemishes on apples using digital image processing", Cornell University, 1982.

Hu, G. and Stockman, G. "3D surface solution using structured light and constrain propagation", IEEE Trans. on PAMI, vol. 4, 390–402, 1989.

Miller, B. K. and Delwiche, M. J., "A color vision system for peach grading", Trans. of the ASAE, vol. 32(4), 1484–1490, 1989.

Rehkugler, G. E. and Throop, J. A., "Apple sorting with machine vision", Trans. of the ASAE, vol. 29(5), 1388–1397, 1986.

Rehkugler, G. E. and Throop, J. A., "Image processing algorithm for apple defect detection", Trans. of the ASAE, vol. 32(1), pp. 267–272, 1989.

Sarker, N. and R. R. Wolfe, "computer vision based system for quality separation of fresh market tomatoes", Trans. ASAE, vol. 28, pp. 1714–1718, 1985.

Shrikhande, N. and Stockman, G., "Surface orientation from a projected grid", IEEE Transactions on pattern analysis and machine intelligence, vol. 11 (6), Jun. 1989.

Upchurch B. L., et al, "Spectophotometric study of bruises on whole, red delicious apples", Transactions of the ASAE, 33(2), Mar.–Apr. 1990.

Wolf, R. R. and Sandler, W. E., "An algorithm for stem detection using digital image processing", Trans. ASAE, 28, pp. 641–644, 1984.

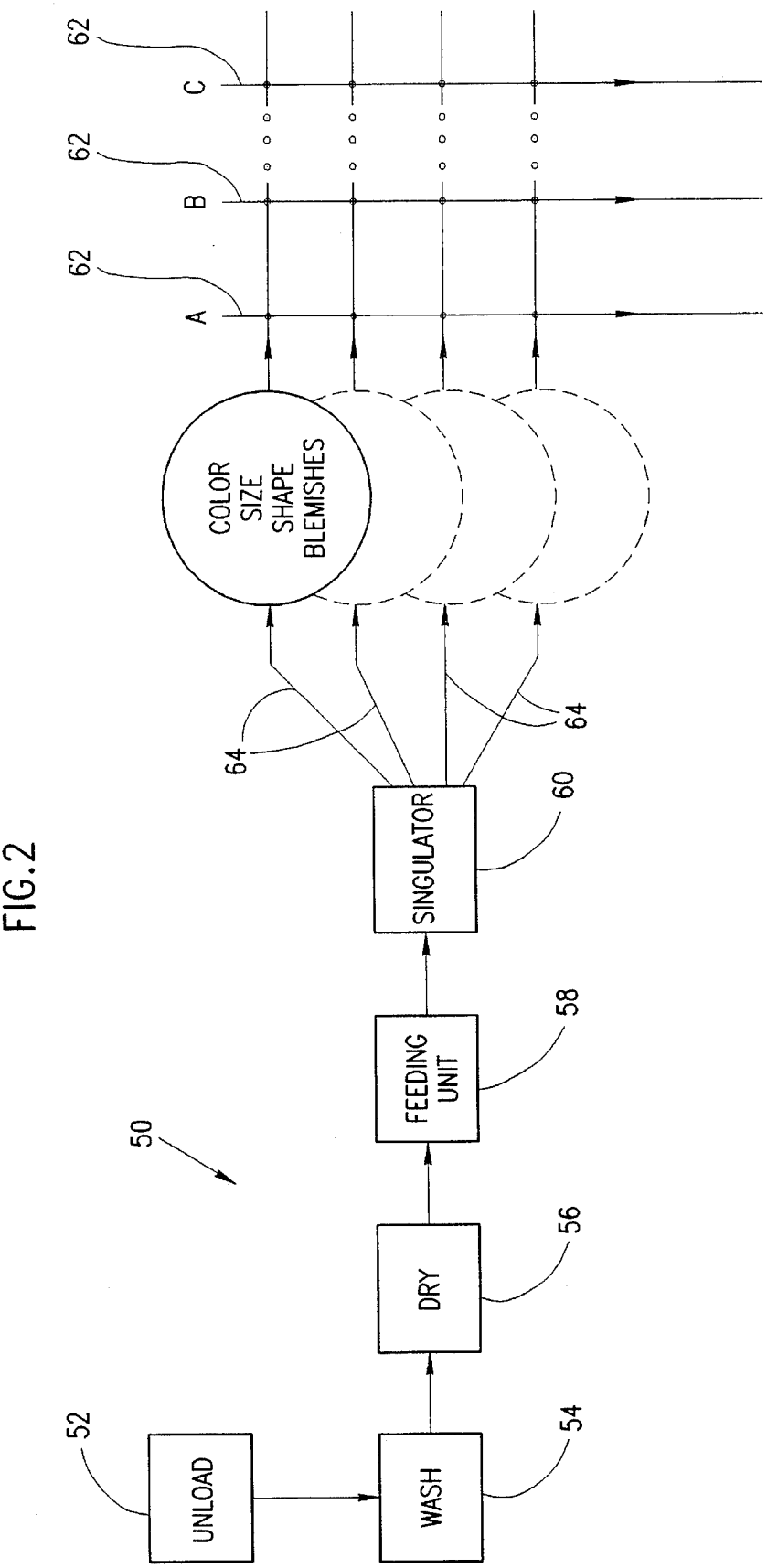

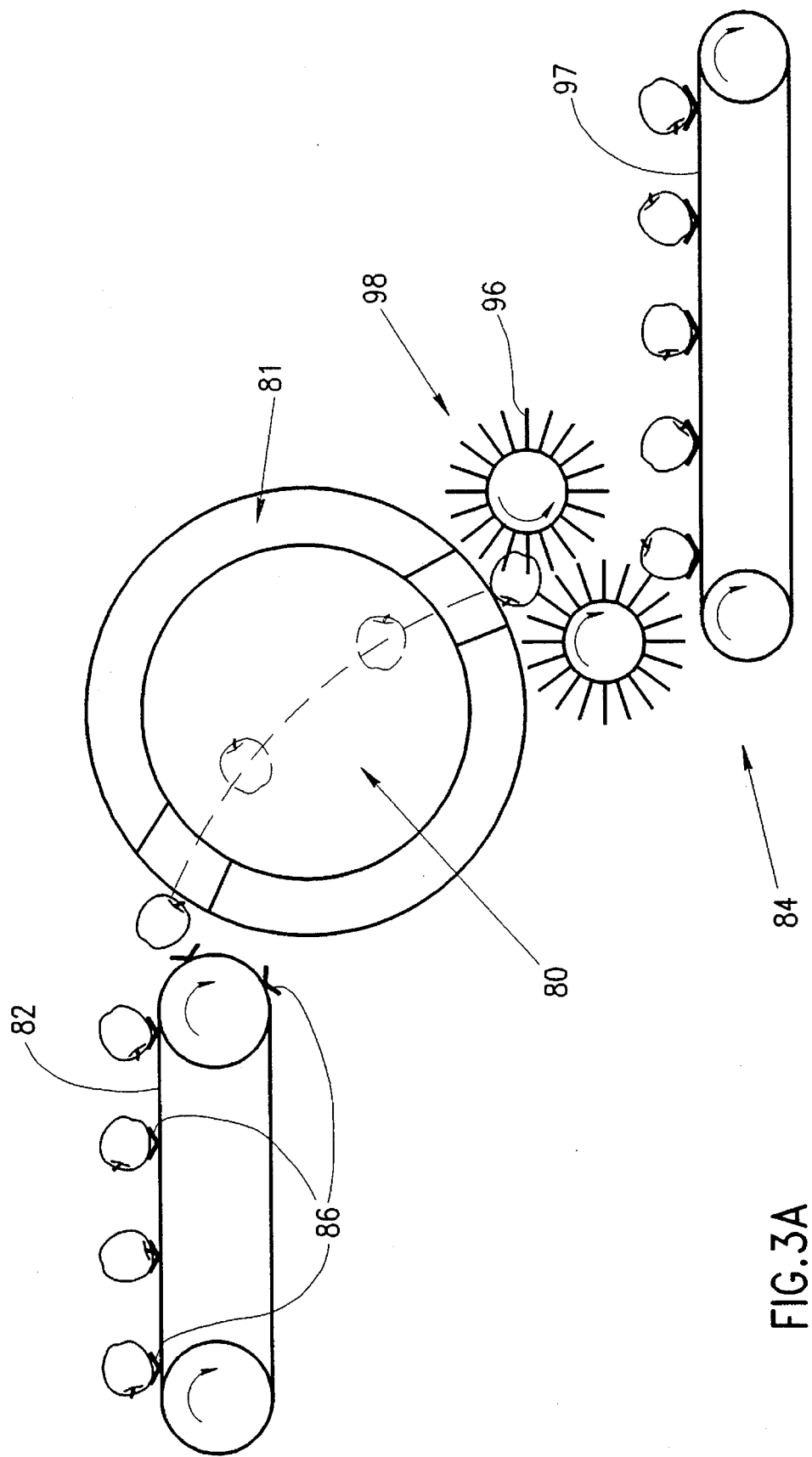

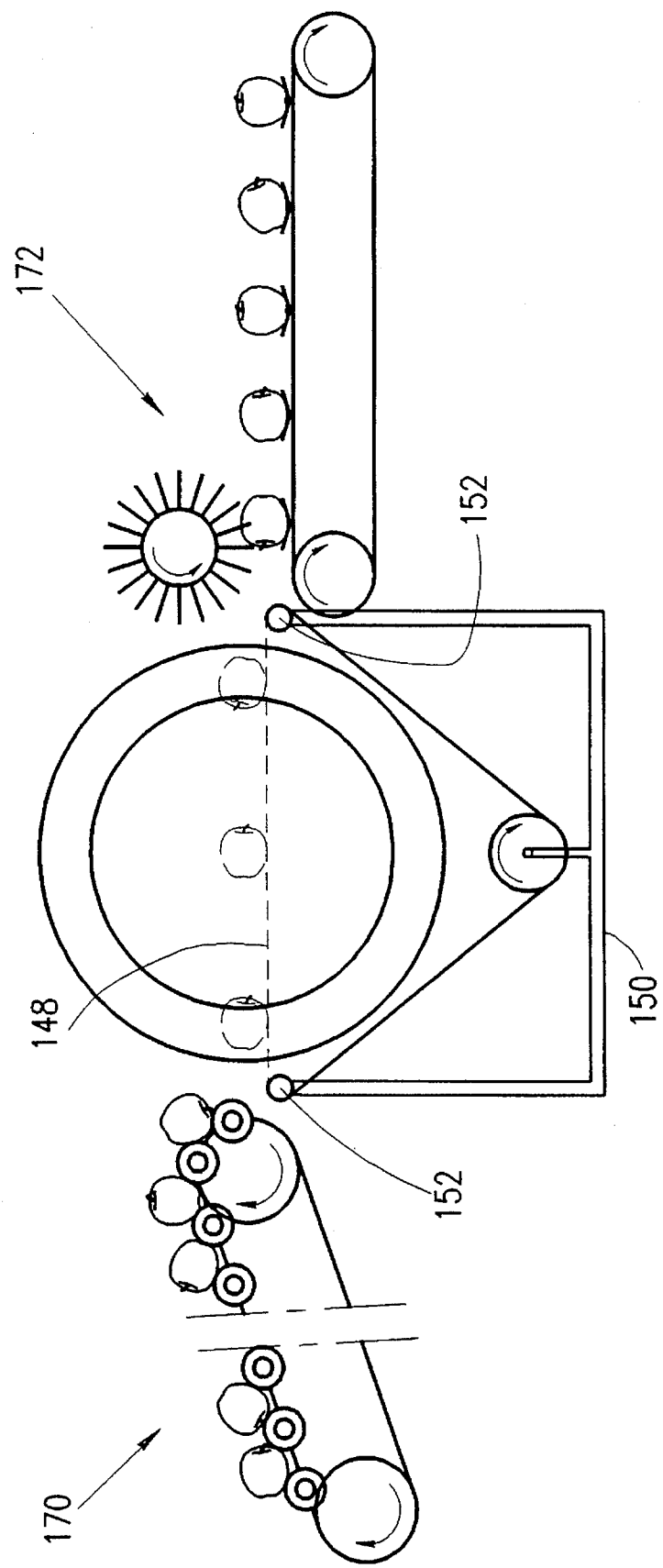

APPARATUS & METHOD FOR INSPECTING ARTICLES SUCH AS AGRICULTURAL PRODUCE

FIELD OF THE INVENTION

The present invention relates generally to apparatus for inspecting articles in motion and particularly to apparatus for sorting and grading agricultural produce.

BACKGROUND OF THE INVENTION

In the present specification and claims, the term "sorting" is used to mean categorization of articles by size and/or color and the term "grading" is used to mean categorization of articles by quality and/or type.

Systems for sorting and grading of apples based on computing thinness ratios for blemishes are described in the following two publications by Rehkugler, G. E. and Throop, J. A.:

"Image processing algorithm for apple defect detection", Trans. of the ASAE, Vol. 32(1), pp. 267–272, 1989, and "Apple sorting with machine vision", Trans. of the ASAE, Vol. 29(5), 1388–1397, 1986. In this reference, diffuse illumination is provided by a translucent acrylic box.

A Ph.D. dissertation by G. L. Graf ("Automatic detection of surface blemishes on apples using digital image processing", Cornell University, 1982, available from UMI Dissertation Information Service, 300 N. Zeeb Rd. Ann Arbor, Michigan 48106) discloses in FIG. 4—4 a generally cylindrical diffuser and apparatus for illuminating the diffuser from the exterior thereof, for inspecting an apple which has been manually placed within the cylindrical diffuser.

Another cylindrical diffused light system is described in Sarker, N. and R. R. Wolfe, "Computer vision based system for quality separation of fresh market tomatoes", Trans. ASAE, Vol. 28, pp. 1714–1718, 1985. The Sarker et al system includes mechanical apparatus for aligning tomatoes along the stem/calyx axis and a defect detection subsystem which employs adaptive thresholding of a gradient image.

Color inspection methods for peaches in which peaches are viewed from more than one angle using multiple sensors, a frame grabber, a CCD camera, one-sided diffuse illumination and color grading and feature extraction algorithms are mentioned in Miller, B. K. and Delwiche, M. J., "A color vision system for peach grading", Trans. of the ASAE, Vol. 32(4), 1484–1490, 1989.

An EO commercial development of a sorter and grader system employing solid-state CCD cameras in which blemishes are detected on fruit rolling on bicone rollers is described in A. Davenel et al, "Automatic detection of surface defects on fruit by using a vision system", J Agricultural and Engineering Research, 41, 1–9, 1988.

Methods for identifying bruised apple tissue using reflected light of one, two or three normalized wavelengths, including computations of differences or ratios between 2 wavelengths, are discussed in B. L. Upchurch et al, "Spectrophotometric study of bruises on whole, red delicious apples", Transactions of the ASAE, 33(2), Mar.–Apr. 1990.

Upchurch et al describe various models for distinguishing bruised from nonbruised areas on Red Delicious apples. One such model is set forth in Equation 5 and comprises a two wavelength such model is set forth in Equation 5 and comprises a two wavelength difference which is divided by a normalizing wavelength to take into account illumination changes. Upchurch et al propose to cancel out differences in reflectance levels, due to factors other than tissue condition, by division.

U.S. Pat. No. 5,085,325 to Jones et al discusses color sorting of articles and use of a camera and flash to image moving articles. Color analysis is performed on the basis of RGB color imaging and spherical color coordinates.

U.S. Pat. No. 5,012,116 to Russell discusses a system for detecting defects in diffusely illuminated bearing balls which roll along a pair of parallel rails.

U.S. Pat. No. 5,010,247 to Smith et al discloses a system in which objects are dropped through a viewing zone and are viewed by three viewers arranged along 3 mutually orthogonal axes using radiation of different wavelengths.

A method for deriving information regarding convexity/concavity of an article by projecting a grid pattern on the article is disclosed in N. Shrikhande and G. Stockman, "Surface orientation from a projected grid", IEEE Transactions on pattern analysis and machine intelligence, Vol. 11(6), June 1989.

Attempts to detect fruit stems using image processing are reported in Wolf, R. R and Sander, W. E, "An algorithm for stem detection using digital image processing", Trans. ASAE, 28, pp. 641–644, 1984.

U.S. Pat. No. 4,863,041 to Bailey discloses a system for observing an article from 4 sides without imaging, using a color background which is dynamically controlled. The system is triggered as a response to intercepted light beams.

U.S. Pat. No. 5,078,258 to Van Der Shoot discloses a system which orients apples by mechanical apparatus and subsequently picks the apple. The system includes a color camera which identifies "red cheek" on an apple.

U.S. Pat. No. 4,940,850 to Satake discloses a system of 3 detectors which "look" at an article in vertical free fall through 2 spectral filters.

U.S. Pat. No. 4,878,582 to Codding discloses a bichromatic sorter in which an article is seen from 3 coplanar directions, on a color background.

U.S. Pat. No. 4,741,042 to Throop et al discloses a software system for analyzing size and shape of bruises on fruit by creating a binary image of bruises.

U.S. Pat. No. 4,645,080 to Scopatz discusses a system for grading non-orienting articles. Specifically, the system grades oranges on the basis of information from three overhead and side sensors.

U.S. Pat. No. 4,515,275 to Mills et al discloses a system for processing fruit such as lemons. Polarized illumination of the fruit is provided from 4 sides and a single video camera or line scanner is employed.

U.S. Pat. No. 4,204,950 to Burford, Jr. discloses a grading system using four spectral bands, of which two are visible.

A state of the art system for conveying fruit is marketed by Accu Pak Systems.

Published PCT Application WO 91/04803 describes apparatus for weighing, sizing and defect sorting of fruit including one or more singulators, a conveyor for passing the fruit under a CCD array camera, means for rotating the fruit under the camera, an image processor including a master processor passing signals to a vision processr and 8 object processors which divide the captured image into image sections each representing only one piece of fruit, and ejectors spaced along the conveyor which eject the fruit to outfeed conveyors corresponding to sorting categories.

SUMMARY OF THE INVENTION

The present invention seeks to provide an improved system for inspecting articles such as but not limited to agricultural produce, including apples.

According to a preferred embodiment of the present invention, a complete sorting system is provided herein including a sequence of interlacing cable conveyors for conveying objects to be sorted, such as apples or other agricultural produce, from bulk storage at the input to the system, through the system, and along to drops at the output of the system. The cable conveyors are configured and arranged to handle even delicate agricultural produce without damage and at high speed. The produce or objects which are conveyed typically do not roll along the conveyors. Preferably, objects of substantially any shape can be conveyed along the system.

There is also provided in accordance with a preferred embodiment of the present invention apparatus for inspecting agricultural produce having a stem and a calyx including a stem/calyx identifier for determining the locations of the stem and the calyx of the agricultural produce, and a blemish detector, cooperative with the stem/calyx detector, for detecting blemishes and avoiding false detections of the stem and calyx as blemishes.

Further in accordance with a preferred embodiment of the present invention the blemish detector is also operative to ignore certain color variations in the vicinity of the stem and calyx.

Still further in accordance with a preferred embodiment of the present invention the stem/calyx identifier includes a valley contour detector.

There is additionally provided in accordance with a preferred embodiment of the present invention apparatus for inspecting and handling agricultural produce having a stem and a calyx including a stem/calyx identifier for determining the locations of the stem and the calyx of the agricultural produce, and a mechanical operator, receiving an output of the stem/calyx identifier, for carrying out a mechanical operation on the agricultural produce which takes into account the locations of the stem and the calyx.

Also in accordance with a preferred embodiment of the present invention the mechanical operator includes a cutter.

Moreover in accordance with a preferred embodiment of the present invention the mechanical operator includes a produce marker.

Further in accordance with a preferred embodiment of the present invention the mechanical operator includes a produce packer.

Still further in accordance with a preferred embodiment of the present invention the mechanical operator includes a produce sorter.

There is also provided in accordance with a preferred embodiment of the present invention apparatus for inspecting articles including a camera, and a spectral filter defining a plurality of light paths from an article to be inspected to the camera, the plurality of light paths having different spectral characteristics, wherein the spectral filter includes a prism operative to provide a plurality of images of the article having different spectral characteristics and being disposed in generally non-overlapping positions on an image plane of the camera.

There is further provided in accordance with a preferred embodiment of the present invention apparatus for inspecting articles including an enclosure formed of a generally translucent light diffusing material, an external illuminator for illuminating the enclosure from the exterior thereof, an article driver for causing articles to be inspected to pass through the enclosure, and a camera for inspecting the articles as they pass through the enclosure.

Also in accordance with a preferred embodiment of the present invention the enclosure is generally spherical.

Additionally in accordance with a preferred embodiment of the present invention the external illuminator includes a plurality of light sources surrounded by a reflector.

Further in accordance with a preferred embodiment of the present invention the enclosure and the external illuminator are operative to provide generally uniform illumination of the article as it is inspected.

Still further in accordance with a preferred embodiment of the present invention the enclosure and the external illuminator are operative to provide a generally uniform background for the article, as the article is inspected.

Also in accordance with a preferred embodiment of the present invention the article driver includes a non-contact passage provider operative to provide non-contact passage of the articles through the enclosure.

Moreover in accordance with a preferred embodiment of the present invention the external illuminator is sealed from the inside of the enclosure.

Additionally in accordance with a preferred embodiment of the present invention the camera is operative to inspect generally all exposed surfaces of the article generally simultaneously.

Further provided in accordance with a preferred embodiment of the present invention is apparatus for inspecting articles including a camera operative to inspect generally all exposed surfaces of the article generally simultaneously.

Still further in accordance with a preferred embodiment of the present invention the apparatus includes an article supporter/conveyer for supporting and conveying articles to be inspected on an article bearing element configured such that substantially insignificant portions of the surfaces of the article are obscured from inspection.

Also in accordance with a preferred embodiment of the present invention the article bearing element has a generally horizontal configuration and wherein the article supporter/conveyer also includes apparatus for driving the articles along the article bearing element.

Additionally provided in accordance with a preferred embodiment of the present invention is apparatus for inspecting articles including an IR imager for generating an IR image of an article, a color imager for generating a color image of an article, and a defect detector receiving outputs from the IR imager and from the color imager for-combining the outputs and for providing an output indication of defects based on information including information derived from combining the outputs.

Further in accordance with a preferred embodiment of the present invention the article bearing element has a mesh configuration.

Still further in accordance with a preferred embodiment of the present invention the apparatus includes a camera operative to inspect generally all exposed surfaces of the article, and an image processor for providing a reconstruction of the exposed surfaces of an article in which substantially every point on the exposed surfaces of the article is reconstructed exactly once.

Also in accordance with a preferred embodiment of the present invention the apparatus include an image processor for providing a reconstruction of the exposed surfaces of an article in which substantially every point on the exposed surfaces of the article is reconstructed exactly once, wherein the camera is operative to inspect generally all exposed surfaces of an article.

There is further provided in accordance with a preferred embodiment of the present invention apparatus for inspecting articles including a camera operative to inspect generally all exposed surfaces of the article, and an image processor for providing a reconstruction of the exposed surfaces of an article in which substantially every point on the exposed surfaces of the article is reconstructed exactly once.

Further in accordance with a preferred embodiment of the present invention the camera is operative to inspect generally all exposed surfaces of an article generally simultaneously.

Still further in accordance with a preferred embodiment of the present invention the camera includes at least first and second camera units.

Also in accordance with a preferred embodiment of the present invention the image processor includes apparatus for reconstructing predetermined at least first and second substantially nonoverlapping portions of the article in accordance with the images generated by the at least first and second camera units respectively.

Also in accordance with a preferred embodiment of the present invention the predetermined portions of the article are determined in accordance with a predetermined model of the shape of the article, the model defining at least one model parameter.

Additionally in accordance with a preferred embodiment of the present invention the at least first and second camera units includes at least first, second and third camera units.

Moreover in accordance with a preferred embodiment of the present invention the camera is operative to inspect at least 70 percent of the exposed surface of an article.

Further in accordance with a preferred embodiment of the present invention the camera is operative to inspect at least 80 percent of the exposed surface of an article.

Still further in accordance with a preferred embodiment of the present invention the camera is operative to inspect at least 90 percent of the exposed surface of an article.

Also in accordance with a preferred embodiment of the present invention the camera is operative to inspect at least 95 percent of the exposed surface of an article.

Additionally in accordance with a preferred embodiment of the present invention the apparatus includes an image-model comparison unit for comparing an image of at least a portion of the article to the predetermined model of the shape of the article and for correcting the determination of the predetermined portions of the article to take into account discrepancies between the actual shape of the article and the predetermined model thereof.

Moreover in accordance with a preferred embodiment of the present invention the image processor includes apparatus for comparing first and second images of first and second respective portions of the article generated by the first and second camera units respectively, thereby to identify overlap between the first and second images.

Further in accordance with a preferred embodiment of the present invention the article is supported by an article supporting element disposed intermediate the article and the camera and wherein the image processor includes an article supporting element identifier for differentiating an image of the article supporting element from the image of the article.

Still further in accordance with a preferred embodiment of the present invention the stem/calyx identifier also includes apparatus for inspecting a putative location of the stem and of the calyx relative to the shape of the fruit and for rejecting putative locations which are not located generally one opposite the other.

There is also provided in accordance with a preferred embodiment of the present invention internal referenced apparatus for inspecting the color of an agricultural product including a spectral standard device, a product and spectral standard imager operative to image an agricultural product together with the spectral standard device, and a product-spectral standard comparator operative to determine the spectral characteristics of the agricultural product relative to the spectral standard device by comparing images thereof.

Also in accordance with a preferred embodiment of the present invention the at least one model parameter includes at least one parameter which is derived from images of individual articles.

Additionally in accordance with a preferred embodiment of the present invention the plurality of images of the article includes at least one IR image of the article.

Further in accordance with a preferred embodiment of the present invention the article bearing element includes a plurality of elongate elements in generally parallel orientation.

There is still further provided in accordance with a preferred embodiment of the present invention apparatus for inspecting agricultural produce substantially without bruising or squashing, including a camera for inspecting delicate agricultural produce, a non-Contact passage provider operative to provide substantially non-contact passage of the delicate agricultural produce through the field of view of the camera, and a damper for receiving the delicate agricultural produce from the non-contact passage provider substantially without bruising or squashing the delicate agricultural produce.

Also in accordance with a preferred embodiment of the present invention the damper includes at least one brush element.

Additionally in accordance with a preferred embodiment of the present invention the damper includes an enclosure containing liquid.

Further in accordance with a preferred embodiment of the present invention the damper includes a sequencer for receiving the delicate agricultural produce in sequence and for maintaining the sequence.

Still further in accordance with a preferred embodiment of the present invention the sequencer includes a container of liquid for sequentially flushing away a sequence of agricultural products.

Also in accordance with a preferred embodiment of the present invention the article bearing element has an inclined configuration.

There is additionally provided in accordance with a preferred embodiment of the present invention apparatus for imaging articles in motion for subsequent inspection including a camera for imaging an article in motion, an article entry detector for repeatedly analyzing a small portion of the field of view of the camera in order to detect entry of the article thereto.

Moreover in accordance with a preferred embodiment of the present invention the apparatus includes a low-level illuminator for providing a low level of illumination sufficient for detecting the presence of the article, a high-level illuminator for providing a high level of illumination sufficient for inspecting characteristics of the article, and a high illumination trigger which receives an indication of the entry of the article into the small portion of the field of view from the article entry detector and triggers the high-level illuminator.

Further in accordance with a preferred embodiment of the present invention the apparatus includes an article characteristic analyzer for analyzing characteristics of the article, and an analyzer trigger for receiving an indication of the entry of the article into the small portion of the field of view from the article entry detector and for triggering the characteristics analyzer.

Still further in accordance with a preferred embodiment of the present invention the article entry detector includes apparatus for repeatedly computing a difference between a digitized first image of the field of view and a digitized subsequent image of the field of view.

There is additionally provided in accordance with a preferred embodiment of the present invention a singulation method including the steps of conveying articles in sequence without physically separating adjacently disposed articles along the conveyor.

There is further provided in accordance with a preferred embodiment of the present invention a singulation method including the steps of conveying articles in sequence without controlling the distances between adjacent article positions.

There is still further provided in accordance with a preferred embodiment of the present invention an agricultural produce inspection method including the steps of inspecting a representation of an entity forming at least a portion of an agricultural product, and employing fuzzy logic criteria in order to classify the entity according to a predetermined classification scheme.

Also in accordance with a preferred embodiment of the present invention the small portion of the field of view includes a one-dimensional array of pixels.

Additionally in accordance with a preferred embodiment of the present invention the camera is operative to inspect the agricultural produce by imaging.

Further provided in accordance with a preferred embodiment of the present invention is a method for inspecting agricultural produce having a stem and a calyx including the steps of optically determining the locations of the stem and the calyx of the agricultural produce, and detecting blemishes by cooperating with the optical determining step in order to avoid false detections of the stem and calyx as blemishes.

Still further provided in accordance with a preferred embodiment of the present invention is a method for inspecting and handling agricultural produce having a stem and a calyx including the steps of optically determining the locations of the stem and the calyx of the agricultural produce, and employing the results of the determining step in order to carry out a mechanical operation on the agricultural produce.

There is also provided in accordance with a preferred embodiment of the present invention a method for imaging articles in motion for subsequent inspection including the steps of providing a camera for imaging an article in motion, and repeatedly analyzing a small portion of the field of view of the camera in order to detect entry of the article thereto.

There is additionally provided in accordance with a preferred embodiment of the present invention a method for inspecting articles including the steps of illuminating an enclosure, formed of a generally translucent light diffusing material, from the exterior of the enclosure, causing articles to be inspected to pass through the enclosure, and inspecting the articles as they pass through the enclosure.

There is moreover provided in accordance with a preferred embodiment of the present invention a method for inspecting articles including the step of inspecting generally all exposed surfaces of the article generally simultaneously.

There is still further provided in accordance with a preferred embodiment of the present invention a method for inspecting articles including the steps of generating at least one IR image of an article, generating a color image of an article, and analyzing the images and providing an output indication of defects in the articles.

Also provided in accordance with a preferred embodiment of the present invention is an internally referenced method for inspecting the color of an agricultural product including the steps of imaging an agricultural product together with a spectral standard device, and determining the spectral characteristics of the agricultural product relative to the spectral standard device by comparing images thereof.

Additionally provided in accordance with a preferred embodiment of the present invention is a method for inspecting delicate agricultural produce substantially without bruising or squashing, including the steps of providing a camera for inspecting delicate agricultural produce, providing for substantially non-contact passage of the delicate agricultural produce through the field of view of the camera, and receiving the delicate agricultural produce following the non-contact passage substantially without bruising or squashing the delicate agricultural produce.

In accordance with a preferred embodiment of the present invention the camera includes a line scanner.

There is provided in accordance with a preferred embodiment of the present invention a method for inspecting agricultural produce including the steps of associating an indication of at least one characteristic of an individual item of agricultural produce with the individual item of produce.

Further in accordance with a preferred embodiment of the present invention the step of associating includes the step of affixing a sticker to the individual item of produce, wherein the sticker bears an indication of at least one characteristic of the individual item.

There is additionally provided in accordance with a preferred embodiment of the present invention apparatus for inspecting agricultural produce including a produce labelling unit operative to associate an indication of at least one characteristic of an individual item of agricultural produce with the item of produce, and a produce inspection unit operative to automatically inspect at least one characteristic of an individual item of produce and to provide an indication of the at least one characteristic to the produce labelling unit.

Further in accordance with a preferred embodiment of the present invention the at least one characteristic includes at least one of the following characteristics variety, size, weight, grade, color, and price.

There is also provided in accordance with a preferred embodiment of the present invention a singulator including a conveyor configured and arranged to convey articles in sequence, characterized in that no element is provided to separate adjacently disposed articles along the conveyor.

There is additionally provided in accordance with a preferred embodiment of the present invention a singulator including a conveyor configured and arranged to convey articles in sequence without controlling the distances between adjacent article positions.

Further in accordance with a preferred embodiment of the present invention the conveyor includes a plurality of elongate elements arranged in the direction in which the articles are conveyed.

Still further in accordance with a preferred embodiment of the present invention the plurality of elongate elements includes a plurality of cables.

There is further provided in accordance with a preferred embodiment of the present invention a singulator including a conveyor configured and arranged to convey articles in sequence, wherein the conveyor includes a plurality of strings of beads.

There is also provided in accordance with a preferred embodiment of the present invention a method for inspecting agricultural produce including the steps of generating an image of individual agricultural products, and automatically grading agricultural products by receiving the image generated by the imager and providing an output indication of a grade for the individual agricultural product.

There is further provided in accordance with a preferred embodiment of the present invention an agricultural produce inspection system including a fuzzy logic image entity classifier which employs fuzzy logic criteria in order to inspect a representation of an entity forming at least a portion of an agricultural product and to classify the entity according to a predetermined classification scheme.

Additionally in accordance with a preferred embodiment of the present invention the agricultural product is expected to have at least one discolored area on its surface and wherein the entity includes a discolored portion of the agricultural product and wherein the predetermined classification scheme includes two classes: expected discoloration, and unexpected discoloration.

Further in accordance with a preferred embodiment of the present invention the entity includes a pair of discolored areas and the predetermined classification scheme includes a binary classification scheme including a first class of stem/calyx and a second class of not stem/not calyx.

Still further in accordance with a preferred embodiment of the present invention the predetermined classification scheme includes a plurality of classes corresponding to a plurality of types of blemishes.

Also in accordance with a preferred embodiment of the present invention the entity includes the agricultural product and wherein the predetermined classification includes a plurality of classes corresponding to a plurality of grades of agricultural produce.

Additionally in accordance with a preferred embodiment of the present invention the representation of the entity is derived by employing fuzzy logic criteria in order to inspect a representation of at least one subentity forming a portion of the entity.

There is also provided in accordance with a preferred embodiment of the present invention an agricultural produce inspection system including an imager for generating an image of individual agricultural products, and an automatic agricultural product grading unit including an image processor receiving the image generated by the imager and providing an output indication of a grade for the individual agricultural product.

Further in accordance with a preferred embodiment of the present invention the grading unit is user-tunable such that criteria employed by the grading unit may be modified by the user.

Still further in accordance with a preferred embodiment of the present invention the grading unit includes a user-tunable fuzzy logic unit.

Also in accordance with a preferred embodiment of the present invention the fuzzy logic image entity classifier includes an entity representation fuzzification unit, entity classification rule inference logic, and an entity classification defuzzification unit.

Additionally in accordance with a preferred embodiment of the present invention a plurality of classification rules are employed, each rule corresponding to an individual class and having associated therewith, for each entity to be classified, a degree of belief, wherein the entity classification defuzzification unit is operative to identify, for each entity, a classification rule having a maximal degree of belief and to associate the entity with the class corresponding to the classification rule having the maximal degree of belief.

There is further provided in accordance with a preferred embodiment of the present invention apparatus for detecting blemishes on agricultural produce, the apparatus including a dual IR illumination system operative to provide IR band I and IR band II illumination of the agricultural produce, and a sensor operative to receive first and second images of the agricultural produce as illuminated by the IR band I and IR band II illumination respectively, a comparison operator operative to compare the first and second images and to generate an output indication of blemishes, wherein the wavelength bands of the band I IR and band II IR illuminations are selected such that artifacts resembling blemishes are similarly detected by the two illuminations whereas blemishes are differently detected in the two illuminations.

Still further in accordance with a preferred embodiment of the present invention the wavelength band of the band I IR illumination includes approximately 0.67–0.77 microns and the wavelength band of the band II IR illumination includes approximately 0.77–0.95 microns.

Moreover in accordance with a preferred embodiment of the present invention the comparison operator includes an arithmetic operation.

Further in accordance with a preferred embodiment of the present invention the article includes an agricultural produce.

Still further in accordance with a preferred embodiment of the present invention the agricultural produce includes an apple.

Also in accordance with a preferred embodiment of the present invention the article includes a round article.

Additionally in accordance with a preferred embodiment of the present invention the agricultural produce includes a round article.

There is also provided in accordance with a preferred embodiment of the present invention conveying apparatus for agricultural produce including a produce supporting cable assembly including a plurality of cables arranged to support agricultural produce.

Further in accordance with a preferred embodiment of the present invention the conveying apparatus includes an additional cable assembly interlaced with the produce supporting cable assembly.

Still further in accordance with a preferred embodiment of the present invention the conveying apparatus includes a kicker element, and a kicker element activator operative to slide the kicker element between the produce supported by the cable assembly so as to allow the kicker element to engage the produce and to remove the produce from the plurality of cables.

Also in accordance with a preferred embodiment of the present invention the spectral filter includes a non-pyramidal prism.

BRIEF DESCRIPTION OF THE DRAWINGS

The present invention will be understood and appreciated from the following detailed description, taken in conjunction with the drawings in which:

FIG. 2 is a block diagram of a sorting and grading line constructed and operative in accordance with a preferred embodiment of the present invention and including the electro-optic sorting and grading system of FIG. 1;

FIG. 3A is a side view illustration of conveying apparatus for conveying or transporting agricultural produce substantially without contacting or obscuring the agricultural produce during imaging, useful in the embodiment of FIG. 1, which is constructed and operative in accordance with a first preferred embodiment of the present invention;

FIG. 7 is a schematic illustration of conveying apparatus useful in the embodiment of FIG. 1 which is constructed and operative in accordance with a preferred embodiment of the present invention wherein agricultural produce to be imaged is actively conveyed along a generally horizontal pathway defined by a plurality of elongate elements having a downward projection of relatively small area;

Figure 23:
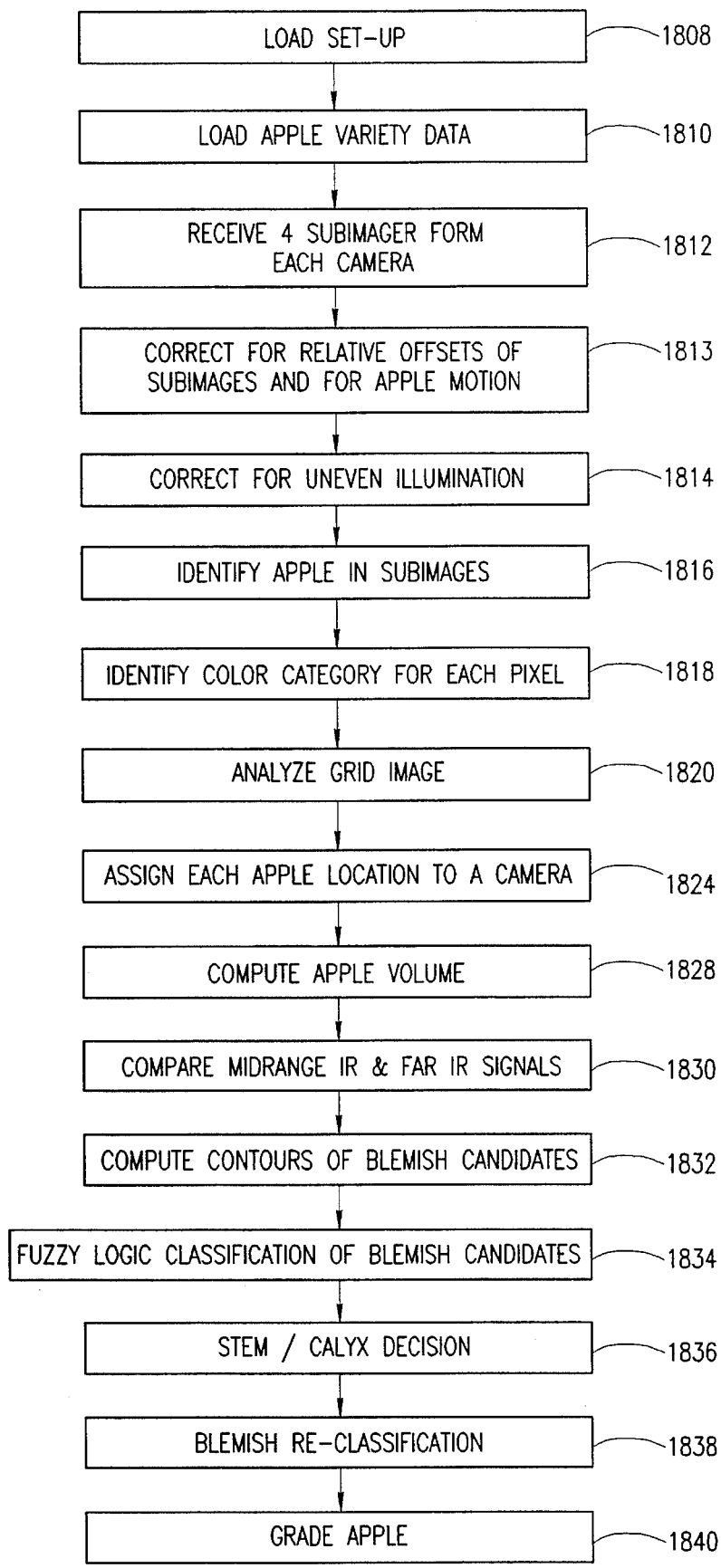
FIG. 23 is a simplified flowchart of a preferred method for implementing the image processing unit 18 of FIG. 1.
Figure 24:
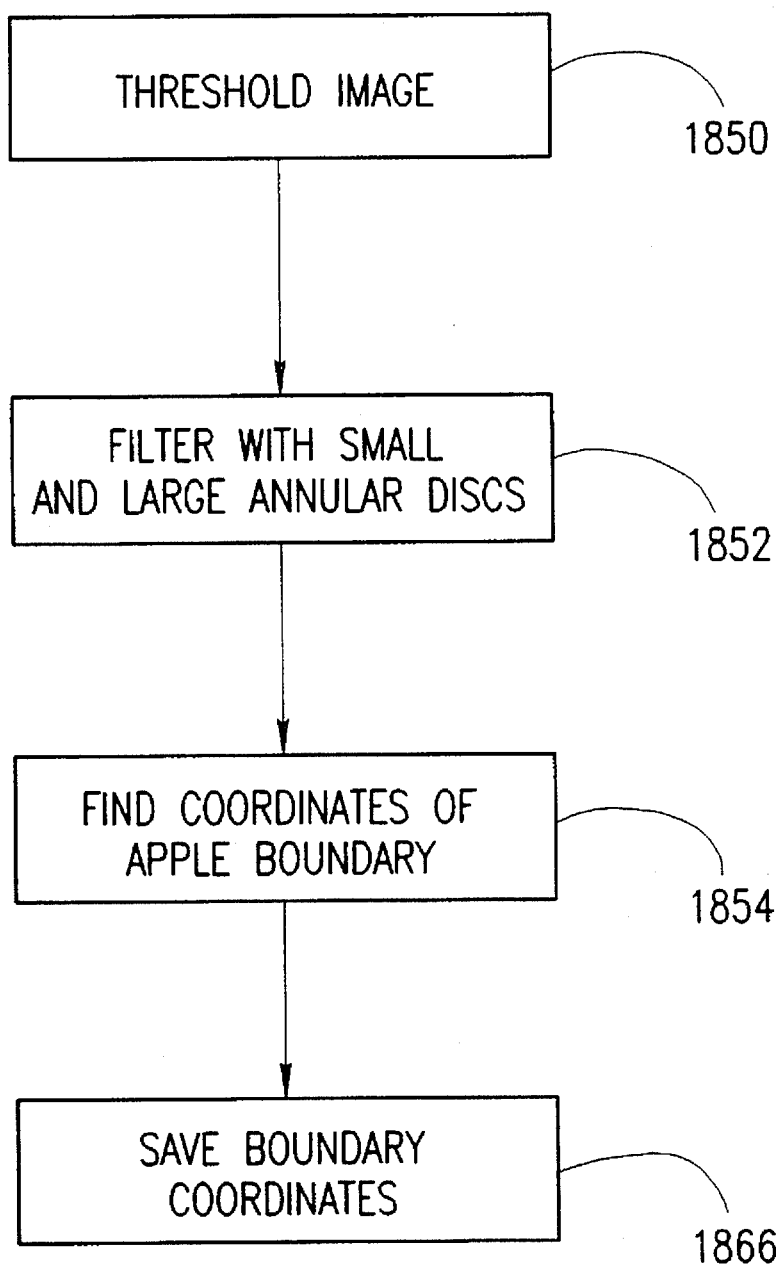
FIG. 24 is a simplified flowchart of a preferred method for finding the boundary of an article using an image of the article and a grid projected onto the article which is suitable for implementing step 1816 of FIG. 23.
Figure 25:
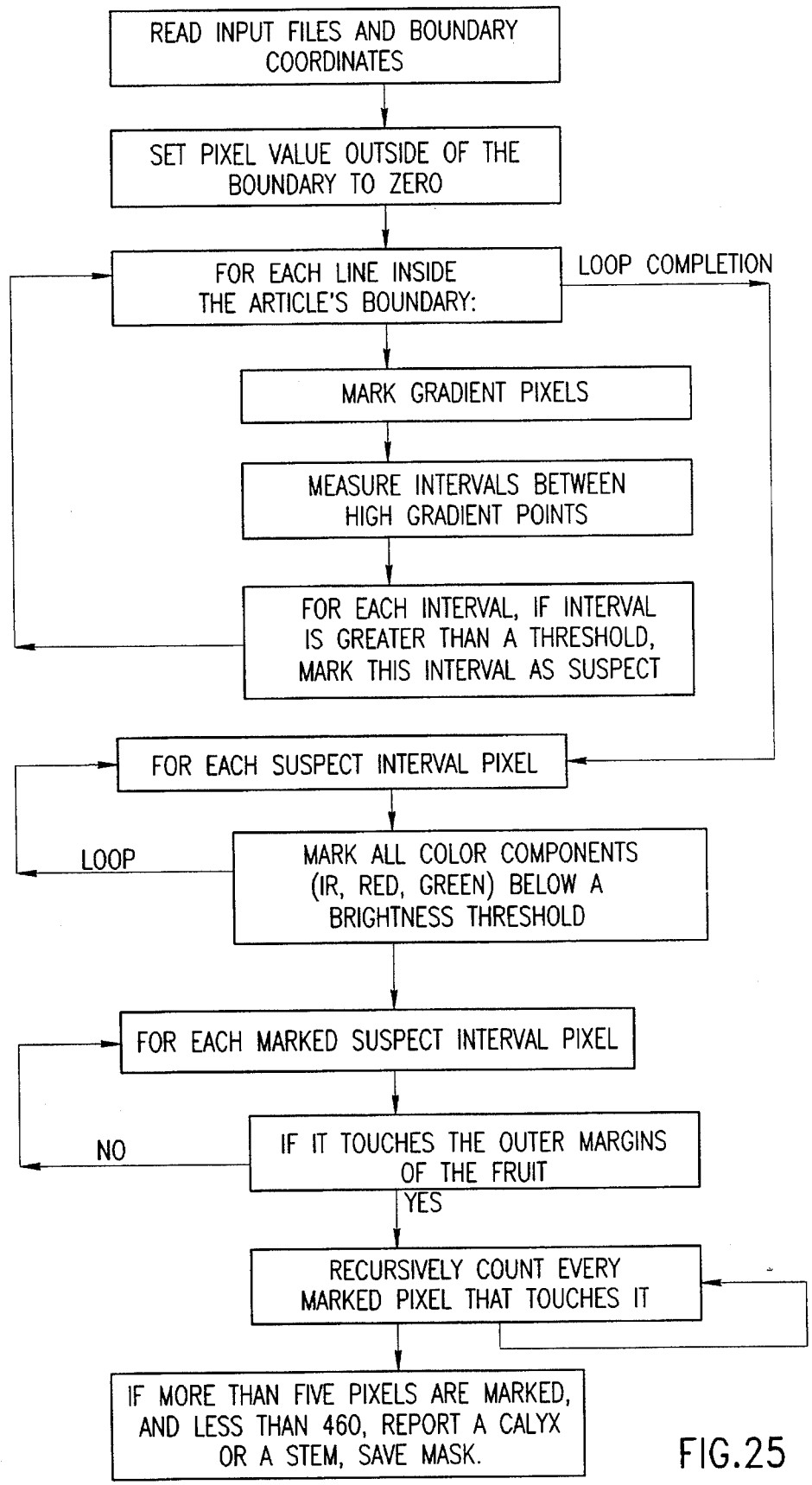
FIG. 25 is a simplified flowchart of a preferred method for implementing step 1820 of FIG. 23.

Also submitted herewith are the following appendices:

Appendix A is a computer listing of a software implementation of a preferred method for implementing steps 1813 and 1814 of FIG. 23;

Appendix B includes a computer listing of a main program for an article inspecting system constructed and operative in accordance with a preferred embodiment of the present invention;

Appendix C is a computer listing of a software implementation of a sample method for implementing the method of FIG. 24;

Appendix D is a computer listing of a software implementation of a sample method for assigning identifying color codes to each of a plurality of locations in imaged StarKing apples;

Appendix E is a computer listing of a software implementation of a sample method for implementing the method of FIG. 25;

Appendix F is a computer listing of a software implementation of a preferred method for implementing steps 1824 and 1828 of FIG. 23;

Appendix G is a computer listing of a software implementation of a preferred method for implementing steps 1830 and 1832 of FIG. 23;

Appendix H, taken together with Appendix I is a computer listing of a software implementation of a preferred method for implementing step 1834 of FIG. 23;

Appendix I includes a computer listing which, taken together with Appendix H, forms a computer listing of a software implementation of a preferred method for implementing step 1834 of FIG. 23, and also includes a computer listing of a software implementation of a preferred method for implementing steps 1836 and 1838 of FIG. 23.

Appendix J includes computer listings of helper routines useful in conjunction with the other computer listings appended hereto;

Appendix K includes computer listings of "include files" useful in conjunction with the other computer listings appended hereto; and Appendix L is a computer listing of a batch file useful in generating executable programs from the other computer listings appended hereto, and a DOS configuration file.

DETAILED DESCRIPTION OF PREFERRED EMBODIMENTS

Figure 1:
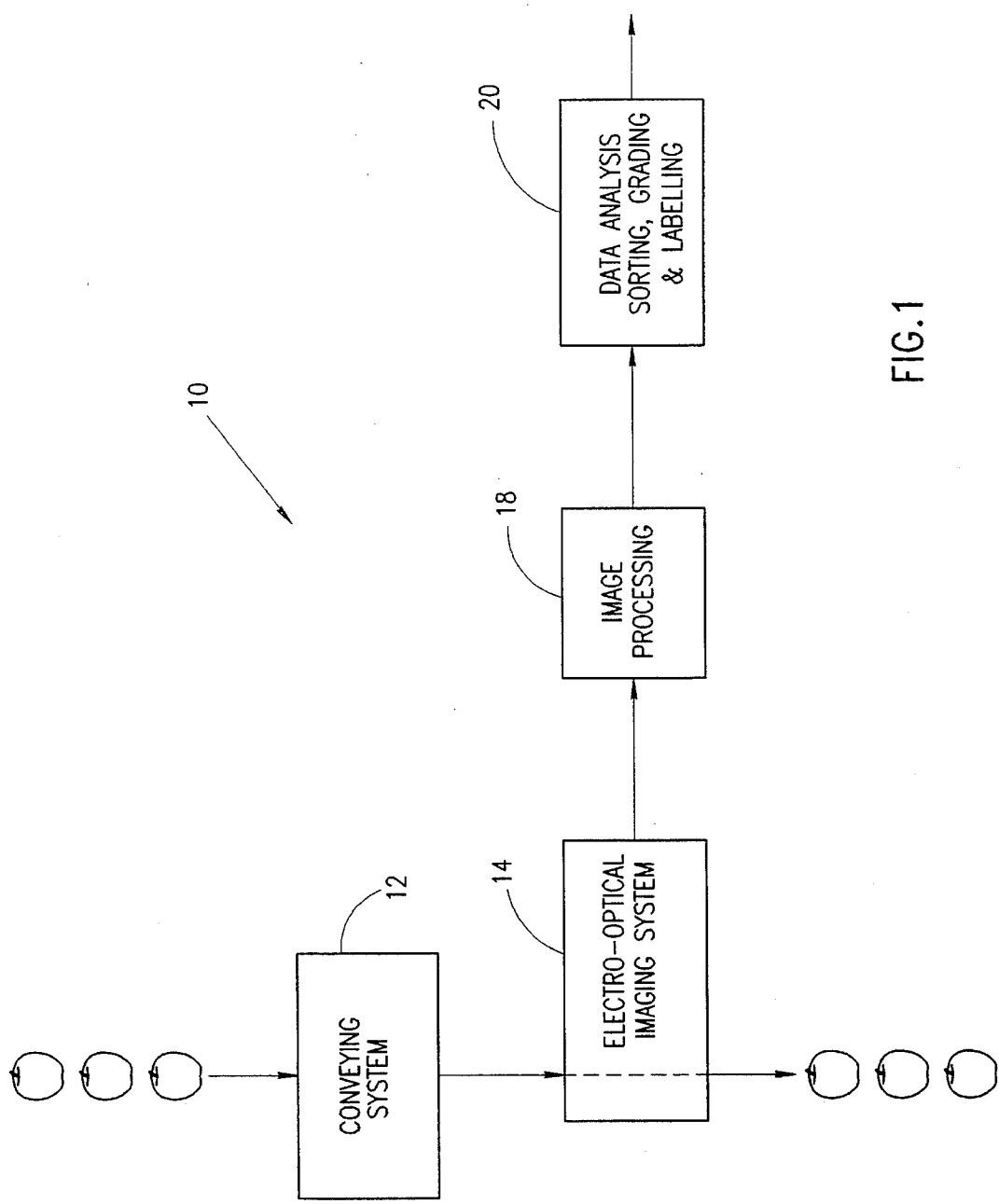
FIG. 1 is a block diagram of an electro-optic sorting and grading system constructed and operative in accordance with a preferred embodiment of the present invention.

Reference is now made to FIG. 1 which is a block diagram of an electro-optic sorting and grading system referenced generally 10 which is constructed and operative in accordance with a preferred embodiment of the present invention. The apparatus of FIG. 1 comprises a conveying unit 12 which receives a sequence of articles to be sorted and graded and conveys the articles past an electro-optical imaging system 14. Preferably, conveying unit 12 conveys the articles so as to allow simultaneous imaging of substantially every point along the surfaces of the articles. Conveying unit 12 may receive singulated articles or may receive articles in bulk. Various embodiments for conveying unit 12 are described below with reference to FIGS. 3A–9 and 30–33.

Electro-optical imaging system 14 preferably includes a plurality of simultaneously operative electro-optical imaging units for imaging each article in the sequence of articles from a corresponding plurality of angles. Preferably, each imaging unit comprises a monochromatic camera unit and a spectral splitting or spectral separation element. Each monochromatic camera unit may comprise any suitable camera apparatus such as one or more line scanner cameras or such as, in the illustrated embodiment, as explained below with reference to FIG. 17, a CCD, CID or vidicon camera. The spectral splitting or spectral separation element, typically a prism, is operative to provide a plurality of nonoverlapping images of each article, each image having different spectral characteristics. Imaging system 14 also preferably includes an illumination subsystem including a plurality of light sources, provided externally of an article-containing enclosure and sealed from the inside thereof.

The light sources are preferably surrounded by a diffusive reflector which provides generally uniform illumination of the article and of the internal surface of the article-containing enclosure which serves as a background when the article is imaged. Preferably, the article-containing enclosure is formed of a translucent material which diffuses light arriving from the light sources, thereby enhancing uniformity of illumination of the article. Electro-optical imaging system 14 is described in detail below with reference to the embodiments of FIGS. 10 and 13.

The images of each article generated by imaging system 14 are provided to an image processing unit 18 which is described below with reference to FIG. 23. Image processing unit 18 is operative to combine the outputs of the plurality of imaging units in order to quantify a plurality of features of the inspected articles. Preferably, almost every point along the surface of each article is represented exactly once in the analysis of image processing unit 18.

The feature information generated by image processing unit 18 is received by an article data analysis and sorting/grading/labelling unit 20. Analysis and sorting/grading/labelling unit 20 comprises a sorting and grading decision tree and is operative to categorize articles using a plurality of predetermined categories which may be based on size and/or shape and/or spectral characteristics such as color and/or presence of blemishes upon the articles.

Preferably, unit 20 is also operative to label or otherwise mark each individual article with an indication of an individual feature thereof as determined by the sorting and grading decision tree, such as the grade thereof.

It is appreciated that the apparatus of FIG. 1 may be used to form part of a fruit sorting and grading line such as the fruit sorting and grading line 50 of FIG. 2. As shown, fruit sorting/grading line 50 may include some or all of the following units in addition to the sorting and grading system 10 of FIG. 1, not necessarily in the illustrated sequence: an unloading unit 52, a fruit washing unit 54, a fruit drying tunnel 56, a fruit feeding unit or bulk conveyor 58, a singulator 60, optionally, and conveyor belts 62 for conveying the fruit to outlets for sorted, graded and, preferably, labelled fruits.

Singulator 60 is operative to sequence a stream of fruit by creating parallel "lanes" 64 of fruit. Each fruit preferably has a well-defined position such as between two particular bicone rollers or within a particular cup or pocket. Typically, one electro-optical imaging unit 14 is provided per lane and the configuration of electro-optical imaging unit 14 is such that the lanes may be disposed relatively close together, as explained below in more detail with reference to FIG. 13.

A mechanical kicker or air jet or other suitable means may be provided (not shown) which, in response to a suitable command from electro-optical unit 14, kicks or otherwise conveys an apple to an individual one of outlet conveyors 62.

FIG. 3A is a side view illustration of conveying unit 12 of FIG. 1 which is constructed and operative in accordance with a first preferred embodiment of the present invention. A particular feature of the embodiment of FIG. 3A is that the articles to be inspected are conveyed substantially without contact therewith during imaging, thereby minimizing obscuring of the articles to be inspected. As shown, the apparatus of FIG. 3A comprises an imaging space 80 in which the articles move substantially without being contacted and therefore substantially without being obscured from imaging apparatus. The imaging space 80 may be enclosed by an enclosure 81 which may be identical to enclosure 230 of FIG. 10 or enclosure 300 of FIG. 13, both of which are described in detail below with reference to FIGS. 10 and 13 respectively.

A conveying and launching unit 82, typically configured as an endless driving chain, conveys articles, such as fruit arriving from lane conveyor 64 of FIG. 2, toward the imaging space 80 and provides horizontal velocity to the articles, thereby enabling them to move in a generally parabolic trajectory through the imaging space 80. An unloading unit 84 receives articles which have travelled through imaging space 80 substantially without damaging the articles upon impact. Unloading unit 84 may also convey the articles to a desired location, such as to conveyor 62 of FIG. 2. Conveying and launching unit 82 may comprise an array of article supporting elements 86 such as but not limited to cylindrical or biconical rollers, rubber cups, plastic cups or trays, or flexible pockets.

Unloading unit 84 preferably comprises a damping element 96, for receiving a sequence of articles following passage of the articles through imaging space 80, and a conveyor 97. Damping element 96 typically receives the articles without substantially damaging the article upon impact, and conveyor 97 then conveys articles onward while maintaining the sequence in which they were received. Conveyor 97 may be similar to conveying and launching unit 82.

According to one preferred embodiment of the present invention, damping element 96 may comprise a brush array 98. Brush array 98 may include two or more cylindrical brushes arranged parallel to one another and rotating in opposite directions at a suitable speed such as 45 rpm. Any suitable size and type of brush may be employed, such as a 25 cm diameter, 20 cm long nylon brush with split hair so as not to damage delicate produce. The distance between axes of adjacent cylindrical brushes may be approximately 50 cm.

Alternatively, damping element 96 may comprise deformable cushions or bean bags (not shown) for damping articles, such as those described in U.S. Pat. No. 3,961,701 to Paddock et al, the disclosure of which is incorporated herein by reference.

Figure 3B:
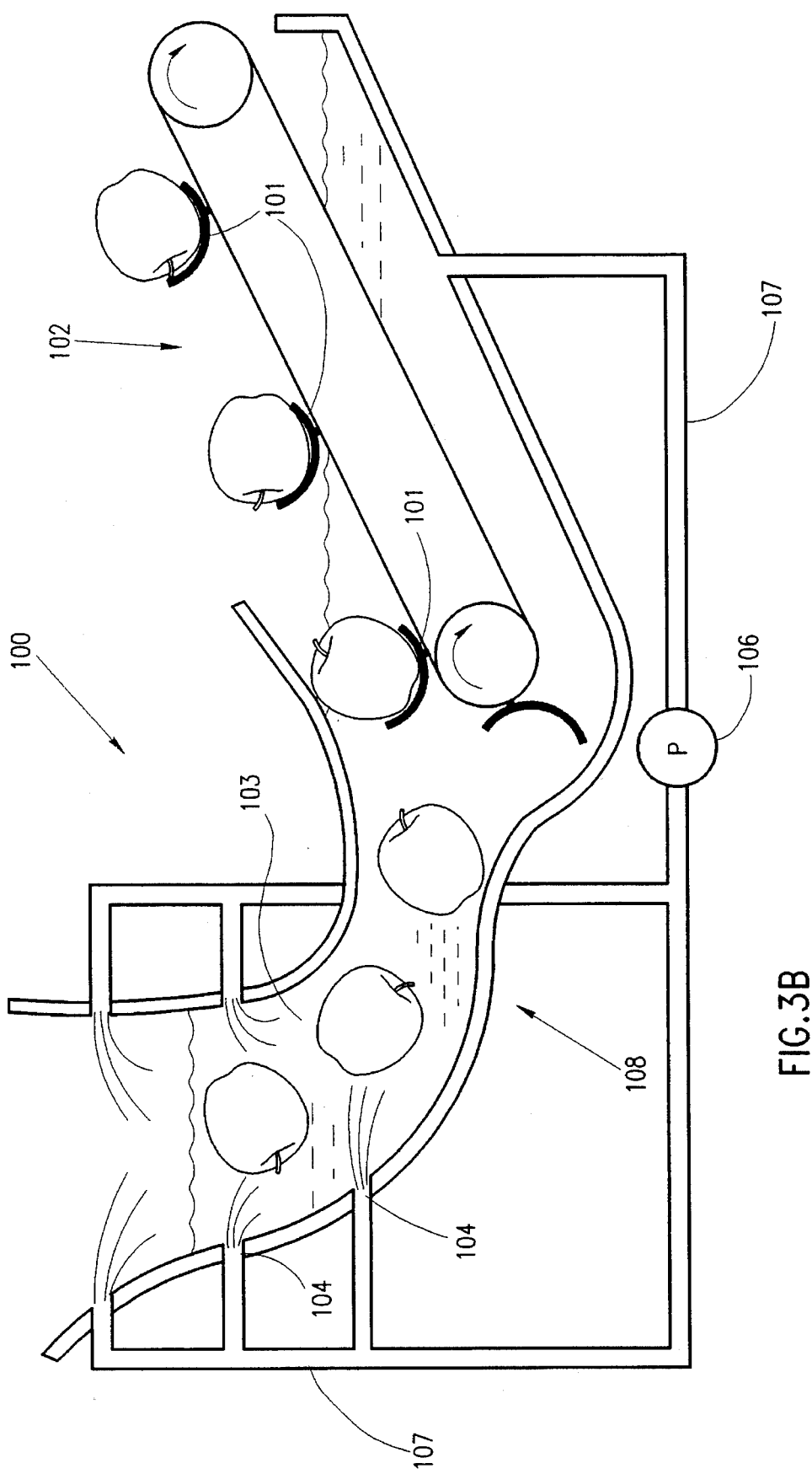
FIG. 3B is a cross sectional schematic illustration of an article receiving system which is a portion of the apparatus of FIG. 3A and is constructed and operative in accordance with a second preferred embodiment of the present invention.

Reference is now made to FIG. 3B which is a cross-sectional illustration of a portion of conveying unit 12 which is operative to convey agricultural produce away from electro-optical imaging system 14. The embodiment of FIG. 3B is substantially identical to the embodiment of FIG. 3A except that brush array 98 is replaced by a liquid based damping unit 100 and unloading unit 84 is replaced with a liquid-immersed unloading unit 102 which may be substantially similar to unloading unit 84 except as specified hereinbelow:

Liquid based damping unit 100 preferably comprises an open enclosure portion 103 within which airborne articles land one at a time in a liquid such as water.

Unloading unit 102 is immersed in approximately 30 cm of water and includes cups 101, or any other suitable element for scooping up articles from the water, which are configured so as to prevent disengagement of the articles from the cups due to water resistance to motion of the articles and of unloading unit 102. Preferably, cups 101 are perforated so that water may drain as articles are conveyed out of the water.

An array of liquid jet outlets 104 is arranged along the interior walls of enclosure 103 in fluid communication with a liquid circulator 106 via a piping system 107. Liquid circulator 106 may comprise a high capacity centrifugal pump which generates liquid circulation at a suitable rate such as 5 liter/sec. Liquid outlets 104 provide liquid fountains or streams which are operative to flush away an article which has landed within enclosure 103 before the next article lands.

Articles are flushed along a predetermined trajectory, in sequence, through a conduit portion 108 toward unloading unit 102 and eventually are conveyed out of damping unit 100 in sequence by unloading unit 102. The operation of unloading unit 102 is typically synchronized relative to the flow of articles to the system, so as to scoop up each article as it flows toward unloading unit 102. Preferably, the velocity of the article relative to the velocity of unloading unit 102 at the moment the article is scooped up by unloading unit 102 is zero. For apples and other articles which are lighter than water, the article has an upward component which is matched by the upward velocity component of unloading unit 102.

Reference is now made to FIGS. 4A–4C and 5 which illustrate conveying unit 12 of FIG. 1 constructed and operative in accordance with a third preferred embodiment of the present invention. In the embodiment of FIGS. 4A–4C and 5, agricultural produce rolls down an inclined pathway defined by a plurality of elongate elements which are configured to conceal a very small portion of the agricultural produce from imaging system 14 of FIG. 1.

As shown, the apparatus of FIGS. 4A–4C and 5 comprises an inclined unit 110, a loading unit or singulator 112 and an unloading unit 114 which may be similar to unloading unit 84 of FIG. 3A. Singulator 112 may comprise a roller conveyor as shown or a cups conveyor such as conveyor 82 in FIG. 3A or more generally any suitable conveying element such as a conveyor forming part of an existing sorting and grading line.

Inclined unit 110 typically includes a plurality of cables 120 which are arranged substantially parallel to one another and to the path along which the articles are to be conveyed. Any suitable number of suitable spaced cables may be employed, such as three cables spaced 20–40 mm apart. Each cable may be formed from any suitable material which is preferably relatively strong so as to allow the cross sectional diameter of the cables to be Small, such as approximately 1–3 mm, thereby minimally obscuring the articles when viewed through the cables. For example, cables may be formed of nylon or plastic coated steel, or of plastic coated polysterene or aramid fibers. The length of cables 120 may be approximately 100–120 cm.

Figure 4A:
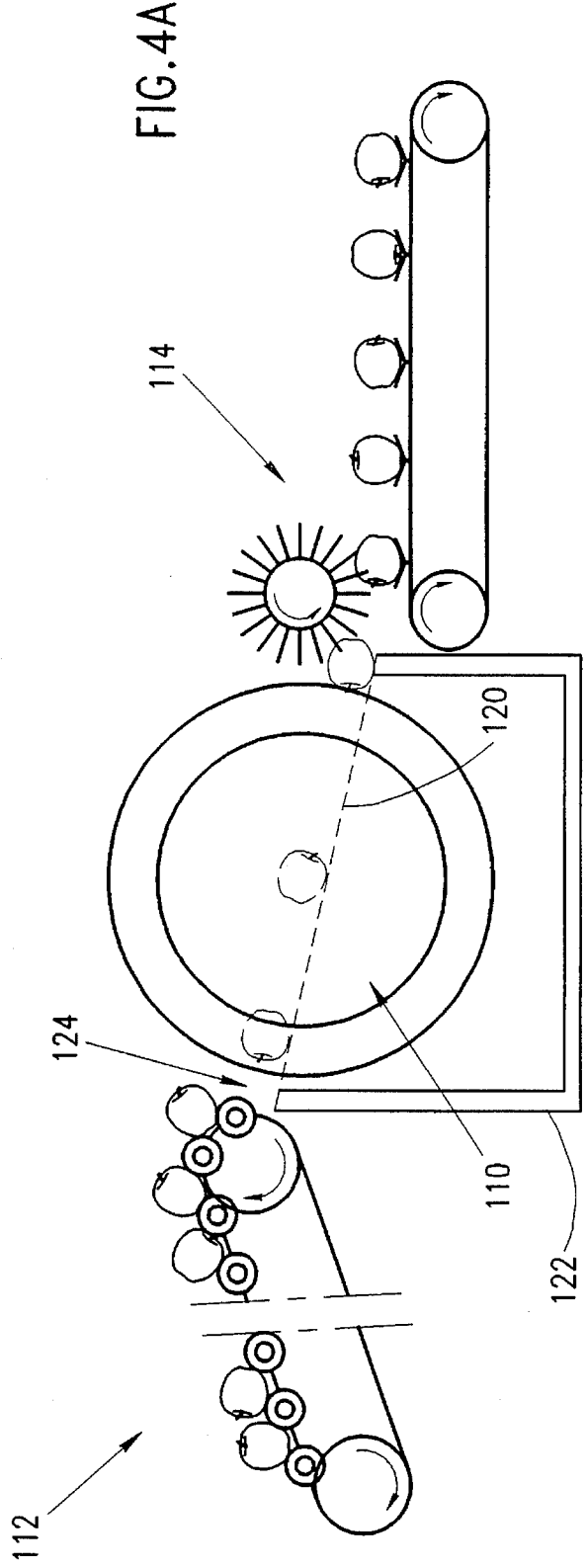
FIG. 4A is a schematic illustration of conveying apparatus useful in the embodiment of FIG. 1 which is constructed and operative in accordance with a preferred embodiment of the present invention wherein agricultural produce rolls down an inclined plane defined by a plurality of elongate elements having a downward projection of relatively small area.
Figure 4C:
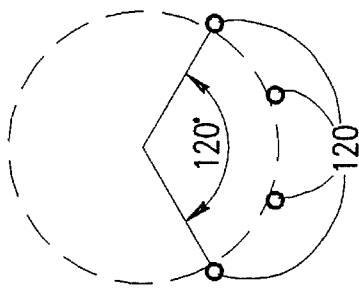
FIGS. 4B and 4C are cross-sectional illustrations of the plurality of elongate elements of FIG. 4A, arranged in accordance with alternative embodiments of the present invention.
Figure 4B:
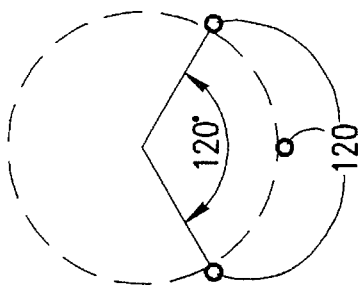

As shown in FIGS. 4B and 4C, the cables 120 when viewed in cross section may for example be arranged at equal intervals along an approximately 120 degree arc of an 8 cm diameter circle.

Cables 120 are typically arranged at a suitable angle such as approximately 20–40 degrees from the horizontal. The cables may be supported by a rigid frame 122 which maintains a suitable level of tension such as approximately 50 kg by means of suitable tensioning elements such as an array 123 of springs. The articles, as they roll down the cables, gain velocity and the angle and length of the cables are preferably selected such that only one article is in the field of the view of the imaging cameras at any one time.

Loading unit 112 is positioned as close as possible to the high end 124 of the cables, at an elevation the same as or slightly exceeding the height of the high end 124 of the cables, so that articles will tend to be deposited from loading unit 112 directly onto the cables 120.

Figure 5:
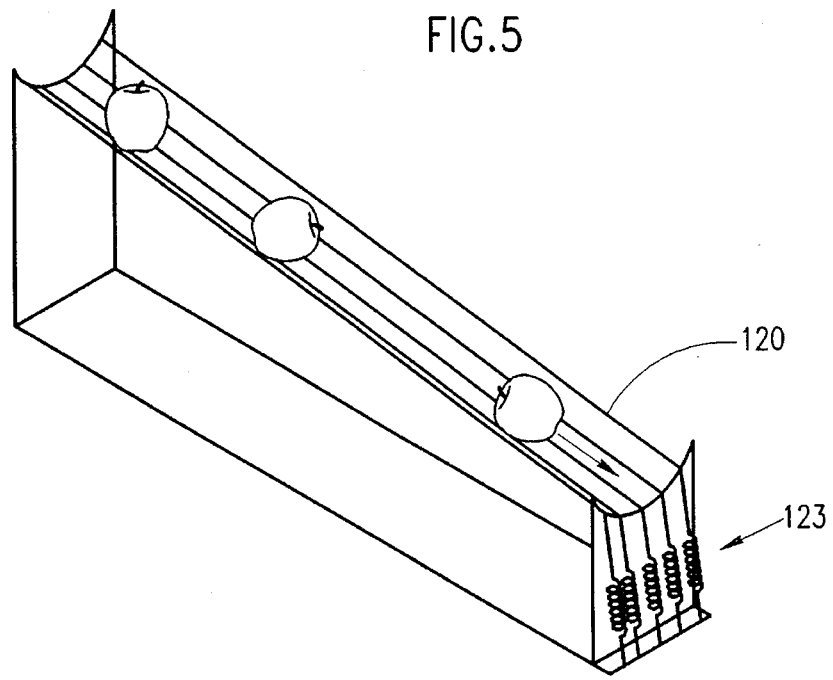
FIG. 5 is a perspective illustration of a portion of the apparatus of FIG. 4A.
Figure 6:
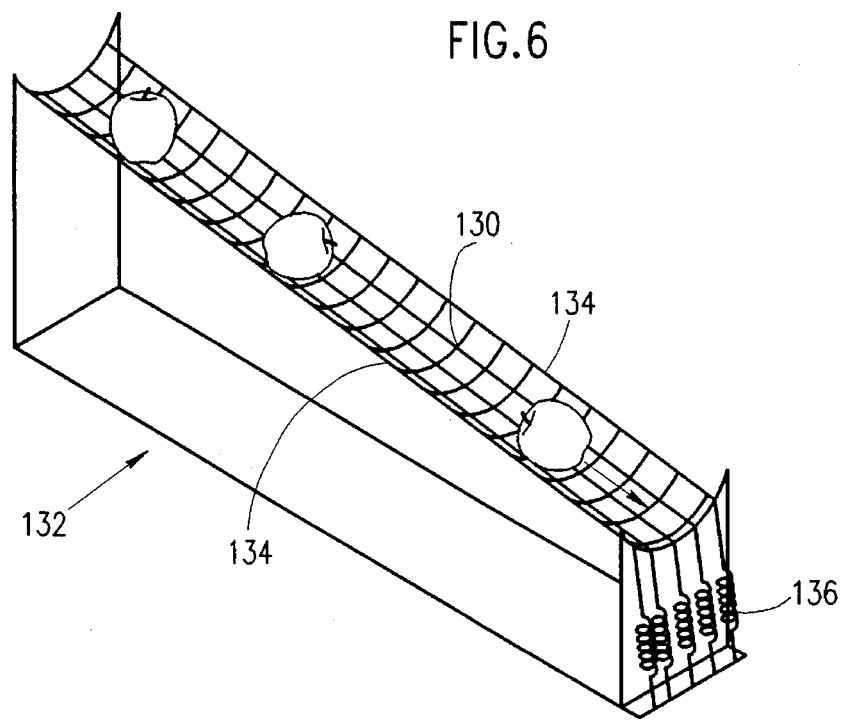
FIG. 6 is a side view illustration of conveying apparatus similar to the apparatus of FIG. 4A but wherein the plurality of generally parallel elogate elements is replaced by an element having a screen or mesh type configuration.

FIG. 6 illustrates an alternative embodiment of conveying unit 12 of FIG. 1. The embodiment of FIG. 6 is similar to the embodiment of FIGS. 4 and 5, however, the cables 120 are replaced by a net 130 arranged at a suitable angle to the horizontal, such as 40–50 degrees. The articles roll down the length of the net, which may be approximately 110–130 cm long. Loading onto the net and unloading therefrom may be as described above with reference to FIGS. 4A–4C and 5.

Any suitable net or mesh may be employed which obscures the articles as little as possible when the articles are viewed through the net. For example, a net or mesh may be formed of nylon threads 0.3–0.8 mm in diameter and spaced appproximately 20 to 30 mm apart. The net 130 may be supported by a rigid frame 132 which preferably includes means, such as an array 136 of springs, for maintaining the net 130 at a level of tension sufficient to ensure that articles rolling along the net depress the net by no more than approximately 2 cm.

According to one embodiment of the present invention, the frame 132 comprises a pair of net-supporting cables 134 disposed on both sides of the net 130. Cables 134 may be approximately 20 cm apart and provide a suitable level of tension such as approximately 20 kg such that, when the net 130 is supporting an article, the lowest point of the net 130 is approximately 3 cm below the cables 134.

Alternatively, the cables may be eliminated and tension in the net may be provided by springs 136.

Figure 8:
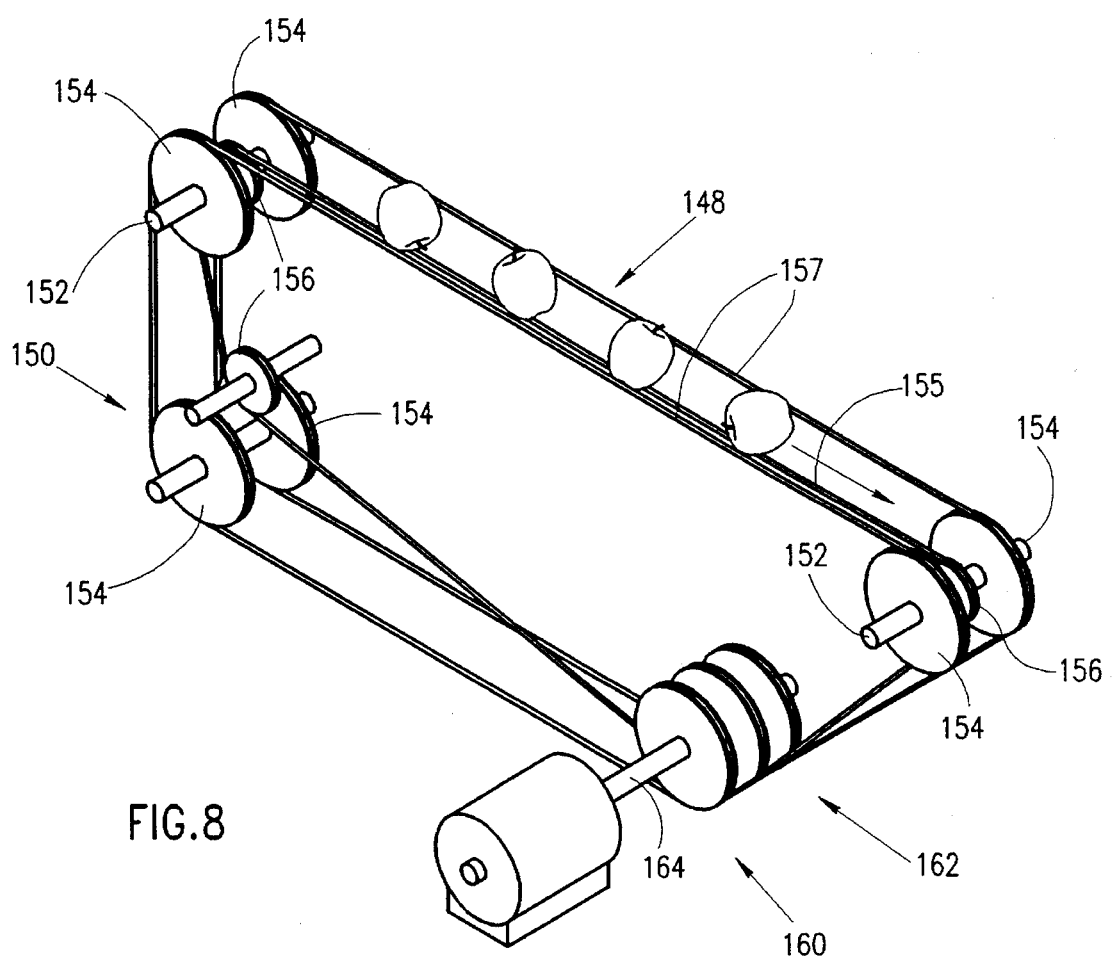
FIG. 8 is a perspective illustration of apparatus similar to the apparatus of FIG. 7 except that 4 pulleys are employed rather than 3 pulleys as in FIG. 7.

FIGS. 7 and 8 illustrate an alternative embodiment of conveying unit 12 of FIG. 1. The embodiment of FIGS. 7 and 8 is similar to the embodiment of FIGS. 4A–C and 5 except for the following differences. The cables 120 of FIGS. 4A–C and 5 are replaced by driven cables 148 which may be oriented generally horizontally rather than being arranged along an inclined plane. Typically, the angle between cables 148 and the horizontal is within the range of +/–5 degrees. Cables 148 are preferably closed loops formed of a suitable material such as plasticized PVC or such as steel or polyester or aramid fibers coated with plasticized PVC or nylon or polyurethane.

A cable supporting unit 150 is provided for tensioning the pulleys at about 30–50 kg. Cable supporting unit 150 preferably comprises an array of coaxial guiding pulleys 152 comprising outer pulleys 154 and inner pulleys 156. Inner pulleys 156, which support central cables 155, are typically smaller than outer pulleys 154, which support peripheral cables 157, such that central cables 155 are supported below peripheral cables 157, providing a cradle-like configuration of cables 148. For example, outer pulleys 154 may have diameters of approximately 100 mm and inner pulleys 156 may have diameters of approximately 70 mm. Each pulley is preferably independent or disengaged relative to the other pulleys.

A cable driving unit 160 is provided for driving the cables 148. Cable driving unit 160 preferably comprises an array 162 of drive/power pulleys which are coaxially mounted on an electric motor shaft 164. Preferably, all drive/power pulleys have the same diameter, such as approximately 100 mm, in order to maintain a uniform linear speed for all of cables 148, such as approximately 1.2–1.4 m/sec.

Preferably, a loading unit or singulator 170 is provided which is generally similar to singulator 112 of FIGS. 4A–5. However, loading unit 170 is configured and arranged relative to cables 148 such that, once loaded onto the cables, articles remain generally stationary relative to the cables and do not roll. Also, preferably, the cables move the articles such that only one article at a time is within the field of view of the imaging apparatus. The velocity of loading unit 170 is preferably approximately 50 cm/sec.

An unloading unit 172 is provided which may be similar to unloading unit 114 of FIG. 4A.

Figure 9:
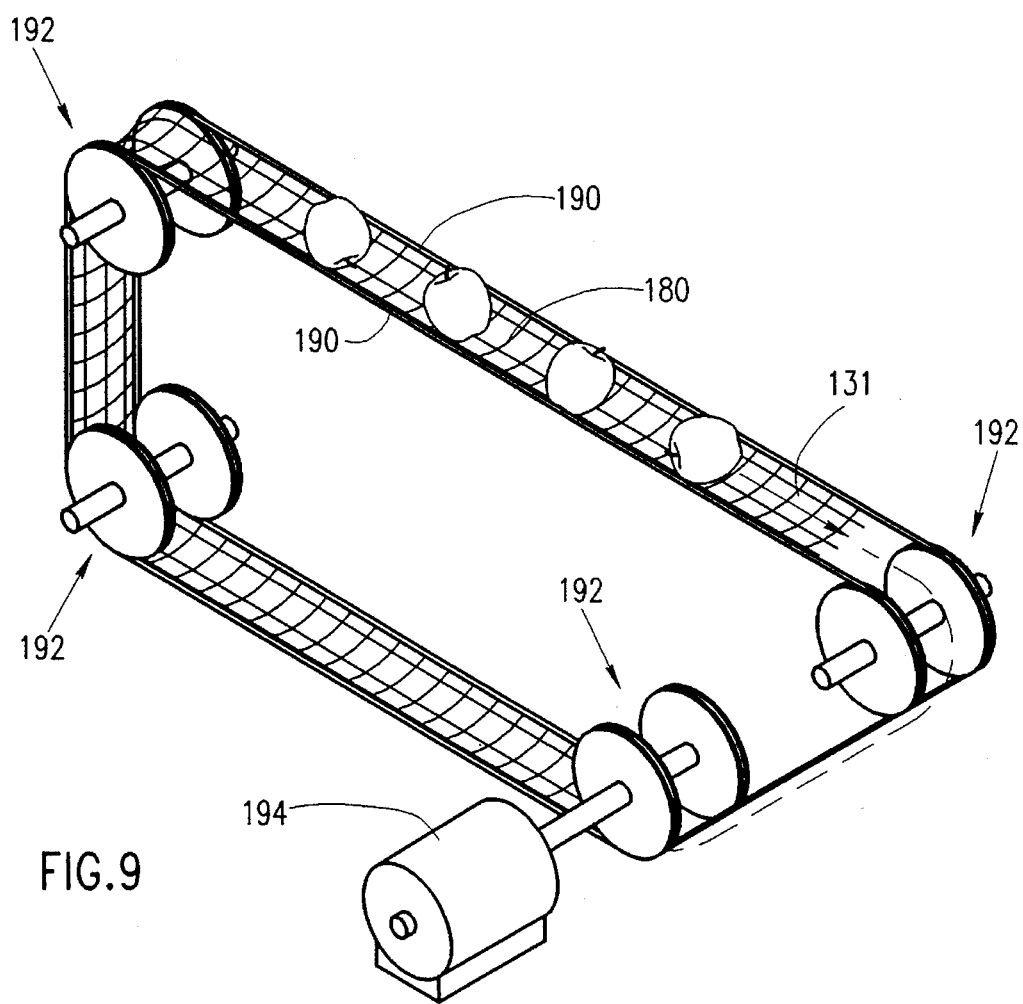
FIG. 9 is a side view illustration of conveying apparatus similar to the apparatus of FIG. 7 but having a screen or mesh type configuration rather than an elongate configuration.

FIG. 9 illustrates an embodiment of conveying unit 12 of FIG. 1 which is a variation on the embodiment of FIGS. 7 and 8. The embodiment of FIG. 9 is similar to the embodiment of FIGS. 7 and 8 except for the following differences.

The cables 148 are replaced with a net 180 which may be similar to net 130 of FIG. 6 and which may be supported at a tension level of approximately 10 kg.

According to one embodiment of the present invention, cables 190 which are similar to cables 134 of FIG. 6 support both sides of the net and are supported by pulleys 192 associated with a motor 194. Motor 194 via pulleys 192 convey the cables 190 in endless motion at a suitable linear velocity such as approximately 0.4 m/sec.

According to an alternative embodiment of the present invention, cables 190 are omitted. In this embodiment, the tension of the net 180 is relatively low, such as approximately 5 kg.

The linear speed at which articles are conveyed along the net may be approximately 0.4 m/sec.

A particular feature of the embodiments of FIGS. 3A–9 is that a large proportion of the surface area of the articles to be inspected is unobscured from any angle and may be imaged, such as 80%, 90%, 95% or more of each article. A plurality of imaging units may be employed such as two, three, four or more imaging units arranged to image the article from different angles.

Figure 10:
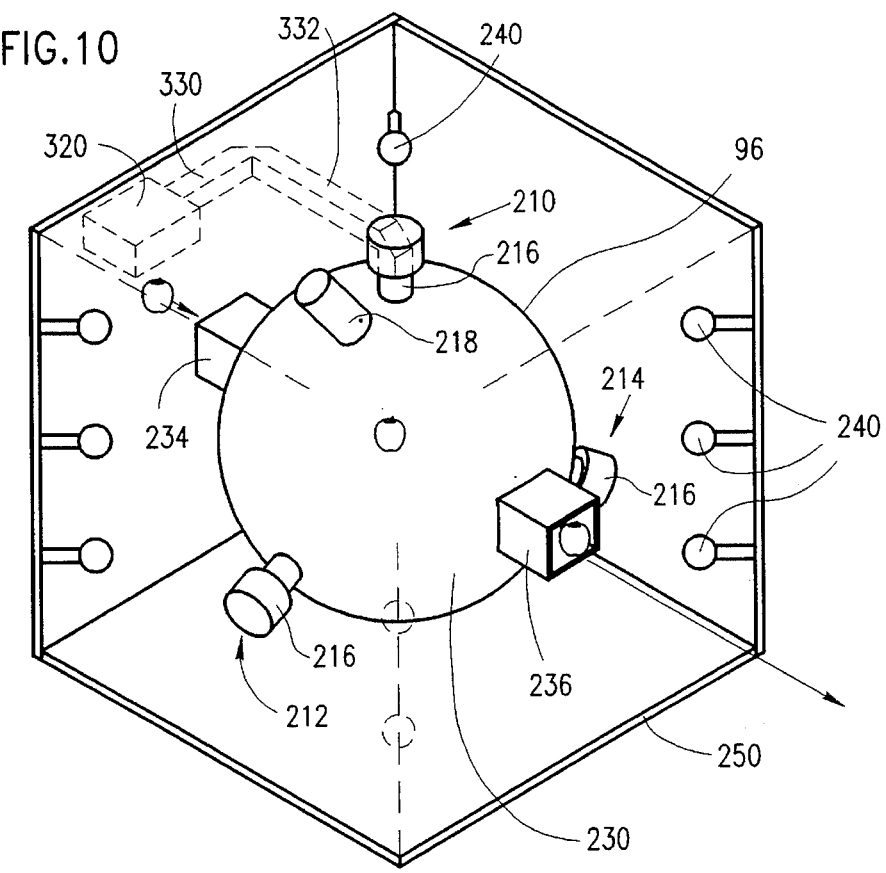
FIG. 10 is a perspective view partially cut away illustration of a diffuse illumination and imaging enclosure useful in the embodiment of FIG. 1.

Reference is now made to FIG. 10 which is a perspective view partially cut away illustration of electro-optical imaging system 14 of FIG. 1 constructed and operative in accordance with a preferred embodiment of the present invention. The apparatus of FIG. 10 preferably includes a plurality of simultaneously operative electro-optical imaging units for imaging each article in the sequence of articles from a corresponding plurality of angles. In the illustrated embodiment, four electro-optical imaging units are provided of which three are shown, referenced 210, 212 and 214. Preferably, each imaging unit includes a camera unit 216 described in detail below with reference to FIG. 17.

Optionally, associated with each imaging unit is a light projector 218 equipped with a grid-shaped mask (not shown) which projects a grid image onto the article and onto a background surface such as the inner surface of an imaging enclosure 230, so that the camera unit 216 may image the grid image superimposed onto each article. The lines or stripes of the grid, when superimposed on the article, are distorted as a function of convexity/concavity of the article. Therefore, by projecting a predetermined pattern, such as a grid pattern, onto an article, convexity/concavity information regarding the article may be derived. Specifically, grid projection is useful in detecting local depressions or "valleys" on an otherwise generally spherical surface, which valleys are putative locations of a fruit stem or calyx.

Methods for analyzing 3D surfaces using projected light grids are discussed in the following reference, the disclosure of which is incorporated herein by reference: Hu, G. and Stockman, G. "3D surface solution using structured light and constraint propagation", IEEE Trans. on PAMI, Vol. 4, 390–402, 1989.

A typical light projector is described in detail below with reference to FIG. 22.

Articles may travel into enclosure 230 for imaging through an entrance opening 234 and may exit enclosure 230 after being imaged through an exit opening 236. Preferably a pair of imaging apertures 237 and 238 (FIG. 12) each of suitable shape and size such as a 7 cm diameter circle are defined in enclosure 230 for each imaging unit. Apertures 237 and 238 provide optical communication between the interior of imaging enclosure 230, and camera unit 216 and optional grid projector 218, respectively, of each imaging unit. Each imaging aperture may be fitted with an optical glass window 239 (FIG. 12) of suitable thickness such as 3 mm. Each window 239 may be attached, preferably sealingly attached, to the enclosure 230 by any suitable means. For example, windows 239 may be glued into apertures 237 and 238 or alternatively may be attached by means of O-rings and brackets.

The apparatus of FIG. 10 also preferably includes an illumination subsystem including a plurality of light sources 240, provided externally of generally spherical enclosure 230 and sealed from the inside thereof. Any suitable number of light sources may be provided, such as 18 50 W light sources, generally symmetrically arranged along the internal surface of a diffusive reflective housing 250 so as to be generally equidistant from the surface of enclosure 230 and so as to be as distant as possible therefrom, thereby enhancing diffuseness of illumination and providing generally uniform illumination of the article. The light sources may comprise conventional incandescent, tungstenhalogen, fluorescent, rare-earth xenon or krytpon arc lamps or flash lamps and are preferably operative to provide a relatively flat spectrum of light ranging from green to near infra-red.

The imaging units 210, 212 and 214 are preferably supported by the housing 250 or alternatively, as shown, may be supported by enclosure 230.

The diffusive reflector housing 250 may be formed of structural panels of metal, plastic or wood which are coated from the inside with a white scatterer/diffuser material such as white alkyd non-glossy paint or white laminated thermosetting panels. Typically, cooling fans or other cooling means (not shown) are provided externally to housing 250 to cool the sealed space between enclosure 230 and housing 250. Alternatively or in addition, fanning or ventilation of the sealed space are provided.

According to a preferred embodiment of the invention, enclosure 230 is formed of a translucent material such as ground glass, opal glass or a plastic such as polycarbonate, polyethylane, high impact polystyren or acrylic. Enclosure 230 diffuses light arriving from light sources 240, thereby enhancing uniformity of illumination of articles inside enclosure 230.

The diffusive reflector housing 250 also preferably provides generally uniform illumination of the internal surface of the enclosure 230 thereby providing a generally uniformly illuminated background for imaging of articles inside the enclosure 230.

A suitable diameter for enclosure 230 is approximately 60 cm. Suitable dimensions for housing 250 is 80 cm×80 cm×80 cm. It is appreciated that the housing 250 need not be in the shape of a cube. Any suitable shape may be employed, such as a sphere or right cylinder having circular or polygonal cross-section. According to a preferred embodiment of the present invention, the cross section of the right cylinder, which defines side surfaces of the imaging enclosure, is a circle or a polygon having a number of sides which is an integer multiple of the number of imaging units, for reasons of symmetry. For example, if three imaging units are employed, the cross-section may be an equilateral hexagon.

Figure 11:
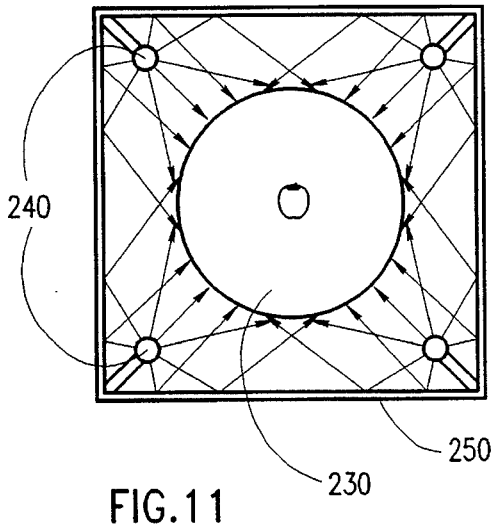
FIG. 11 is an optical diagram of the illumination apparatus of FIG. 10.

FIG. 11 is an optical diagram of the illumination apparatus of FIG. 10. As shown, illumination is preferably provided from a plurality of symmetric directions such as four symmetric directions, if four coplanar imaging units are employed.

Figure 12:
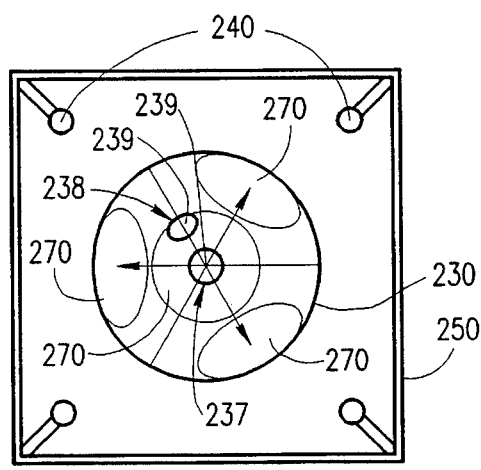
FIG. 12 is a schematic illustration of the fields of view of each of the cameras of the imaging apparatus of FIG. 10.

FIG. 12 is a schematic illustration of the intersections 270 of the internal surface of enclosure 230 with the fields of view of the four imaging units of FIG. 10. Each of the four intersections 270 serves as a background on which the article is imaged by the corresponding imaging unit. The backgrounds are preferably back-illuminated by light travelling between spherical enclosure 230 and housing 250, and further illuminated by light scattered within enclosure 230, as explained above. Preferably, the backgrounds are homogeneously bright within a range of +/–5%.

Preferably, each background is brighter than the brightest location on the article because the backgrounds, and not the articles, are backlit. The difference in lighting between article and background facilitates easy distinction between article and background in image processing.

Optionally, a spectral standard, serving as an internal, on-line imaged reference to which the image of the article may be compared, is placed along the interior surface of enclosure 230, within each of backgrounds 270. Each spectral standard is positioned at a suitable location such as adjacent the edge of the respective background 270 such that the corresponding imaging unit may simultaneously image an article to be inspected and the spectral standard. Each spectral standard may be reflective or transparent and may be attached as by an adhesive to the internal surface of the imaging enclosure 230. A sample spectral standard is described below with reference to FIG. 16.

Figure 13:
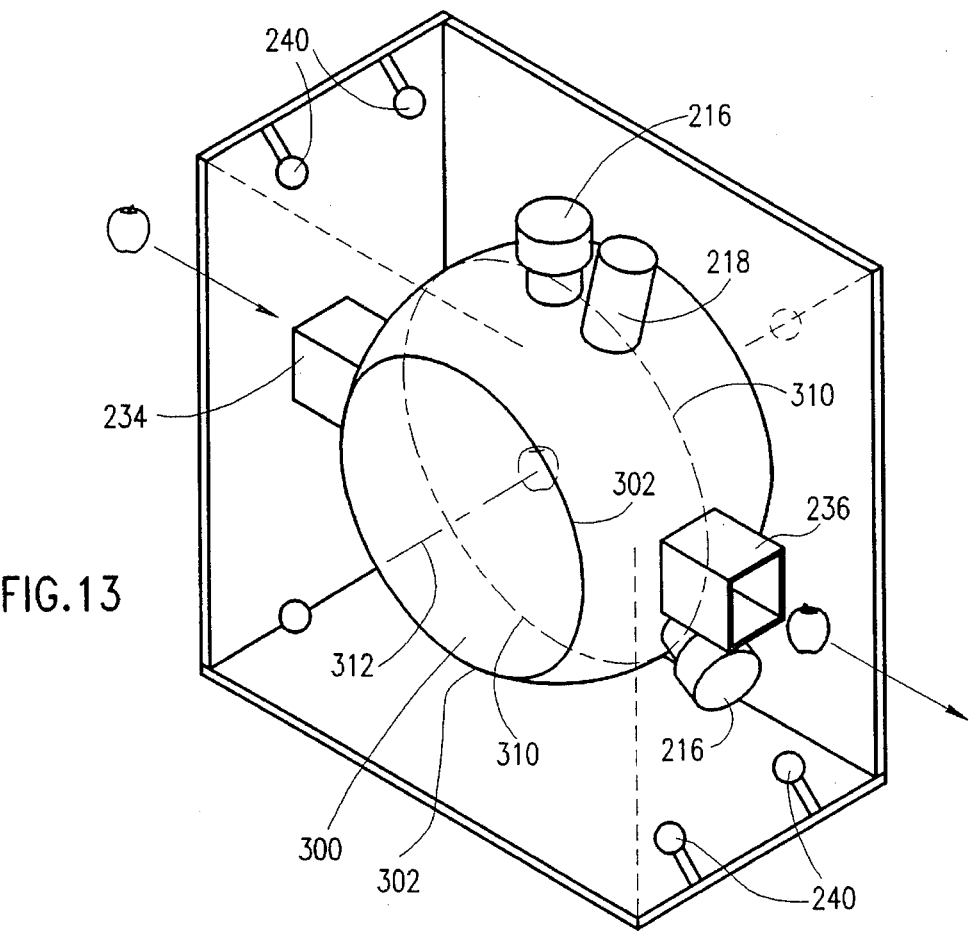
FIG. 13 is a perspective view partially cut away illustration of a generally truncated spherical diffuse illumination and imaging apparatus useful in the embodiment of FIG. 1.
Figure 14:
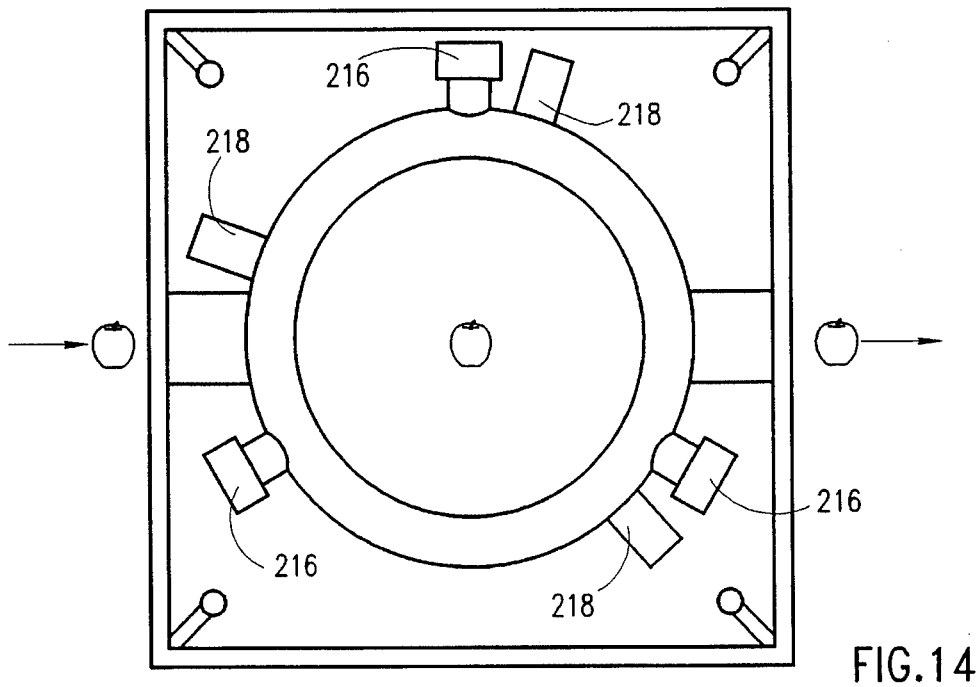
FIG. 14 is a cross sectional illustration of the apparatus of FIG. 13.

FIGS. 13 and 14 are a perspective view partially cut away illustration and a cross sectional illustration, respectively, of apparatus which is a variation of the apparatus of FIG. 10. The apparatus of FIG. 13 is similar to the apparatus of FIG. 10, however, spherical enclosure 230 is replaced by an enclosure 300 which resembles spherical enclosure 230 except that its configuration is that of a truncated sphere. The circumference 302 of the circle of truncation may be approximately 65 percent of the circumference 310 of the spherical portion of truncated sphere 300. Imaging units may be positioned at equal intervals along the circumference 310.

Preferably, the enclosure 300 has a plane of symmetry defined by circumference 310 on which three imaging units are centered. In this embodiment, the two locations intersecting an axis 312 which is perpendicular to the plane defined by circumference 310 are typically not imaged and therefore, relatively poor illumination of these locations does not adversely affect operation.

According to a preferred embodiment of the present invention, images of the articles travelling through enclosure 230 of FIG. 10 or enclosure 300 of FIG. 13 which are employed for subsequent analysis of the articles are generated in accordance with a predetermined time schedule. The predetermined time schedule ensures that at the moment of imaging, the article being imaged is correctly positioned relative to the imaging units.

Figure 15:
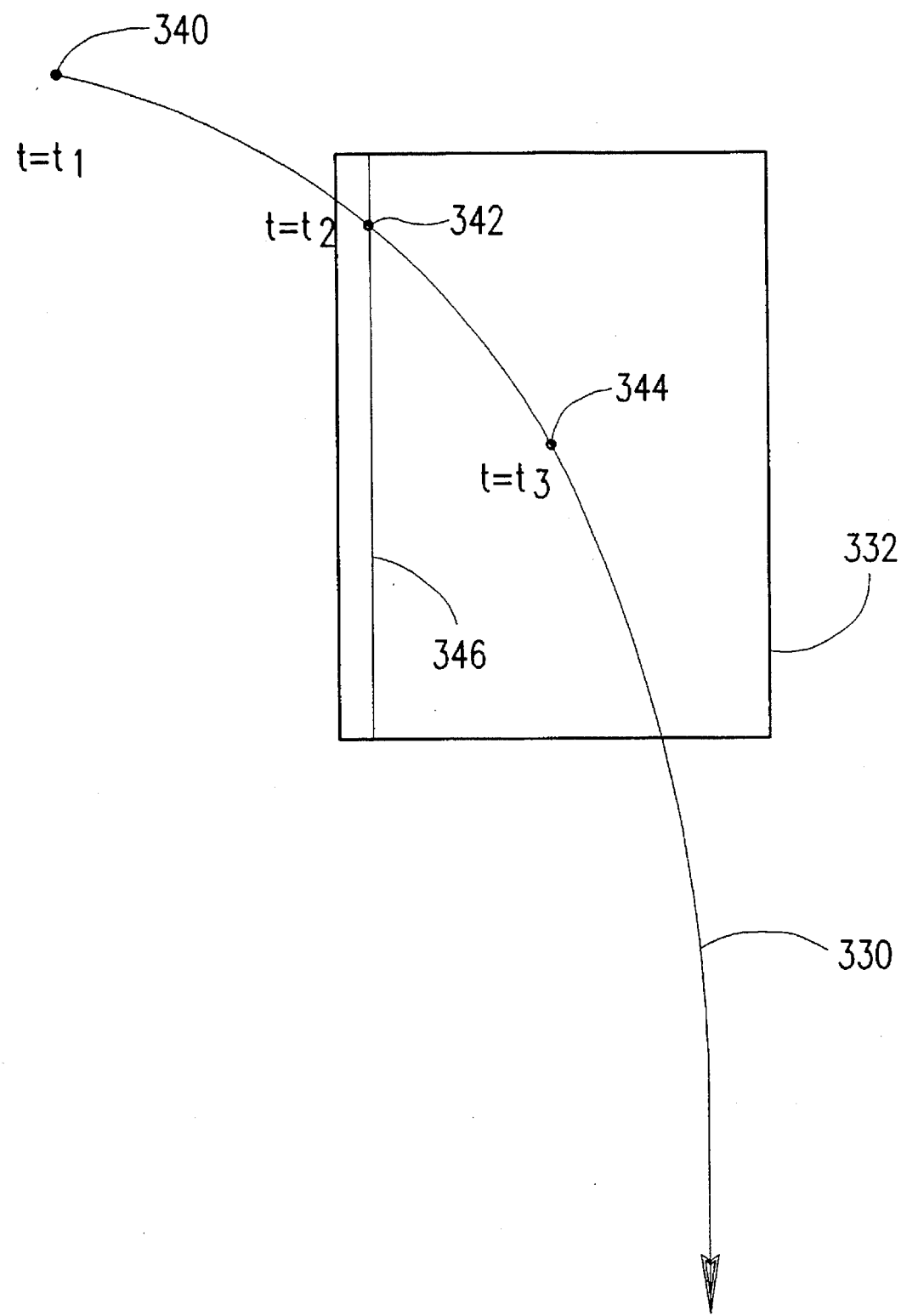
FIG. 15 is a pictorial illustration of an article in motion within the illumination and imaging apparatus of FIGS. 10–12 and a method for triggering illumination or article inspection when the article in motion reaches a predetermined position along its trajectory.

FIG. 15 is a pictorial illustration of an article in motion within the illumination and imaging apparatus of FIGS.

10–13 and a method for triggering the imaging units when the article in motion reaches a predetermined position along its trajectory. The method of FIG. 15 may be employed for triggering a high level of illumination or for triggering the imaging-for-analysis of the article in motion or for triggering any other system response.

Optionally, one or more imaging unit digitizes a predetermined portion of its field of view generally continuously, whereas the remainder of the imaging units only digitize their fields of view upon triggering by the continuously digitizing imaging unit. The continuously digitizing imaging unit may trigger the remainder of the imaging units either directly or via a central control mechanism such as a computer. The continuously digitizing imaging unit preferably digitizes at a relatively low resolution when digitizing in order to monitor article position and digitizes at a relatively high resolution when digitizing for analysis.

When digitizing in order to monitor article position, the imaging unit preferably analyzes only a single column or row of the field of view, such as a column close to the left boundary of the field of view, if the article enters the field of view from the left, or a row close to the top boundary of the field of view, if the article enters the field of view from the top. Preferably, a row or column which is near the relevant boundary but not so near as to be subject to edge effects, if present, is selected, such as the fourth row or column. Triggering occurs if a predetermined result is obtained from digitization of the monitored row or column in an individual frame, such as presence of at least ten consecutive pixels having reflectance values which differ from the reflectance values of the same pixels in the previous frame.

FIG. 15 shows the trajectory 330 of an object, which may have any shape such as a substantially straight line, in relation to the field of view 332 of an imaging unit (not shown), and three positions 340, 342 and 344 of the object along the trajectory 330, which the object reaches at times $t_1$, $t_2$ and $t_3$, respectively. At time $t_1$, the object is external to the field of view 332 and therefore, monitoring of the fourth column from the left, referenced 346, of the field of view, will not result in triggering. At time $t_2$, the object has reached a vertical location corresponding to the fourth column 346 of the field of view 332 and therefore, triggering will result in the time interval between $t_2$ and $t_3$. At time $t_3$, the object has reached the center 344 of the field of view of the imaging unit and is imaged for analysis by all imaging units (not shown).

A particular feature of the method of FIG. 15 is that only a small portion of the field of view of the illumination and imaging apparatus, and only a small portion of the trajectory of the articles in motion, need be monitored. Also, only a single one of a plurality of imaging-for-analysis units need be employed in implementing the method of FIG. 15. The individual unit may trigger operation of the remaining units when the article to be imaged has been detected at the predetermined location along its trajectory.

It is appreciated that the triggering method of FIG. 15 is suitable not only for triggering imaging units as shown. The triggering method of FIG. 15 has more general applications such as triggering a momentary high illumination level of an article which is normally illuminated at a low level. For example, a suitable level of illumination for imaging fruit for analysis is approximately 3000 lux. A suitable level of illumination for imaging fruit merely in order to detect the time at which the fruit reaches a predetermined position along its trajectory is approximately 10 lux.

Alternatively, the method of FIG. 15 for triggering a high level of illumination or for triggering the imaging-for-analysis of the article in motion or for triggering any other system response may be eliminated. Instead, a time schedule for imaging articles may be implemented by a microswitch or by employing any other suitable device for physically sensing that the article in motion has reached a predetermined position along its trajectory, such as entry to enclosure 230 of FIG. 10. Microswitches must be delicate enough not to damage delicate articles such as fruit.

Figure 16:
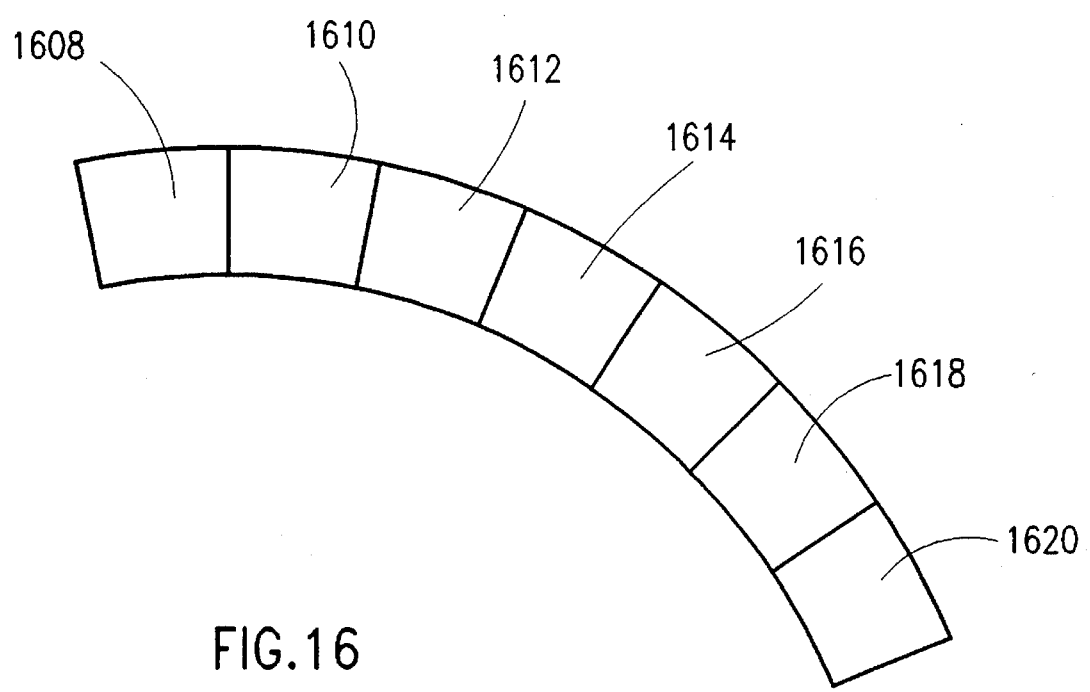
FIG. 16 is a pictorial illustration of a spectral standard useful in conjunction with the illumination and imaging apparatus of FIGS. 10–14.

FIG. 16 is a pictorial illustration of a sample configuration for a spectral standard useful in conjunction with the apparatus of FIGS. 10–14, as described above with reference to FIG. 12. As explained above, each spectral standard is preferably utilized as an on-line internal reference to which each article may be compared, and thereby serves to standardize imaging over time by overcoming variations in optical conditions over time.

As shown, the spectral standard may comprise a plurality of patches having different spectral bands. The patches may serve as standards for intensity and/or dynamic range and/or spectral content. A sample plurality of materials which may be cut to size in order to form patches suitable for inspecting apples includes the following:

1608: A white opaque diffuser formed of Alumina or $BaSO_4$.

1610: A neutral density filter having 3 db attenuation such as a GD-30-S.

1612: A red filter such as a a CA-600.

1614: A green filter such as a CA-550.

1616: An IR filter such as an LG-697.

1618: An IR filter such as an LG-790.

1620: A black scatterer or black paint such as Krylon black enamel.

All filters described above are commercially available from Corion Corp., Mass., USA.

Each patch may be approximately square in configuration with suitable dimensions such as 7 mm×7 mm. However, the exact configuration of each patch is preferably not exactly square but rather curved so as to correspond to the curvature of the boundary of backgrounds 270 of FIG. 12.

It is appreciated that the particular spectral bands and arrangement of spectral patches specified hereinabove are merely exemplary and are not intended to be limiting. Selection of spectral patches is preferably determined by at least the type of article being graded, including variety of fruit if the article is a fruit, and the types of blemishes and color variations to be detected.

Figure 17:
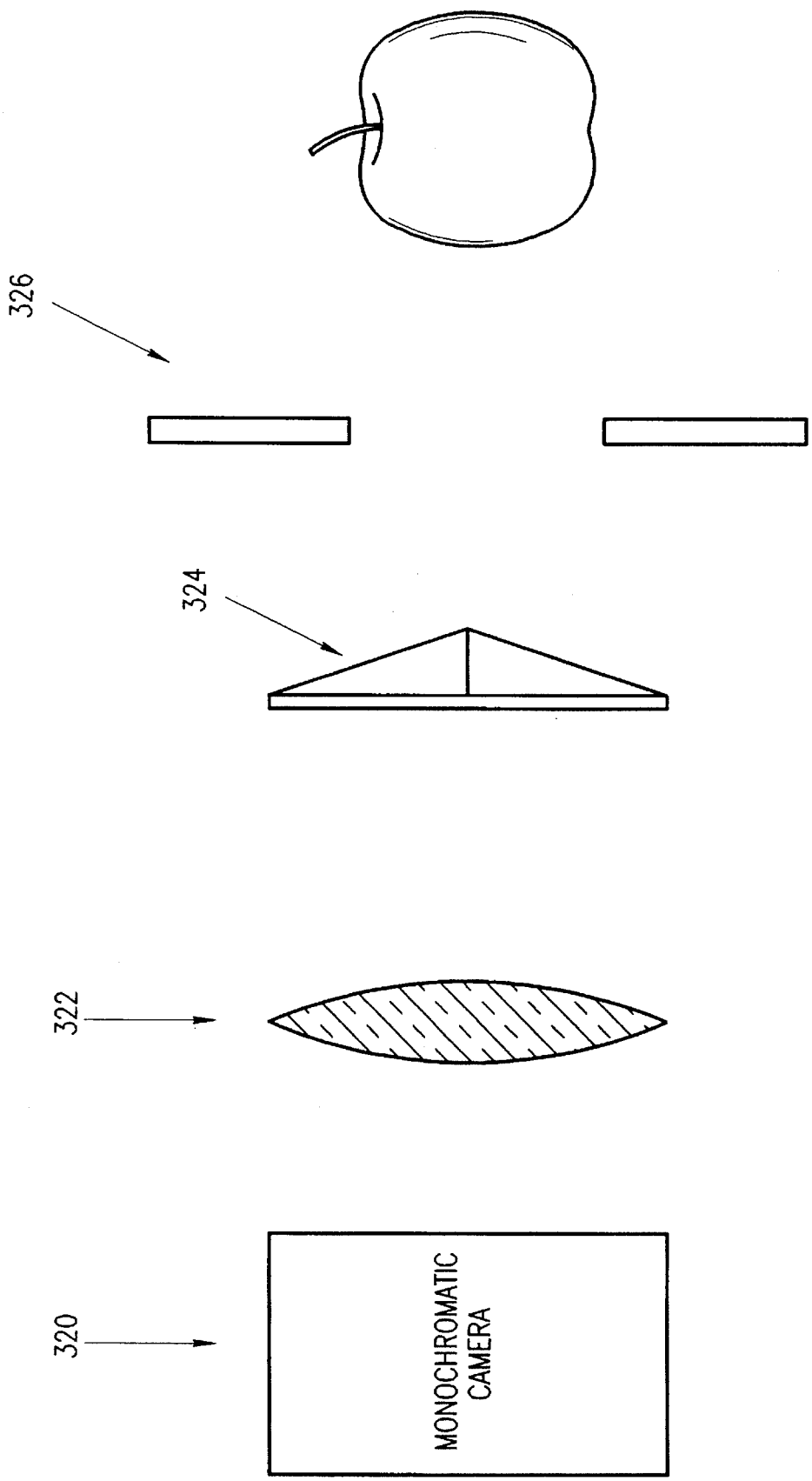
FIG. 17 is an optical schematic diagram of an electro-optical imaging unit forming part of the apparatus of FIGS. 10 and 13, constructed and operative in accordance with a preferred embodiment of the present invention.

FIG. 17 is an optical schematic diagram, not to scale, of an individual camera unit 216 constructed and operative in accordance with a preferred embodiment of the present invention. As shown, each camera unit preferably comprises a monochromatic camera 320 such as a Model TC 655EC, commercially available from Burle Industries, Middlesex, England, an imaging lens 322, a spectral separation element 324 preferably including a prism as described in detail below, and an aperture 326.

Camera 320 preferably has a spectral response in the visible and near-IR portions of the spectrum and is actuated by external triggering in accordance with a suitable method such as the method described herein with reference to FIG. 15. If high intensity continuous illumination is employed, a camera with a short duration shutter may be employed.

Imaging lens 322 preferably comprises a high quality imaging lens with a relatively low F-number such as a P/N 71846, commercially available from JML Optical Industries, Inc., N.Y., USA, which has a focal length of 12.5 mm and an F-number of 1.3. Spectral separation element 324 is operative to provide a plurality of non-overlapping subimages of each article, each subimage having different spectral characteristics. A preferred embodiment of spectral separation element 324 is described in detail below with reference to FIG. 18.

Figure 21:
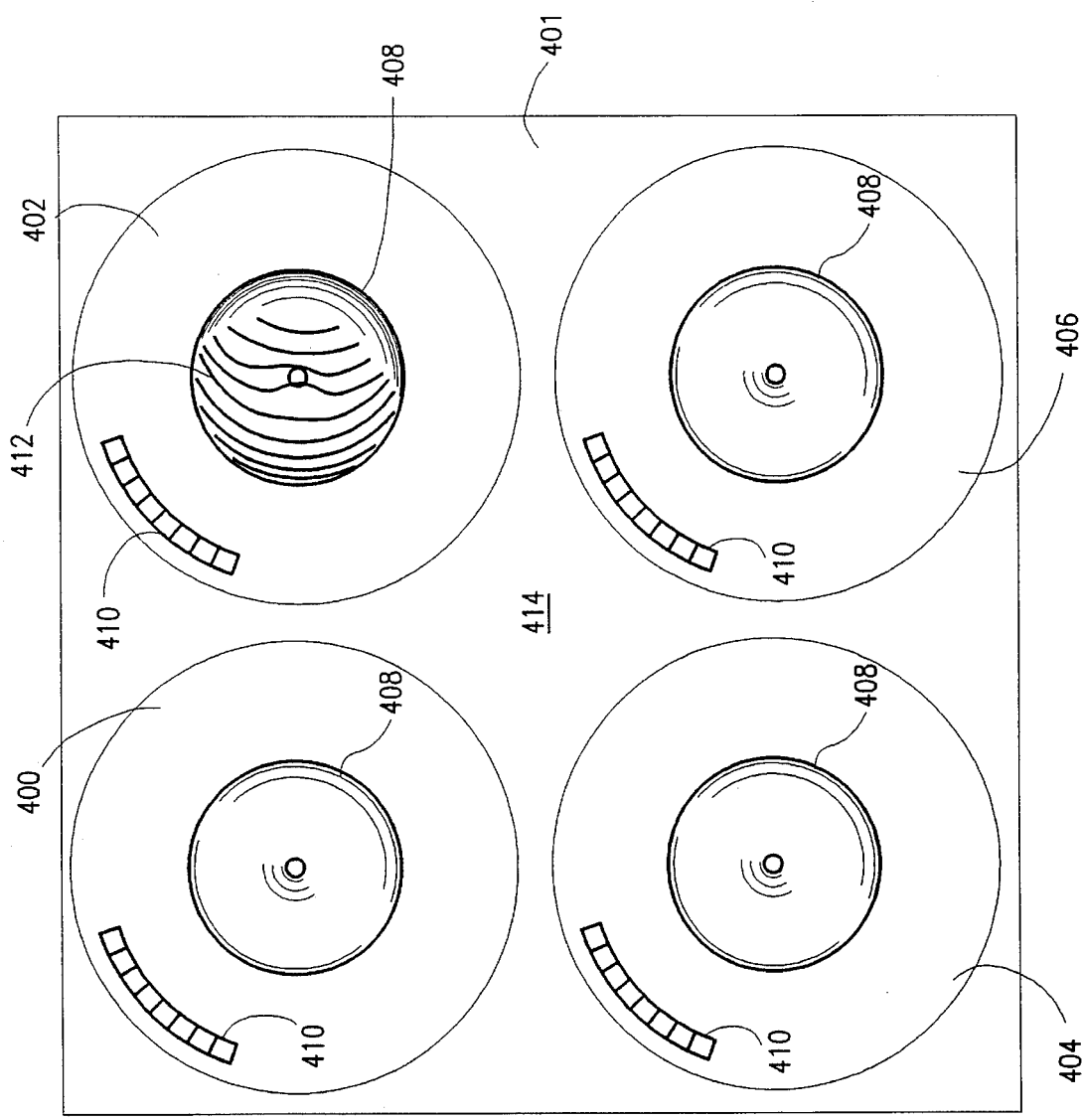
FIG. 21 is a pictorial illustration of an image generated by imaging an apple and a spectral standard using the apparatus of FIG. 18.

Aperture 326 typically comprises a black panel having a central aperture whose diameter may be approximately 7 cm. Due to provision of aperture 326, the periphery of each subimage of the article is black, as best seen in FIG. 21. Therefore, the plurality of subimages of each article typically do not cover one another despite a small amount of overlap therebetween.

Reference is made briefly back to FIG. 10. Preferably, the optical path from the camera 320 to the imaging enclosure 230 of FIG. 10 is relatively long in order to provide a relatively small viewing angle such that a plurality of subimages of each article may be imaged. In order to provide a relatively long optical path without greatly enlarging the dimensions of housing 250, the optical path from camera 320 to enclosure 230 may be broken into path segments, such as path segments 330 and 332 of FIG. 10, which are optically associated with one another by means of mirrors (not shown).

Figure 18:
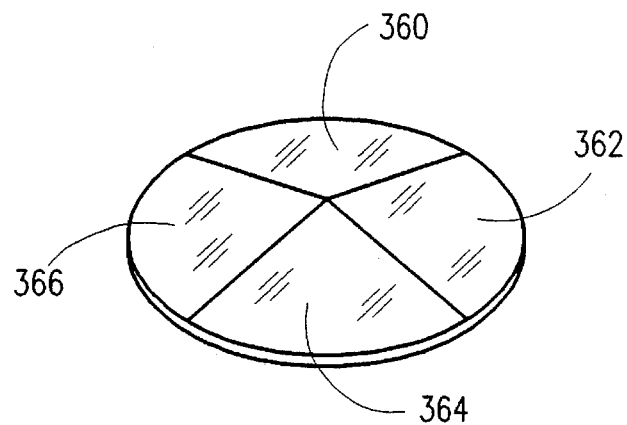
FIG. 18 is a perspective illustration of a spectral splitting element which is useful in conjunction with the apparatus of FIG. 17, which is constructed and operative in accordance with a first preferred embodiment of the present invention.
Figure 19:
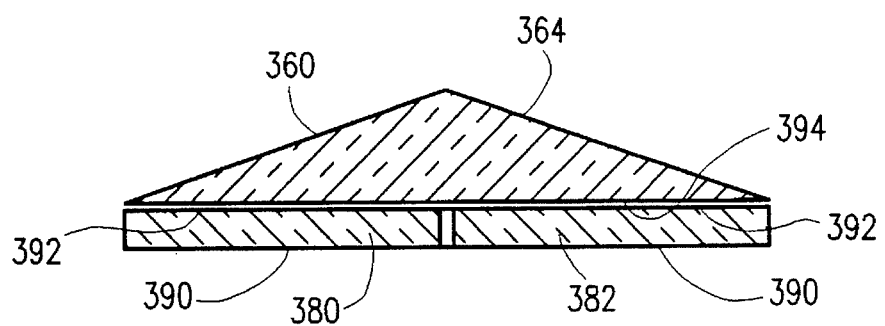
FIG. 19 is a cross sectional illustration of the apparatus of FIG. 18.

FIGS. 18 and 19 are perspective and cross-sectional illustrations, respectively, of spectral splitting element 324 of FIG. 17, constructed and operative in accordance with a first preferred embodiment of the present invention. As shown, the spectral splitting element preferably has a pyramid configuration comprising a plurality of facets such as 4 facets 360, 362, 364 and 366. The spectral splitting element of FIGS. 18 and 19 is operative to provide 4 partially overlapping or nonoverlapping images.

The spectral splitting element may be similar in construction to photographic multiple image elements such as Filter 201 of the Cokin Creative Filters System, commercially available from Cromofilter S. A., RC, Paris, France, except that the pyramid need not be truncated at its top.

A plurality of filters generally corresponding in number to the number of pyramid facets is operatively associated with the pyramid facets. For example, two filters 380 and 382 are visible in FIG. 19 which are operatively associated with pyramid facets 360 and 364 respectively. Each filter may be attached by an adhesive or by any suitable mechanical means. The filters may be replaced or augmented by a dielectric or absorptive optical coating deposited on one or both surfaces 390 and 392 of each of the filters and/or deposited on one or more pyramid facets such as facets 360, 364 and 394.

Figure 28:
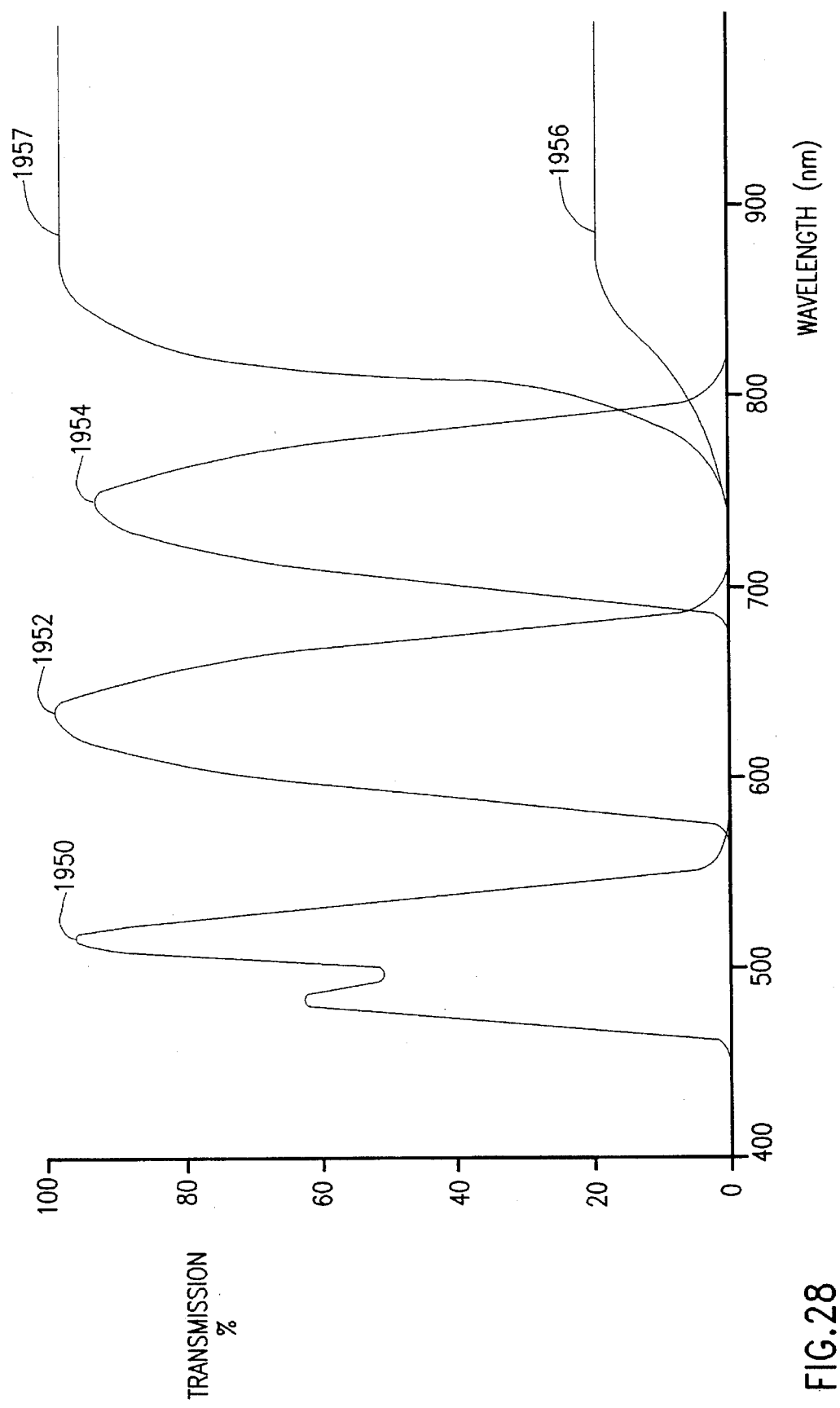
FIG. 28 is a graph of spectral characteristics of each of a plurality of filters employed in the apparatus of FIG. 18.

According to one preferred embodiment of the present invention, each filter and/or optical coating defines a spectral waveband which substantially do not overlap with the spectral waveband of any of the other filters. A sample set of 4 spectral profiles for 4 filters corresponding to the four facets of the pyramid of FIG. 4, which filters are particularly suitable for inspecting certain varieties of apples, is illustrated in FIG. 28.

Figure 20:
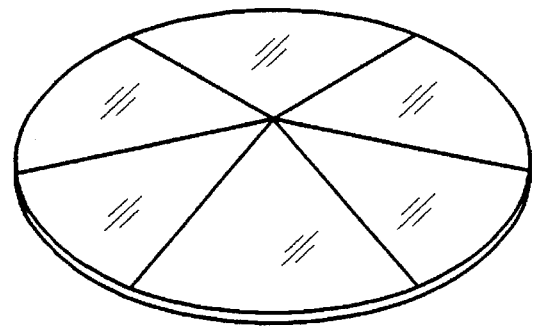
FIG. 20 is a perspective illustration of a spectral splitting element which is useful in conjunction with the apparatus of FIG. 17, which is constructed and operative in accordance with a second preferred embodiment of the present invention.

FIG. 20 is a perspective illustration of a spectral splitting element which is constructed and operative in accordance with an alternative embodiment of the present invention. The spectral splitter of FIG. 20 is similar to the spectral splitter of FIG. 18 except that 6 facets are provided instead of 4, thereby providing 6 images of an article, each having different spectral characteristics. More generally, any suitable number of facets may be employed, depending on the number of differently characterized images required in a particular application.

It is appreciated that the spectral splitting elements employed in the apparatus of the present invention need not be pyramidal in configuration, as shown in FIGS. 18–20 which are merely exemplary of suitable spectral splitting elements.

It is appreciated that spectral splitting elements such as the spectral splitting elements illustrated in FIGS. 18–20 may be useful in a wide variety of contexts other than imaging agricultural produce, particularly applications in which it is desired to capture an image of a fast moving article which is spectrally separated to a plurality of full relatively high resolution "subimages" thereof, as shown in FIG. 21.

FIG. 21 is a pictorial illustration of an image generated by imaging an apple using the apparatus of FIG. 18. As shown, the image comprises four non-overlapping subimages 400, 402, 404 and 406, each of which may have different spectral characteristics. For example, subimage 400 may be red, subimage 404 may be green, subimage 406 may be IR and the waveband of subimage 402 may be a waveband which corresponds to the wavelength of light projector 218 of FIG. 10 and which substantially does not overlap the wavebands of subimages 400, 404 and 406 as shown in detail below with reference to FIG. 28.

Providing an IR image in combination with at least one colored image is particularly advantageous for fruit inspection because blemishes may effectively be detected by comparing the IR image of the fruit to the colored images thereof.

It is appreciated that an image generated using the apparatus of FIG. 20 would include 6 subimages rather than 4 subimages as in FIG. 18.

Each subimage preferably comprises an image 408 of an apple and an image 410 of a spectral standard, such as the spectral standard of FIG. 16, which serves as an internal reference for evaluating image 408. In subimage 402, the imaged apple 408 may be illuminated via a grid, as explained above. The image 412 of the grid is preferably a mask comprising a plurality of alternating dark and bright stripes. For example, the bright stripes may be approximately one-quarter the width of the dark stripes.

As explained above, the four subimages are separated by a black region 414 due to provision of aperture 326 of FIG. 17.

Figure 22:
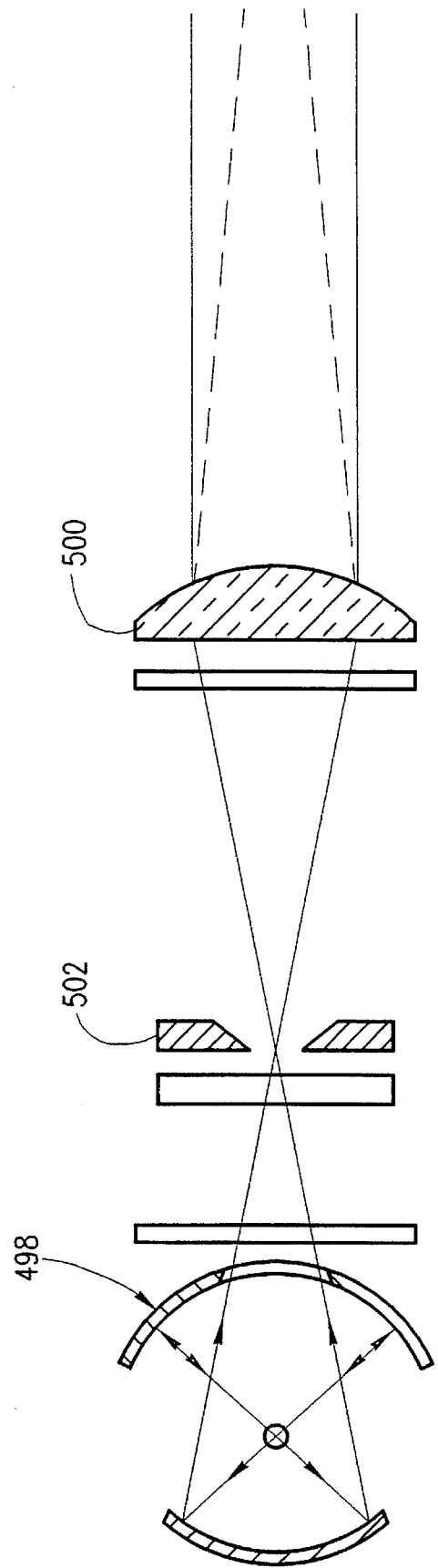
FIG. 22 is an optical schematic diagram of a light projector forming part of the apparatus of FIGS. 10 and 13.

FIG. 22 is an optical schematic diagram of a commercially available projector, the model 790 Xenon Arc lamp source, commercially available from Newport Corporation, Calif., USA, which may be employed to implement light projector 218 of FIGS. 10 and 13, with the following modifications:

Transmitting filters, such as an OG-580 and an RG-780, both commercially available from Schott, Pa., USA, are placed adjacent the lamp assembly 498 and the projection lens 500 respectively. A grid slide comprising a black or opaque mask of stripes is placed adjacent the aperture plate 502.

Reference is now made to FIG. 23 which is a simplified flowchart of a preferred method for implementing image processing unit 18 of FIG. 1. FIG. 23 is described with reference to sorting and grading apples, specifically, however, it is appreciated that the method of FIG. 23 is generally appropriate for a wide variety of article inspection procedures. The method of FIG. 23, as specifically described below with reference to the Appendices, is suitable for an article inspection system which includes three imaging units, however, it is appreciated that the method may be suitably modified by the ordinarily skilled man of the art in order to apply to an article inspection system including any other number of cameras, such as four or more cameras.

The method of FIG. 23 preferably comprises the following steps:

Step 1808: Set-up data is loaded into the system. Set-up data preferably includes the following items of information: a. Data regarding the position, relative to the cameras' field of view, of the element if any which supports the article to be imaged, during imaging. For example, the set-up data may indicate whether or not cables supporting the article are visible by one of the cameras.

If support elements are visible, data is preferably provided which identifies the location of support elements. Preferably, each camera generates a binary mask for each subimage, using the following steps: i. All pixels are compared to a suitable threshold value, such as a gray level value of 100, thereby to define a binary mask. For example, pixels exceeding the threshold may be marked with a 0 gray level value, and pixels falling below the threshold may be marked with a 255 gray level value. ii. A dilation procedure is performed and then repeated on the binary mask in order to compensate for lateral movement of the cables or nets.

Any conventional method for binary image dilation may be employed. b. Data regarding the spectral band and the location within the field of view of the camera, in camera coordinates, of each of a plurality of spectral patches to which each location of each article is compared. Suitable pluralities of spectral patches are described above with reference to FIG. 16. c. Data identifying subimages to be analyzed. For example, the number of subimages to be analyzed may be specified as 4 and the 4 subimages may be identified as IR, red, green and grid subimages, where the grid subimage refers to the subimage in which the article to be imaged is illuminated through a grid. The first three subimages are collectively termed herein "the spectral subimages", and are used for size, shape, color and blemish categorizations. The subimage data preferably includes, for each camera, an indication of fixed offsets generated between subimages due to optical effects of the beam splitter.

Alternatively, the grid subimage may be omitted or may be replaced by an additional IR subimage. The two IR subimages, also termed herein the "IR band I" and "IR band II" subimages, are useful in detecting blemishes as described below with reference to step 1830 of FIG. 1830.

Step 1810: Optionally, profile data characterizing the variety of article to be inspected is loaded in image processing unit 18. For example, if the articles to be inspected are apples, substantially any variety of apple may preferably be processed, such as Red Delicious, Ida Red, Smith, Hermon, Golden Delicious, McIntosh and Jonathan. Sample data for a profile of a particular variety may include the following: a. Definitions, preferably expressed as computational formulae, for each of a plurality of color gradings of a variety to be processed.

Color gradings may be based on accepted standards such as, for apples, the U.S.D.A. Standards for Grades of Apples. b. Definitions, preferably comprising a fuzzy logic expert system rule base, for each of a plurality of types of blemishes which occur in a particular variety to be processed. c. A computational formula for correcting the volume of the article, based on an assumption regarding the article in question, such as the assumption that the article is smoothly contoured or spherical. The correction preferably is based upon more accurate knowledge of the shape of a typical article of the particular variety in question, relative to the assumed geometric shape of articles which are not classified by variety.

A sample method for generating profile data for an undocumented type of article, such as a not-yet-profiled apple variety, is described below with reference to FIG. 26.

Step 1812: A plurality of digitized subimages is received from each of the plurality of cameras in electro-optical imaging unit 16 of FIG. 1. In the present example, it is assumed that 3 cameras are employed, each providing 4 subimages, termed herein the red, green, IR and grid subimages, giving a total of 12 subimages of each apple of which 9 are spectral subimages and 3 are grid subimages.

Step 1813: Since the four subimages are typically offset relative to one another, a suitable correction is preferably provided. Also, motion of the produce is compensated for.

Step 1814: Each of the spectral subimages is corrected to compensate for uneven illumination or shading of the imaged apple, using any suitable method. A suitable shading correction algorithm is described in the following publication, the disclosure of which is incorporated herein by reference:

Ballard, D. H. and Brown, C. M., Computer Vision, pp. 72–73, Prentice-Hall, Englewood Cliffs, N.J., 1982.

Appendix A, when used in conjunction with Appendix B, is a computer listing of a software implementation of a preferred method for implementing steps 1813 and 1814 of FIG. 23.

Step 1816: The boundaries of each of the 12 subimages are located.

Step 1816 may be performed only once per camera per article, preferably on the green subimage provided by each camera or on a subimage generated by averaging the green and red subimages provided by each camera. Once identified, the boundary of the green subimage or of the green/red subimage for each camera is then modified in order to generate the boundaries of the remaining subimages provided by the same camera. Typically, a predetermined x-y shift is sufficient in order to obtain the boundary of the red, grid or IR subimages from the boundary of the green subimage from the same camera.

As explained above, set-up step 1808 preferably includes the step of loading, for each camera, an indication of predetermined x-y shifts generated between subimages due to optical effects of the beam splitter.

A representation of the boundary, in suitable form such as an XY list or in vector form, is stored in memory.

Preferably, all steps from here on are performed only for pixels lying within the boundary as stored in memory, in order to eliminate unnecessary computations.

A suitable method for implementing step 1816 is described below with reference to FIG. 24 and Appendix C.

Step 1818: For each pixel in the image of the article, the color of that pixel is determined. For example, the pixels within each of the spectral subimages may be compared to a spectral standard such as the spectral standard of FIG. 16. A particular advantage of performing this step by comparison to a spectral standard is that on-line comparison with a spectral standard placed within the same optical chamber used to image the apples cancels out errors due to temporal variations in the illumination of the interior of the optical chamber and due to dirt.

Preferably, the spectral standard comprises a plurality of spectral patches, as illustrated in FIG. 16, each of which is assigned an identifying code. Each pixel within each of the spectral subimages is compared to the corresponding subimage of each of the plurality of spectral patches in order to identify the spectral patch whose subimage is closest in color or spectral characteristics to the subimage pixel. For example, if a brown color patch is provided, a bruise location on an apple will normally be found to be closest in color to the brown color patch. The subimage pixel is then assigned the identifying code of that patch.

A computer listing of a software implementation of a sample method for assigning identifying color codes to each of a plurality of locations in imaged StarKing apples which does not employ the method of comparison to a spectral standard is provided herein and is referenced Appendix D.

Step 1820: The grid subimage generated by each camera may be analyzed in order to either identify stem and calyx locations or to identify an absence of stem or calyx in the portion of the article viewed by the camera. Preferably, one or more of the spectral subimages are also analyzed in order to facilitate identification of stem and calyx. A preferred method for implementing step 1820 is explained in more detail below with reference to FIG. 25.

Optionally, if step 1836 below is included in the method of FIG. 23, step 1820 may be eliminated.

Step 1824: Each location along the apple surface is preferably assigned to exactly one of the three cameras before the fruit feature computation step described below is carried out.

According to one preferred embodiment of the present invention, predetermined portions of the article surface are assigned to each camera in accordance with a predetermined model of the shape of the article, such as a sphere.

A computer listing of a software implementation of a sample method for implementing step 1824, using a generally spherical model of the article, is provided herein and is referenced Appendix F. More specifically, the listing of Appendix F assumes that the cross sectional portion of the article corresponding to each line of the image is circular in shape.

Preferably, an image of at least a portion of the article is compared to the predetermined model of the shape of the article in order to determine discrepancies between the actual shape of the article and the predetermined model thereof. The determination of the predetermined portions of the article may then be corrected to take into account these discrepancies.

According to an alternative embodiment of the present invention, subimages generated by adjacent cameras are compared in order to identify registration therebetween, which typically defines areas of overlap therebetween. The overlap is taken into account such that each location is analyzed by taking into account only one image thereof generated by only one of the three cameras. Methods for determining the relative alignment of two subimages are described in the following publication, the disclosure of which is incorporated herein by reference:

Barnard, S. T. and Fischler, M. A., "Computational stereo", Computing Surveys, 14(4), 553–572, 1982.

Preferably, step 1824 comprises the step of identifying, for each of a majority of individual locations within an area of overlap between two camera units, the camera unit which images the individual location at the smallest angle to a normal to the surface of the article at the individual location.

Figure 27:
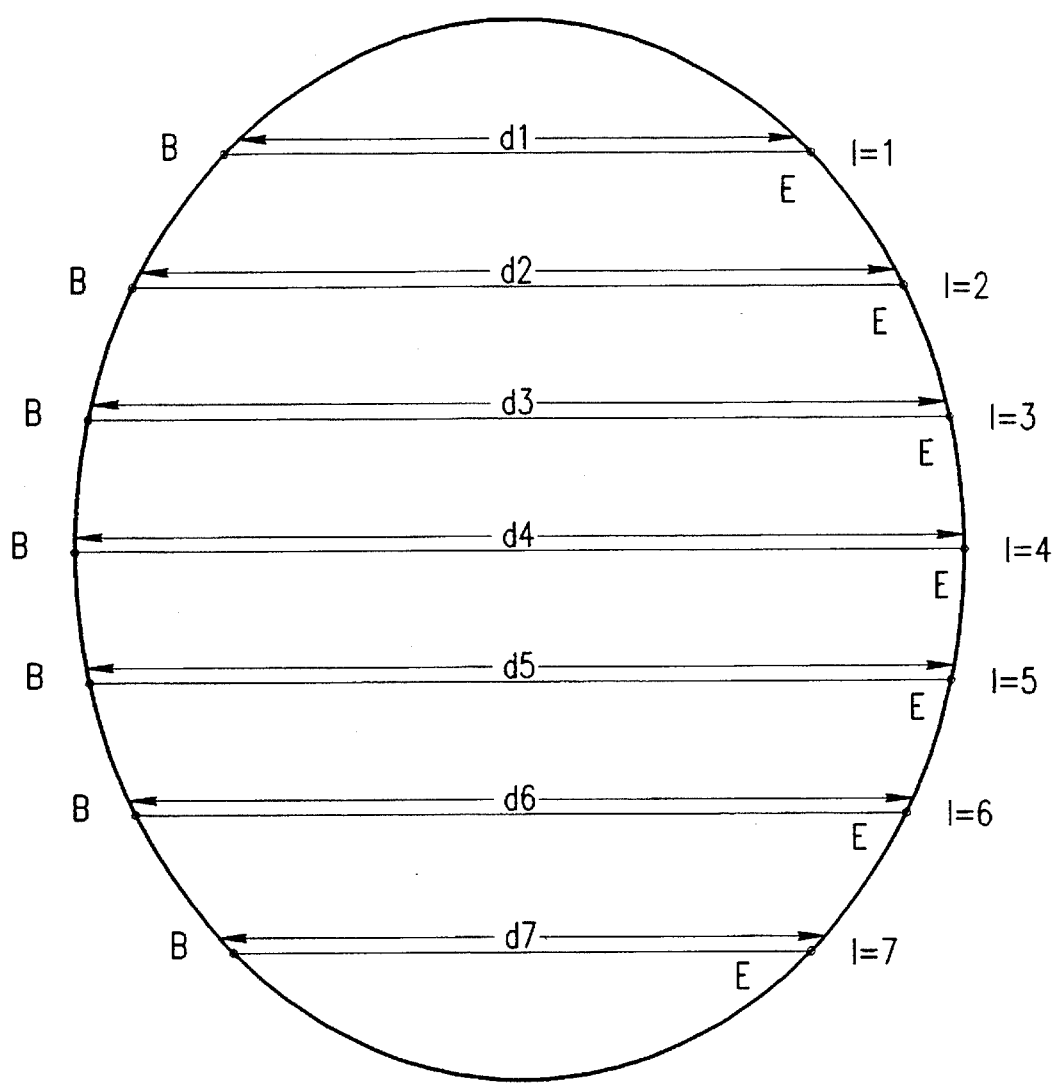
FIG. 27 is a pictorial illustration illustrating a preferred method for implementing step 1828 of FIG. 23.

Step 1828: The volume of the apple is computed, using any suitable method such as the following: a. Each of the imaging units may compute, for each line 1 of the image generated thereby, the distance $d_1$ between a "begin article" point B and an "end article" point E, as shown in FIG. 27. b. For each line 1, a value $D_1$ is computed as the product of the distance $d_1$ and a constant factor F which compensates for the fact that the imaging unit generally images less than half of the article. F may be computed by imaging a spherical article of known diameter and computing the ratio between the known diameter and the diameter of the imaged article. c. For each imaging unit, an approximation to the volume of the apple in pixel units is computed, using the following formula:

$$pixsum_1 (D_1)^2$$

d. For each imaging unit, the volume in pixel units computed in step c is converted to $mm^3$ by multiplying the value generated in step c by a scaling factor. e. The values generated in step c for each of the imaging units is averaged over imaging units to obtain an approximate value for the volume of the article in $mm^3$.

A software implementation of steps a - d for a three camera system is provided herein in Appendix F.

In step 1830, an image is generated by combining the IR band I and IR band II images so as to obtain differences therebetween. The image may be generated by dividing the IR band I image by the IR band II image, or by subtracting the IR band I image from the IR band II image.

In step 1832, the image generated in step 1830 is inspected to identify blemish candidates which differ in appearance from the expected appearance of the apple. Specifically, contours for each discolored portion of the apple, also termed herein "blemish candidates", are identified.

A commercially available chip which is suitable for identifying contours is the L64290 chip, commercially available from LSI Logic Corporation, Milpitas, Calif., USA. Preferably, for each blemish candidate, features are recorded such as the area, perimeter, darkness inside the area, darkness outside the area and an aspect ratio, i.e. the ratio between the horizontal and vertical dimensions of the area.

Appendix G is a computer listing of a software implementation of a preferred method for implementing steps 1830 and 1832 of FIG. 23.

In step 1834, each blemish candidate is fuzzy-logic processed so as to classify it as one of a plurality of blemish types such as russeting, bruise and bitter pit.

Appendix H, taken together with Appendix I, is a computer listing of a software implementation of a preferred method for implementing step 1834 of FIG. 23.

Step 1836: The information regarding absence of or location of stem and calyx for each of the cameras, generated in step 1820, is combined over all cameras, in order to make a final identification of the locations of the stem and calyx. Preferably, the final identification of stem and calyx locations takes into account some or all of the following data: a. A comparison of the green, red and IR outputs of the stem and calyx locations to a predetermined dark color which is known to be characteristic of stems and calyxes. b. The shape of the fruit, such that an identification of a pair of stem and calyx locations which are not located along a central axis of the fruit, will be rejected.

It is appreciated that the information regarding the locations of the stem and calyx may be utilized in performing subsequent operations on the fruit, such as cutting, marking and packing the fruit.

Preferably, each of a plurality of pairs of blemish candidates is fuzzy-logic processed to identify one of the pairs of blemish candidates as including a stem and a calyx. Preferably, the results of step 1834 are employed to filter out blemish candidates which do not resemble stems and calyxes and therefore need not be fuzzy-logic processed.

If three cameras are employed, the set of blemish candidates, each pair of which is fuzzy-logic processed in step 1836, preferably includes two "dummy" blemish candidates positioned at the two blind spots of the imaging apparatus. Thereby, the system takes into account the possibility that the stem or calyx or both may be located at one or both of the two blind spots of the imaging apparatus.

Optionally, if step 1820 above is included in the method of FIG. 23, step 1836 may be eliminated.

Preferably, in step 1838, the classification of blemishes is reviewed and modified to take into account the stem/calyx position as determined by step 1836. For example, a blemish candidate which was classified in step 1834 as russeting may now be reclassified as a non-blemish if it surrounds the stem position.

As explained above, Appendix I includes a computer listing which, taken together with Appendix H, forms a computer listing of a software implementation of a preferred method for implementing step 1834 of FIG. 23. However, Appendix I also includes a computer listing of a software implementation of a preferred method for implementing steps 1836 and 1838 of FIG. 23.

In step 1840, the apples are graded based on the characteristics of the blemishes on each apple, as derived in steps 1832 and 1838.

Fuzzy logic technology is discussed generally in the following publication, the disclosure of which is hereby incorporated by reference:

Bezdek, J. C. and Sankar, K. Pal, Fuzzy models for pattern recognition, IEEE Pres 1992, ISBN 0-7803-0422-5.

Commercially available development packages include TILShell together with FCDS (Fuzzy C Development System), commercially available from Togay InfraLogic, Irvine, Calif., USA and the ADS 230 development system, commercially available from American NeuraLogix Inc., Sanford, FA, USA.

It is appreciated that the steps of the flowcharts described in the present specification need not be performed in the illustrated order and specifically, the steps of the method of FIG. 23 need not be performed in the illustrated order. For example, step 1818 may be performed after step 1824 in order to save computing time. Also, steps 1820 and 1826 may be performed in parallel to steps 1818 and 1824 or after steps 1818 and 1824. Many other modifications of the illustrated order are possible.

Reference is made briefly to FIG. 24 which is a simplified flowchart of a preferred method for implementing step 816 of FIG. 23. A computer listing of a software implementation of a sample method for implementing the method of FIG. 24 is provided herein and is referenced Appendix C.

Using the method of FIG. 24, the boundary of the apple may be found. In step 1850, at least one of the subimages of the apple is transformed into a binary image, comprising object pixels and background pixels, by a thresholding procedure. For example, if the pixels of the subimages are represented in 8 bits, a suitable threshold is a gray level of 200. Preferably, the green subimage is binarized because the green subimage has been found to differentiate well between the apple and its background.

In step 1852, a filtering procedure is employed to remove images of the support elements and artifactual images. The filtering procedure is operative to remove all portions of the image which are smaller than a selected filter.

According to one alternative embodiment of the present invention, filtering is initially carried out using a first annular disc defining a one-pixel wide ring and the filtering procedure includes a single step in which, for each location within the image for which the one-pixel wide ring is not entirely covered by a non-background entity, the entire portion of the image underlying the ring is removed.

If the width of the support elements supporting the agricultural produce is 5 pixels, a suitable radius for the first annular filter is, for example, 6 pixels.

Preferably, a second annular filter with a larger radius such as, for example, 20 pixels, is additionally employed in order to round off edges left by the small radius filter.

According to another alternative embodiment of the present invention, step 1852 is replaced by the step of employing a round disc filter. In this case, the filtering procedure includes two steps: an erosion step in which centers of portions which are smaller than the filter are removed; and a dilation step in which edges of large portions are restored, since these edges tend to be eroded in the erosion step. This embodiment may, for example, be implemented using a L64230 chip, commercially available from LSI Logic.

Typically, there is a tradeoff between the accuracy of the filtering operation which is achieved by employing a large filter, and between simplicity of computation which is achieved by employing a small filter.

In step 1854, the coordinates of the apple boundary, typically cartesian coordinates, are identified. Typically, the algorithm positions itself on the top line of the binary subimage. If no object pixel is encountered in the top line, the algorithm advances to and through the next line, and so on, until on a particular line, the first object pixel is encountered. When this occurs, the border pixels on the left and on the right for that line are identified and the algorithm then advances to the next line until a line is found on which, again, there are no object pixels. At this point, the boundary coordinates are stored (step 1866).

Reference is now made to FIG. 25 which is a simplified flowchart of a preferred method, suitable for implementing step 1820 of FIG. 23, for analyzing a grid image generated by each camera in order to identify absence of or location of stem and calyx. The grid image may comprise a grid of bright lines super-imposed on a dark background. Before employing the method of FIG. 5, the edges of the bright lines may be sharpened by using any suitable method such as application of an edge-enhancement operator to the image.

The method of step 1820 then generates, for each camera, an indication of a putative stem location or of an absence of stem, and an indication of a putative calyx location or of an absence of calyx. Locations are identified as putative stem or calyx locations if the curvature of the grid lines, superimposed on those locations, changes relatively sharply thereat.

A computer listing of a software implementation of a preferred method for implementing the method of FIG. 25 is appended hereto and is referenced Appendix E.

Figure 26:
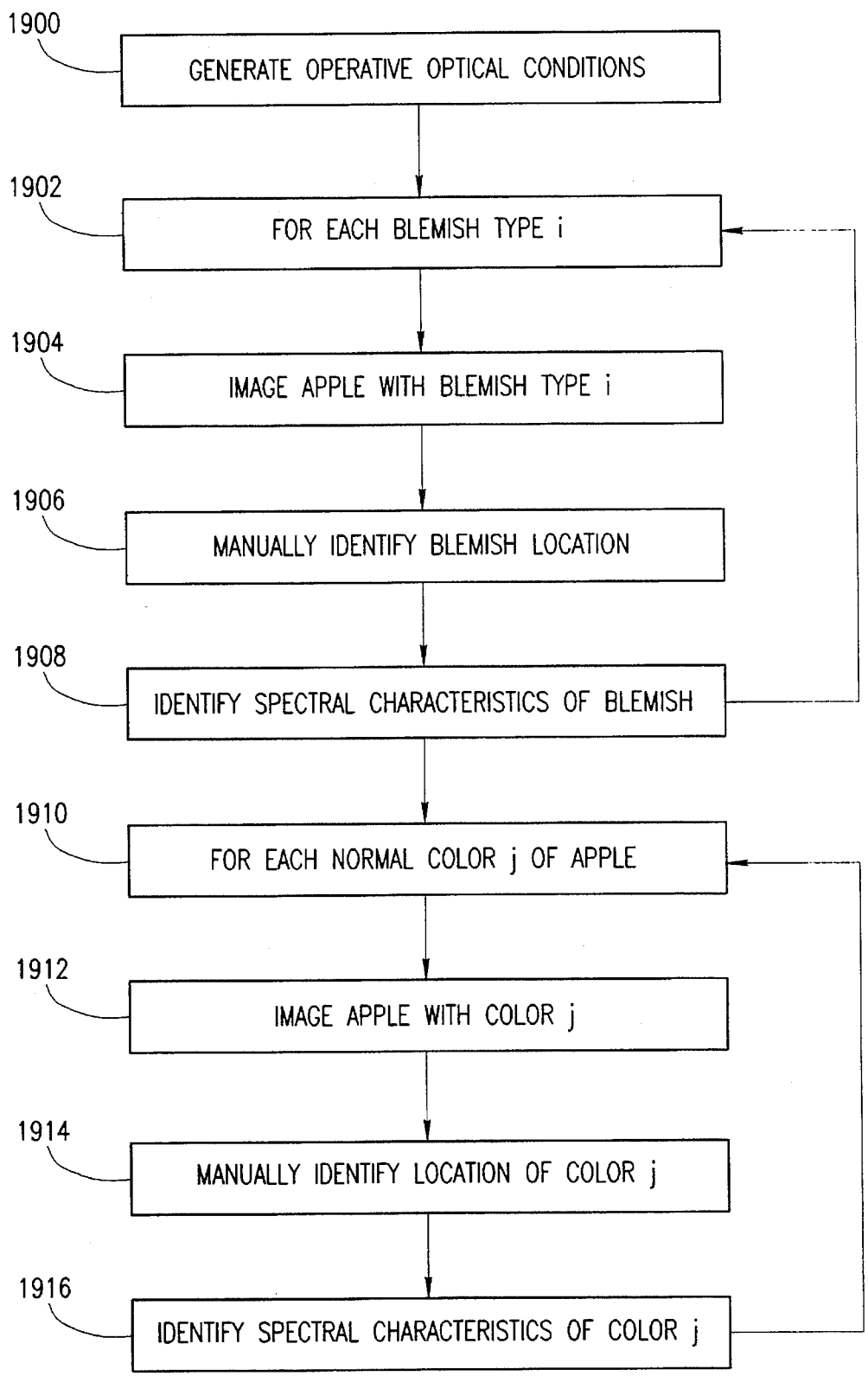
FIG. 26 is a simplified flowchart of a preferred method for generating apple variety data to be loaded in step 1810 of FIG. 23.

Reference is now made to FIG. 26 which is a simplified flowchart of a method whereby a human operator "teaches" the system about an individual type of article, such as an individual variety of agricultural produce such as an apple variety, and the system generates profile data for the apple variety.

The method of FIG. 26 preferably comprises the following steps:

Step 1900: The learning process preferably takes place with illumination and other optical conditions that resemble operative conditions as closely as possible.

Step 1902: Steps 1904, 1906 and 1908 are performed for each of a plurality of blemish types which it is desired to define.

Step 1904: An article of the appropriate variety, such as an apple, is imaged.

Step 1906: A human operator identifies the location of a blemish within the image of the apple, using suitable means such as a mouse.

Step 1908: The system analyzes the spectral characteristics of the location indicated in step 1906. For example, the system may compare the color/spectral value of each of a plurality of pixels within the location indicated in step 1906, to the spectral patches of a spectral standard such as the spectral standard of FIG. 16, and identify the spectral patch that best characterizes the type of blemish under consideration.

Steps 1910–1916: Each of a plurality of colors which characterize the apple variety, such as red, green and yellow, may be learned in steps similar to blemish learning steps 1902–1908 above.

Reference is now made to FIG. 28 which includes four graphs 1950, 1952, 1954 and 1956 of spectral characteristics of the four filters of FIG. 18 respectively, for applications in which a projected light grid is employed in conjunction with filter 1956. For applications in which a projected light grid is not employed, the fourth filter, instead of having the spectral characteristics of graph 1956, may have the spectral characteristics of graph 1957. According to one preferred embodiment of the present invention, the spectral profiles of the four filters are generally nonoverlapping. It is appreciated that the filters defined by the spectral characteristics of FIG. 28 are merely exemplary of suitable filters.

According to a preferred embodiment of the present invention, the four filters of FIG. 18 comprises a combination of filters, preferably including at least one IR filter, which is designed to facilitate distinction of bruised tissue from non-bruised tissue, as described below in detail with reference to FIG. 28. Reflectance spectra for bruised and non-bruised tissue are described in the following publication, the disclosure of which is incorporated herein by reference:

B. L. Upchurch et al, "Spectrophotometric study of bruises on whole, red delicious apples", Transactions of the ASAE, 33(2), March-April 1990.

Providing an IR filter is particularly advantageous for detecting blemished regions such as russeting, sun-burn, rot and bruising on apples.

Figure 29:
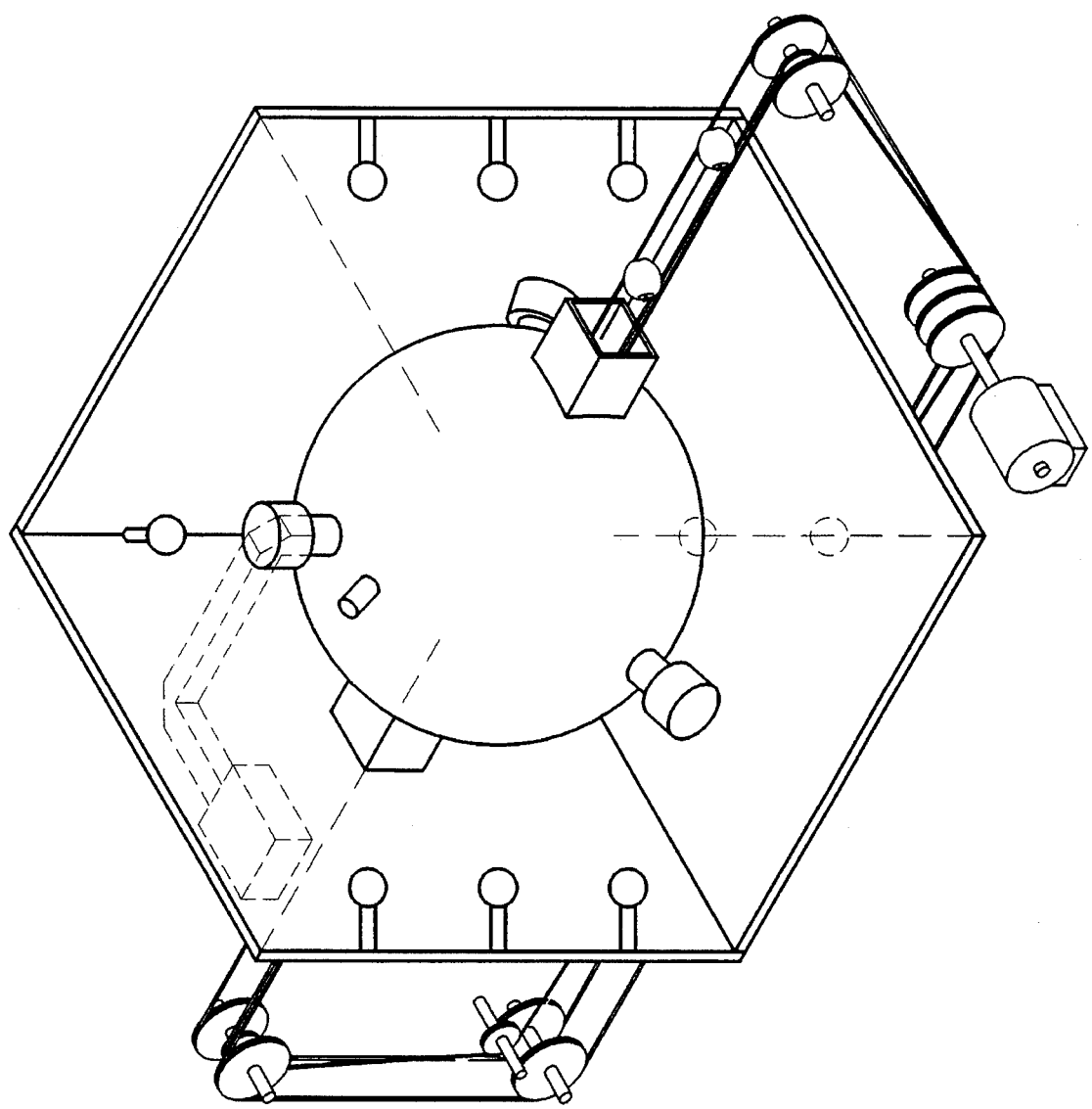
FIG. 29 is a perspective illustration of the conveying apparatus of FIG. 7 in operative association with the imaging apparatus of FIG. 10.

FIG. 29 illustrates the conveying apparatus of FIG. 7 in operative association with the imaging apparatus of FIG. 10. It is appreciated that conveying apparatus constructed and operative in accordance with any of the embodiments shown and described herein may be similarly combined with imaging apparatus constructed and operative in accordance with any of the embodiments shown and described herein. A particular feature of the apparatus of FIG. 29 is that only the elements, if any, directly supporting the article to be inspected, such as the nets and cables shown and described above, are disposed interiorly of the imaging enclosure and therefore there is relatively little obscuring of the article.

Figure 30A:
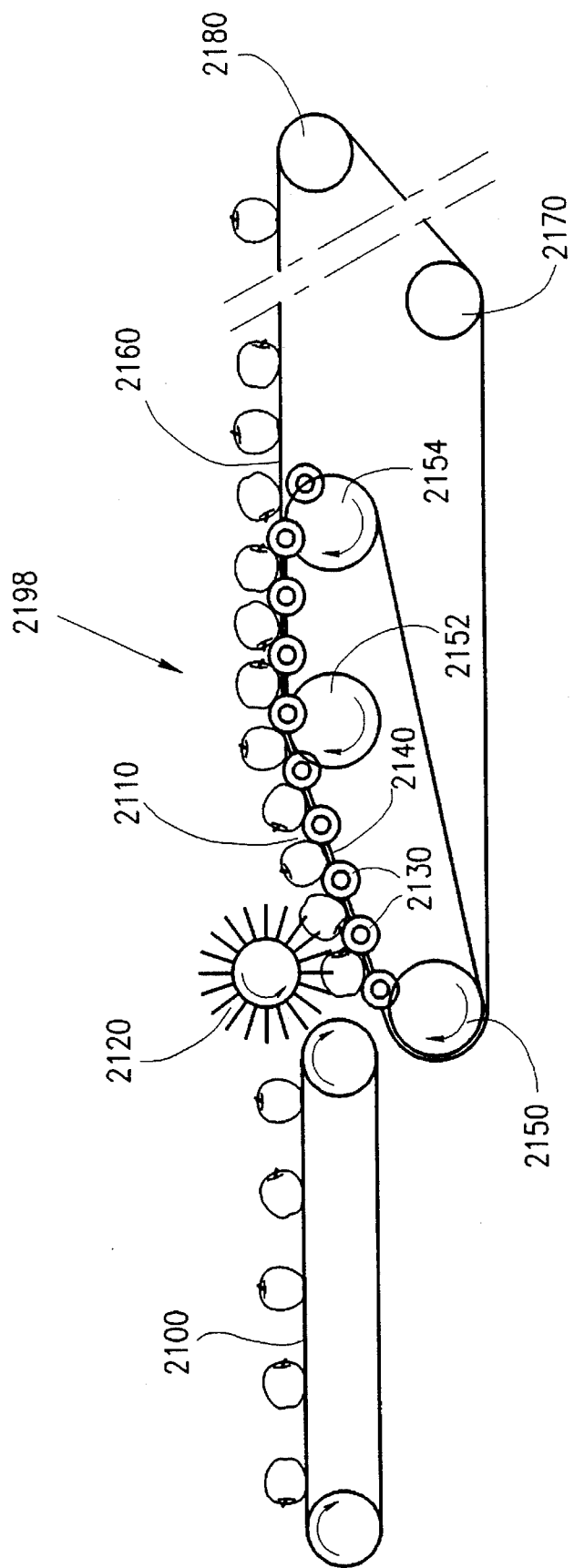
FIG. 30A is a simplified side view illustration of singulating apparatus including a conveying junction comprising an interlaced pair of conveyors.

Reference is now made to FIG. 30A which is a simplified side view illustration of singulating apparatus including a conveying junction 2098 comprising an interlaced pair of conveyors 2110 and 2160 suitable for conveying agricultural produce such as apples. Conveyors 2110 and 2160 may replace conveyors 170 and 148, respectively, of FIG. 7. Alternatively, conveyors 2110 and 2160 may replace conveyor 170, only, of FIG. 7.

The singulating apparatus of FIG. 30A receives non-singulated produce from a bulk conveyor 2100 which may comprise a conventional strip conveyor such as the strip conveyor commercially available from Matechet Rishon, Rishon Le Zion, Israel. The bulk conveyor 2100 feeds onto ascending singulating conveyor 2110. Preferably, means are providing adjacent the junction between conveyors 2100 and 2110 for urging apples from conveyor 2100 onto conveyor 2110, such as a brush 2120.

The singulator of FIG. 30A is also suitable for applications in which the ascending conveyor 2110 is partly submerged in water, and the non-singulated produce is provided within the water and is scooped up therefrom by ascending conveyor 2110, as explained above with reference to FIG. 3B.

The ascending conveyor 2110 typically comprises a plurality of rotating roller assemblies 2130 which are mounted on a guiding chain or belt 2140 in operative association with a plurality of guiding pulleys such as pulleys 2150, 2152 and 2154. Ascending conveyor 2110 is preferably inclined so as to allow apples to roll or slide backwards into spacings between the roller assemblies 2130. Rotation of the roller assemblies 2130 need not be linked with the motion of the guiding chain 2140.

Each roller assembly is configured for supporting an apple or other item of produce. Preferably, each roller assembly may be constructed as illustrated in detail in FIG. 30B.

Ascending conveyor 2110 interlaces with a cable conveyor 2160 including a plurality of cables such as 3 or 4 cables which may, for example, be similar to the cable conveyor shown and described above with reference to FIG. 5. The cables may be formed of any suitable material such as rubber or polystyrene. Cable conveyor 2160 is mounted on and driven on pulleys 2150, 2152, 2154, 2170 and 2180. In other words, cable conveyor 2160 and ascending conveyor 2110 have guiding pulleys in common.

Sample dimensions for the apparatus of FIG. 30A include: rollers: outer diameter—5 cm, width—6 cm, inter-roller spacing—8 cm; brush: diameter—25 cm; speed—30 rpm; length of ascending conveyor—50 cm; angle of ascending conveyor—13 degrees; diameter of pulleys—15 cm; apple conveying speed—5 apple/sec.

It is appreciated that singulation of the produce in the produce inspection system shown and described herein may occur at any suitable point. Conveyor 2110 of FIG. 30A may be, but need not be, a singulator. If conveyor 2110 is not a singulator, the dimensions of the rollers 2130 thereof may be, for example, approximately 2 cm, and the separation therebetween may be, for example, approximately 1 cm. Alternatively, rollers 2130 may be eliminated. In this case, singulation of the produce is provided at the junction 2098 between conveyors 2110 and 2160 by causing the velocity of conveyor 2160 to exceed the velocity of conveyor 2110. For example, the velocities of conveyors 2110 and 2160 may be 40 cm/sec and 150 cm/sec, respectively.

According to still a further alternative, singulation may not be performed by the apparatus of FIG. 30A. Instead, singulation may be performed by the apparatus of FIG. 32, as explained in detail below with reference to FIG. 32.

Figure 30B:
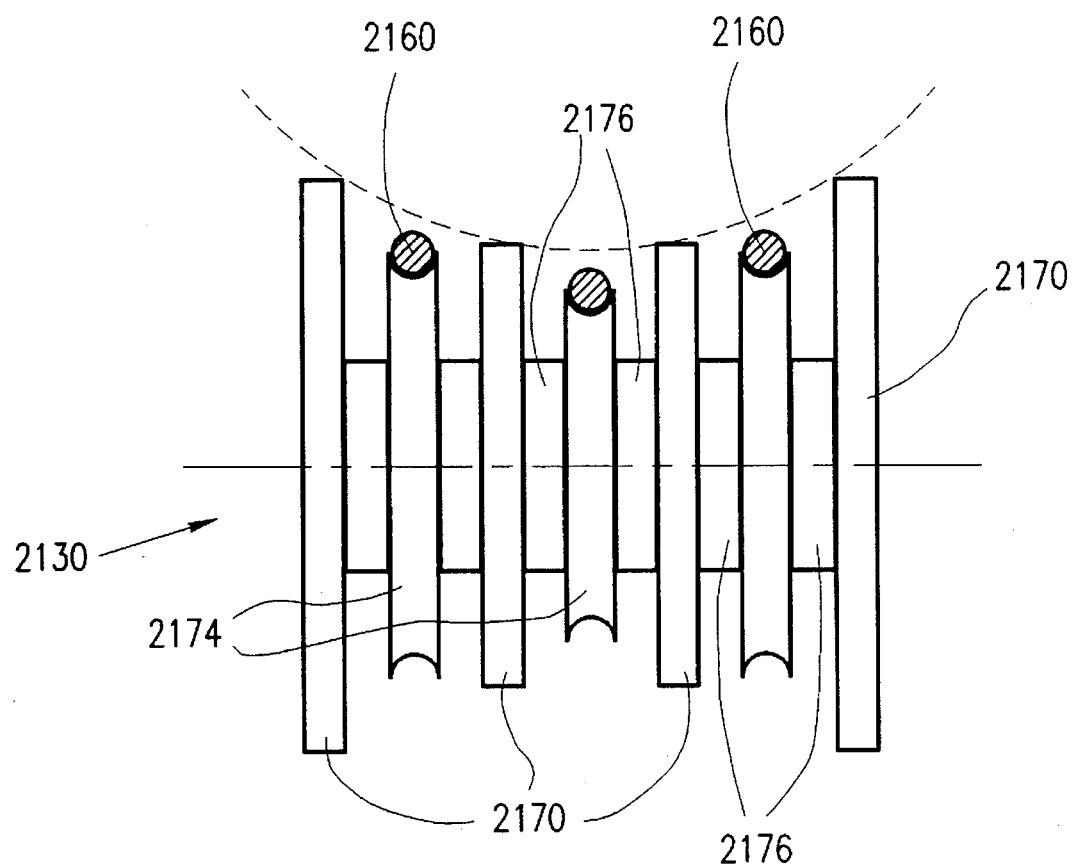
FIG. 30B is a detailed cross-sectional illustration of a preferred implementation of one of the roller assemblies of FIG. 30A.

Reference is now made to FIG. 30B which illustrates an individual one of roller assemblies 2130, constructed and operative in accordance with one preferred embodiment of the present invention. Each roller assembly comprises a plurality of coaxial elements including article supporting discs 2170 defining a cradle 2172 for supporting an article such as an apple, cable supporting pulleys 2174 for supporting cables 2160 below cradle 2172, and, preferably, spacers 2176.

Article supporting discs 2170 may, for example, be formed of rubber and they may rotate at a suitable speed, such as 100 rpm, if it is desired to rotate the articles as they are conveyed. Cable supporting pulleys 2174 may, for example, be formed of a suitable low-friction metal or plastic. Spacers 2176 may, for example, be formed of a suitable metal or plastic.

It is appreciated that due to the configuration of FIG. 30B, the cables 2160 are below and spaced away from the apples being conveyed, until junction 2098 is reached, from which point the apples are supported by cables 2160.

Figure 31A:
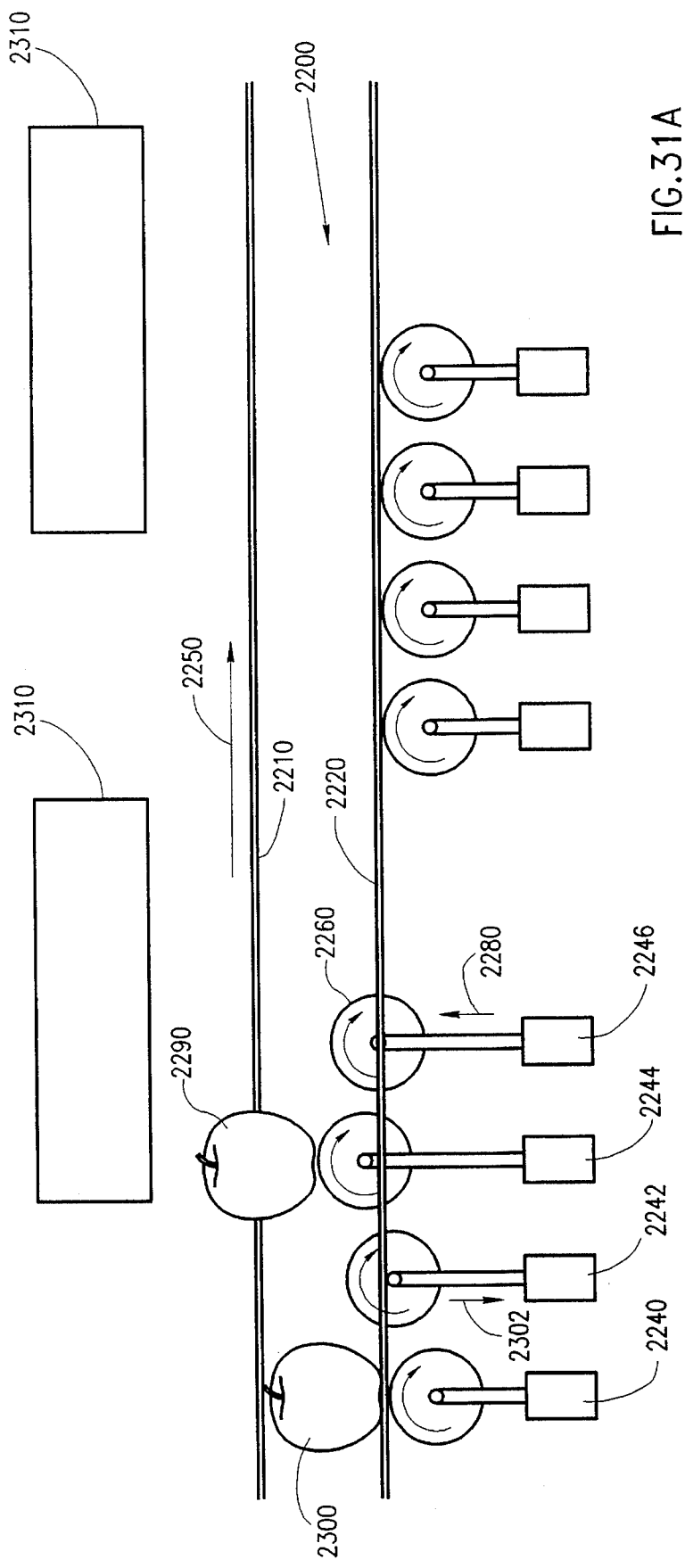
FIGS. 31A–31C illustrate apparatus for selectably ejecting articles from a cable conveyor onto a selected one of a plurality of bins corresponding to a plurality of categories into which the apples have been categorized.
Figure 31B:
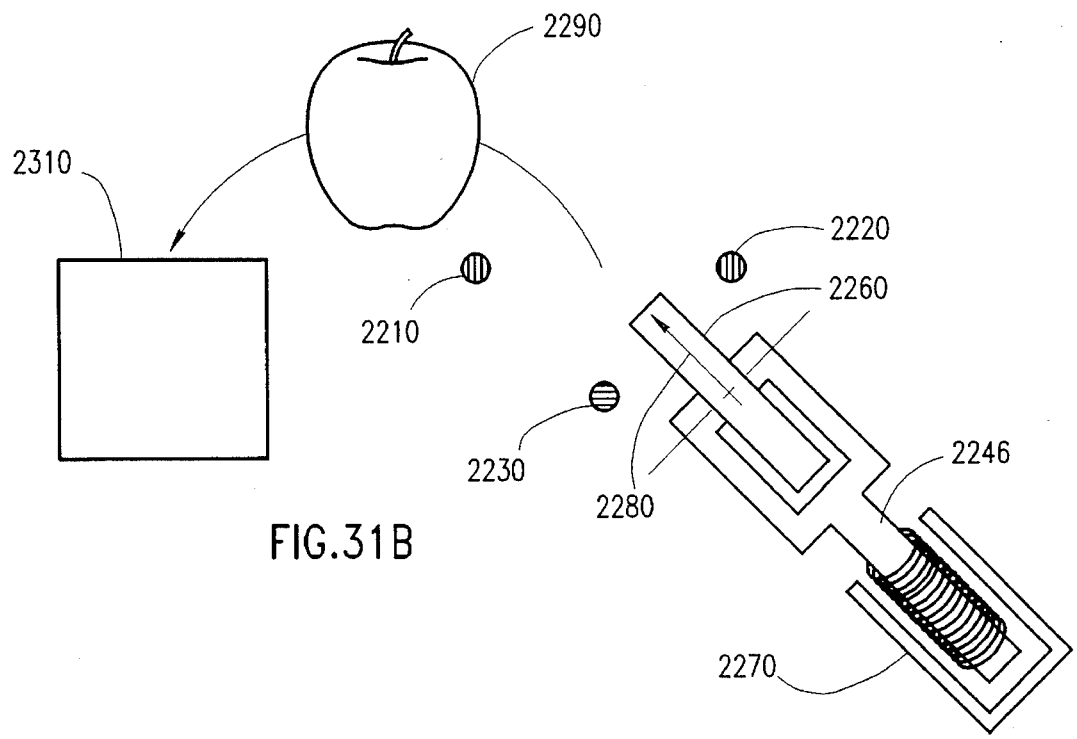
Figure 31C:
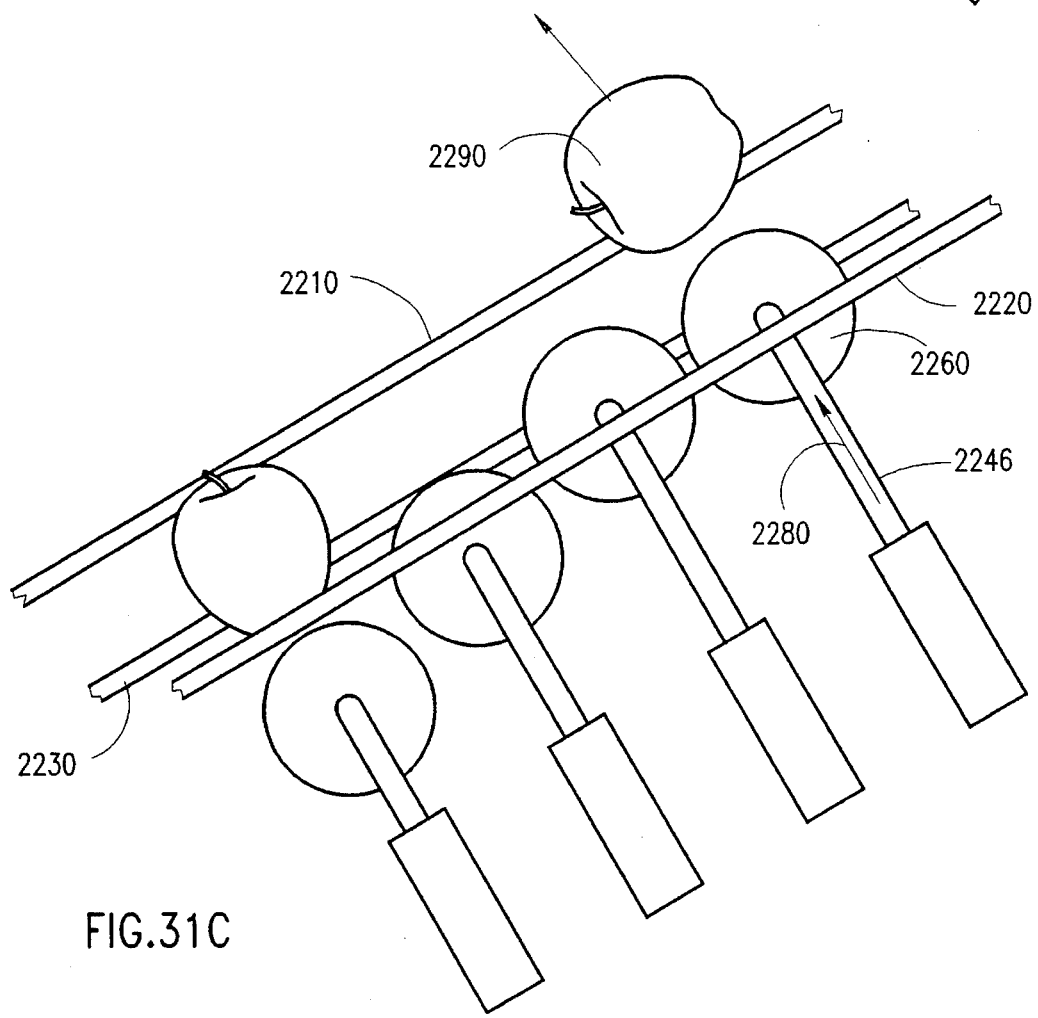

FIGS. 31A–31C illustrate apparatus for selectably ejecting apples from a cable conveyor 2200 into a selected one of a plurality of bins 2310 corresponding to a plurality of categories into which the apples have been categorized. Typically, apple categorization and control of the ejecting apparatus of FIGS. 31A–31C is by means of an automatic unit such as data analysis/sorting/grading unit 20 of FIG. 1.

The cable conveyor 2200 includes a plurality of cables such as 3, 4 or more cables. In the illustrated embodiment, the cable conveyor 2200 includes first, second and third cables 2210, 2220 and 2230. In FIG. 31A, the produce is moving from left to right, as indicated by an arrow 2250. In FIG. 31B, the produce is moving into the plane of the page. The rate at which the produce is conveyed is typically relatively high, such as 5 articles per second.

The produce ejecting apparatus of FIGS. 31A–31C includes, opposite each of bins 2310, at least one kicker 2240 and preferably a plurality of kickers, such as four kickers 2240, 2242, 2244 and 2246. Each kicker preferably includes a rotating disc 2260 which is arranged such that its tangential velocity substantially equals the velocity of the moving produce, as indicated by arrow 2250.

The magnitude of the velocity vector is preferably equal to the linear velocity of the produce, so as to prevent damage to the produce when engaged by the kicker. Disc 2260 may be formed of a soft rubber or plastic such as polyurethane. Sample dimensions for each disc 2260 are a diameter of 5 cm and a width of 2 cm. The separation between adjacent discs may be 6 cm center to center, or a 1 cm separation between perimeters.

Each kicker is actuated by suitable means such as a solenoid or pneumatic piston 2270 which causes the kicker to pass smoothly between two extreme positions: a first inactive, withdrawn position, such as the position of kicker 2240 of FIG. 31A, and a second active, protruding position, such as the position of kicker 2246 of FIGS. 31A and 31B. The amplitude of motion between the first and second positions is preferably 3 cm–5 cm.

When a kicker is in its inactive, withdrawn position, it does not interfere with the passage of an item of produce along the cables 2200. When a kicker is in its active, protruding position, it protrudes between cables 2220 and 2230 and engages a passing item of produce, acting to eject the item sideways, over cable 2210. Each kicker passes from its inactive position to its active position by extending along a direction indicated by an arrow 2280.

In FIG. 31A, a first apple 2290 is shown which is to be ejected and a second apple 2300 is shown, following the first apple, which is not to be ejected. Kicker 2240 is stationary, in its inactive position, since apple 2300 is not to be ejected. Kicker 2242 is withdrawing after ejecting apple 2290, as indicated by arrow 2302, since apple 2300 is not to be ejected. Kicker 2244 is in its active position, since apple 2290 is to be ejected, and kicker 2246 is moving into its active position, as indicated by arrow 2280, in anticipation of the arrival of apple 2290.

It is appreciated that, if desired, bins may be placed on both sides of the cable conveyer. In this case, kickers corresponding to the bins on one side of the cable conveyor, such as bin 2310, will protrude between cables 2220 and 2230 when active, whereas kickers corresponding to the bins on the other side of the cable conveyor will protrude between cables 2210 and 2230 when active.

Figure 32:
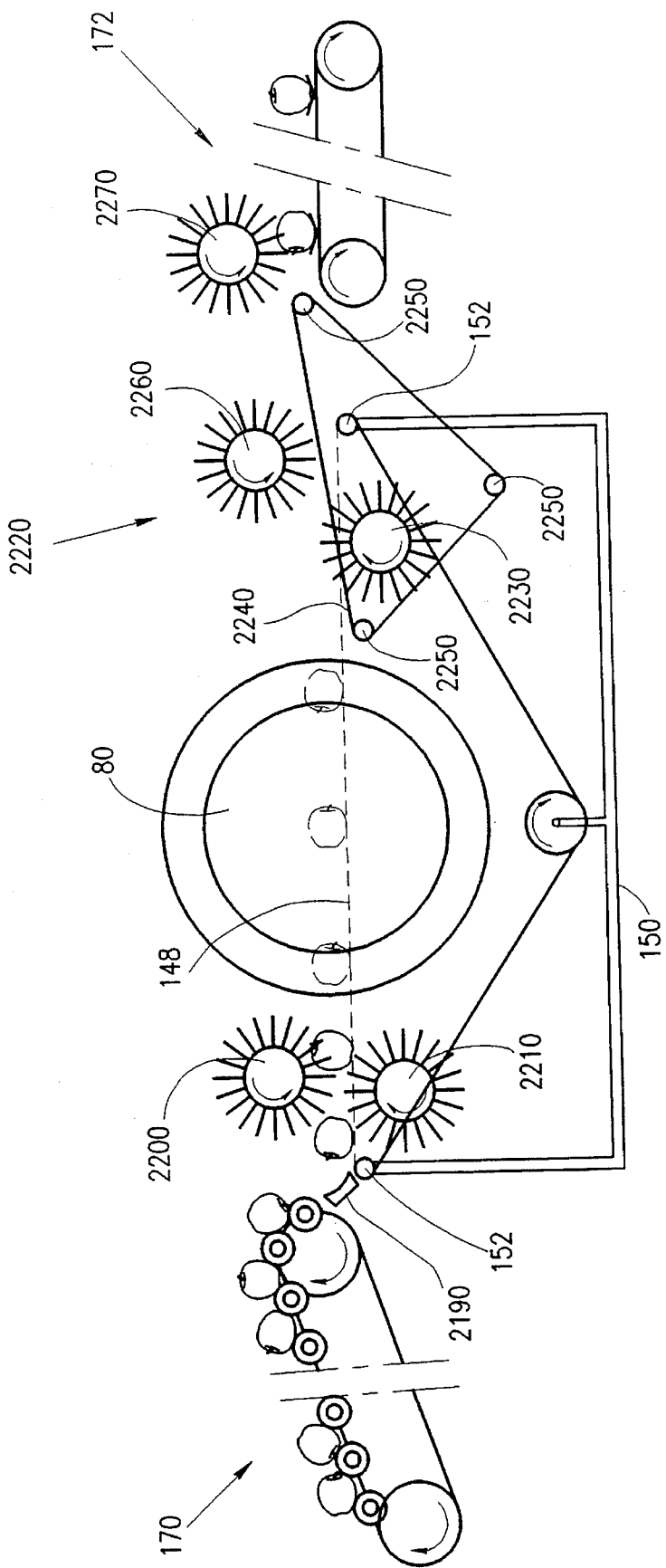
FIG. 32 illustrates a preferred alternative to the conveying apparatus of FIG. 7.

FIG. 32 illustrates a preferred alternative to the active conveying apparatus of FIG. 7 which is similar to the apparatus of FIG. 7 except that a cushioning element and brushes are provided to facilitate the transition of apples from one conveying device to another. Elements in FIG. 32 which are similar to corresponding elements in FIG. 7 bear identical reference numbers for convenience.

In the illustrated embodiment, a cushioned landing pad 2190 is provided adjacent to and downstream of conveyor 170. The width W of the cushion 2190 is preferably relatively small, such as 2 cm, so that even articles which are not round tend to fall off the cushion 2190 toward a brush array comprising, in the illustrated embodiment, first and second brushes 2200 and 2210.

The first and second brushes 2200 and 2210 are provided upstream of cable conveyor 148, above and below cushioned landing pad 2190 or above and below a location slightly downstream of cushion 2190. A suitable separation between the brushes is, for example, 2 cm. The highest point of lower brush 2210 is typically slightly elevated relative to the plane defined by cable conveyors 148, such as at an elevation of 1 cm relative to the plane of conveyors 148. The linear velocity of the brushes is typically equal to the linear velocity of cables 148.

During operation, apples are deposited from loading conveyor 170 onto the cushioned landing pad 2190 from which they fall toward the brushes 2200 and 2210. The brushes facilitate transfer of the apples onto driven cables 148. Preferably, brushes 2200 and 2210 accelerate the top and bottom portions, respectively, of the apples to a horizontal velocity suitable for conveyance along cables 148, such as 1.2 m/sec. Brushes 2200 and 2210 preferably place the articles onto cables 148, rather than rolling them thereon, such that the separation between apples on cables 148 is maintained because the apples do not roll therealong.

It is appreciated that the brushes 2200 and 2210 may, alternatively, be replaced with functionally equivalent elements such as assemblies of soft plastic or rubber disks or sheets.

Preferably, a decelerating assembly 2220 is provided for decelerating apples arriving from cables 148 and facilitating the sequential transfer of these apples onto unloader 172. The decelerating assembly 2220 typically comprises a first brush 2230, a cable conveyor 2240, a pulley array 2250 for supporting and driving cable conveyor 2240, a second brush 2260 and a third brush 2270.

Cable conveyor 2240 may be approximately 60 cm long and comprise a plurality of rubber or polysterene cables which are typically thick relative to cables 148 and may, for example, have a cross-section of approximately 6 mm. The cables 2240 are associated with pulleys 2250 and are meshed or interlaced at their upstream end with the downstream end of cables 148 and at their downstream end with the upstream end of unloader 172. The association between adjacent conveyors may be similar to that illustrated in FIGS. 33A and 33B. The speed of the cable conveyor 2240 is preferably similar to the speed of unloader 172, such as approximately 0.7 m/sec. The separation between the tips of brushes 2230 and 2260 is typically approximately 2 cm.

The operation of the decelerating assembly 2220 is as follows: The brush 2230 lifts an apple riding off cables 148 onto cable-conveyor 2240, also decelerating the bottom portion of the apple to the speed of the cable conveyor 2240.

Brush 2260 decelerates the upper portion of each apple so as to prevent it from rolling forward. In other words, the function of brush 2260 is substantially the reverse of the function of accelerating brush 2200.

Brush 2270 cushions the apple as it is transferred from conveyor 2240 to conveyor 172.

According to an alternative embodiment of the present invention, any of the various brushes in FIG. 32 may be omitted.

According to one alternative embodiment of the present invention, loading conveyor 170 conveys the articles in bulk and the articles are singulated in the course of being transferred to cables 148. For example, conveyor 170 may be a bulk conveyor, and a funnel may be provided upstream of cushioning pad 2190, such that the produce fall one at a time onto cushion 2190 and therefore are transferred one at a time onto cables 148. Separation between produce may be provided by having conveyor 148 move much faster than does conveyor 170. For example, the velocities of conveyors 148 and 170 may be 150 cm/sec and 40 cm/sec, respectively.

Figure 33A:
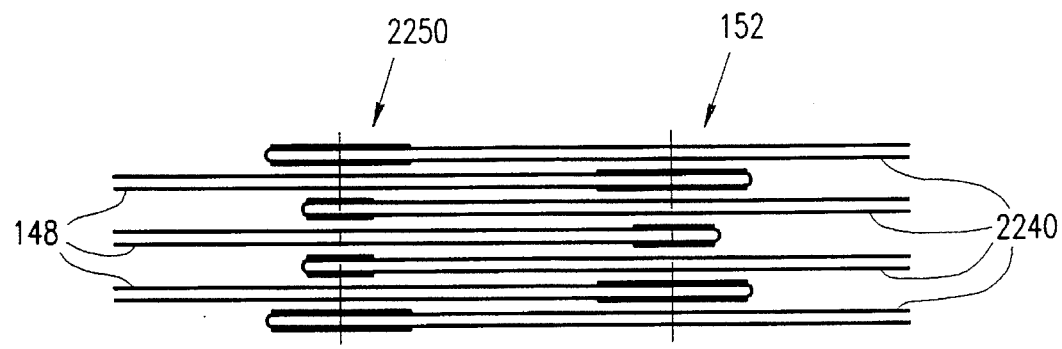
FIG. 33A and FIG. 33B illustrate interlacing cables 2240 and 148 of FIG. 32.
Figure 33B:
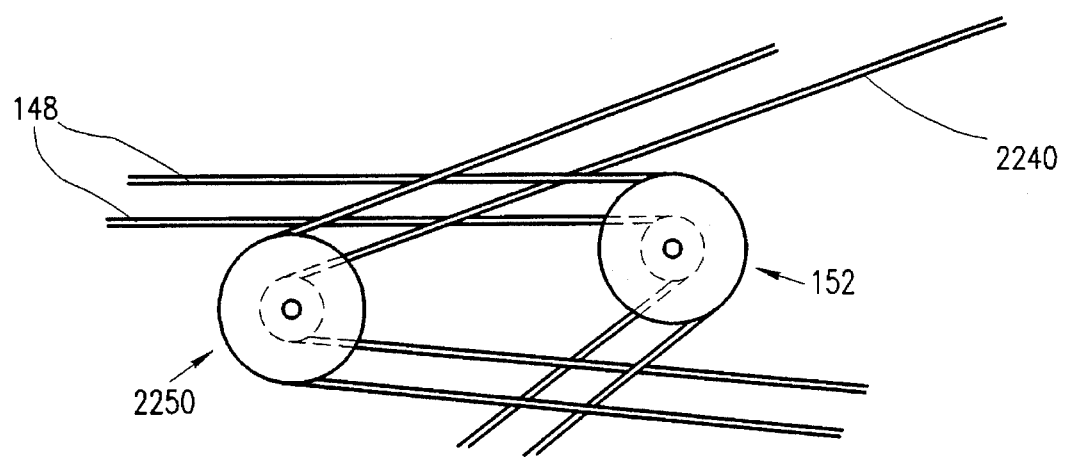

FIGS. 33A and 33B illustrate interlacing of cable 148 and associated pulleys 152; with cables 2240 and associated pulleys 2250. As shown, conveyor 148 is angled relative to conveyor 2240, for example at a 5 degree angle, so that the apples do not come into contact with the pulleys.

It is appreciated that a pair of meshed or interlaced cable conveyors such as those illustrated in FIGS. 33A–33B may be utilized more than once within a single produce sorting system and that one or more sequences of three, four or more pairs of interlaced cable conveyors may be provided within a single produce sorter.

A computer listing of a software implementation of a preferred method for implementing steps 1824 and 1828 of FIG. 23, is provided herein and is referenced Appendix F. The listing of Appendix F relies on a model of object contour according to which the object under inspection is smoothly contoured.

Appendix B includes a computer listing of a main program for an article inspecting system constructed and operative in accordance with a preferred embodiment of the present invention.

Appendix J includes computer listings of helper routines useful in conjunction with the other computer listings appended hereto, as explained in more detail below.

Appendix K includes computer listings of "include files" useful in conjunction with the other computer listings appended hereto, as explained in more detail below.

A suitable environment for running the listings appended hereto is a 486 AT with 16 megabytes of memory, an Imaging Technology CFG frame grabber board, a PCL 720 digital I/O board, commercially available from Advantech, Taipei, Taiwan, and a color screen, the following software products being installed on the 486 AT:

a. ITEX-CFG, commercially available from Imaging Technology, Boston, Mass., USA;
b. Fuzzy C Development System, commercially available from Togai Infralogic; and
c. Microsoft C compiler, Version 6.00.

The frame grabber board may be configured as follows:
Base address—E0000, I/O address—240.

The PCL 720 board may be configured as follows:
I/O address—2A0.

Figure 34A:
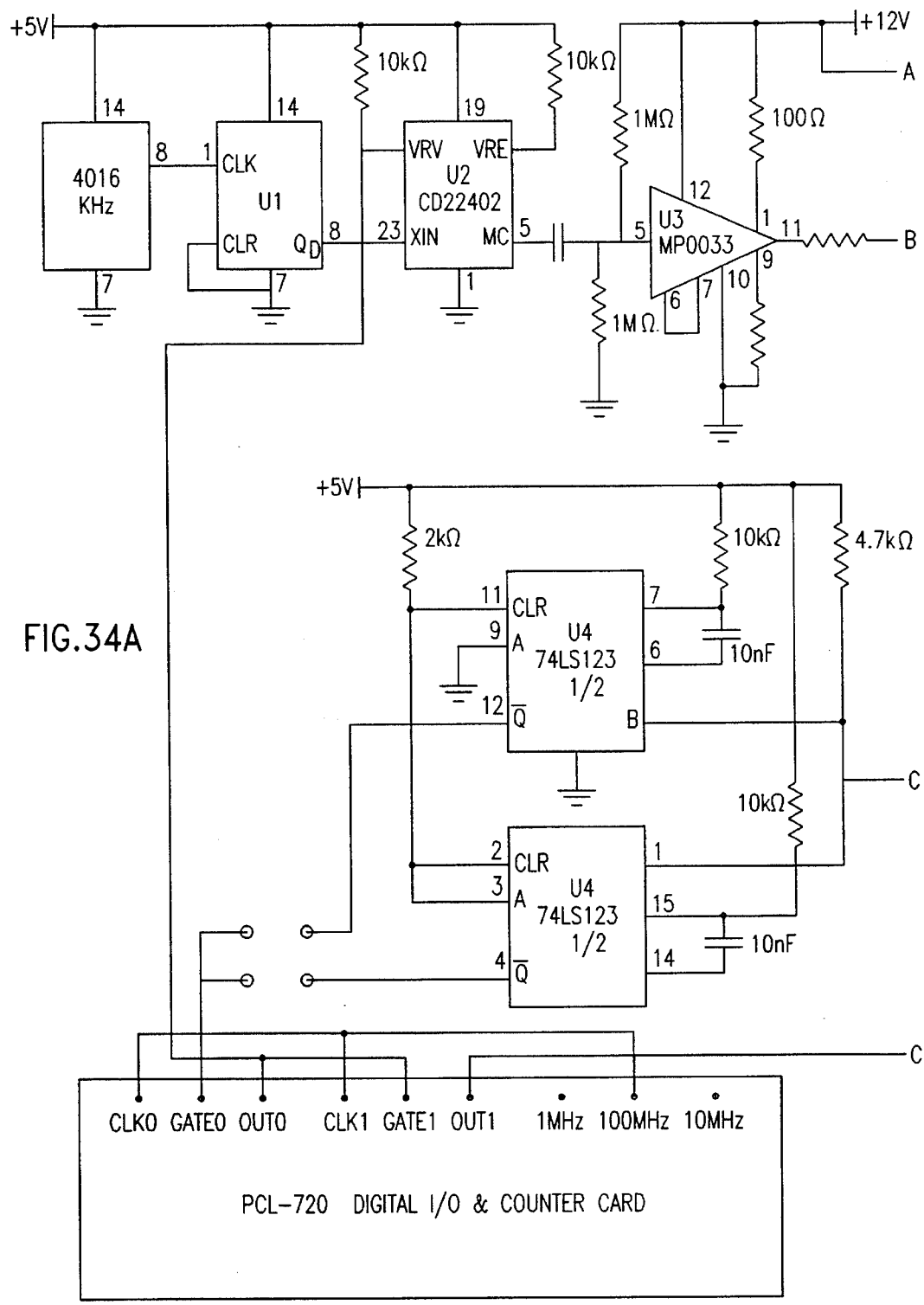
FIGS. 34A and 34B, taken together, form an electronic schematic diagram of components which are not commercially available and which are useful in conjunction with the Appendices attached herewith.
Figure 34B:
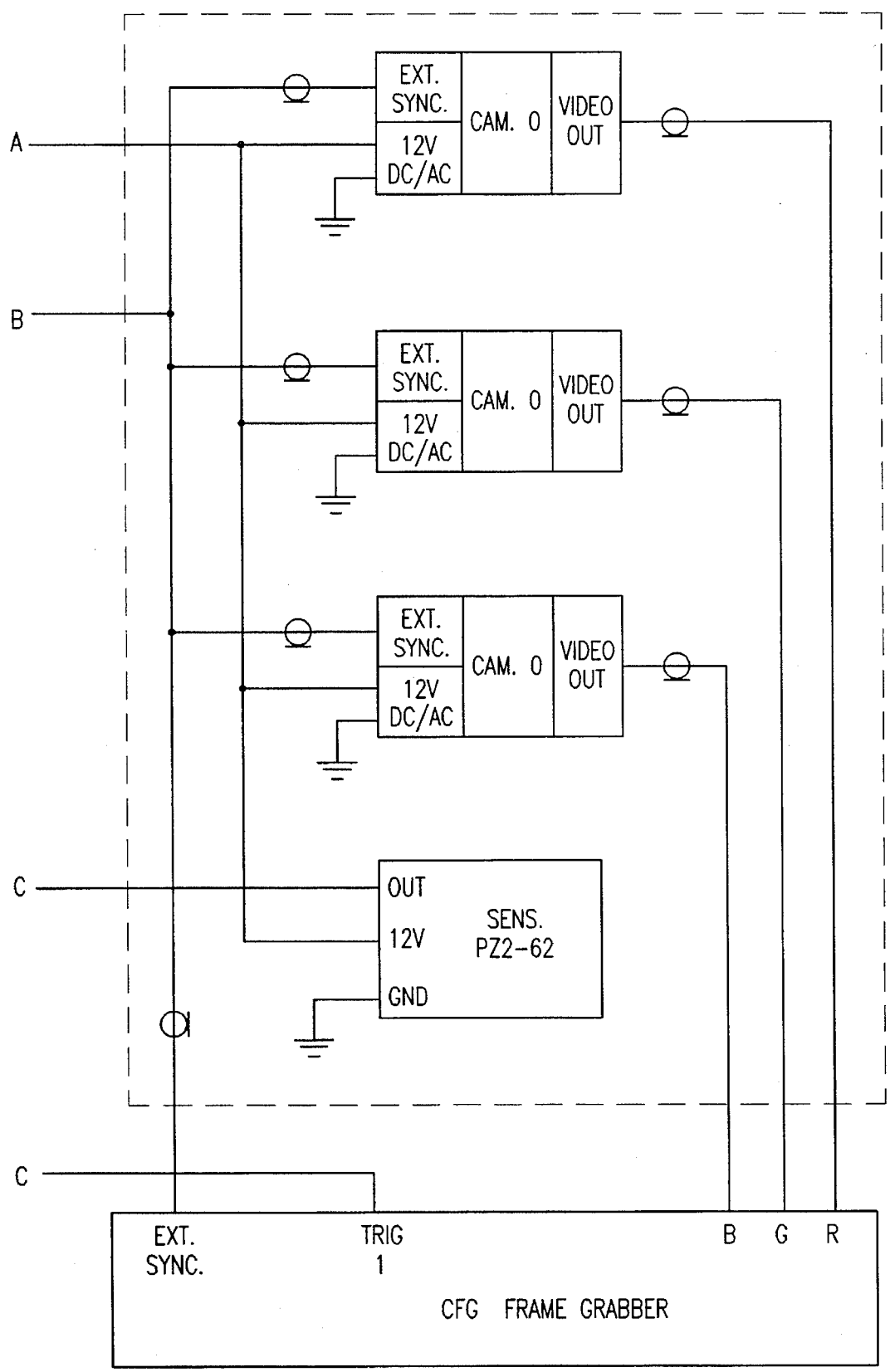

The electronic components diagrammed in FIGS. 34A and 34B may be built and connected to the above commercially available components and to Cohu Model 4912 cameras, commercially available from Cohu, San Diego, Calif., USA, as shown in FIGS. 34A and 34B.

To load and operate any of the computer listings appended herewith, the following steps may be performed:

a. Generate a computer file of the listing. At the top of each listing in each Appendix, a title appears which should be the name of the computer file.
b. Use the batch file and DOS configuration file, a computer listing of which is appended herewith and is referenced Appendix L, to generate an executable program.

It is appreciated that the various appendices enclosed herewith are merely intended to provide an extremely detailed sample implementation of various preferred aspects of the present invention and are not intended to be limiting.

It is appreciated that features of the present invention that have been described in combination with other features may also be employed separately wherever suitable and that features which have been described separately may also be employed in combination with other features wherever suitable. For example, although the simultaneous inspection of generally all exposed areas of the inspected article is the preferred embodiment, alternatively, a plurality of portions of the exposed area of the inspected article may be inspected sequentially.

The present invention is operative in the context of apple inspection and has been described in relation to apple inspection. However, it is appreciated that the invention shown and described herein has a wide variety of applications in inspecting other articles such as but not limited to agricultural products generally and delicate agricultural products specifically, and also to round or spherical objects generally.

It will be appreciated by persons skilled in the art that the present invention is not limited to what has been particularly shown and described hereinabove. Rather, the scope of the present invention is defined only by the claims that follow:

APPENDIX A

```c
/*
                ID: 016
   File name is: app16.c
-----------------------------------------------------------------
*/
#define Q1_IMAGE green
#define Q2_IMAGE ir
#define Q3_IMAGE grid
#define Q4_IMAGE red
#include "adapter.h"
#include <stdio.h>
#include <string.h>
extern struct single_view_info   view_info[N_CAMERAS];
struct {int y,x; } splitter_correction[N_CAMERAS][4] =
                { { 0,  0,  -2,  5,    6,  1,  5,  5    },
                  { 0,  0,   2,  7,   11,  2,  4,  8    },
                  { 0,  0,  -5,  7,    9,  2,  7,  7    }
                  }   ;
static int dc_level[] = {22, 15, 22 };
#define IR_PLATE_FACTOR      1.5
#define GRID_PLATE_FACTOR    2.0
#define GREEN_PLATE_FACTOR   1.5
#define RED_PLATE_FACTOR     1.5
struct boundary_data pip_h;
test_leading_field(image, cam)
          PIXEL   image[L_FR_Y_SIZE][L_FR_X_SIZE];
{
int c_x, c_y, s_x, s_y, y1, i;
      swap_in(&pip_h, view_info[cam].xms_handle, (long)sizeof(struct boundary_dat
              view_info[cam].splitter[0]);
   c_x = (pip_h.out_rect.x2 + pip_h.out_rect.x1) >> 1;
   c_y = (pip_h.out_rect.y2 + pip_h.out_rect.y1) >> 1;
   s_x = c_x - L_FR_X_SIZE/2;
   s_y = c_y - L_FR_Y_SIZE/2;
#ifdef CFG
   cfg_2_ram(image,0,0, L_FR_Y_SIZE, L_FR_X_SIZE,s_x,s_y);
#endif
   for (i = 8 ; i < L_FR_Y_SIZE ; ++i)    {
       printf("\n %3d %3d",i, image[i][L_FR_X_SIZE >> 1]);
       if (image[i][L_FR_X_SIZE >> 1] < 200) break;
       }
printf("\nend line: %d", (i+s_y));
   if (i > 25) return (((i+s_y) & 1));
   return(((i+s_y) & 1)+1);
}
get_cam_splitter_images(image, cam, debug_flag, processing_mode, r_image,field)
          PIXEL   image[L_FR_Y_SIZE][L_FR_X_SIZE];
          PIXEL   r_image[L_FR_Y_SIZE][L_FR_X_SIZE];
{
int j;
double div_fact;
    set_channel(cam);
    for (j = 0 ; j < 4 ; ++j)
    {
       swap_in(&pip_h, view_info[cam].xms_handle, (long)sizeof(struct boundary_dat
               view_info[cam].splitter[j]);
       switch (j) {
          case 0:
                  SWAP_IN_SIZE(r_image, cam, r_images.Q1_IMAGE, L_FR_X_SIZE*L_FR_
                  div_fact = GREEN_PLATE_FACTOR;
                  break;
          case 1:  SWAP_IN_SIZE(r_image, cam, r_images.Q2_IMAGE, L_FR_X_SIZE*L_FR
                  div_fact = IR_PLATE_FACTOR;
                  break;
```

```
            case 2:   SWAP_IN_SIZE(r_image, cam, r_images.Q3_IMAGE, L_FR_X_SIZE*L_FR
                        div_fact = GRID_PLATE_FACTOR;
                        break;
            case 3:   SWAP_IN_SIZE(r_image, cam, r_images.Q4_IMAGE, L_FR_X_SIZE*L_FR
                        div_fact = RED_PLATE_FACTOR;
                        break;
            }
        get_rect_nl(image, pip_h.boundary, pip_h.boundary_index, pip_h.out_rect,
                    splitter_correction[cam][j].x,
                    splitter_correction[cam][j].y,
                    processing_mode, field);
        l_shadow_norm(image, r_image, cam, div_fact);
        if (j == 0)
            SWAP_OUT_SIZE(image, cam, w_images.Q1_IMAGE, L_FR_Y_SIZE*L_FR_X_SIZE);
        else if (j == 1)
            SWAP_OUT_SIZE(image, cam, w_images.Q2_IMAGE,   L_FR_Y_SIZE*L_FR_X_SIZE)
        else if (j == 2)
            SWAP_OUT_SIZE(image, cam, w_images.Q3_IMAGE,   L_FR_Y_SIZE*L_FR_X_SIZE);
        else if (j == 3)
            SWAP_OUT_SIZE(image, cam, w_images.Q4_IMAGE,   L_FR_Y_SIZE*L_FR_X_SIZE);
        if (debug_flag)
            draw_boundary(pip_h.boundary, pip_h.boundary_index,
                                    pip_h.out_rect, 0, 0, 251+j, 254);
    }
}
l_shadow_norm(image, ref_image, cam, factor)
        PIXEL *image, *ref_image;   double factor;
{
unsigned int i;
double f, r;
    for (i = 0 ; i < (L_FR_X_SIZE * L_FR_Y_SIZE) ; ++i)
        {
            if (*image > 253) { ++image; ++ref_image; continue; }
            f= (double)(*image - dc_level[cam]);
            f= (double)(*image - dc_level[cam]);
            r= (double)(*ref_image  - dc_level[cam]);
            r= r*factor;
            if (r < 1) r = 1.;
            f= f / r;
            f= f * 200.;
            if (f > 253.) f = 253.;
            *image = (PIXEL)(f+0.5);
            ++image;
            ++ref_image;
        }
    return(1);
}
static int sss = 1;
get_rect_nl(image, boundary, boundary_index, out_rect, off_x, off_y,
            processing_mode, field)
    PIXEL image[L_FR_Y_SIZE][L_FR_X_SIZE];
    struct line_pair boundary[];
    struct rect out_rect;
{
int c_x, c_y, s_x, s_y;
char t[16];
    c_x = (out_rect.x2 + out_rect.x1) >> 1;
    c_y = (out_rect.y2 + out_rect.y1) >> 1;
    s_x = c_x - L_FR_X_SIZE/2 + off_x;
    s_y = c_y - L_FR_Y_SIZE/2+ off_y;
    if (processing_mode == MANUAL_MODE)
        get_block_dc(image,0,0, s_x,s_y);
    else if (processing_mode == AUTO_MODE)
        get_block_field0_dc(image,0,0, s_x,s_y, field);
```

```
    else {
        fprintf(stderr, "Unknown P-mode"); exit(1);
    }
    correct_pip_hole_n(image, boundary, boundary_index, s_x-off_x, s_y-off_y, out_
}
get_block_field0_dc(image,k,l, s_x, s_y, field)
            PIXEL image[L_FR_Y_SIZE][L_FR_X_SIZE];
{
#define N_C 4
int i,j, cam_col, cam_line, dc, p, a, b;
PIXEL norms[N_C][640];
#ifdef _CFG
    get_dfield(image,k,l, L_FR_Y_SIZE, L_FR_X_SIZE, s_x, s_y, field);
#endif
#ifdef NORM_MIDDLE_LINE
    get_block(norms,k,l, N_C, 640, 0, 228);
    cam_col = s_x;
    for (j = 0 ; j < L_FR_X_SIZE ; ++j)
        {
            dc = 0;
            for (a = cam_col-1 ; a <= cam_col+2 ; ++a)
                for (b = 0 ; b < N_C ; ++b)
                    dc += norms[b][a];
            dc = dc >> 4;
            for (i = 0 ; i < L_FR_Y_SIZE ; ++i)
            {
                p = image[i][j];
                p = p-dc;
                if (p < 0) p = 0;
                image[i][j] = (PIXEL)p;
            }
            ++cam_col;
        }
#endif
}
get_block_dc(image,k,l, s_x,s_y)
            PIXEL image[L_FR_Y_SIZE][L_FR_X_SIZE];
{
int i,j, cam_col, cam_line, dc, p, a,b;
#define N_C 4
PIXEL norms[N_C][640];
    get_block(image,k,l, L_FR_Y_SIZE, L_FR_X_SIZE,s_x,s_y);
#ifdef NORM_MIDDLE_LINE
    get_block(norms,0,0, N_C, 640, 0, 228);
    cam_col = s_x;
    for (j = 0 ; j < L_FR_X_SIZE ; ++j)
        {
            dc = 0;
            for (a = cam_col-1 ; a <= cam_col+2 ; ++a)
                for (b = 0 ; b < N_C ; ++b)
                    dc += norms[b][a];
            dc = dc >> 4;
 if (dc > 60)
     printf("\nDC: %d %d", dc, cam_col);
            for (i = 0 ; i < L_FR_Y_SIZE ; ++i)
            {
                p = image[i][j];
                p = p-dc;
                if (p < 0) p = 0;
                image[i][j] = (PIXEL)p;
            }
            ++cam_col;
        }
#endif
```

```
}
correct_for_saturation(image)
          PIXEL image[L_FR_Y_SIZE][L_FR_X_SIZE];
{
int i,j;
     for (i = 0 ; i < L_FR_Y_SIZE ; ++i)
       for (j = 0 ; j < L_FR_Y_SIZE ; ++j)
          if (image[i][j] > 253) image[i][j] = 253;
}
Xdraw_boundary(boundary, boundary_index, out_rect, off_x, off_y, b_color, rect_co
     struct line_pair boundary[];
     struct rect out_rect;
{
int i,x1,x2,y;
     for (i = 0 ; i < boundary_index ; ++i)
     {
        y = boundary[i].y + off_y;
        x1 = boundary[i].x1 + off_x;
        x2 = boundary[i].x2 + off_x;
printf("\n +++ %d %d %d %d",i, y,x1,x2); if (x2 <= x1) printf("+++");
        wpixel(x1,y,b_color);
        wpixel(x2,y,b_color);
     }
     if (rect_color >= 0) {
        dline(out_rect.x1+off_x, out_rect.y1+off_y, out_rect.x2+off_x, out_rect.y1+o
        dline(out_rect.x2+off_x, out_rect.y1+off_y, out_rect.x2+off_x, out_rect.y2+o
        dline(out_rect.x2+off_x, out_rect.y2+off_y, out_rect.x1+off_x, out_rect.y2+o
        dline(out_rect.x1+off_x, out_rect.y2+off_y, out_rect.x1+off_x, out_rect.y1+o
     }
}
```

APPENDIX B

```c
/*
                        ID: 015
   File name: app15.c
------------------------------------------------------------------------
*/
#define REAL_GRAB
#include "adapter.h"
#include <stdio.h>
#include <process.h>
#include <io.h>
#include <conio.h>
#include <time.h>
#include <string.h>
#include <math.h>
#include <setjmp.h>
#define D_ST_CA     12
#define D_ROT       45
#define D_MOTH      65
#define D_LROT      101
#define D_RUSSET    131
#define D_BRUISE    161
#define D_PIT       191
#define D_PARLAT    220
#define D_NOTHING   241
#define BLEMISH_KINDS_N 9
extern jmp_buf jmp_mark;
static int line = 100, col = 30;
static int display_index = 1;
double apple_volume;
struct prog_settings prog_consts;
struct setup_data    settings;
struct spot spots[MAX_SPOTS];
struct spot final_spots[MAX_FINAL_SPOTS];
int         spots_index=0;
long        Dark_Red ,Simple_red, Yellow, Green, Orange, Sat;
double      dist = 80.;
int   do_not_display_calyx_cam;
static int  display_line_count, display_col_count;
extern struct single_view_info   view_info[N_CAMERAS];
struct {
        PIXEL image0[FR_Y_SIZE][FR_X_SIZE];
        PIXEL image1[FR_Y_SIZE][FR_X_SIZE];
        PIXEL image2[FR_Y_SIZE][FR_X_SIZE];
        struct boundary_data bnd;
        } mem0;
struct {
        PIXEL image0[FR_Y_SIZE][FR_X_SIZE];
        PIXEL image1[FR_Y_SIZE][FR_X_SIZE];
        PIXEL image2[FR_Y_SIZE][FR_X_SIZE];
        } mem1;
struct c_dat candidates[MAX_CANDIDATES];
int cand_index;
int n_stems, stem_index, calyx_index;
int global_color_grade, apple_size;
int p_errno;
int debug_flag;
static char last_key[4];
char *args[16];
#ifdef IP8
#define gtext(a,b,c,d,e,f) write_str(a,b,c,d,e);
#endif
static char *f_text[] = { "Get Data", "Size", "Blemish", "Color",
       "", "3D Save", "", "Roll" };
static char *k_text[] = { "F1", "F2", "F3", "F4", "F5", "F6", "F7", "F8" };
```

```c
static struct { int xs, ys, xf, yf;
                unsigned char on_off;
                int f_color, b_color;
                char *act_button, *text; } buttons[16];
#ifdef VGA
static short screen_lut[256][4];
#endif
#define DISP_X 640
#define DISP_Y 480
#define GRAB_X 0
#define GRAB_Y 0
#define UP_ARROW        1
#define RIGHT_ARROW     2
#define DOWN_ARROW      3
#define LEFT_ARROW      4
#define HOME_KEY        5
#define END_KEY         6
#define PgDn_KEY        7
#define PgUp_KEY        8
#define CTRL_F1_KEY     40
#define CTRL_F8_KEY     41
#define CTRL_F6_KEY     99
#define ALT_F8_KEY      61
#define F1_KEY          9
#define F2_KEY          10
#define F3_KEY          11
#define F4_KEY          12
#define F5_KEY          13
#define F6_KEY          14
#define F7_KEY          15
#define F8_KEY          16
#define F9_KEY          17
#define F10_KEY         18
#define CNTRL_Z         19
#define ESCAPE          20
#define CNTRL_D         21
#define HOME_HEY        71
#define END_HEY         79
#define BOT_20          ((int)(DISP_Y / 5))
#define START_Y         ((int)(DISP_Y - BOT_20))
#define END_Y           ((int)(DISP_Y - 1))
#define Y_INCREMENT     ((int)((END_Y-START_Y)/2 + 1))
#define START_X         10
#define END_X           ((int)(DISP_X ))
#define X_INCREMENT     ((int)(DISP_X / 4 + 2))
#define D_X             ((int)(X_INCREMENT*0.80))
#define D_Y             ((int)(Y_INCREMENT*0.70))
#ifdef IP8
static short grab_lut[256][4];
static short screen_lut[256][4];
static short blank_lut[256][4];
#endif
#define TEXT_X1   25
#define TEXT_Y1   290
#define TEXT_X2   615
#define TEXT_Y2   360
#define TEXT_BACK     176
#define SHAD 5
#define STAT_FILE_NAME "s_file.dat"
FILE *stat_file;
struct {
    int size;
    int volume;
    int color_index_1;
```

```c
        int color_index_2;
        int color_index_3;
        int color_index_4;
        int n_rot;
        int n_bruise;
        int n_moth;
        int n_st_ca;
    } statistics;
static char *apple_brands[] = ("Smith",      "Hermon",    "Ana", "Orleans", NUL
int apple_brand;
static int auto_mode;
int grade_1, grade_2;
main(argc,argv )              char *argv[];
(
int exit_flag, ret, off_x, off_y;
    if (argc < 4) { printf("\n Usage: %s apple-brand debug auto",argv[0]); exit(1)
        sp_init_xms();

debug_flag = atoi(argv[2]);
    auto_mode = atoi(argv[3]);
    init_statistics();
    init_exception_handlers();
    reinit_storage();
    process_command_file(SETUP_FILE, &prog_consts, &settings);
    load_splitter_locations();
    load_no_zone_images(&mem0);
    if (debug_flag) show_setup(&settings);
    apple_brand = match_apple_brand(argv[1]);
    if (apple_brand < 0) ( printf("\n Unfamiliar apple brand"); exit(1); }
    init_display();
#define SCREEN_COLOR    118
#define TEXT_COLOR      255
#define KEY_COLOR        14
#define SHADOW_COLOR      0
#ifdef IP8
    load_luts();
    set_lut_active(screen_lut);
#endif
#ifdef VGA
    init_vga_display(5,2);
    load_luts();
      vga_clear_screen(7);
    vga_set_pallate(screen_lut);
#endif
#ifndef TEXT_COLOR
#define TEXT_COLOR      255
#define KEY_COLOR        14
#define SHADOW_COLOR      0
#endif
    zoom_window(0);
    pan_window(0,0);
    demo_screen();
    exit_flag = 0;
     display_header(argv[1]);
    if (auto_mode)  {
       do_auto_mode(argv[1]);
       auto_mode = 0;
       }
    auto_mode = atoi(argv[3]);
    do (
     p_errno = 0;
     switch (select_menue())
     (
       case CTRL_F1_KEY: on_indicator("F1");
```

```
                              get_data_all(MANUAL_MODE);
#ifdef IP8
                              set_lut_active(screen_lut);
#endif
                              break;
          case F2_KEY       : on_indicator("F2");
                              line = 100, col = 30; display_index = 1;
                              display_header(argv[1]);
                              do_measure_all();
                              break;
          case F3_KEY       : on_indicator("F3");
                              bruise_all();
                              break;
          case F4_KEY       : on_indicator("F4");
                              do_global_all();
                              break;
          case F5_KEY       : on_indicator("F5");
                              break;
          case F6_KEY       : on_indicator("F6");
                               produce_3d_file(FILE_3D_NAME);
                              break;
          case CTRL_F6_KEY  : on_indicator("F6");
                              do_save_data(mem0.image0);
                              break;
          case F7_KEY       : on_indicator("F7");
                              write_statistics();
                              break;
          case CTRL_F8_KEY  : on_indicator("F8");
                              if (wait_for_apple())
                                    extract_regions_all(AUTO_MODE);
                              break;
          case ALT_F8_KEY   :
                                do_calibrate_all();
                                break;
          case ESCAPE:
                                exit_flag = 1;
                                break;
          case PgDn_KEY:
          case PgUp_KEY:
                                break;
          case CNTRL_Z:
                                auto_mode = 0;
                                break;
          case CNTRL_D:
                                auto_mode = 1;
                                do_auto_mode(argv[1]);
                                break;
      }
      off_indicator(last_key);
    } while (!exit_flag) ;
#ifdef IP8
    set_lut_active(grab_lut);
#endif
#ifdef VGA
  finit_vga();
#endif
}
static int off_x, off_y;
toggle_display_image()
{
int off_x, off_y;
      ++display_index;
      if (display_index > 2) display_index = 0;
      off_x = atoi(prog_consts.T_WIN_X_OFF[CAM_2]);
```

```
        off_y = atoi(prog_consts.T_WIN_Y_OFF[CAM_2]);
        if      (display_index == 0) display_cam_full(CAM_1, off_x, off_y);
        else if (display_index == 1) display_cam_full(CAM_2, off_x, off_y);
        else if (display_index == 2) display_cam_full(CAM_3, off_x, off_y);
}
do_auto_mode(brand)        char *brand;
{
int ret, off_x, off_y;
   do {
           vga_filled_rectangle(7+4, 7+4, 7+10, 7+10, 90);
           p_errno = 0;
           on_indicator("F8");
more_wait: ;
           if (wait_for_apple())
                   extract_regions_all(AUTO_MODE);
           if (kbhit()) {   ret = getch();
                           if (kbhit())  {   ret = getch();
                               if (ret == 81 || ret == 73) {
                                  goto more_wait; }
                               if (ret == 71 ) {
                                  goto more_wait; }
                               if (ret ==CTRL_F6_KEY) {
                                       on_indicator("F6");
                                       do_save_data(mem0.image0);
                                       on_indicator("F8");
                                       goto more_wait;
                                  }
                               else continue;
                           }
                           else break;
                   }
           if (kbhit()) break;
#ifdef FOR_DATA_TAKING
                                     on_indicator("F6");
                                     do_save_data(mem0.image0);
                                     on_indicator("F8");
#else
           on_indicator("F2");
           display_header(brand);
           line = 100, col = 30; display_index = 1;
           ret = do_measure_all();
           if (ret != SUCCESS) continue;
           if (kbhit()) break;
       on_indicator("F3");
           bruise_all();
           if (kbhit()) break;
       on_indicator("F4");
           do_global_all();
       on_indicator("F6");
           write_statistics();
           do_save_data(mem0.image0);
           produce_3d_file(FILE_3D_NAME);
#endif
    }  while (!kbhit());
   off_indicator(last_key);
   while (kbhit()) getch();
   vga_filled_rectangle(7+4, 7+4, 7+10, 7+10, 0);
}
bruise_all()
{
int cam, count, ca_index, mate_index, cam_dist, third_index;
int old_chan, cam_i;
int cam_redirection[] = { 0, 1, 2 };
   old_chan = get_channel();
```

```
spots_index = 0;
for (cam_i = 0 ; cam_i < N_CAMERAS ; ++cam_i) {
    cam = cam_redirection[cam_i];
    set_channel(cam);
    count = do_bruse_1(cam, &mem0.bnd,
                mem0.image0 ,
                mem0.image1 ,
                mem0.image2 ,
                 mem1.image0 ,
                mem1.image1 ,
                mem1.image2 ,
                spots);
    spots_index += convert_spots(spots, &final_spots[spots_index], count);
    SWAP_OUT_SIZE(mem1.image1, cam, spots_2, FR_Y_SIZE*FR_X_SIZE);
    if (cam == CAM_2)
         display_single_object(mem1.image1, BRUSE_MARK, 0,
                atoi(prog_consts.T_WIN_X_OFF[1]),atoi(prog_consts.T_WIN_Y_OFF[1])
    else if (debug_flag || !auto_mode)
         display_single_object(mem1.image1, BRUSE_MARK, 0,
                atoi(prog_consts.T_WIN_X_OFF[cam]),atoi(prog_consts.T_WIN_Y_OFF[c
}
if(debug_flag) {
    printf("\n3-D data:");
    printf("\n=========");
    display_found_contours(final_spots, spots_index, &mem0.image1);
}
cam_dist = prog_consts.camera_distance[CAM_1];
spots_index = fill_3d_info(final_spots, spots_index,
            &mem0.bnd, &mem0.image0, &mem0.image1, 0);
ca_index = choose_stem_calyx(final_spots, spots_index, 0);
if (ca_index >= 0)  {
    mate_index = final_spots[ca_index].mate;
    printf("\nLooking for third");
    third_index = look_for_third(final_spots,
                        spots_index, ca_index, mate_index);
}
else   {
    ca_index = third_index = mate_index = -1;
}
printf("\nfound : ca_index= %d  mate_index= %d third_index= %d",
    ca_index,mate_index,third_index);
pre_re_classify(final_spots, spots_index, &ca_index, &mate_index, &third_index
re_classify(final_spots, spots_index, ca_index, mate_index, third_index);
cancel_no_zone_litter(final_spots, spots_index, &mem0);
if (dump_spots("F_SPT.DAT", final_spots, sizeof(struct spot) * MAX_FINAL_SPOTS
 {
    printf("\n ERROR : dump final spots failure");
    exit(1);
}
if (debug_flag && ca_index >= 0) {
    if (final_spots[ca_index].flag4 == REAL_BLEMISH)
        display_single(&final_spots[ca_index], 254, ca_index);
    if (final_spots[mate_index].flag4 == REAL_BLEMISH)
        display_single(&final_spots[mate_index], 254, mate_index);
    if (third_index >= 0)
        if (final_spots[third_index].flag4 == REAL_BLEMISH)
            display_single(&final_spots[third_index], 254, mate_index);
}
fill_blem_stat(final_spots, spots_index,
                    ca_index, mate_index, third_index);
display_found_contours_on(final_spots, spots_index,
                    ca_index, mate_index, third_index);
if (ca_index >= 0)  {
   if (final_spots[ca_index].flag4 == REAL_BLEMISH)
```

```c
        display_single_on(&final_spots[ca_index], 122, ca_index);
      if (final_spots[mate_index].flag4 == REAL_BLEMISH)
           display_single_on(&final_spots[mate_index], 122, mate_index);
     if (third_index >= 0)
        if (final_spots[third_index].flag4 == REAL_BLEMISH)
            display_single_on(&final_spots[third_index], 122, third_index);
    }
    display_reading();
    stem_index=mate_index;   calyx_index=ca_index;
    set_channel(old_chan);
    return(1);
}
display_found_contours_on(spots, spt_index, ind1, ind2, ind3)
          struct spot spots[];
{
int i, color;
    for (i = 0 ; i < spt_index ; ++i)
       {
          if (i != ind1 && i != ind2 && i != ind3)
            {
              if (final_spots[i].flag4 == REAL_BLEMISH
                           && final_spots[i].flag2 != D_NOTHING) {
                  if ((!debug_flag && auto_mode) && spots[i].cam_number != CAM_2)
                  color = get_display_color(spots[i].flag2);
                  display_single_on(&spots[i], color, i);
              }
           }
       }
}
get_display_color(blemish)
{
int color;
    switch(blemish)
       {
           case D_PARLAT:    color = 41; break;
           case D_BRUISE:    color = 64; break;
           case D_ST_CA:
           case D_LROT:
           case D_ROT:       color = 18;  break;
           case D_MOTH:       color = 95;  break;
           case D_PIT:      color = 113; break;
           default:         color = 253; break;
       }
printf("\ncolor: %d", color);
    return(color);
}
display_reading()
{
char tmp[64];
int x, y, color;
#define D_DEL 15
    x = 500;
    y = 200;
    color = get_display_color(D_BRUISE); gtext_demo(x, y, "Bruise", 1, color, 1);
    y += D_DEL;
    color = get_display_color(D_ROT);    gtext_demo(x, y, "Rot", 1, color, 1);
    y += D_DEL;
    color = get_display_color(D_MOTH);   gtext_demo(x, y, "Moth", 1, color, 1);
    y += D_DEL;
    color = get_display_color(D_PIT);    gtext_demo(x, y, "Pit", 1, color, 1);
    y += D_DEL;
    color = get_display_color(D_PARLAT); gtext_demo(x, y, "Parlat", 1, color, 1);
}
display_single_on(spot, color, ind)
```

```c
    struct spot *spot;

int off_x, off_y;
char name[16];
        if ((!debug_flag && auto_mode) && spot->cam_number != CAM_2) return(1);
        switch (spot->cam_number)
            {
            case 0:
                    off_x = atoi(prog_consts.T_WIN_X_OFF[CAM_1]);
                    off_y = atoi(prog_consts.T_WIN_Y_OFF[CAM_1]);
                    break;
            case 1:
                    off_x = atoi(prog_consts.T_WIN_X_OFF[CAM_2]);
                    off_y = atoi(prog_consts.T_WIN_Y_OFF[CAM_2]);
                    break;
            case 2:
                    off_x = atoi(prog_consts.T_WIN_X_OFF[CAM_3]);
                    off_y = atoi(prog_consts.T_WIN_Y_OFF[CAM_3]);
                    break;
            }
        draw_contour_file_on(spot, spot->flag3, color, spot->cam_number,
                                                    1, off_x, off_y);
}
draw_contour_file_on(spot, id, color, cam_number, magni, off_x, off_y)
        struct spot *spot;
{
int j, ret, per, i;
char c_name[24];
#define CHAIN_SIZE 2048
char chain[CHAIN_SIZE], *p;
int xybuf[1024][2];
int min_i, min_j, max_i, max_j;
#define _UP_ARROW       'U'
#define _DOWN_ARROW     'D'
#define _LEFT_ARROW     'L'
#define _RIGHT_ARROW    'R'
    sprintf(c_name, "%s%ld_%ld.cnt", TMP_DEVICE, cam_number, id);
    ret = undump_spots(c_name, chain, CHAIN_SIZE, &per);
    if (ret != SUCCESS) {
            printf("\nContour file %s not found", c_name); return(1);
        }
    i = spot->start_i + off_y;
    j = spot->start_j + off_x;
    chain_to_raster(i, j,chain, xybuf, &min_i, &min_j, &max_i, &max_j);
    plot_buf_on(xybuf, per, color, 1, 5);
#ifdef OLD
    for (p = chain; *p ; ++p)
    {
        switch(*p)
        {
        case _UP_ARROW:         --i ; break;
        case _DOWN_ARROW:       ++i ; break;
        case _LEFT_ARROW:       --j; break;
        case _RIGHT_ARROW:      ++j ; break;
        }
        wpixel_demo(j,i,color);
    }
#endif
}
plot_buf_on(circle_buf,buf_pointer,color,magni,smooth_d)
        int circle_buf[][2];
{
int i;
int k,l,il,j;
```

```
float dividor1 = (smooth_d*2.+1) / (float)magni;
float dividor2 = (smooth_d*2.+1) / (float)magni;
   if (buf_pointer < smooth_d ) { buf_pointer = 0 ; return(0); }
   k = l = 0;
   for (i = -smooth_d ; i <= smooth_d ; ++i )
   {
      if ( i < 0 ) j = buf_pointer+i ; else j = i;
      k +=  circle_buf[j][0] ;
      l += circle_buf[j][1] ;
   }
   l = (int) ((float)l/dividor1) + 0;
   k = (int) ((float)k/dividor2) + 0;
   wpixel_demo(l,k,color);
   for (i1 = 1 ; i1 <= buf_pointer ; ++i1)
   {
      k = l = 0;
      for (i=i1-smooth_d ; i <= i1+smooth_d ; ++i )
      {
         if ( i<0 ) j = buf_pointer+i ;
         else if (i >= buf_pointer ) j = i-buf_pointer ;
         else j = i;
         k +=  circle_buf[j][0] ; l += circle_buf[j][1] ;
      }
      l = (int) ((float)l/dividor1) + 0;
      k = (int) ((float)k/dividor2) + 0;
      wpixel_demo(l,k,color);
   }
   buf_pointer = 0;
return(1);
}
produce_3d_file(name)     char *name;
{
char *p;
char name1[32];
double t_volume;
int    fill_color_mask();
int    spt_index;
      if (undump_spots("F_SPT.DAT", final_spots, sizeof(final_spots),
                                    &spt_index)== FAILURE)
         {  printf("\n Final_spots file not found"); exit(1);    }
      spots_index=spt_index;
      fill_color_mask(final_spots, spt_index, mem0.image0);
   p = &mem0.image0[0][0];
   p += sizeof(struct boundary_data);
   if (strlen(settings.demo_file_command) > 0)
                sprintf(name1,"%s",name);
   else strcpy(name1, name);
printf("\n #DNAME: %s", name1);
   do_3dfile(name1, (struct boundary_data *)&mem0.bnd,
             (struct boundary_data *)&mem0.image0,
             (PIXEL *)p,
             mem0.image1, mem0.image2, mem1.image1,mem1.image0, &t_volume);
   printf("\n Volume : %4d cc\n",(int)(t_volume/1000.));
}
display_cam_full(cam, off_x, off_y)
{
   switch(apple_brand) {
      case SMITH_TYPE:
         SWAP_IN_SIZE(mem1.image1, cam,  normal_images.green, FR_Y_SIZE*FR_X_SIZ
         break;
      case HERMON_TYPE:
      case ORLEANS_TYPE:
         SWAP_IN_SIZE(mem1.image1, cam,  normal_images.red, FR_Y_SIZE*FR_X_SIZE)
            break;
```

```
        }
        SWAP_IN_SIZE(mem0.image0, cam, enhanced_images.green, FR_Y_SIZE*FR_X_SIZE);
        show_squeesed_image(mem0.image0, "0", off_x, off_y);
        SWAP_IN_SIZE(mem1.image1, cam, stem_mask, FR_Y_SIZE*FR_X_SIZE);
        display_single_object(mem1.image1, CALYX_MARK, 0, off_x, off_y, 118);
}
colect_color_inf(cam_number,Dark_Red,Simple_red,Yellow,Green,Orange,Sat,changes,n
int     cam_number;
long    *Dark_Red,*Simple_red,*Yellow,*Green,*Orange,*Sat,*changes,*no_color;
{
int     display_flag = 1;
        SWAP_IN_SIZE(&mem0.bnd,  cam_number, bnd, sizeof(struct boundary_data));
        SWAP_IN_SIZE(mem0.image0, cam_number, raw_images.green, FR_X_SIZE * FR_Y_SI
        SWAP_IN_SIZE(mem0.image1, cam_number, raw_images.red,   FR_X_SIZE * FR_Y_SI
        SWAP_IN_SIZE(mem0.image2, cam_number, raw_images.grid,  FR_X_SIZE * FR_Y_S
        global_color_analysis(cam_number, &mem0.bnd, mem0.image0,mem0.image1,mem0.i
                        ,Dark_Red,Simple_red,Yellow,Green,Orange,Sat,changes,n
        SWAP_OUT_SIZE(mem1.image0, cam_number, spots_1, FR_Y_SIZE*FR_X_SIZE);
}
int  do_global_all()
{
   int        p2;
   char       tmp[64];
   long       changes=0,no_color=0;
        float     tmporal;
   Dark_Red=0;   Simple_red=0;
   Yellow=0; Green=0;   Orange=0;  Sat=0;
   colect_color_inf(CAM_1,&Dark_Red,&Simple_red,&Yellow,&Green,&Orange,&Sat,&chan
   colect_color_inf(CAM_2,&Dark_Red,&Simple_red,&Yellow,&Green,&Orange,&Sat,&chan
   colect_color_inf(CAM_3,&Dark_Red,&Simple_red,&Yellow,&Green,&Orange,&Sat,&chan
   if (debug_flag)    printf("\n\n     COLOR ANALYSIS RESULTS   pixel counters :\
            \n Green=%ld dark_red=%ld simple_red=%ld   Yellow=%ld Orange=%ld
            \n Sat=%ld Changes=%ld   no_color=%ld",
            Green,Dark_Red,Simple_red,Yellow,Orange,Sat,changes,no_color);
      changes = (long) (100 * changes/(float) (Dark_Red + Simple_red +1) + 0.5);
      tmporal=(float)(Dark_Red+Simple_red+Yellow+Green+Orange + no_color);
      Simple_red=(long)( 100.*Simple_red/tmporal +0.5);
      Dark_Red=(long)( 100.*Dark_Red/tmporal +0.5);
      Green=(long)( 100.*Green/tmporal +0.5);
      Orange=(long)( 100.*Orange/tmporal +0.5);
      Yellow=(long)( 100.*Yellow/tmporal +0.5);
      no_color=(long)( 100.*no_color/tmporal +0.5);
      if (debug_flag)    printf("\n\n    NORMALIZED COLOR ANALYSIS  : \
            \n Green=%ld dark_red=%ld simple_red=%ld   Yellow=%ld Orange=%ld
            \n Sat=%ld Changes=%ld   no_color=%ld",
            Green,Dark_Red,Simple_red,Yellow,Orange,Sat,changes,no_color);
      switch (apple_brand)
         {
         case SMITH_TYPE:
            {
              p2 = Green;
              p2=(p2<5)?5:p2;
              p2=(p2>95)?95:p2;
              sprintf(tmp, "Green Coverage");  off_x = 60; off_y = 200;
              make_rouler_p(off_x, off_y, off_x+160, off_y+20,
                 20, p2, tmp, 57, 38);
                    return(0 );
                    break;
            }
         case ANA_TYPE:
         case HERMON_TYPE:
         case ORLEANS_TYPE:
            {
              p2 = Dark_Red+Simple_red + (Orange>>1);
```

```
                    p2=(p2<5)?5:p2;
                    p2=(p2>95)?95:p2;
                    sprintf(tmp, "Red Coverage"); off_x = 60; off_y = 200;
                    make_rouler_p(off_x, off_y, off_x+160, off_y+20,
                        20, p2, tmp, 57, 38);
                    statistics.color_index_1 = p2;
                     p2 = Dark_Red;
                    p2=(p2<5)?5:p2;
                    p2=(p2>95)?95:p2;
                    sprintf(tmp, "Red Saturation Area"); off_x = 60; off_y =.240;
                    make_rouler_p(off_x, off_y, off_x+160, off_y+20,
                        20, p2, tmp, 57, 38);
                    statistics.color_index_2 = p2;
                    p2 = Sat;
                    p2=(p2<5)?5:p2;
                    p2=(p2>95)?95:p2;
                    sprintf(tmp, "Saturation Strength"); off_x = 260; off_y = 200;
                    make_rouler_p(off_x, off_y, off_x+160, off_y+20,
                        20, p2, tmp, 57, 38);
                    statistics.color_index_3 = p2;
                    p2 = changes;
                    p2=(p2<5)?5:p2;
                    p2=(p2>95)?95:p2;
                    sprintf(tmp, "Stripeness"); off_x = 260; off_y = 240;
                    make_rouler_p(off_x, off_y, off_x+160, off_y+20,
                        20, p2, tmp, 57, 38);
                    statistics.color_index_4 = p2;
                }
            }
    }
get_data_all(flag)
{
int ret, old, cam_number;
    zoom_window(0);
#ifdef _CFG
    set_dac_limits_all(prog_consts.dac_low_lim[CAM_1],
                       prog_consts.dac_high_lim[CAM_1],
                       prog_consts.dac_low_lim[CAM_2],
                       prog_consts.dac_high_lim[CAM_2],
                       prog_consts.dac_low_lim[CAM_3],
                       prog_consts.dac_high_lim[CAM_3]);
#endif
#ifdef REAL_GRAB
    cont_grab(0);
    while(!kbhit()) ; if (getch() == 27) {
                                            freese(); return(1); }
    snap(0);
#endif
        old = get_channel();
        extract_regions_all(flag);
        set_channel(old);
}
wait_for_apple()
{
int ret;
#ifdef _CFG
    set_dac_limits_all(prog_consts.dac_low_lim[CAM_1],
                       prog_consts.dac_high_lim[CAM_1],
                       prog_consts.dac_low_lim[CAM_2],
                       prog_consts.dac_high_lim[CAM_2],
                       prog_consts.dac_low_lim[CAM_3],
                       prog_consts.dac_high_lim[CAM_3]);
    ret = grab_moving_apple(prog_consts.apple_travel_time_interval,
                       prog_consts.frame_time_interval, 0);
```

```
        return(ret);
=endif
        return(0);
}
extract_regions_all(processing_mode)
{
int ret, cam_number, field;
static int count = 0;
char t1[4];
    field = test_leading_field(&mem0, CAM_1);
    printf("\nfield: %d", field);
    for (cam_number = 0 ; cam_number < 3 ; ++cam_number)
    {
        set_channel(cam_number);
        get_cam_splitter_images(&mem0, cam_number,
                                debug_flag, processing_mode, &mem1, field);
    }
    return(SUCCESS);
}
do_calibrate_all()
{
    fprintf(stderr, "\nThis option exists as a utility program only");
}
zero_all_masks(image)      PIXEL *image;
{
int cam;
    clear_mat(image);
    for (cam = 0 ; cam < N_CAMERAS ; ++cam)
    {
        SWAP_OUT_SIZE(image, cam, spots_1, FR_Y_SIZE*FR_X_SIZE);
        SWAP_OUT_SIZE(image, cam, spots_2, FR_Y_SIZE*FR_X_SIZE);
        SWAP_OUT_SIZE(image, cam, combi_map, FR_Y_SIZE*FR_X_SIZE);
    }
}
do_measure_all()
{
int precent, i;
int mean[N_CAMERAS], mad[N_CAMERAS], min[N_CAMERAS], max[N_CAMERAS];
int mean_mean, mean_mad;
    if (p_errno == 0) test_for_miss_feed(apple_brand, mem0.image0);
    printf("\n -1)) befor normal_for...");
    for (i = 0 ; i < N_CAMERAS ; ++i)
        {
          if (p_errno == 0)
             do_measure(i, &mem0, &mem1, mem1.image0, mem1.image1,
                   &mem0.bnd, 50,
                   &mean[i], &mad[i], &min[i], &max[i],
                   mem1.image2, apple_brand);
             if (p_errno) { display_error("Error: Apple Miss Feed");
                        return(FAILURE);
                }
           normal_for_shadows(i, mem0.image1, mem0.image2, mem1.image0, mem1.image1,
                          &mem0.bnd);
        }
    printf("\n 0)) after normal_for...");
    mean_mean = mean_mad = 0;
    for (i = 0 ; i < N_CAMERAS ; ++i)
        {
        mean_mean += mean[i];
        mean_mad  += mad[i];
        }
    mean_mean = (int)((double)mean_mean / N_CAMERAS + 0.5);
    mean_mad  = (int)((double)mean_mad  / N_CAMERAS + 0.5);
    if (!debug_flag && auto_mode)     display_in_auto_mode(mean_mean, mean_mad);
```

```
      else              display_all(mean_mean, mean_mad);
        do_3d_all(&mem0.bnd, &mem1.image0, &mem1.image1,
                                        mem0.image0, mem0.image1, mem0.image2);
      return(SUCCESS);
}
display_error(text)     char *text;
{
        gtext_demo(30, 100, text, 1, 0, 1);
}
test_for_miss_feed(apple_brand, l_image)
        PIXEL l_image[L_FR_Y_SIZE][L_FR_X_SIZE];
{
int i,j, count;
#define N_LINES 18
#define MIN_T 170
      switch (apple_brand) {
         case SMITH_TYPE:
               SWAP_IN_SIZE(l_image, CAM_2, w_images.green, L_FR_Y_SIZE*L_FR_X_SI
               break;
         case HERMON_TYPE:
         case ORLEANS_TYPE:
         case ANA_TYPE:
               SWAP_IN_SIZE(l_image, CAM_2, w_images.green, L_FR_Y_SIZE*L_FR_X_SI
               break;
      }
      for (count = i = 0 ; i < N_LINES ; ++i)
          for (j = 0 ; j < L_FR_X_SIZE ; ++j)
               if (l_image[i][j] < MIN_T) ++count;
      if (count > 50*N_LINES)    ( printf("\nAbove: %d",count);p_errno = 1; return
      count = 0;
      for (i = L_FR_Y_SIZE-1 ; i > L_FR_Y_SIZE-N_LINES ; --i)
          for (j = 0 ; j < L_FR_X_SIZE ; ++j)
               if (l_image[i][j] < MIN_T)  ++count;
      if (count > 60*2*N_LINES)    ( printf("\nBelow: %d",count); p_errno = 1; ret
      return(SUCCESS);
}
display_all(mean_mean, mean_mad)
{
int i;
   for (i = 0 ; i < N_CAMERAS ; ++i)
   {
   switch(apple_brand) {
      case SMITH_TYPE:
         SWAP_IN_SIZE(mem1.image1, i,  normal_images.green, FR_Y_SIZE*FR_X_SIZE)
         break;
      case HERMON_TYPE:
      case ORLEANS_TYPE:
         SWAP_IN_SIZE(mem1.image1, i,  normal_images.red, FR_Y_SIZE*FR_X_SIZE);
         break;
   }
     show_squeesed_image(mem1.image1, "0",
        atoi(prog_consts.T_WIN_X_OFF[i]),atoi(prog_consts.T_WIN_Y_OFF[i]));
   }
}
display_in_auto_mode(mean_mean, mean_mad)
{
int i;
   i = 1;
   {
   switch(apple_brand) {
      case SMITH_TYPE:
         SWAP_IN_SIZE(mem1.image1, i,  normal_images.green, FR_Y_SIZE*FR_X_SIZE)
         break;
      case HERMON_TYPE:
```

```c
            case ORLEANS_TYPE:
                SWAP_IN_SIZE(mem1.image1, i, normal_images.red, FR_Y_SIZE*FR_X_SIZE);
                    break;
        }
        show_squeesed_image(mem1.image1, "0",
            atoi(prog_consts.T_WIN_X_OFF[i]),atoi(prog_consts.T_WIN_Y_OFF[i]));
    }
}
do_3d_all(bnd0, bnd1, bnd2, image0, image1, image2)
                        PIXEL image0[FR_Y_SIZE][FR_X_SIZE];
                        PIXEL image1[FR_Y_SIZE][FR_X_SIZE];
                        PIXEL image2[FR_Y_SIZE][FR_X_SIZE];
                        struct boundary_data *bnd0;
                        struct boundary_data *bnd1;
                        struct boundary_data *bnd2;
{
char header[64];
        SWAP_IN_SIZE(bnd0,   CAM_1, bnd, sizeof(struct boundary_data));
        SWAP_IN_SIZE(bnd1,   CAM_2, bnd, sizeof(struct boundary_data));
        SWAP_IN_SIZE(bnd2,   CAM_3, bnd, sizeof(struct boundary_data));
        SWAP_IN_SIZE(image0, CAM_1, enhanced_images.green, FR_Y_SIZE*FR_X_SIZE);
        SWAP_IN_SIZE(image1, CAM_2, enhanced_images.green, FR_Y_SIZE*FR_X_SIZE);
        SWAP_IN_SIZE(image2, CAM_3, enhanced_images.green, FR_Y_SIZE*FR_X_SIZE);
#ifdef EYAL_OLDDD
        glob_all(bnd0, bnd1, bnd2, image0, image1, image2, &apple_volume);
#else
        glob_all(bnd0, bnd1, bnd2, &apple_volume);
#endif
        SWAP_OUT_SIZE(bnd0, CAM_1,  bnd_z, sizeof(struct boundary_data));
        SWAP_OUT_SIZE(bnd1, CAM_2,  bnd_z, sizeof(struct boundary_data));
        SWAP_OUT_SIZE(bnd2, CAM_3,  bnd_z, sizeof(struct boundary_data));
        dist = 2.*(pow(apple_volume / 3.14 * 3. / 4., 0.33));
        if (apple_volume <= 120000) dist = dist*1.09;
        else if (apple_volume <= 150000) dist = dist*1.04;
        else dist = dist*1.00;
        dist += 3;
        apple_size = (int)(dist + 0.5);
         apple_volume=apple_volume*1.17 + 16470.0;
        printf("\nVolume:%4d", (int)(apple_volume / 1000.));
        print_demo(70,"Volume:", "%4d","cc", (int)(apple_volume / 1000.));
        print_demo(70, "Apple width:", "%4d", "mm",(int)(dist+0.5));
        statistics.volume = (int)(apple_volume / 1000.);
        statistics.size = (int)(dist+0.5);
        return(SUCCESS);
}
print_demo(color, header, form, trailer, num1, num2, num3, num4)
        char *header, *form, *trailer;
{
char tmp[80];
int i;
    if (display_line_count >= 300+3*20) {
        display_line_count = 300;
        display_col_count += 300;
        }
    gtext_demo(display_col_count+30, display_line_count, header, 1, color, 1);
    sprintf(tmp, form, num1, num2, num3, num4);
    gtext_demo(display_col_count+200, display_line_count-5, tmp, 1, color, 2);
    gtext_demo(display_col_count+260, display_line_count, trailer, 1, color, 1);
    display_line_count += 20;
}
load_luts()
{
#define LOAD_LUT(h,l)   if (read_map_file(h,l) == 0) { printf("\n Unable to read
                }
```

```
#ifdef IP8
      LOAD_LUT("grab.lut",  grab_lut);
      LOAD_LUT("measure.lut", screen_lut);
      LOAD_LUT("blank.lut", blank_lut);
#endif
#ifdef VGA
      LOAD_LUT("measure.lut", screen_lut);
#endif
}
spawn_pass(args)
        char *args[];
{
      fprintf(stderr, "Not implemented ");
}
spawn_pass_1(args)
        char *args[];
{
int ret;
char st[30];
int i;
      if (debug_flag) { printf("\n About to run phase: %s\n",args[0]);
             for (i = 0 ; args[i] != NULL ; ++i)    printf("%s\t",args[i]);
      }
      sprintf(st,"Can't run %s:", args[0]);
#ifndef EY_NNIOS
      finit_display();
#endif
      fflush(stdout);
      ret = spawnvp(P_WAIT, args[0], args);
      fflush(stdout);
      if (ret == -1) { perror(st); }
#ifndef EY_NNIOS
      init_display();
#endif
      return(ret);
}
on_indicator(key)    char key[];
{
int f;
  strcpy(last_key, key);
  for (f = 0 ; f < 8 ; ++f)
  {
        if (buttons[f].on_off == 1)  release_button(f);
        if (strcmp(key,buttons[f].act_button) == 0)
                                press_button(f);
  }
}
off_indicator(key)    char key[];
{
int f;
  for (f = 0 ; f < 8 ; ++f)
  {
        if (strcmp(key,buttons[f].act_button) == 0)
                                release_button(f);
  }
}
demo_screen()
{
int x,y,f;
char t[10];
#ifdef IP8
      clear_screen(SCREEN_COLOR);
#endif
      for (f = 0, y = START_Y; y < END_Y ; y += Y_INCREMENT)
```

```c
        for (x = START_X ; x < END_X && f < 12 ; x += X_INCREMENT)
        {
          buttons[f].xs = x;
          buttons[f].ys = y;
          buttons[f].xf = x+D_X;
          buttons[f].yf = y+D_Y;
          buttons[f].f_color = KEY_COLOR;
          buttons[f].b_color = SHADOW_COLOR;
          buttons[f].act_button = k_text[f];
          buttons[f].text = f_text[f];
          buttons[f].on_off = 1;
          release_button(f);
          ++f;
        }
}
release_button(f)
{
int x1,y1,x2,y2;
        if (buttons[f].on_off == 0) return(0);
        x1 = buttons[f].xs;
        y1 = buttons[f].ys;
        x2 = buttons[f].xf;
        y2 = buttons[f].yf;
#ifdef IP8
        filled_rectangle(x1-3,y1-3,x2-3,y2-3,SCREEN_COLOR);
        filled_rectangle(x1+3,y1+3,x2+3,y2+3,buttons[f].b_color);
        filled_rectangle(x1,y1,x2,y2,buttons[f].f_color);
        gtext(x1+5,y1-15,buttons[f].act_button,2,64,1);
        gtext(x1+5+45,y1+5,buttons[f].text,1,64,1);
#endif
#ifdef VGA
        vga_filled_rectangle(x1-SHAD,y1-SHAD,x2-SHAD,y2-SHAD, 7);
        vga_filled_rectangle(x1+SHAD,y1+SHAD,x2+SHAD,y2+SHAD, 0);
        vga_filled_rectangle(x1,y1,x2,y2,buttons[f].f_color);
        vga_rectangle(x1-1,y1-1,x2,y2,0);
        gtext_vga(x1+5,y1-15,buttons[f].act_button,2,64,1);
        gtext_vga(x1+5+45,y1+5,buttons[f].text,1,64,1);
#endif
        buttons[f].on_off = 0;
        return(1);
}
press_button(f)
{
int x1,y1,x2,y2;
        if (buttons[f].on_off == 1) return(0);
        x1 = buttons[f].xs;
        y1 = buttons[f].ys;
        x2 = buttons[f].xf;
        y2 = buttons[f].yf;
#ifdef IP8
        filled_rectangle(x1+SHAD,y1+SHAD,x2+SHAD,y2+SHAD, 7);
        filled_rectangle(x1-3,y1-SHAD,x2-3,y2-SHAD, 0);
        filled_rectangle(x1,y1,x2,y2, 115);
        gtext(x1+5,y1-15,buttons[f].act_button,2,64,1);
        gtext(x1+5+45,y1+5,buttons[f].text,1,64,1);
#endif
#ifdef VGA
        vga_filled_rectangle(x1+SHAD,y1+SHAD,x2+SHAD,y2+SHAD, 7);
        vga_filled_rectangle(x1-SHAD,y1-SHAD,x2-SHAD,y2-SHAD, 0);
        vga_filled_rectangle(x1,y1,x2,y2, 115);
        vga_rectangle(x1-1,y1-1,x2,y2,0);
        gtext_vga(x1+5,y1-15,buttons[f].act_button,2,64,1);
        gtext_vga(x1+5+45,y1+5,buttons[f].text,1,64,1);
#endif
```

```
                buttons[f].on_off = 1;
                speaker_beep(800+f*100, 80, 0, 1);
                return(1);
}
#define LK201
select_menue()
{
char ch;
        while (1)
            {
    ch = getch();
#ifdef LK201
    switch (ch)
      {
        case 26: return(CNTRL_Z);
        case 4:  return(CNTRL_D);
        case 27: return(ESCAPE);
        case 0 : break;
        default: printf ("%c",7); continue;
      }
#endif
    ch = getch();
    switch(ch)
      {
          case 72: return(UP_ARROW);
          case 77: return(RIGHT_ARROW);
          case 80: return(DOWN_ARROW);
          case 75: return(LEFT_ARROW);
          case 71: return(HOME_KEY);
          case 79: return(END_KEY);
          case 81: return(PgDn_KEY);
          case 73: return(PgUp_KEY);
          case 59: return(F1_KEY);
          case 60: return(F2_KEY);
          case 61: return(F3_KEY);
          case 62: return(F4_KEY);
          case 63: return(F5_KEY);
          case 64: return(F6_KEY);
          case 65: return(F7_KEY);
          case 66: return(F8_KEY);
          case 67: return(F9_KEY);
          case 68: return(F10_KEY);
          case 94: return(CTRL_F1_KEY);
          case 99: return(CTRL_F6_KEY);
          case 101:return(CTRL_F8_KEY);
          case 111:return(ALT_F8_KEY);
          default: fprintf (stderr,"%c",7);
      }
    }
}
display_header(h)   char *h;
{
#define D 7
int i;
static int first_time = 1;
            display_line_count = 300;
            display_col_count  = 0;
#ifdef VGA
        if (!first_time)  {
          vga_filled_rectangle(D, D, 640-D, START_Y-2*D ,121);
          vga_rectangle(D, D, 640-D, START_Y-2*D ,0);
          vga_filled_rectangle(TEXT_X1, TEXT_Y1, TEXT_X2, TEXT_Y2, TEXT_BACK);
          vga_filled_rectangle(TEXT_X1+SHAD, TEXT_Y2, TEXT_X2+SHAD, TEXT_Y2+SHAD,
          vga_filled_rectangle(TEXT_X2, TEXT_Y1+SHAD, TEXT_X2+SHAD, TEXT_Y2, 115);
```

```
            vga_rectangle(TEXT_X1-1, TEXT_Y1-1, TEXT_X2, TEXT_Y2, 0);
            }
            gtext_vga(520,  0,  h, 2, 63, 0);
            for (i = 1 ; i < 6 ; ++i )
                gtext_vga(10+6-i, 0+6-i, "PriOp-1", 4, 129+i*20, 0);
#endif
            first_time = 0;
}
match_apple_brand(name)      char *name;
{
int i;
        for (i = 0 ; apple_brands[i] != NULL ; ++i)
            if (stricmp(apple_brands[i], name) == 0) return(i);
        return(-1);
}
do_save_data(image)    PIXEL image[L_FR_Y_SIZE][L_FR_X_SIZE];
{
static unsigned int count = 0;
FILE *fp;
char tmp[64], header[FR_HEADER_SIZE];
int cam, x, y, i;
    if (count == 0) {
        fp = fopen("c:\\apples\\count.dat", "r");
        if (fp == NULL)  count = 0;
        else { fscanf(fp,"%d",&count); fclose(fp); }
        }
#define get_and_write(buf, i_name, o_name, cam) SWAP_IN_SIZE(buf, cam, i_name, L_\
                sprintf(tmp, "F:\\apl\\%s.%ld", o_name, cam); \
                printf("\nSaving %s",tmp);\
                write_fr_pic(tmp, buf, L_FR_X_SIZE, L_FR_Y_SIZE,header);
        header[0] = 0;
        for (cam = 0 ; cam < N_CAMERAS ; ++cam) {
           get_and_write(image, w_images.green, "w_green", cam);
           get_and_write(image, w_images.red,   "w_red",   cam);
           get_and_write(image, w_images.ir,    "w_ir",    cam);
           get_and_write(image, w_images.grid,  "w_grid",  cam);
        }
#ifdef OLD
        sprintf(tmp, "c:\\apples\\G_MTH%2d",count);
        for (i = 0 ; i < strlen(tmp) ; ++i)
                { if (tmp[i] == ' ') tmp[i] = '0'; }
         args[0] = "pkzip.exe";
        args[1] = tmp;
        args[2] = "w_red.1 w_green.1 w_ir.1 w_grid.1";
        args[3] = NULL;
        spawn_pass_1(args);
#ifdef VGA
        sprintf(tmp, "Save Name: %ld",count);
        gtext_vga(400,  30, tmp, 1, 63, 0);
#endif
        ++count;
        fp = fopen("c:\\apples\\count.dat", "w");
        fprintf(fp,"%d",count);
        fclose(fp);
#endif
}
show_squeesed_image(image, headline,off_x, off_y)   char *headline;
        PIXEL    image[FR_Y_SIZE][FR_X_SIZE];
{
int i,j;
        for (i = 0 ; i < FR_Y_SIZE ; ++i)
          for (j = 0 ; j < FR_X_SIZE ; ++j)
             image[i][j] = (image[i][j] >> 1) + 128;
        display_image_demo(off_x,off_y,image,FR_X_SIZE,FR_Y_SIZE,headline);
```

```
        vga_filled_rectangle(off_x+SHAD, off_y+FR_Y_SIZE, off_x+SHAD+FR_X_SIZE, off
        vga_filled_rectangle(off_x+FR_X_SIZE, off_y+SHAD, off_x+SHAD+FR_X_SIZE, off
        vga_rectangle(off_x-1, off_y-1, off_x+FR_X_SIZE, off_y+FR_Y_SIZE, 0);
}
display_datum_line_demo(x,y,val,header)   char *header;
{
char s[32];
    sprintf(s, "%s: %4d", header, val);
    gtext_demo(x, y, s, 1, 36, 1);
}
display_single_object(image, foreground, background, off_x, off_y, color)
     PIXEL   image[FR_Y_SIZE][FR_X_SIZE];
{
int i,j;
   for (i = 1 ; i < FR_Y_SIZE-1 ; ++i)
      for (j = 1 ; j < FR_X_SIZE-1 ; ++j)
      {
         if ( image[i][j] == foreground &&
             ( (image[i-1][j]   != foreground ) ||
               (image[i][j-1]   != foreground ) ||
               (image[i-1][j+1] != foreground ) ||
               (image[i+1][j]   != foreground ) ||
               (image[i+1][j+1] != foreground ) ||
               (image[i+1][j-1] != foreground ) ||
               (image[i-1][j+1] != foreground ) ||
               (image[i-1][j-1] != foreground ) ))
#ifdef AAA
             ( image[i-1][j]   == background ||
               image[i][j-1]   == background ||
               image[i-1][j+1] == background ||
               image[i+1][j]   == background ||
               image[i+1][j+1] == background ||
               image[i+1][j-1] == background ||
               image[i-1][j+1] == background ||
               image[i-1][j-1] == background))
#endif
                 wpixel_demo(j+off_x, i+off_y, color);
      }
}
display_single_object_1(image, foreground, background, off_x, off_y, color)
     PIXEL   image[FR_Y_SIZE][FR_X_SIZE];
{
int i,j;
   for (i = 1 ; i < FR_Y_SIZE-1 ; ++i)
      for (j = 1 ; j < FR_X_SIZE-1 ; ++j)
      {
         if ( image[i][j] == foreground &&
             ( (image[i-1][j]   == background ) ||
               (image[i][j-1]   == background ) ||
               (image[i-1][j+1] == background ) ||
               (image[i+1][j]   == background ) ||
               (image[i+1][j+1] == background ) ||
               (image[i+1][j-1] == background ) ||
               (image[i-1][j+1] == background ) ||
               (image[i-1][j-1] == background ) ))
                  wpixel_demo(j+off_x, i+off_y, color);
      }
}
do_grade_all()
{
   if (spots_index==0)
   {
      if (debug_flag) printf("\nERROR v1: There is not Spots info to grade");
      return(0);
```

```c
        }
        do_simple_grade(final_spots,spots_index,Dark_Red,Simple_red,Yellow,Green,Ora
}
close_stat()
{
    fclose(stat_file);
    printf("\nStat closed");
}
init_statistics()
{
    stat_file = fopen(STAT_FILE_NAME, "a");
    if (stat_file == NULL) {
        printf("\nCan't open stat"); exit(1);
    }
    atexit(close_stat);
    return(1);
}
write_statistics()
{
int running_index;
FILE *fp;
    fp = fopen("count.dat", "r");
    fscanf(fp,"%d", &running_index);
    fclose(fp);
    fp = fopen("f:\\apl\\pkcount.dat", "w");
    fprintf(fp,"%d", running_index);
    fclose(fp);
    fp = fopen("count.dat", "w");
    fprintf(fp,"%d", running_index+1);
    fclose(fp);
    fprintf(stat_file, "%3d    %3d %3d %3d %3d %3d %3d %3d %3d %3d %3d\n",
            running_index,
            statistics.size,
            statistics.volume,
            statistics.color_index_1,
            statistics.color_index_2,
            statistics.color_index_3,
            statistics.color_index_4,
            statistics.n_rot,
            statistics.n_bruise,
            statistics.n_moth,
            statistics.n_st_ca);
}
fill_blem_stat(spots, spt_index, ind1, ind2, ind3)
            struct spot spots[];
{
int i;
    statistics.n_st_ca  =
    statistics.n_rot    =
    statistics.n_bruise =
    statistics.n_moth   = 0;
    for (i = 0 ; i < spt_index ; ++i)
    {
        if (final_spots[i].flag4 != REAL_BLEMISH) continue;
        switch(final_spots[i].flag2)
        {
            case D_ST_CA:   ++statistics.n_st_ca;   break;
            case D_ROT:
            case D_LROT:    ++statistics.n_rot;     break;
            case D_BRUISE:  ++statistics.n_bruise;  break;
            case D_MOTH:    ++statistics.n_moth;    break;
        }
    }
}
```

```
sp_init_xms()
{
int ret;
  init_xms();
  init_storage(0);
  ret = dump_into_file(STORAGE_FILE);
  if (ret != SUCCESS)  {
        printf ("\nError in dumping into file "); exit(1);
        }
}
```

APPENDIX C

```
/*
                         ID: 001
   File name is: app01.c
----------------------------------------------------------------
*/
#include "adapter.h"
#define INTERLACE_OPTIMIZATION
extern int debug_flag;
extern int norm_raw[N_CAMERAS][4];
extern int p_errno;
extern struct single_view_info  view_info[N_CAMERAS];
#define RADIUS 20
#ifdef INTERLACE_OPTIMIZATION
#define I_STEP 2
#else
#define I_STEP 1
#endif
do_measure(cam, l_image, l_image_1, s_image, s_image_1, bnd, precent,
             mean_p, mad_p, min_p, max_p, s_image_2, apple_brand)
        PIXEL l_image[L_FR_Y_SIZE][L_FR_X_SIZE];
        PIXEL l_image_1[L_FR_Y_SIZE][L_FR_X_SIZE];
        PIXEL s_image[FR_Y_SIZE][FR_X_SIZE];
        PIXEL s_image_1[FR_Y_SIZE][FR_X_SIZE];
        PIXEL s_image_2[FR_Y_SIZE][FR_X_SIZE];
        struct boundary_data *bnd;
        int *mean_p, *mad_p, *min_p, *max_p;
{
char s[16];
int ret, old, precet, u_thresh, l_thresh, x_off, y_off;
int i1,i2,i3,i4;
        old = get_channel();
        set_channel(cam);
        SWAP_IN_SIZE(l_image, cam, w_images.green, L_FR_X_SIZE*L_FR_Y_SIZE);
        ret = find_boundary(l_image, l_image_1, precent, bnd,
                      &u_thresh, &l_thresh, cam);
        if (ret != SUCCESS)   { p_errno = NO_PER; return(ret); }
        SWAP_IN_SIZE(l_image, cam, w_images.green, L_FR_X_SIZE*L_FR_Y_SIZE);
#define   GREEN_PIC  0
#define     RED_PIC  1
#define      IR_PIC  2
#define    GRID_PIC  3
        cvt_sml_boundary(bnd, &x_off, &y_off);
        SWAP_OUT_SIZE(bnd, cam, bnd, sizeof(struct boundary_data));
        extract_reg_image(l_image, s_image, x_off, y_off);
        cancel_wires_n(s_image, s_image_2, bnd, cam, GREEN_PIC,x_off);
        clear_x_sel_color(s_image_2, bnd->boundary, bnd->boundary_index, 255);
        SWAP_OUT_SIZE(s_image_2, cam, raw_images.green, FR_X_SIZE*FR_Y_SIZE);
        if (apple_brand == SMITH_TYPE)
              z_transform(s_image_2, s_image_2, mean_p, mad_p, min_p, max_p);
        else
              z_transform_f(s_image_2, s_image_2, mean_p, mad_p, min_p, max_p);
        SWAP_OUT_SIZE(s_image_2, cam, enhanced_images.green, FR_X_SIZE*FR_Y_SIZE);
#define    CVT_ALL(src, dst1, dst2 ,pic) SWAP_IN_SIZE(l_image, cam, src, L_FR_X_S
        extract_reg_image(l_image, s_image_1, x_off, y_off); \
        cancel_wires_n(s_image_1, s_image_2, bnd, cam, pic,x_off);   \
        clear_x_sel_color(s_image_2, bnd->boundary, bnd->boundary_index, 255); \
        SWAP_OUT_SIZE(s_image_2, cam, dst1, FR_X_SIZE*FR_Y_SIZE); \
        if (apple_brand == SMITH_TYPE) \
           z_transform(s_image_2, s_image_2, &i1, &i2, &i3, &i4); \
        else \
           z_transform_f(s_image_2, s_image_2, &i1, &i2, &i3, &i4); \
        SWAP_OUT_SIZE(s_image_2, cam, dst2, FR_X_SIZE*FR_Y_SIZE);
        CVT_ALL(w_images.grid, raw_images.grid, enhanced_images.grid , GRID_PIC);
        CVT_ALL(w_images.red,  raw_images.red,  enhanced_images.red, RED_PIC);
```

```
        CVT_ALL(w_images.ir,   raw_images.ir,   enhanced_images.ir, IR_PIC);
        set_channel(old);
        return(SUCCESS);
}
normal_for_shadows(cam, green, red, ir, grid, bnd)
        struct boundary_data *bnd;
        unsigned char green[FR_Y_SIZE][FR_X_SIZE];
        unsigned char red[FR_Y_SIZE][FR_X_SIZE];
        unsigned char ir[FR_Y_SIZE][FR_X_SIZE];
        unsigned char grid[FR_Y_SIZE][FR_X_SIZE];
{
        SWAP_IN_SIZE(green,    cam, raw_images.green, FR_X_SIZE*FR_Y_SIZE);
        SWAP_IN_SIZE(red,      cam, raw_images.red,   FR_X_SIZE*FR_Y_SIZE);
        SWAP_IN_SIZE(ir,       cam, raw_images.ir,    FR_X_SIZE*FR_Y_SIZE);
        SWAP_IN_SIZE(grid,     cam, raw_images.grid,  FR_X_SIZE*FR_Y_SIZE);
        do_normal(green, red, ir, grid, cam);
        SWAP_OUT_SIZE(green, cam, normal_images.green,  FR_X_SIZE*FR_Y_SIZE);
        SWAP_OUT_SIZE(red,   cam, normal_images.red,    FR_X_SIZE*FR_Y_SIZE);
        SWAP_OUT_SIZE(ir,    cam, normal_images.ir,     FR_X_SIZE*FR_Y_SIZE);
        SWAP_OUT_SIZE(grid,  cam, normal_images.grid,   FR_X_SIZE*FR_Y_SIZE);
}
do_normal(green, red, ir, grid, cam)
        PIXEL green[FR_Y_SIZE][FR_X_SIZE];
        PIXEL red[FR_Y_SIZE][FR_X_SIZE];
        PIXEL ir[FR_Y_SIZE][FR_X_SIZE];
        PIXEL grid[FR_Y_SIZE][FR_X_SIZE];
{
int i,j;
double g,r,a,f;
}
find_boundary(l_image, l_image_1, precent, bnd, u_thresh, l_thresh, cam)
          int *u_thresh, *l_thresh;
          PIXEL l_image[L_FR_Y_SIZE][L_FR_X_SIZE];
          PIXEL l_image_1[L_FR_Y_SIZE][L_FR_X_SIZE];
          struct boundary_data *bnd;
{
int margins = RADIUS;
   if (debug_flag)
        display_image(0,0,l_image,L_FR_X_SIZE,L_FR_Y_SIZE,"l_image");
   bnd->boundary_index = locate_boundary(l_image, l_image_1, margins, precent,
                bnd->boundary, &(bnd->out_rect),
                            u_thresh, l_thresh, debug_flag, cam);
   if (bnd->boundary_index == FAILURE) return(FAILURE);
   if (debug_flag)
        draw_boundary(bnd->boundary, bnd->boundary_index, bnd->out_rect, 300,200, 2
   return(SUCCESS);
}
cancel_wires(l_image, l_image_1, u_thresh, l_thresh, bnd, cam_number)
          PIXEL l_image[L_FR_Y_SIZE][L_FR_X_SIZE];
          PIXEL l_image_1[L_FR_Y_SIZE][L_FR_X_SIZE];
          struct boundary_data *bnd;
{
   u_thresh = 160;
   threshold_image_pip(l_image, u_thresh, l_thresh, 1);
   if (debug_flag)
        display_image(0,0,l_image,L_FR_X_SIZE, L_FR_Y_SIZE,"t_image");
   cancel_wires_ad(l_image, l_image_1, bnd->out_rect, cam_number);
   return(SUCCESS);
}
#ifdef AUTO_WIRES
cancel_wires_auto(t_image, image, bnd, cam_number)
          PIXEL   image[L_FR_Y_SIZE][L_FR_X_SIZE];
          PIXEL   t_image[L_FR_Y_SIZE][L_FR_X_SIZE];
          struct boundary_data *bnd;
```

```
{
int i,j, y, x1, x2, ret, ret1, j1, j2, t, tc;
#define DIST 6
#define MAX_WIRE_WIDTH (WIRE_WIDTH + 4)
    if (debug_flag)
        display_image(200,200,t_image,L_FR_X_SIZE, L_FR_Y_SIZE,"w_image");
    j2 = 0;
    while(1)
        {
        ret = locate_wire_adaptive(t_image, bnd, &i, &j1, &j2);
        if (ret != SUCCESS) break;
            t = 160;
            for(tc = 0 ; i >= bnd->out_rect.y1 ; --i, ++tc)
            {
              for (j = j1 ; j <= j2 ; ++j)
                {
                    image[i][j] = WIRE_MARK;
                    if (debug_flag) wpixel(j,i,255);
                    if (tc >= t) {   tc = 0; j1 -= 1; j2 -= 1;   }
                }
#ifdef DO_INTERPOLATION
            do_interpolation(image, i, j1, j2);
#endif
            }
        }
#undef DIST
#undef MAX_WIRE_WIDTH
}
locate_wire_adaptive(t_image, bnd, ip, j1p, j2p)
        int *ip, *j1p, *j2p;
        PIXEL   t_image[L_FR_Y_SIZE][L_FR_X_SIZE];
        struct boundary_data *bnd;
{
int i, index, i1, j, ret;
    for (i = 0 ; i < bnd->boundary_index ; ++i) {
        if (bnd->boundary[i].x1 <= bnd->out_rect.x1 ||
            bnd->boundary[i].x2 >= bnd->out_rect.x2 )    index = i;
    }
    if (*j2p > 0) j = *j2p; else j = bnd->out_rect.x1;
    for ( ; j < bnd->out_rect.x2 ; ++j)
        {
        for (i = index ; i < bnd->boundary_index ; ++i) {
            if (bnd->boundary[i].x1 == j || bnd->boundary[i].x2 == j) break;
        }
        if (i == bnd->boundary_index)   { fprintf(stderr,"HELP"); continue; }
        i1 = bnd->boundary[i].y;
        ret = locate_wire(t_image, j, j, i1+10, j1p, j2p);
        if (ret == SUCCESS) return(SUCCESS);
        }
    return(FAILURE);
}
#endif
#define DIST 4
#define MAX_WIRE_WIDTH (WIRE_WIDTH + 6)
locate_wire(image, x1, x2, y, x3p, x4p)
        PIXEL image[L_FR_Y_SIZE][L_FR_X_SIZE];
        int *x3p, *x4p;
{
int k1, k2;
    for (k1 = x1-DIST ; k1 < x2+DIST ; ++k1)
    {   if (debug_flag) wpixel(k1,y,0);
      if (image[y][k1] == LOW_MARK && image[y][k1-1] == HIGH_MARK)
        {
        for (k2 = k1 ; k2 < k1 + MAX_WIRE_WIDTH ; ++k2 )
```

```
                if (image[y][k2] == LOW_MARK && image[y][k2+1] == HIGH_MARK)
                {
                    if (debug_flag) {    wpixel(k1,y,55);    wpixel(k2,y,55);    }
                    *x3p = k1;
                    *x4p = k2;
                    return(SUCCESS);
                }
            }
        }
        *x3p = x1-2;
        *x4p = x1+4;
        return(SUCCESS);
    }
    #undef DIST
    #undef MAX_WIRE_WIDTH
    locate_boundary(image, image_1, margins, thresh_precent,
                            boundary, out_rect, utp, ltp, debug_flag, cam)
        struct rect *out_rect;
        struct line_pair boundary[MAX_BOUNDARY];
        PIXEL   image[L_FR_Y_SIZE][L_FR_X_SIZE];
        PIXEL   image_1[L_FR_Y_SIZE][L_FR_X_SIZE];
        int *utp, *ltp;
    {
    int u_thresh, l_thresh, per;
    struct point points[RADIUS * 2 * 4];
        if (cam == CAM_1)      u_thresh = 200;
        if (cam == CAM_2)      u_thresh = 200;
        if (cam == CAM_3)      u_thresh = 200;
        l_thresh = 0;
        threshold_image_pip(image, u_thresh, l_thresh, I_STEP);
        if (debug_flag)
            display_image(200,0,image,L_FR_X_SIZE,L_FR_Y_SIZE,"1");
        filter_with_disc(image, image_1, RADIUS, points);
        if (debug_flag) {
            printf("\n Thresh: %d %d", u_thresh, l_thresh);
            display_image(400,0,image_1,L_FR_X_SIZE,L_FR_Y_SIZE,"2");
        }
        per = encirc_outer_gradient(image_1, out_rect,
                L_FR_X_SIZE, L_FR_Y_SIZE, RADIUS, boundary);
        *utp = u_thresh;
        *ltp = l_thresh;
        if (per < 20) return(FAILURE);
        return(per);
    }
    filter_with_disc(src, dst, radius, points)
        struct point points[];
        PIXEL   src[L_FR_Y_SIZE][L_FR_X_SIZE];
        PIXEL   dst[L_FR_Y_SIZE][L_FR_X_SIZE];
    {
    int circle_len, i,j;
        circle_len = circle_points(0, 0, 6, 200, points);
        open_image_circle_p(src, dst, points, circle_len, radius);
        if (debug_flag == 2)
            display_image(0,0, dst, 192,192,"*");
        circle_len = circle_points(0, 0, radius, 200, points);
        open_image_circle_p(dst, src, points, circle_len, radius);
                for (i = 0 ; i < L_FR_Y_SIZE ; ++i)
                    for (j = 0 ; j < L_FR_X_SIZE ; ++j)
                        dst[i][j] = src[i][j];
    }
    #ifdef NOT_IN_USE
    open_image_circle(src, dst, points, len, radius)
        struct point points[];
        PIXEL   src[L_FR_Y_SIZE][L_FR_X_SIZE];
```

```
        PIXEL   dst[L_FR_Y_SIZE][L_FR_X_SIZE];
{
int i,j,k, dy, dx, flag, w;
        for (i = 0 ; i < L_FR_Y_SIZE ; ++i)
           for (j = 0 ; j < L_FR_X_SIZE ; ++j)
              dst[i][j] = HIGH_MARK;
        for (i = radius ; i < L_FR_Y_SIZE - radius ; i+= 1)
        {
           for (j = radius ; j < L_FR_X_SIZE - radius ; j += 1)
           {
#define STEP 1
              if (src[i][j] != LOW_MARK) continue;
              flag = 1;
                 for (k = 0 ; k < len ; k += (8*STEP))
                 {
                    dy = i+points[k+2].y;
                    for (w = j+points[k+2].x ; w < j+points[k+0].x ; w += STEP)
                         if (src[dy][w] != LOW_MARK) {flag = 0 ; goto next; }
                    dy = i+points[k+3].y;
                    for (w = j+points[k+3].x ; w < j+points[k+1].x ; w += STEP)
                         if (src[dy][w] != LOW_MARK) {flag = 0 ; goto next; }
                    dy = i+points[k+7].y;
                    for (w = j+points[k+7].x ; w < j+points[k+5].x ; w += STEP)
                         if (src[dy][w] != LOW_MARK) {flag = 0 ; goto next; }
                    dy = i+points[k+4].y;
                    for (w = j+points[k+6].x ; w < j+points[k+4].x ; w += STEP)
                         if (src[dy][w] != LOW_MARK) {flag = 0 ; goto next; }
                 }
#undef STEP
next:
              if (flag) {
                 for (k = 0 ; k < len ; k += 1)
                 {
                    dx = points[k].x;
                    dy = points[k].y;
                    dx = j + dx ;
                    dy = i + dy ;
                    dst[dy][dx] = LOW_MARK;
                    if (debug_flag == 2)
                         wpixel(dx,dy,19);
                 }
              }
           }
        }
}
#endif
open_image_circle_p(src, dst, points, len, radius)
        struct point points[];
        PIXEL   src[L_FR_Y_SIZE][L_FR_X_SIZE];
        PIXEL   dst[L_FR_Y_SIZE][L_FR_X_SIZE];
{
int i,j,k, dy, dx, flag, w;
        for (i = 0 ; i < L_FR_Y_SIZE ; ++i)
           for (j = 0 ; j < L_FR_X_SIZE ; ++j)
              dst[i][j] = HIGH_MARK;
        for (i = radius ; i < L_FR_Y_SIZE - radius ; i += I_STEP)
        {
           for (j = radius ; j < L_FR_X_SIZE - radius ; j += 1)
           {
#define STEP 1
              if (src[i][j] != LOW_MARK) continue;
              flag = 1;
                 for (k = 0 ; k < len ; k += 1)
                 {
```

```c
                        dy = points[k].y;
#ifdef INTERLACE_OPTIMIZATION
                        if (dy & 1) continue;
#endif
                        dx = points[k].x;
                        dx = j + dx;
                        dy = i + dy;
                         if (src[dy][dx] != LOW_MARK) {flag = 0 ; goto next; }
                    }
#undef STEP
next:
                if (flag) {
                    for (k = 0 ; k < len ; k += 1)
                    {
                        dy = points[k].y;
#ifdef INTERLACE_OPTIMIZATION
                        if (dy & 1) continue;
#endif
                        dx = points[k].x;
                        dx = j + dx ;
                        dy = i + dy ;
                        dst[dy][dx] = LOW_MARK;
                        if (debug_flag == 2)
                                wpixel(dx,dy,19);
                    }
                }
            }
        }
}
encirc_outer_gradient(image, enclosing, x_dim, y_dim, margin, boundary)
            struct line_pair boundary[MAX_BOUNDARY];
            PIXEL   image[L_FR_Y_SIZE][L_FR_X_SIZE];
            struct rect *enclosing;
{
int i, j1, j2, flag, area = 0, s_i, len, d, tr, tr1, pix, pix0;
int min_i, max_i, min_j = 999, max_j = -1;
int pix1, pix2, pix3, grad, grad0, p1, p2, boundary_index;
    tr = 0;
    tr1 = 0;
    len = 255;
    boundary_index = 0;
    for (s_i = 0, i = margin ; i < y_dim-margin ; i += I_STEP)
    {
        flag = 0;
        for (j1 = margin ; j1 < x_dim-margin ; j1 += 1)
        {
#define MIN_GRAD 40
#define ENV 1
            pix = image[i][j1];
            pix1= image[i-ENV][j1];
            pix2= image[i][j1+ENV];
            pix3= image[i+ENV][j1];
            grad = MAX((pix1-pix), (pix-pix2));
            grad = MAX(grad, (pix3-pix));
            if (grad > MIN_GRAD)     { flag = 1 ;
                if (grad == (pix-pix2)) j1 += ENV;
#ifdef DEBUG
                wpixel(j1,i,grad); printf("\n %d %d    %d",j1,i,grad);
#endif
                          break; }
        }
        if (!flag && boundary_index > 1) {
                    if(debug_flag) printf("\n break");  break; }
        if (!flag) continue;
```

```
        flag = 0;
        for (j2 = x_dim-margin ; j2 >= j1 ; --j2)
        {
            pix  = image[i][j2];
            pix1 = image[i-ENV][j2];
            pix2 = image[i][j2-ENV];
            pix3 = image[i+ENV][j2];
            grad = MAX((pix1-pix), (pix-pix2));
            grad = MAX(grad, (pix3-pix));
            if (grad > MIN_GRAD)   {
                flag = 1 ;
                if (grad == (pix-pix2)) j2 -= (ENV-1);
#ifdef DEBUG
                wpixel(j2,i,grad); printf("\n %d %d    %d",j2,i,grad);
#endif
                                break; }
        }
        if (!flag && s_i) { if(debug_flag) printf("\n Error #1!");
                if (boundary_index > 40) break;
                else exit(0); }
        if (!flag) continue;
        ++s_i;
        if (debug_flag && 0) { wpixel(j1,i,255); wpixel(j2,i,254);   }
        if (boundary_index > 0) { d = len - (j2-j1); if (d < 0) d = -d;
                if (d > 60)
                  if (boundary_index > 10) { if(debug_flag) printf("\n dist: %d", d)
                        else { boundary_index = 0; continue; }
                len = j2-j1;
        }
        else len = j2-j1;
        boundary[boundary_index].y = i;
        boundary[boundary_index].x1 = j1;
        boundary[boundary_index].x2 = j2;
        ++boundary_index;
#ifdef INTERLACE_OPTIMIZATION
        boundary[boundary_index].y = i+1;
        boundary[boundary_index].x1 = j1;
        boundary[boundary_index].x2 = j2;
        ++boundary_index;
#endif
        if (boundary_index >= MAX_BOUNDARY) { printf("\n Boundary too long");
                                              exit(0); }
        area += (j2-j1+1);
        max_i = i;
        if (j1 < min_j) min_j = j1;
        if (j2 > max_j) max_j = j2;
    }
    min_i = max_i - I_STEP*s_i;
    enclosing -> x1 = min_j;
    enclosing -> x2 = max_j;
    enclosing -> y1 = min_i;
    enclosing -> y2 = max_i;
    if (debug_flag)
        printf("\n %d %d %d %d    %d",min_j, max_j, min_i, max_i, boundary_index);
    return(boundary_index);
#undef ENV
}
#ifdef NOT_USED
choose_threshold_level_1(image, mar, thresh_precent)
        PIXEL   image[L_FR_Y_SIZE][L_FR_X_SIZE];
{
double sum;
int i,j;
unsigned int n, n1, thresh, count;
```

```
      n = 0;
      sum = 0;
      for (i = mar ; i < L_FR_Y_SIZE-mar ; i += 2)
         for (j = mar ; j < L_FR_X_SIZE-mar ; ++j)
         {
            if (image[i][j] > 253) continue;
                  sum += (double)image[i][j]; ++n;
         }
      sum = sum / (double)n;
      thresh = 0;
      n = (int)((double)n * (double)thresh_precent / 100. + 0.5);
      count = 0;
   do {
      thresh += ((int)sum * 0.1);
      ++count;
      nl = 0;
      for (i = mar ; i < L_FR_Y_SIZE-mar ; ++i)
         for (j = mar ; j < L_FR_X_SIZE-mar ; ++j)
         {
            if (image[i][j] > 253 || image[i][j] < 10) continue;
            if (image[i][j] < thresh) ++nl;
         }
      } while (nl < n && thresh < 255);
   if (thresh > 253) { printf("\n Thresh set to default"); return(250); }
   return(thresh);
}
#endif
choose_threshold_level_u(image, mar, thresh_precent)
         PIXEL    image[L_FR_Y_SIZE][L_FR_X_SIZE];
{
double sum;
int i,j;
unsigned int n, nl, thresh, count;
#define DEF_TR 240
      n = 0;
      sum = 0;
      for (i = mar ; i < L_FR_Y_SIZE-mar ; i += I_STEP)
         for (j = mar ; j < L_FR_X_SIZE-mar ; ++j)
         {
            if (image[i][j] > 253 || image[i][j] < 10) continue;
            sum += (double)image[i][j]; ++n;
         }
      sum = sum / (double)n;
      thresh = ((int)sum * 0.8);
      n = (int)((double)n * (double)thresh_precent / 100. + 0.5);
      count = 0;
   do {
      thresh += ((int)sum * 0.05);
      ++count;
      nl = 0;
      for (i = mar ; i < L_FR_Y_SIZE-mar ; i += I_STEP)
         for (j = mar ; j < L_FR_X_SIZE-mar ; ++j)
         {
            if (image[i][j] > 253 || image[i][j] < 10) continue;
            if (image[i][j] < thresh) ++nl;
         }
      } while (nl < n && thresh < 255);
   if (thresh > DEF_TR) { printf("\n Thresh set to default"); return(DEF_TR); }
   return(thresh);
}
threshold_image_pip(image, u_thresh, l_thresh, i_step)
         PIXEL    image[L_FR_Y_SIZE][L_FR_X_SIZE];
{
int i,j;
```

```c
    for (i = 0 ; i < L_FR_Y_SIZE ; i += i_step)
        for (j = 0 ; j < L_FR_X_SIZE ; ++j)
            if (image[i][j] < u_thresh && image[i][j] >= l_thresh)
                                              image[i][j] = LOW_MARK;
            else if (image[i][j] < 255) image[i][j] = HIGH_MARK;
}
int circle_length;
static
Wput_dot(x,y,color,circle_points)
    struct point circle_points[];
{
    circle_points[circle_length].x = x;
    circle_points[circle_length].y = y;
    ++circle_length;
}
static
Wcircle_dot(x,y,c_x,c_y,color,circle_points)
    struct point circle_points[];
    int x,y,c_x,c_y;
{
    Wput_dot(x+c_x,y+c_y,color,circle_points);
    Wput_dot(y+c_x,x+c_y,color,circle_points) ;
    Wput_dot(-x+c_x,y+c_y,color,circle_points) ;
    Wput_dot(-y+c_x,x+c_y,color,circle_points) ;
    Wput_dot(x+c_x,-y+c_y,color,circle_points);
    Wput_dot(y+c_x,-x+c_y,color,circle_points);
    Wput_dot(-x+c_x,-y+c_y,color,circle_points);
    Wput_dot(-y+c_x,-x+c_y,color,circle_points) ;
  return(1);
}
#define COS45    .707
circle_points(c_x,c_y,r,color,circle_points)
    struct point circle_points[];
    int c_x,c_y,r;
{
int   x , y = r ,
    di = 3-2*r ;
int lim_x = (int)(COS45 * (float)r + 0.5);
    circle_length = 0;
    for (x = 0 ; x <= lim_x ; ++x)
    {
        if (di > 0)
        {
            di += 4*(x-y)+6;
            Wcircle_dot(x,--y,c_x,c_y,color, circle_points);
        }
        else
        {
            di += 4*x+2;
            Wcircle_dot(x,y,c_x,c_y,color,circle_points);
        }
    }
    return(circle_length);
}
struct point w_adhok[] = {  44, WIRE_MARK ,   61, WIRE_MARK,    0, 0,
                           146, WIRE_MARK ,    0, 0,            0, 0,
                            55, WIRE_MARK ,  112, WIRE_MARK,  150, WIRE_MARK };
cancel_wires_ad(t_image, image, out_rect, cam_number)
    PIXEL   image[L_FR_Y_SIZE][L_FR_X_SIZE];
    PIXEL   t_image[L_FR_Y_SIZE][L_FR_X_SIZE];
    struct rect out_rect;
{
int i;
    for (i = cam_number*3 ; i < (cam_number+1)*3 ; ++i)
```

```c
        {
            if (w_adhok[i].x == 0) continue;
            cancel_wires_adhok(t_image, image, out_rect.y2+4,
                        w_adhok[i].x, cam_number, w_adhok[i].y);
        }
}
cancel_wires_adhok(t_image, image, i0, j0, cam, mark_color )
        PIXEL   image[L_FR_Y_SIZE][L_FR_X_SIZE];
        PIXEL   t_image[L_FR_Y_SIZE][L_FR_X_SIZE];
{
int i,j, y1, y2, x1, x2, x3, x4, x5, x6, ret, ret1, j1, j2, t, tc, delta;
#define DIST 4
#define MAX_WIRE_WIDTH (WIRE_WIDTH + 4)
        if (i0 & 1) ++i0;
        ret = locate_wire(t_image, j0-4, j0+4, i0, &x3, &x4);
        if (ret == SUCCESS) {
            x5 = x3 ; x6 = x4;
                j1 = MIN(x3,x5);
                j2 = MAX(x4,x6)+1;
                if (cam == CAM_1) t = 80;
                if (cam == CAM_2) t = 200;
                if (cam == CAM_3) t = 200;
                delta = -1;
            if (j1 <= (L_FR_X_SIZE / 2))  { j2 += 1;   }
            else                          ( j2 -= 1;   )
                for(tc = 0, i = L_FR_Y_SIZE-1 ; i > 0 ; --i, ++tc)
                {
                    for (j = j1 ; j < j2 && j < L_FR_X_SIZE; ++j)
                    {
                            image[i][j] = mark_color;
                            if (debug_flag) wpixel(j,i,255);
                            if (tc >= t) {
                                tc = 0; j1 -= delta; j2 -= delta;   }
                    }
                }
        }
}
cvt_sml_boundary(bnd, x_off, y_off)
        struct boundary_data *bnd;
        int *x_off, *y_off;
{
int sum_x, sum_y, i;
    sum_x = sum_y = 0.;
    for (i = 0 ; i < bnd->boundary_index ; ++i)
        sum_x += (bnd->boundary[i].x1 + bnd->boundary[i].x2);
    *y_off = (bnd->boundary[0].y + bnd->boundary[bnd->boundary_index-1].y) >> 1;
    *x_off = (int)(sum_x / (double)(i+i) + 0.5);
    *x_off -= ((FR_X_SIZE) >> 1);
    *y_off -= ((FR_Y_SIZE) >> 1);
    modify_bnd(bnd->boundary, &(bnd->out_rect), bnd->boundary_index, *x_off, *y_of
}
modify_bnd(boundary, out_rect, boundary_index, off_x, off_y)
        struct line_pair boundary[];
        struct rect *out_rect;
{
int i;
    for (i = 0 ; i < boundary_index ; ++i)
    {
        boundary[i].y  -= off_y;
        boundary[i].x1 -= off_x;
        boundary[i].x2 -= off_x;
    }
    out_rect -> x1 -= off_x;
    out_rect -> x2 -= off_x;
```

```
    out_rect -> y1 -= off_y;
    out_rect -> y2 -= off_y;

extract_reg_image(image, image_reg, x_off, y_off)
        unsigned char image[L_FR_Y_SIZE][L_FR_X_SIZE];
        unsigned char image_reg[FR_Y_SIZE][FR_X_SIZE];
{
int i,j;
    for (i = 0 ; i < FR_Y_SIZE ; ++i)
       for (j = 0 ; j < FR_X_SIZE ; ++j)
          image_reg[i][j] = image[i+y_off][j+x_off];
}
copy_wire_mark(image, mask)
        unsigned char image[FR_Y_SIZE][FR_X_SIZE];
        unsigned char mask[FR_Y_SIZE][FR_X_SIZE];
{
int i,j;
    for (i = 0 ; i < FR_Y_SIZE ; ++i)
       for (j = 0 ; j < FR_X_SIZE ; ++j)
          if (mask[i][j] == WIRE_MARK) image[i][j] = WIRE_MARK;
          else if (mask[i][j] == 255) image[i][j] = 255;
}
```

APPENDIX D

```c
/*
                                        ID: 009
    File name is: app06.c
-----------------------------------------------------------------
*/
#include "adapter.h"
#include <limits.h>
#include <stdio.h>
#define STEM
extern struct prog_settings prog_consts;
extern int debug_flag;
extern int norm_raw[N_CAMERAS][4];
make_rouler_p(xs,ys,xend,yend,step, grade, header,c1,c2)   char *header;
{
}
global_color_analysis(cam_num, bnd, green_image,red_image,grid_image,color_mask,
                      Dark_Red,Simple_Red,Yellow,Green,Orange,Sat,Changes,no
int                cam_num,apple_brand,no_color;
long               *Dark_Red,*Simple_Red,*Yellow,*Green,*Orange,*Sat,*Changes,*
PIXEL               red_image[FR_Y_SIZE][FR_X_SIZE];
PIXEL               green_image[FR_Y_SIZE][FR_X_SIZE];
PIXEL               grid_image[FR_Y_SIZE][FR_X_SIZE];
PIXEL               color_mask[FR_Y_SIZE][FR_X_SIZE];
struct boundary_data *bnd;
{
    int     i,j,max_y,r;
    PIXEL   Level_thresh;
    float   R_Gd,G_Gd,RTL,RTM,RTH,GTL,GTM,GTH, satu=0.;
#define  SAMPLE_STEP_SIZE  2
        switch (apple_brand) {
            case SMITH_TYPE:
                {
                Level_thresh=SMITH_GRID_THRESH;
                RTL=SMITH_RED_THRESH_LOW;
                RTM=SMITH_RED_THRESH_MEDIUM;
                RTH=SMITH_RED_THRESH_HIGH;
                GTL=SMITH_GREEN_THRESH_LOW;
                GTM=SMITH_GREEN_THRESH_MEDIUM;
                GTH=SMITH_GREEN_THRESH_HIGH;
                break;
                }
            case HERMON_TYPE:
            case ANA_TYPE:
            case ORLEANS_TYPE:
                {
                Level_thresh=ORLEANS_GRID_THRESH;
                RTL=ORLEANS_RED_THRESH_LOW;
                RTM=ORLEANS_RED_THRESH_MEDIUM;
                RTH=ORLEANS_RED_THRESH_HIGH;
                GTL=ORLEANS_GREEN_THRESH_LOW;
                GTM=ORLEANS_GREEN_THRESH_MEDIUM;
                GTH=ORLEANS_GREEN_THRESH_HIGH;
                break;
                }
            }
        for (i=0 ; i < FR_Y_SIZE ;i++)
        for (j=0 ; j < FR_X_SIZE ;j++) color_mask[i][j]=0;
        r=1;
        max_y=bnd->boundary[bnd->boundary_index-1].y-r;
        for (i=bnd->boundary[r].y ; i < max_y ; i+=SAMPLE_STEP_SIZE)
            {
            for (j=bnd->boundary[r].x1+2 ;j <= bnd->boundary[r].x2-2 ;j+=SAMPLE_STEP
                {
                if (grid_image[i][j] > Level_thresh)
```

```
                {
                R_Gd=red_image[i][j]/(float)grid_image[i][j];
                G_Gd=green_image[i][j]/(float)grid_image[i][j];
                if (R_Gd <= RTL  && G_Gd    <= GTL)
                    {
                    color_mask[i][j]=DARK_RED_COLOR;
                    (*Dark_Red)++;
                    if ( R_Gd < 0.7) satu+=(0.7-R_Gd);
                    }
                else if (R_Gd <= RTH && G_Gd > GTH)
                    {
                    color_mask[i][j]=GREEN_COLOR;
                    (*Green)++;
                    }
                else if (R_Gd >  RTH && G_Gd > GTH)
                    {
                    color_mask[i][j]=YELLOW_COLOR;
                    (*Yellow)++;
                    }
                else if (R_Gd > RTM && G_Gd > GTM  && G_Gd <= GTH)
                    {
                    color_mask[i][j]=ORANGE_COLOR;
                    (*Orange)++;
                    }
                else
                    {
                    color_mask[i][j]=SIMPLE_RED_COLOR;
                    (*Simple_Red)++;
                        if (color_mask[i-SAMPLE_STEP_SIZE][j] != SIMPLE_RED_COLOR )
                        (*Changes)++;
                        if (color_mask[i][j-SAMPLE_STEP_SIZE] != SIMPLE_RED_COLOR )
                        (*Changes)++;
                    if ( R_Gd < 0.7) satu+=(0.7-R_Gd);
                    }
                }
            else (*no_color)++;
            }
        r+=SAMPLE_STEP_SIZE;
        }
    satu/=(float)((*Simple_Red) + (*Dark_Red));
    satu-=0.2;
    if (satu <= 0.) satu= 0.01;
    satu/=0.07;
    (*Sat)+= (long) ( satu*33. +0.5);
}
```

APPENDIX E

```c
/*
                              ID: 002
                              File Name is: app02.c
*/
#include "adapter.h"
#include <math.h>
#include <stdio.h>
#define CALYX_GAP    5
#define MAX_RECURSE 604
PIXEL   grid[FR_Y_SIZE][FR_X_SIZE];
PIXEL   green[FR_Y_SIZE][FR_X_SIZE];
PIXEL   red[FR_Y_SIZE][FR_X_SIZE];
PIXEL   aa[FR_Y_SIZE][FR_X_SIZE];
PIXEL   res[FR_Y_SIZE][FR_X_SIZE];
char header[FR_HEADER_SIZE];
static struct line_pair boundary[MAX_BOUNDARY];
static int boundary_index;
static struct rect out_rect;
static int debug_flag;
static int rec_depth;
cancel_touch_frame(mat, boundary, boundary_index)
    PIXEL mat[][FR_X_SIZE];
    struct line_pair boundary[];
{
int i, i1, j2, j1, l, count;
    for (i = 0 ; i < boundary_index ; ++i)
    {
      i1 = boundary[i].y;
      j1 = boundary[i].x1;
      j2 = boundary[i].x2;
      if (mat[i1][j1+1] > 0) { rec_depth = 0; cancel_grow(i1, j1+1); }
      if (mat[i1][j2-1] > 0) { rec_depth = 0 ; cancel_grow(i1, j2-1); }
      for (l = j1 ; l < j2 ; ++l)
            if (res[i1][l] == 99 && aa[i1][l] > 0)
                  { rec_depth = 0 ; cancel_grow(i1,l); }
    }
    for (count = i = 0 ; i < boundary_index ; ++i)
    {
      i1 = boundary[i].y;
      j1 = boundary[i].x1;
      j2 = boundary[i].x2;
      for (l = j1 ; l < j2 ; ++l) if (aa[i1][l] > 0) ++count;
    }
  return(count);
}
cancel_grow(i0,j0)
{
    if (i0 < 0 || j0 < 0 || i0 >= FR_Y_SIZE || j0 >= FR_X_SIZE) return(1);
    if (aa[i0][j0] > 0) {
                if (rec_depth > MAX_RECURSE) {  return(0); }
                ++rec_depth;
                aa[i0][j0] = 0;
                cancel_grow(i0-1, j0);
                cancel_grow(i0+1, j0);
                cancel_grow(i0, j0+1);
                cancel_grow(i0, j0-1);
                cancel_grow(i0-1, j0-1);
                cancel_grow(i0-1, j0+1);
                cancel_grow(i0+1, j0-1);
                cancel_grow(i0+1, j0+1);
                --rec_depth;
        }
}
final_decision(res, green, red, aa, boundary, boundary_index,out_mask)
```

```
    PIXEL res[][FR_X_SIZE];
    PIXEL green[][FR_X_SIZE];
    PIXEL red[][FR_X_SIZE];
    PIXEL aa[][FR_X_SIZE];
    PIXEL out_mask[FR_Y_SIZE][FR_X_SIZE];
    struct line_pair boundary[];
{
int i,y,x1,x2,j;
    clear_mat(out_mask);
       for (i = 0 ; i < boundary_index ; ++i)
         {
            y = boundary[i].y;
         x1 = boundary[i].x1;
         x2 = boundary[i].x2;
            for (j = x1 ; j < x2 ; ++j)
              {
                 if (res[y][j] == 253)  (rec_depth = 0 ; grow(y,j); }
              }
         }
}
dialate(mat, mat1)
    PIXEL mat[][FR_X_SIZE];
    PIXEL mat1[][FR_X_SIZE];
{
int i,j, count = 0;
    for (i = 1 ; i < FR_Y_SIZE-1 ; ++i)
       for (j = 1 ; j < FR_X_SIZE-1 ; ++j)
              if (mat[i-1][j] == 200 || mat[i][j-1] == 200 ||
                  mat[i+1][j] == 200 || mat[i][j+1] == 200)
                       { mat1[i][j] = 200; ++count; }
                     else mat1[i][j] = mat[i][j];
    return(count);
}
clear_mat(m) long *m;
{
long *p;
       p = FR_X_SIZE / sizeof(long) * FR_Y_SIZE + m;
       for ( ; m < p ; ++m) *m = 0;
}
d00(grid, boundary, boundary_index, out_rect, res)
         PIXEL    grid[FR_Y_SIZE][FR_X_SIZE];
         PIXEL    res[FR_Y_SIZE][FR_X_SIZE];
         struct line_pair boundary[];
         struct rect out_rect;
         int boundary_index;
{
int i,j, x1, v_index;
unsigned char vec[FR_X_SIZE], mark[FR_X_SIZE];
       for (i = 0 ; i < boundary_index; ++i)
         {
            x1 = boundary[i].x1 + 2;
            v_index = horizontal_walk(grid, i, vec, boundary, x1);
            anal_vec(vec, v_index, boundary[i].y, x1, res, mark);
         }
}
horizontal_walk(grid, i, vec, boundary, x2)
         PIXEL    grid[FR_Y_SIZE][FR_X_SIZE];
         struct line_pair boundary[];
         unsigned char vec[];
{
int y,j,l, x1, v_index, min_p, max_p;
         y = boundary[i].y;
         if (debug_flag)     wpixel(x2, y, 255);
         v_index = 0;
```

```
            for (j = x2+1 , l = y; grid[l][j]  ; ++j)
                {
                    if (debug_flag == 2) wpixel(j,l,254);
                    vec[v_index] = grid[l][j];
                    ++v_index;
                }
        return(v_index);
}
#ifdef GRID_HORIZONTAL
d90(grid, boundary, boundary_index, out_rect, res)
        PIXEL   grid[FR_Y_SIZE][FR_X_SIZE];
        PIXEL   res[FR_Y_SIZE][FR_X_SIZE];
        struct line_pair boundary[];
        struct rect out_rect;
        int boundary_index;
{
int i,j, x1, v_index, x2;
unsigned char vec[128], min_p, max_p;
     for (i = 0 ; i < boundary_index; ++i)
        {
            x1 = boundary[i].x1;
            if (x1 <= out_rect.x1+2)
                        break;
        }
        if (i == boundary_index) { printf("\n Warning: Unable to find place in Lt. c
                                }
        for ( ; i > 0 ; --i)
        {
         for (x2 = boundary[i].x1 ; x2 < boundary[i-1].x1 ; ++x2)
          {
           v_index = vertical_walk(grid, i, vec, boundary, &min_p, &max_p, x2);
           anal_vec(vec, v_index, min_p, max_p, boundary[i].y, x2, res);
          }
        }
        for (x2 = boundary[0].x1 ; x2 < boundary[0].x2 ; ++x2)
        {
            v_index = vertical_walk(grid, 0, vec, boundary, &min_p, &max_p, x2);
            anal_vec(vec, v_index, min_p, max_p, boundary[i].y, x2, res);
        }
        for (i = 1 ; i < boundary_index ; ++i)
        {
         for (x2 = boundary[i-1].x2 ; x2 < boundary[i].x2 ; ++x2)
           {
             v_index = vertical_walk(grid, i, vec, boundary, &min_p, &max_p, x2);
             anal_vec(vec, v_index, min_p, max_p, boundary[i].y, x2, res);
           }
        }
}
vertical_walk(grid, i, vec, boundary, min_pp, max_pp, x2)
        PIXEL   grid[FR_Y_SIZE][FR_X_SIZE];
        struct line_pair boundary[];
        unsigned char vec[];
        int *min_pp, *max_pp;
{
int y,j,l, x1, v_index, min_p, max_p;
        y = boundary[i].y;
        if (debug_flag)    wpixel(x2, y, 255);
        v_index = 0;
        min_p = 255; max_p = 0;
        for (j = x2 , l = y+1 ; grid[l][j]  ; ++l )
            {
                if (debug_flag == 2) wpixel(j,l,254);
                vec[v_index] = grid[l][j];
                if (vec[v_index] > max_p) max_p = vec[v_index];
```

```
            else if (vec[v_index] < min_p) min_p = vec[v_index];
            ++v_index;
        }
    *min_pp = min_p;
    *max_pp = max_p;
    return(v_index);
}
#endif
#ifdef GRID_45
d45(grid, boundary, boundary_index, out_rect, res)
        PIXEL   grid[FR_Y_SIZE][FR_X_SIZE];
        PIXEL   res[FR_Y_SIZE][FR_X_SIZE];
        struct line_pair boundary[];
        struct rect out_rect;
        int boundary_index;
{
int i,j, x1, v_index, x2;
unsigned char vec[128], min_p, max_p;
    for (i = 0 ; i < boundary_index; ++i)
    {
        x1 = boundary[i].x1;
        if (x1 <= out_rect.x1+2)
                break;
    }
    if (i == boundary_index) { printf("\n Warning: Unable to find place in Lt. c
                    }
    for ( ; i ; --i)
    {
       x2 = boundary[i].x1;
       v_index = diagonal_walk(grid, i, vec, boundary, &min_p, &max_p, x2);
       anal_vec(vec, v_index, min_p, max_p, boundary[i].y, x2, res);
    }
    for (x2 = boundary[0].x1 ; x2 < boundary[0].x2 ; ++x2)
    {
        v_index = diagonal_walk(grid, 0, vec, boundary, &min_p, &max_p, x2);
        anal_vec(vec, v_index, min_p, max_p, boundary[i].y, x2, res);
    }
    for (i = 0 ; i < boundary_index ; ++i)
    {
        x2 = boundary[i].x2;
        v_index = diagonal_walk(grid, i, vec, boundary, &min_p, &max_p, x2);
        anal_vec(vec, v_index, min_p, max_p, boundary[i].y, x2, res);
    }
}
diagonal_walk(grid, i, vec, boundary, min_pp, max_pp, x2)
        PIXEL   grid[FR_Y_SIZE][FR_X_SIZE];
        struct line_pair boundary[];
        unsigned char vec[];
        int *min_pp, *max_pp;
{
int y,j,l, x1, v_index, min_p, max_p;
    y = boundary[i].y;
    if (debug_flag)      wpixel(x2, y, 255);
    v_index = 0;
    min_p = 255; max_p = 0;
    for (j = x2-1 , l = y; grid[l][j]  ; --j, ++l )
        {
            if (debug_flag == 2) wpixel(j,l,254);
            vec[v_index] = grid[l][j];
            if (vec[v_index] > max_p) max_p = vec[v_index];
            else if (vec[v_index] < min_p) min_p = vec[v_index];
            ++v_index;
        }
    *min_pp = min_p;
```

```
            *max_pp = max_p;
        return(v_index);
}
#endif
anal_vec(vec, v_index, y0, x0, res, mark)
             PIXEL res[FR_Y_SIZE][FR_X_SIZE];
             unsigned char vec[];
             unsigned char mark[];
{
int i, l;
#define N 2
    if (v_index < 4) return(1);
    for (i = N ; i < v_index-N ; ++i)
    {
        l = vec[i+1]-vec[i-1];
        if (l < 0) l = -l;
        if (l < 8) continue;
         if (vec[i] > vec[i-N] && vec[i] > vec[i+N] && vec[i] > 10)
                  mark[i] = 1;
             else mark[i] = 0;
    }
    mark_suspicious_intervals(mark,v_index, y0, x0, res, vec);
    if (debug_flag)
        draw_data(v_index, mark, y0, x0, x0);
}
mark_suspicious_intervals(mark1, v_index, y0, x0, res, mark)
             PIXEL res[FR_Y_SIZE][FR_X_SIZE];
             unsigned char mark1[];
             unsigned char mark[];
{
int i,j, r, l;
    v_index = (int)((double)v_index * 0.8);
    for (i = 1 ; i < v_index-1 ; ++i)
            if ( mark1[i-1] || mark1[i+1] || mark1[i])
                         mark[i] = 1;       else mark[i] = 0;
    for (i = 1 ; ! mark[i] && i < v_index ; ++i) ;
    for (i += 2 ; i < v_index ; ++i)
    {
        for (j = i ; ! mark[j] && j < v_index ; ++j) ;
        if (j == v_index) continue;
        r = 0;
        if (j-i >= CALYX_GAP) {
                if (debug_flag) { wpixel(x0+j,y0,253);   wpixel(x0+i,y0,254); }
                for (l = i ; l < j ; ++l)
                              res[y0][x0+l] = 253;
                 for (l = j ; mark[l] && l < v_index ; ++l) ;
                if (l == v_index) continue;
                for ( ; mark[l] == 0 ; ++l)
                              res[y0][x0+l] = 253;
        }
         else { res[y0][x0+i] = 100;    }
         i = j+1;
    }
    for ( ; i < FR_X_SIZE ; ++i) res[y0][x0+i] = 99;
}
draw_data(v_index, mark, y0, x0, x_base)
             unsigned char mark[];
{
int i;
#define X 0
#define Y 200
#define SIZE_X 256
#define SIZE_Y 256
static int height = SIZE_Y;
```

```
    wpixel(x0, y0, 253);
    if (height == SIZE_Y)    filled_rectangle(X,Y,X+SIZE_X,Y+SIZE_Y, 60);
       for (i = 1 ; i < v_index ; ++i)
       {
           if (mark[i] == 1) wpixel(X+i+x_base, Y+height, 255);
           if (mark[i] == 2) wpixel(X+i+x_base, Y+height, 253);
       }
    height -= 1;
}
grow(i0,j0)
{
double r_g;
    if (i0 < 0 || j0 < 0 || i0 >= FR_Y_SIZE || j0 >= FR_X_SIZE) return(1);
    r_g = (double)red[i0][j0] / (double)green[i0][j0];
    if ((green[i0][j0] < 125 && red[i0][j0] < 125 && aa[i0][j0] < 150
         && grid[i0][j0] != 200  && r_g > 1.10  )) {
             grid[i0][j0] = 200 ;
             if (rec_depth > MAX_RECURSE) {   return(0); }
             ++rec_depth;
             grow(i0-1, j0);
             grow(i0+1, j0);
             grow(i0, j0+1);
             grow(i0, j0-1);
             grow(i0-1, j0-1);
             grow(i0+1, j0-1);
             grow(i0-1, j0+1);
             grow(i0+1, j0+1);
             --rec_depth;
    }
}
```

APPENDIX F

```c
/*
                    ID: 010
         File name is: app10.c
-------------------------------------------------------------------------
*/
=include "adapter.h"
=include <math.h>
=include <stdio.h>
extern struct single_view_info   view_info[N_CAMERAS];
static FILE *out_file;
extern struct prog_settings prog_consts;
extern int debug_flag;
double
compute_single_cam(cam, bnd, image, camera_distance)
         int cam, camera_distance;
         struct boundary_data *bnd;
         PIXEL image[FR_X_SIZE][FR_Y_SIZE];
{
int x1, x2, y, ret, x, i, x1z, x2z, old, min_x, max_x;
double volume, area;
float radius, y_height;
    if (debug_flag) { old = get_channel(); set_channel(cam); }
    volume = 0;
    min_x = L_FR_X_SIZE;
    max_x = 0;
    for (i = 1; i < bnd -> boundary_index-1 ; ++i)
    {
       y  = bnd -> boundary[i].y;
       x1 = bnd -> boundary[i].x1;
       x2 = bnd -> boundary[i].x2;
       compute_radius(y, x1, x2, &radius, &y_height, camera_distance);
       set_zone_bounds(radius, y, x1, x2, &x1z, &x2z, camera_distance);
       area = 3.1415*radius*radius;
       volume += (area * y_height);
       if (debug_flag)  { wpixel(x1z, y, 254);
                          wpixel(x2z, y, 255);
                            wpixel(bnd->boundary[i].x1, y, 150);
                            wpixel(bnd->boundary[i].x2, y, 151);
                         }
       if (x1z < min_x) min_x = x1z;
       if (x2z > max_x) max_x = x2z;
       bnd -> boundary[i].x1 = x1z;
       bnd -> boundary[i].x2 = x2z;
    }
   bnd->out_rect.x1 = min_x;
   bnd->out_rect.x2 = max_x;
   if (debug_flag)  {     set_channel(old);
                          printf("\n Volume: %f", volume);
                    }
   return(volume);
}
glob_all(bnd0, bnd1, bnd2, image0, image1, image2, volp)
                     PIXEL image0[FR_Y_SIZE][FR_X_SIZE];
                     PIXEL image1[FR_Y_SIZE][FR_X_SIZE];
                     PIXEL image2[FR_Y_SIZE][FR_X_SIZE];
                     struct boundary_data *bnd0;
                     struct boundary_data *bnd1;
                     struct boundary_data *bnd2;
                     double *volp;
{
double copmute_single_cam();
double t_volume, volume;
char header[32];
     t_volume =
```

```
      compute_single_cam(CAM_1, bnd0, image0, prog_consts.camera_distance[CAM_1
t_volume +=
      compute_single_cam(CAM_2, bnd1, image1, prog_consts.camera_distance[CAM_2
t_volume +=
      compute_single_cam(CAM_3, bnd2, image2, prog_consts.camera_distance[CAM_3
t_volume /= 3.;
   *volp = t_volume;
   return(SUCCESS);
}
assign_global_coordinates_tr(radius, y1, x1, x2, cam_number, cam_distance,
                             y_center, x_center)
           double radius;
{
int xc;
float x, y, z;
     xc = (x2 + x1) >> 1;
     for (++x1 ; x1 < x2 ; x1 += 3)
     {
        glob_coord_single_point(cam_number, y1, x1, xc, y_center,
                        radius, &x, &y, &z, cam_distance, x_center, y_center);
     }
   return(SUCCESS);
}
#define PERSPECTIVE_X(world_coordinate, cam_coordinate, Z)  \
 world_coordinate = (double)( cam_coordinate ) * CCD_SIZE_X / CCD_RESOLUTION_X; \
 world_coordinate = world_coordinate * (Z - CAM_FOCAL_LENGTH) / \ define PERSPECTIVE_Y(world_coordinate, cam_coordinate, Z)  \
 world_coordinate = (double)( cam_coordinate ) * CCD_SIZE_Y / CCD_RESOLUTION_Y; \
 world_coordinate = world_coordinate * (Z - CAM_FOCAL_LENGTH) / \ world_coordinate *= 1.04;
compute_radius(y, x1, x2, rp, y_height, cam_distance)              float *rp
{
double a,b;
int w;
                            /* 1. compute radius in mm ( world coordinates) *
              w = (x2-x1) >> 1;
              PERSPECTIVE_X(b, w, cam_distance);
              *rp = (float)b;
              PERSPECTIVE_Y(a, 1, (cam_distance-*rp)); /* compute height of 1 p
              *y_height = (float)a;
}
#define PERSPECTIVE_X(world_coordinate, cam_coordinate, Z)  \
 world_coordinate = (double)( cam_coordinate ) * CCD_SIZE_X / CCD_RESOLUTION_X; \
 world_coordinate = world_coordinate * (Z - CAM_FOCAL_LENGTH) / \ glob_coord_single_point(cam_number, y1, x1, xc, yc, radius, xp, yp, zp,
                                                       cam_distance, y_c
                      float *xp, *yp, *zp;
                      double radius;
                      int xc, yc, y1, x1;
{
double s, f, a, b, c, q, z, x, y;
              f = CAM_FOCAL_LENGTH;
              s = (double)(x1 - xc);
              s = s * CCD_SIZE_X / CCD_RESOLUTION_X;
              s = s * s;
              a = s / (f*f) + 1.;
              b = 2.*radius - 2.*cam_distance - 2.*s/f;
              c = s + cam_distance*(cam_distance-2.*radius);
              q = -0.5 * (b - sqrt((b * b) - (4.0 * a * c)));
              z = c / q;
              PERSPECTIVE_X(x, (x1-x_center), z);
```

```
                            PERSPECTIVE_Y(y, (y1-yc), z);
                            z = cam_distance-radius-z;
                       if (cam_number == CAM_1) ;
                            if (cam_number == CAM_3)
                            {
#define SIN120 0.866
#define COS120 -0.5
#define SIN240 -0.866
#define COS240 -0.5
#define PLANE_X_Z
#ifdef PLANE_X_Z
                                s = (float)x;
                                x = -(z - 0)*SIN120  + x*COS120;
                            z = (z - 0)*COS120 + s*SIN120;
#endif
#ifdef PLANE_Y_Z
                                s = (float)y;
                                y = -(z - 0)*0.866  + y*(-0.5);
                            z = (z - 0)*(-0.5) + s*0.866;
#endif
                            }
                            else if (cam_number == CAM_2)
                            {
                                s = (float)x;
                                x = -(z - 0)*SIN240  + x*COS240;
                            z = (z - 0)*COS240 + s*SIN240;
                            }
#ifdef NEW
#define PLANE_X_Z
#ifdef PLANE_X_Z
                                s = (float)x;
                                x = -(z - 0)*0.866  + x*(-0.5);
                            z = (z - 0)*(-0.5) + s*0.866;
#endif
#ifdef PLANE_Y_Z
                                s = (float)y;
                                y = -(z - 0)*0.866  + y*(-0.5);
                            z = (z - 0)*(-0.5) + s*0.866;
#endif
                            }
                            else if (cam_number == CAM_2)
                            {
                                s = (float)x;
                                x = -(z - 0)*(-0.866)  + x*(0.5);
                            z = (z - 0)*(0.5) + s*(-0.866);
                            }
#endif
                    y = -y;
                    *xp = (float)x;
                    *yp = (float)y;
                    *zp = (float)z;
        return(SUCCESS);
}
set_zone_bounds(radius, y, x1, x2, x1zp, x2zp, cam_distance)
                       int *x1zp, *x2zp;
                       double radius;
{
double p, w, d2, f, s, alfa;
int pixels;
            f = CAM_FOCAL_LENGTH;
            w = radius * sin(60 * PI / 180.);
            d2 =   cam_distance - f - radius * (1. + sin(30 * PI / 180.));
            p = w * f / d2;
            pixels = (int) (p * CCD_RESOLUTION_X / CCD_SIZE_X + 0.5);
```

```
        *x1zp = ((x1+x2) >> 1) - pixels;
        *x2zp = ((x1+x2) >> 1) + pixels;
    return(pixels);
}
```

```c
/*
                                    ID: 009
    File name is: app06.c
------------------------------------------------------------------
*/
#include "adapter.h"
#include <limits.h>
#include <stdio.h>
#define STEM
extern struct prog_settings prog_consts;
extern int debug_flag;
extern int norm_raw[N_CAMERAS][4];
make_rouler_p(xs,ys,xend,yend,step, grade, header,c1,c2)   char *header;
{
}
global_color_analysis(cam_num, bnd, green_image,red_image,grid_image,color_mask,
                      Dark_Red,Simple_Red,Yellow,Green,Orange,Sat,Changes,no
int              cam_num,apple_brand,no_color;
long             *Dark_Red,*Simple_Red,*Yellow,*Green,*Orange,*Sat,*Changes,*
PIXEL            red_image[FR_Y_SIZE][FR_X_SIZE];
PIXEL            green_image[FR_Y_SIZE][FR_X_SIZE];
PIXEL            grid_image[FR_Y_SIZE][FR_X_SIZE];
PIXEL            color_mask[FR_Y_SIZE][FR_X_SIZE];
struct boundary_data *bnd;
{
    int     i,j,max_y,r;
    PIXEL   Level_thresh;
    float   R_Gd,G_Gd,RTL,RTM,RTH,GTL,GTM,GTH, satu=0.;
#define    SAMPLE_STEP_SIZE  2
        switch (apple_brand) {
           case SMITH_TYPE:
              {
              Level_thresh=SMITH_GRID_THRESH;
              RTL=SMITH_RED_THRESH_LOW;
              RTM=SMITH_RED_THRESH_MEDIUM;
              RTH=SMITH_RED_THRESH_HIGH;
              GTL=SMITH_GREEN_THRESH_LOW;
              GTM=SMITH_GREEN_THRESH_MEDIUM;
              GTH=SMITH_GREEN_THRESH_HIGH;
              break;
              }
           case HERMON_TYPE:
           case ANA_TYPE:
           case ORLEANS_TYPE:
              {
              Level_thresh=ORLEANS_GRID_THRESH;
              RTL=ORLEANS_RED_THRESH_LOW;
              RTM=ORLEANS_RED_THRESH_MEDIUM;
              RTH=ORLEANS_RED_THRESH_HIGH;
              GTL=ORLEANS_GREEN_THRESH_LOW;
              GTM=ORLEANS_GREEN_THRESH_MEDIUM;
              GTH=ORLEANS_GREEN_THRESH_HIGH;
              break;
              }
           }
        for (i=0 ; i < FR_Y_SIZE ;i++)
        for (j=0 ; j < FR_X_SIZE ;j++) color_mask[i][j]=0;
        r=1;
        max_y=bnd->boundary[bnd->boundary_index-1].y-r;
        for (i=bnd->boundary[r].y ; i < max_y ; i+=SAMPLE_STEP_SIZE)
           {
           for (j=bnd->boundary[r].x1+2 ;j <= bnd->boundary[r].x2-2 ;j+=SAMPLE_STEP
              {
              if (grid_image[i][j] > Level_thresh)
```

```
            {
            R_Gd=red_image[i][j]/(float)grid_image[i][j];
            G_Gd=green_image[i][j]/(float)grid_image[i][j];
            if (R_Gd <= RTL   && G_Gd    <= GTL)
                {
                color_mask[i][j]=DARK_RED_COLOR;
                (*Dark_Red)++;
                if ( R_Gd < 0.7) satu+=(0.7-R_Gd);
                }
            else if (R_Gd <= RTH && G_Gd > GTH)
                {
                color_mask[i][j]=GREEN_COLOR;
                (*Green)++;
                }
            else if (R_Gd >  RTH && G_Gd > GTH)
                {
                color_mask[i][j]=YELLOW_COLOR;
                (*Yellow)++;
                }
            else if (R_Gd > RTM && G_Gd > GTM  && G_Gd <= GTH)
                {
                color_mask[i][j]=ORANGE_COLOR;
                (*Orange)++;
                }
            else
                {
                color_mask[i][j]=SIMPLE_RED_COLOR;
                (*Simple_Red)++;
                    if (color_mask[i-SAMPLE_STEP_SIZE][j] != SIMPLE_RED_COLOR )
                    (*Changes)++;
                    if (color_mask[i][j-SAMPLE_STEP_SIZE] != SIMPLE_RED_COLOR )
                    (*Changes)++;
                if ( R_Gd < 0.7) satu+=(0.7-R_Gd);
                }
            }
        else (*no_color)++;
        }
    r+=SAMPLE_STEP_SIZE;
    }
satu/=(float)((*Simple_Red) + (*Dark_Red));
satu-=0.2;
if (satu <= 0.) satu= 0.01;
satu/=0.07;
(*Sat)+= (long) ( satu*33. +0.5);
}
```

APPENDIX G

Mar 17 13:01 1993 appl2.c Page 1

```
/*
                             ID: 012
    File name is: appl2.c
--------------------------------------------------------------
*/
#define SUR 2
#include <math.h>
#include <stdio.h>
#include <conio.h>
#include <malloc.h>
#include <memory.h>
#include <fcntl.h>
#include <limits.h>
#include "adapter.h"
extern struct single_view_info  view_info[N_CAMERAS];
extern struct prog_settings prog_consts;
extern int debug_flag;
extern struct c_dat candidates[MAX_CANDIDATES];
extern int cand_index;
do_bruse_1(cam, bnd, image0, image1, image2, image3, image4, image5, spots)
     int cam;
     PIXEL image0[FR_Y_SIZE][FR_X_SIZE];
     PIXEL image1[FR_Y_SIZE][FR_X_SIZE];
     PIXEL image2[FR_Y_SIZE][FR_X_SIZE];
     PIXEL image3[FR_Y_SIZE][FR_X_SIZE];
     PIXEL image4[FR_Y_SIZE][FR_X_SIZE];
     PIXEL image5[FR_Y_SIZE][FR_X_SIZE];
     struct boundary_data *bnd;
     struct spot spots[MAX_SPOTS];
{
int old, n, i, spt_index;
int ret, old_debug;
char s[16];
   old_debug = debug_flag;
   debug_flag = 0;
     old = get_channel();
     if (debug_flag)    set_channel(cam);
     SWAP_IN_SIZE(image1, cam,  normal_images.green, FR_Y_SIZE*FR_X_SIZE);
     SWAP_IN_SIZE(image2, cam,  normal_images.red,   FR_Y_SIZE*FR_X_SIZE);
     SWAP_IN_SIZE(image3, cam,  normal_images.ir,    FR_Y_SIZE*FR_X_SIZE);
     SWAP_IN_SIZE(image5, cam,  normal_images.grid,  FR_Y_SIZE*FR_X_SIZE);
     SWAP_IN_SIZE(bnd,    cam,  bnd,                 sizeof(struct boundary_data));
#define SH 3
     clear_outside_margin(image1, bnd->boundary, bnd->boundary_index, 255, SH);
     divide_1(image3, image5, image0);
     clear_outside_margin(image0, bnd->boundary, bnd->boundary_index, 255, SH);
     do_smooth_masked(image0, image2);
     change_background(image2);
     dialate_color(image2, image0, 255);
     SWAP_IN_SIZE(image2, cam,  normal_images.red,  FR_Y_SIZE*FR_X_SIZE);
     SWAP_IN_SIZE(image5, cam,  normal_images.grid, FR_Y_SIZE*FR_X_SIZE);
     if (debug_flag || old_debug)
       display_plain_magnified_3(0, 0, image0, FR_X_SIZE, FR_Y_SIZE);
     spt_index = ret = cntr(image0 , image1, image2, image3,
                  cam, image4, spots, image5);
   if (debug_flag)
```

Mar 17 13:01 1993  appli.c Page 2

```
        display_image(430, 0, image4, FR_X_SIZE, FR_Y_SIZE, "final");
    sprintf(s, "SPT_%ld.dat", cam);
    dump_spots(s, spots, sizeof(struct spot) * MAX_SPOTS, &ret);
       if (debug_flag)
       {
            set_channel(old);
       }
    select_contour_1(spots, spt_index, REAL_BLEMISH, 100, cam);
    for (i = 0; i < spt_index ; ++i)
    {
        decide_about_contour(spots, i, 0, cam);
    }
debug_flag = old_debug;
    choose_defects_by_severity(spots, spt_index, cam);
    return(spt_index);
}
dump_spots(name, buf, size, count)         unsigned int size; char *buf;
                                           int *count; char *name;
{
int out_file;
unsigned int bw;
    out_file = open(name, (O_WRONLY | O_CREAT |
                           O_TRUNC | O_BINARY), (0200 | 0400) );
    if (out_file == -1) return(FAILURE);
    bw = write(out_file, buf, size);
    if (bw != size) {    close(out_file);      return(FAILURE); }
    bw = write(out_file, count, sizeof(int));
    if (bw != sizeof(int)) {    close(out_file);     return(FAILURE); }
    close(out_file);
    return(SUCCESS);
}
cntr(spot_image, green, red, ir, cam, whtg, spots, grid)
        int cam;
        PIXEL whtg[FR_Y_SIZE][FR_X_SIZE];
        PIXEL spot_image[FR_Y_SIZE][FR_X_SIZE];
        PIXEL green[FR_Y_SIZE][FR_X_SIZE];
        PIXEL grid[FR_Y_SIZE][FR_X_SIZE];
        PIXEL red[FR_Y_SIZE][FR_X_SIZE];
        PIXEL ir[FR_Y_SIZE][FR_X_SIZE];
        struct spot spots[MAX_SPOTS];
{
int n;
int sp_index;
int start_i, start_j, per, level, offset, ci, cj, ret;
char chain[2048], c_name[16];
long  measure_chain_area(PIXEL *chain);
int area, old_area;
struct spot spot1;
int x1, y1, x2, y2, angle, a1, b1;
struct point xybuf[2048];
    offset = 0;
    sp_index = 0;
    init_contours(spot_image, whtg, 1,
                    1, FR_Y_SIZE-2, FR_X_SIZE-2);
    per = 1;
#define LEVEL_STEP 3
```

```
Mar 17 13:01 1993  appl2.c Page 3 for (level = 200 ; level > 60 && sp_index < (MAX_SPOTS- 1) ; )
       {
          if (kbhit()) {          getch(); return(0);        }
          per = next_contour(level,&start_i,&start_j, &chain[0]);
          if (per == 0) { level -= LEVEL_STEP; continue;}
          area = (int)measure_chain_area(&chain[0]);
          if (area < -10 && area > -5600) {
          spot1.area = ABS(area);
          spot1.per = per;
          mal_contour_features(start_i, start_j, &chain[0],   &spot1);
          enclosing_rectangle_chain(&chain[0], start_i, start_j, &xybuf[0], &x1, &y1, &x2,
          spot1.a1 = x2 - x1 + 1;
          spot1.b1 = y2 - y1 + 1;
          spot1.cam_number = cam;
          a1 = (spot1.a1 > spot1.b1) ? spot1.a1 : spot1.b1;
          b1 = (spot1.a1 < spot1.b1) ? spot1.a1 : spot1.b1;
          spot1.ar = (b1 > 0 ? (float)a1 / (float)b1 : 0.);
          if (debug_flag) {
              draw_contour(offset+start_i, start_j, chain, 3, 1);
              }
          if (1)
              {
old_area = spot1.area;
          do_statistics(cam, green, red, ir, grid, &spot1);
          do_statistics_ring(cam, green, red, ir, grid, &spot1, &chain);
       spot1.area = old_area;
          if(spot1.area != 0)
  spot1.p2a = ((float)spot1.per * (float)spot1.per) / (4.0 * PI *(float)spot1.area);
          memcpy(&spots[sp_index], &spot1, sizeof(struct spot));
          sprintf(c_name, "%s%ld_%ld.cnt", TMP_DEVICE, cam, sp_index);
          dump_spots(c_name, chain, sizeof(chain), &per);
       if (debug_flag)
          draw_contour(offset+start_i, start_j, chain, 3, 254);
              sp_index++;
              if ((sp_index) >= MAX_SPOTS) {
                     cputs("\nToo many spots"); return(sp_index); }
              }
          }
       }
       return(sp_index);
}
mal_contour_features(i, j, chain_buf, spot1)
          int i,j;    char *chain_buf;
          struct spot *spot1;
{
char *p = &chain_buf[0];
double ar;
int min_i, max_i, min_j, max_j;
long cci, ccj;
   min_i = min_j = FR_X_SIZE;
   max_i = max_j = 0;
   cci = ccj = 0;
   spot1->start_i = (unsigned char)i;
   spot1->start_j = (unsigned char)j;
   for ( ; *p ; ++p)
   {
```

```
Mar 17 13:01 1993  appl2.c Page 4 cci += i;
      ccj += j;
      if (i < min_i) min_i = i;
      if (i > max_i) max_i = i;
      if (j < min_j) min_j = j;
      if (j > max_j) max_j = j;
         switch(*p)
         {
         case 'U':       --i ;  break;
         case 'D':       ++i ;  break;
         case 'L':       --j;   break;
         case 'R':       ++j ;  break;
         default:
             printf ("\n Illegal"); exit(0);
         }
      }
if (spot1->per != 0)
   {
     spot1 -> ci = (unsigned char)((double)cci / (double)spot1->per + 0.5);
     spot1 -> cj = (unsigned char)((double)ccj / (double)spot1->per + 0.5);
   }
  spot1 -> min_i = (unsigned char)min_i;
  spot1 -> max_i = (unsigned char)max_i;
  spot1 -> min_j = (unsigned char)min_j;
  spot1 -> max_j = (unsigned char)max_j;
   spot1 ->flag1 = 0;
   spot1 ->flag2 = 0;
   spot1 ->flag3 = 0;
   return(SUCCESS);
}
#ifdef S_ALONE
do_smooth_masked(src,dst)
         PIXEL src[][FR_X_SIZE];
         PIXEL dst[][FR_X_SIZE];
{
int i,j, cnt;
unsigned int n, p;
   for (i = 1 ; i < FR_Y_SIZE-1 ; ++i)
      for (j = 1 ; j < FR_X_SIZE-1 ; ++j)
      {
        p = src[i][j];
        if (p < 253)  { n = p << 2; cnt = 4; }
        else  {  dst[i][j] = (PIXEL)p; continue;    }
#define ADD_COND4(a,b) p = src[a][b]; if (p < 253) {n += (p << 1); cnt += 2;}
#define ADD_COND8(a,b) p = src[a][b]; if (p < 253) {n += p;        cnt += 1;}
        ADD_COND4(i,j-1);
        ADD_COND4(i-1,j);
        ADD_COND4(i+1,j);
        ADD_COND4(i,j+1);
        ADD_COND8(i-1,j-1);
        ADD_COND8(i-1,j+1);
        ADD_COND8(i+1,j-1);
        ADD_COND8(i+1,j+1);
        n = (int)((double)n / (double)cnt + 0.5);
        dst[i][j] = (PIXEL)n;
     }
```

```
Mar 17 13:01 1993  appl2.c Page 5 return(1);
}
#endif
change_background(image)
        PIXEL image[FR_Y_SIZE][FR_X_SIZE];
{
int i,j;
   for (i = 0 ; i < FR_Y_SIZE ; ++i)
       for (j = 0 ; j < FR_X_SIZE ; ++j)
           if (image[i][j] > 253) image[i][j] = 255;
}
divide_1(div1, divisor, result)
        PIXEL div1[FR_Y_SIZE][FR_X_SIZE];
        PIXEL divisor[FR_Y_SIZE][FR_X_SIZE];
        PIXEL result[FR_Y_SIZE][FR_X_SIZE];
{
int i,j;
double d1, d2, d3;
   for (i = 0 ; i < FR_Y_SIZE ; ++i)
       for (j = 0 ; j < FR_X_SIZE ; ++j)
          {
             if (div1[i][j] > 253) {
                result[i][j] = div1[i][j];
                continue;
             }
             if (divisor[i][j] > 253) {
                result[i][j] = divisor[i][j];
                continue;
             }
#define VERY_DARK 110
             if (divisor[i][j] < VERY_DARK || div1[i][j] < VERY_DARK) {
                result[i][j] = 70;
                continue;
             }
              d1 = (double)div1[i][j];
              d2 = (double)divisor[i][j];
             if (d2 < 1.0) d2 = 1.0;
          d3 = d1 / d2;
             d3 = d3 * 100. + 0.5;
             if (d3 > 250.) d3 = 250.;
             result[i][j] = (PIXEL)d3;
          }
}
clear_outside_margin(image, boundary, boundary_index, color, margin)
        PIXEL   image[FR_Y_SIZE][FR_X_SIZE];
        struct line_pair boundary[];
{
int i, y, x1, y1, j, x2;
printf("\n %d %d", boundary_index, margin);
     for (i = 0 ; i < boundary_index ; ++i)
     {
        y = boundary[i].y;
        if (y < 0 || y >= L_FR_Y_SIZE) continue;
        x1 = boundary[i].x1 + margin; if (x1 < 0) x1 = 0;
        x2 = boundary[i].x2 - margin; if (x2 > FR_X_SIZE) x2 = FR_X_SIZE;
        if (x1 > x2) {
```

```
Mar 17 13:01 1993  appl2.c Page 6 x1 = boundary[i].x1;
                x2 = boundary[i].x2;
            }
            if (x1 == 0 && x2 == FR_X_SIZE)
                for (j = 0 ; j < x2 ; ++j) image[y][j] = color;
            else {
                for (j = 0 ; j < x1 ; ++j)          image[y][j] = color;
                for (j = x2 ; j < FR_X_SIZE ; ++j)  image[y][j] = color;
            }
        }
        for (y = 0 ; y < boundary[0].y ; ++y)
            for (j = 0 ; j < FR_X_SIZE ; ++j)
                            image[y][j] = color;
        for (y = boundary[boundary_index-1].y ; y < FR_Y_SIZE ; ++y)
            for (j = 0 ; j < FR_X_SIZE ; ++j)
                            image[y][j] = color;
}
do_statistics(cam, green, red, ir, grid,  spot)
        int cam;
        PIXEL green[FR_Y_SIZE][FR_X_SIZE];
        PIXEL red[FR_Y_SIZE][FR_X_SIZE];
        PIXEL ir[FR_Y_SIZE][FR_X_SIZE];
        PIXEL grid[FR_Y_SIZE][FR_X_SIZE];
        struct spot *spot;
{
int i, j;
float rg, rr, ri, rgrid;
int n, ret;
}
count_spot_point( i, j, image, sum, r, min, max, area)
        int i,j, *area;
        unsigned char *min, *max;
        float *sum, *r;
        PIXEL image[FR_Y_SIZE][FR_X_SIZE];
{
            *sum =*sum + (float)( image[i][j]);
            *r = *r + (float)( image[i][j]) * (float)( image[i][j]);
            *min = ( (*min < image[i][j]) ? *min : image[i][j] );
            *max = ( (*max > image[i][j]) ? *max : image[i][j] );
            *area = *area + 1;
        return(0);
}
do_statistics_ring(cam, green, red, ir, grid, spot, chain)
        int cam;
        PIXEL green[FR_Y_SIZE][FR_X_SIZE];
        PIXEL red[FR_Y_SIZE][FR_X_SIZE];
        PIXEL ir[FR_Y_SIZE][FR_X_SIZE];
        PIXEL grid[FR_Y_SIZE][FR_X_SIZE];
        struct spot *spot;
        char *chain;
{
int i, j, n, p1, p2, p3, p4, d, di, dj, ci, cj, dist_center;
char *p;
unsigned long sum_green, sum_red, sum_ir, sum_grid;
#define SIGN(a) (a < 0 ? -1 : (a > 0 ? 1 : 0))
int g1, g2, g3, g4, per;
```

```
Mar 17 13:01 1993  appl2.c  Page 7 spot->flag_g = 0;
    dist_center = 2;
    count_cgl (green, spot->ci, spot->cj, &spot->green_cgl, dist_center);
    count_cgl (red,   spot->ci, spot->cj, &spot->red_cgl,   dist_center);
    count_cgl (ir,    spot->ci, spot->cj, &spot->ir_cgl,    dist_center);
    count_cgl (grid,  spot->ci, spot->cj, &spot->grid_cgl,  dist_center);
#define NEW
#ifdef NEW
    ci = spot->ci; cj = spot->cj;
    i = spot->start_i; j = spot->start_j;
    sum_green = sum_red = sum_ir = sum_grid = 0;
    n = 0;
    per = 0;
    for (p = chain ; *p ; ++p)
    {
        switch(*p)
        {
        case 'U':       --i ; break;
        case 'D':       ++i ; break;
        case 'L':       --j ; break;
        case 'R':       ++j ; break;
        }
        ++per;
        d = (i-ci); di = SIGN(d);
        d = (j-cj); dj = SIGN(d);
        di = 6*di;
        dj = 6*dj;
        p1 = green[i+di][j+dj];
        p2 = red[i+di][j+dj];
        p3 = ir[i+di][j+dj];
        p4 = grid[i+di][j+dj];
        if (p1 > 253 || p2 > 253 || p3 > 253 || p4 > 253) continue;
        if (p1 < 1 || p2 < 1 || p3 < 1 || p4 < 1) continue;
        sum_green += p1;
        sum_red   += p2;
        sum_ir    += p3;
        sum_grid  += p4;
        ++n;
        g1 = -(ir[i][j] - ir[i-2][j]);
        g2 = -(ir[i][j] - ir[i+2][j]);
        g3 = -(ir[i][j] - ir[i][j-2]);
        g4 = -(ir[i][j] - ir[i][j+2]);
        if (g2 > g1) g1 = g2;
        if (g3 > g1) g1 = g3;
        if (g4 > g1) g1 = g4;
        spot->mate = g1;
        if (debug_flag)
            wpixel(3*(j+dj),3*(i+di),0);
    }
    if (n > ((per >> 1))) {
    spot->grid_ar_mean = (PIXEL) ((double)sum_grid  / (double)n + 0.5);
    spot->g_ar_mean    = (PIXEL) ((double)sum_green / (double)n + 0.5);
    spot->r_ar_mean    = (PIXEL) ((double)sum_red   / (double)n + 0.5);
    spot->i_ar_mean    = (PIXEL) ((double)sum_ir    / (double)n + 0.5);
    }
    else {
```

```
Mar 17 13:01 1993  appld.c  Page 2 spot->grid_ar_mean  = 0;
        spot->g_ar_mean     = 0;
        spot->r_ar_mean     = 0;
        spot->i_ar_mean     = 0;
        }
#endif
        return(SUCCESS);
}
count_cgl (image, ci, cj, cgl, dist_center)
        PIXEL image[FR_Y_SIZE][FR_X_SIZE];
        unsigned char ci, cj, *cgl;
{
int i,j, sum, n;
unsigned char min;
    min = 255;
    sum = 0;
    n = 0;
        for (i = (int)(ci - dist_center); i < (int)(ci + dist_center); i++)
        {
            for (j = (int)(cj - dist_center); j < (int)(cj + dist_center); j++)
            {
                if (image[i][j] < min) min = image[i][j];
            }
        }
    *cgl = min;
    return(1);
}
count_sd (r, area, mean, sd)
    int area;
    unsigned char *mean;
    float *r, *sd;
{
        if (area != 0 )
        {
            *r = *r /(float)(area);
            *mean = (unsigned char) (*r + 0.5);
            *sd = (area > 1) ?
                (*sd - *r * *r * (float)(area)) / (float)(area - 1) : 0.0 ;
            if (*sd < 0.0)
            {
                *sd = 0.0;   return (-2);
            }
            *sd = sqrt (*sd);
        }
    return(SUCCESS);
}
#define IMAGE_X FR_X_SIZE
#define IMAGE_Y FR_Y_SIZE
#define DOWN_BIT        8
#define RIGHT_BIT       1
#define UP_BIT                  2
#define LEFT_BIT        4
#define ALL_BITS        (UP_BIT|DOWN_BIT|LEFT_BIT|RIGHT_BIT)
#define UP_ARROW        'U'
#define DOWN_ARROW      'D'
#define LEFT_ARROW      'L'
```

```
Mar 17 13:01 1993  appl2.c Page 9 define RIGHT_ARROW     'R'
define DISP_I          1
#define DISP_J          0
static PIXEL *_image_p;
static PIXEL *_whtg_p;
static int _last_level;
static int _start_i, _start_j;
static int _begin_i, _begin_j, _end_i, _end_j;
init_contours(image, whtg, x1, y1, x2, y2)
            PIXEL   image[][IMAGE_X] ;
            PIXEL   whtg[][IMAGE_X] ;
{
    _image_p = &image[0][0];
    _whtg_p = &whtg[0][0];
    if (x1 < 1) x1 = 1;
    if (y1 < 1) y1 = 1;
    if (x2 > IMAGE_Y-1) x2 = IMAGE_Y-1;
    if (y2 > IMAGE_X-1) y2 = IMAGE_X-1;
    _begin_i = x1; _begin_j = y1; _end_i = x2; _end_j = y2;
    _start_i = _begin_i; _start_j = _begin_j;
    _last_level = -1;
    frame_with_zeros(_image_p,x1-1,y1-1,x2,y2);
}
next_contour(level,start_i,start_j, chain)
            int *start_i, *start_j;
            char far *chain;
{
int c_length;
    if (level != _last_level) {
        _last_level = level;
        _start_i = _begin_i; _start_j = _begin_j;
        fill_whtg(_image_p,_whtg_p,_start_i-1,_start_j-1,_end_i,_end_j,level);
    }
    if (!find_init_point(&_start_i,&_start_j,_end_i,_end_j,_whtg_p,level))
        {
        return(0); }
    c_length = search(_start_i,_start_j,_whtg_p,chain);
    *start_i = _start_i;
    *start_j = _start_j;
    return(c_length);
}
search(gi,gj,whtg,chain_buf)
            int gi,gj; PIXEL far *chain_buf;
            unsigned char far whtg[][IMAGE_X];
{
PIXEL *p  = &whtg[0][0] + gj + (gi * IMAGE_X), v;
PIXEL *q  = _image_p + gj + (gi * IMAGE_X);
PIXEL *p0 = p;
PIXEL far *pcb;
int len = 0;
#define UNMASK(a,b) v &= (~(a)); *p = v; *pcb++ = (b); ++len;
    p0 = p;
    pcb = chain_buf;
    do {
    v = *p;
if (v == 0) { printf("\n OOPS!"); *pcb = 0 ; return(1); }
```

```
Mar 17 13:01 1993   appl0.c Page 10 if (len >= MAX_LENGTH)
        { printf ("\n too long"); exit(1); }
    if (v & LEFT_BIT )
           { UNMASK(LEFT_BIT,LEFT_ARROW);
              --p;   --gj; }
    else if (v & RIGHT_BIT )
           { UNMASK(RIGHT_BIT,RIGHT_ARROW);
              ++p;   ++gj; }
    else if (v & UP_BIT )
           { UNMASK(UP_BIT,UP_ARROW);
              p -= IMAGE_X;  --gi; }
    else if (v & DOWN_BIT )
           { UNMASK(DOWN_BIT,DOWN_ARROW);
              p += IMAGE_X;  ++gi; }
    }
    while ( p != p0) ;
    *pcb++ = 0;
    return(len);
}
plot_buf(circle_buf,buf_pointer,color,magni,smooth_d)
        int circle_buf[][2];
{
int i;
int k,l,il,j;
float dividor1 = (smooth_d*2.+1) / (float)magni;
float dividor2 = (smooth_d*2.+1) / (float)magni;
    if (buf_pointer < smooth_d ) { buf_pointer = 0 ; return(0); }
    dline(0,482,0,483,color);
    k = l = 0;
    for (i = -smooth_d ; i <= smooth_d ; ++i )
    {
       if ( i < 0 ) j = buf_pointer+i ; else j = i;
       k += circle_buf[j][0] ;
       l += circle_buf[j][1] ;
    }
    l = (int) ((float)l/dividor1) + DISP_I ;
    k = (int) ((float)k/dividor2) + DISP_J;
    MOVE_ABS(k,l);
    for (il = 1 ; il <= buf_pointer ; ++il)
    {
       k = l = 0;
       for (i=il-smooth_d ; i <= il+smooth_d ; ++i )
       {
          if ( i<0 ) j = buf_pointer+i ;
          else if (i >= buf_pointer ) j = i-buf_pointer ;
          else j = i;
          k += circle_buf[j][0] ; l += circle_buf[j][1] ;
       }
       l = (int) ((float)l/dividor1) + DISP_I;
       k = (int) ((float)k/dividor2) + DISP_J;
       DRAW_ABS(k,l,color);
    }
    buf_pointer = 0;
return(1);
}
touch_frame(i,j,chain_buf)
```

Mar 17 13:01 1993 appl2.c Page 11

```c
            PIXEL far *chain_buf;
{
    for ( ; *chain_buf ; ++chain_buf)
    {
        switch(*chain_buf)
        {
        case UP_ARROW:      --i ; break;
        case DOWN_ARROW:    ++i ; break;
        case LEFT_ARROW:    --j; break;
        case RIGHT_ARROW:   ++j; break;
        default:
            printf ("\n Illegal 2"); exit(0);
        }
        if (j <= 1)
            return(1);
        if (j >= IMAGE_X-2)
            return(2);
        if (i <= 1)
            return(3);
        if (i >= IMAGE_Y-2)
            return(4);
    }
    return(0);
}
long
measure_chain_area(chain_buf)       PIXEL  *chain_buf;
{
long area = 0;
int i = 1000;
char c;
    for ( ; (c = *chain_buf++) ; )
    {
        switch(c)
        {
        case UP_ARROW:      --i; --area;    break;
        case DOWN_ARROW:    ++i; ++area;    break;
        case LEFT_ARROW:    area -= i; break;
        case RIGHT_ARROW:   area += i ; break;
        default:
            printf ("\n Illegal 3"); exit(0);
        }
    }
    return(area);
}
draw_contour_nice(i,j,chain_buf,magni,color)
            int i,j; PIXEL far *chain_buf;
{
int xybuf[1024][2];
int min_i, min_j, max_i, max_j;
    chain_to_raster(i,j,chain_buf,xybuf, &min_i, &min_j, &max_i, &max_j);
    plot_buf(xybuf, strlen(chain_buf),color,magni,3);
}
chain_to_raster(i,j,chain_buf,xybuf,min_ip, min_jp, max_ip, max_jp)
                int i,j; PIXEL far *chain_buf;
                int xybuf[][2];
                int *min_ip, *min_jp, *max_ip, *max_jp;
```

```
Mar 17 13:01 1993  appl2.c Page 12

{
PIXEL far *p;
int ind;
int min_i, min_j, max_i, max_j;
   min_i = INT_MAX;
   min_j = INT_MAX;
   max_i = INT_MIN;
   max_j = INT_MIN;
   ind = 0;
   for ( p = chain_buf; *p ; ++p)
   {
        switch(*p)
        {
        case UP_ARROW:        --i ; break;
        case DOWN_ARROW:      ++i ; break;
        case LEFT_ARROW:      --j; break;
        case RIGHT_ARROW:     ++j ; break;
        default:
           printf ("\n Illegal 1"); exit(0);
        }
     xybuf[ind][0] = i;
     xybuf[ind][1] = j;
     if (i < min_i) min_i = i;
     if (i > max_i) max_i = i;
     if (j < min_j) min_j = j;
     if (j > max_j) max_j = j;
     ++ind;
   }
    *min_ip = min_i; *max_ip = max_i+1;  *min_jp = min_j; *max_jp = max_j+1;
        return(ind);
}
draw_contour(i,j,chain_buf,magni,color)
           int i,j; PIXEL far *chain_buf;
{
PIXEL far *p = &chain_buf[0];
   MOVE_ABS((int)((float)i * magni),(int)((float)j * magni));
   for ( ; *p ; ++p)
   {
        switch(*p)
        {
        case 'U':        --i ; break;
        case 'D':        ++i ; break;
        case 'L':        --j; break;
        case 'R':        ++j ; break;
        default:
           printf ("\n Illegal"); exit(0);
        }
     DRAW_ABS((int)((float)i * magni),(int)((float)j * magni),color);
   }
}
fill_whtg(im,whtg,s_i,s_j,max_i,max_j,level)
    PIXEL im[][IMAGE_X] ;
    PIXEL whtg[][IMAGE_X] ;
    int  level , max_i , max_j ;
{
int i,j;
```

```
Mar 17 13:01 1993  appl2.c Page 13 char mask;
short pix1,pix2,pix3,pix4;
    for (i = s_i ; i < max_i ; ++i)
        for (j = s_j ; j < max_j ; ++j)
        {
            pix1 = im[i-1][j-1] ;
            pix2 = im[i-1][j] ;
            pix3 = im[i][j] ;
            pix4 = im[i][j-1] ;
            mask = 0;
            if ( pix1 >= level && pix2 < level ) mask |= UP_BIT ;
            if ( pix3 >= level && pix4 < level ) mask |= DOWN_BIT ;
            if ( pix4 >= level && pix1 < level ) mask |= LEFT_BIT ;
            if ( pix2 >= level && pix3 < level ) mask |= RIGHT_BIT;
            whtg[i][j] = mask ;
        }
}
find_init_point(px,py,max_i,max_j,whtg)
        int *px,*py;   int max_i,max_j;
        PIXEL whtg[][IMAGE_X];
{
int s_r = *px, s_c = *py;
    for ( ; s_r < max_i ; ++s_r)
        {
        for (; s_c < max_j ; ++s_c)
            {
            if (whtg[s_r][s_c] & ALL_BITS)
                { *px = s_r ; *py = s_c ; return(1);}
            }
        s_c = _begin_j;
        }
return(0);
}
frame_with_zeros(image,x1,y1,x2,y2)
    PIXEL image[][IMAGE_X];
{
int i;
    for (i=x1 ; i < x2 ; ++i)
        {
            image[i][y1] = 0;
            image[i][y2-1] = 0;
        }
    for (i = y1 ; i < y2 ; ++i)
        {
            image[x1][i] = 0;
            image[x2-1][i] = 0;
        }
}
```

APPENDIX H

```c
/*
            ID: 013
            File Name: appl3.c
------------------------------------------------------------------
*/
#ifndef ANSI
#define signed
#endif
typedef unsigned char       UBYTE;
typedef signed char         SBYTE;
typedef unsigned short int  UWORD;
typedef signed short int    SWORD;
typedef unsigned long       ULONG;
typedef signed long         SLONG;
typedef double              FLOAT;
typedef UBYTE FUBYTE;
typedef SBYTE FSBYTE;
typedef UWORD FUWORD;
typedef SWORD FSWORD;
struct _UBY_b_point { UBYTE x; FUBYTE y; };
struct _UWO_b_point { UWORD x; FUBYTE y; };
struct _FLO_b_point { FLOAT x; FUBYTE y; };
struct _til_hbinfo { long hcentroid, height; };
struct _til_hfinfo { double hcentroid, height; } ;
#define min(a,b) ((a)<(b)?(a):(b))
#define max(a,b) ((a)<(b)?(b):(a))
#define FUBYTE_CONVERT(a) (((double) a) / 255.0)
static FUBYTE _UBY_b_ploop (UBYTE var, int n, struct _UBY_b_point *pts);
static FUBYTE _UBY_b_ploop (UBYTE var, int n, struct _UBY_b_point *pts)
{
    register int i;
    FUBYTE _alpha;
    SLONG _tmp;
    SLONG _tmp2;
    if (var < pts->x)
        _alpha = ((FUBYTE) 0);
    else if (var == pts->x)
        _alpha = pts->y;
    else {
        _alpha = ((FUBYTE) 0);
        for (i = 0; i < n - 1; i++, pts++)
            if (var > pts->x && var <= (pts+1)->x) {
                _tmp2 = ((SLONG) (pts+1)->x) - ((SLONG) pts->x);
                _tmp =  ((SLONG) pts->y) * _tmp2 +
                        (((SLONG) var) - ((SLONG) pts->x)) * (((SLONG) (pts+1)->
                _alpha = (FUBYTE) (_tmp / _tmp2);
                break;
            }
    }
    return _alpha;
}
static FUBYTE _UWO_b_ploop (UWORD var, int n, struct _UWO_b_point *pts);
static FUBYTE _UWO_b_ploop (UWORD var, int n, struct _UWO_b_point *pts)
{
    register int i;
    FUBYTE _alpha;
    SLONG _tmp;
    SLONG _tmp2;
    if (var < pts->x)
        _alpha = ((FUBYTE) 0);
    else if (var == pts->x)
        _alpha = pts->y;
    else {
        _alpha = ((FUBYTE) 0);
```

```
            for (i = 0; i < n - 1; i++, pts++)
                if (var > pts->x && var <= (pts+1)->x) {
                    _tmp2 =  ((SLONG) (pts+1)->x) - ((SLONG) pts->x);
                    _tmp =   ((SLONG) pts->y) * _tmp2 +
                             (((SLONG) var) - ((SLONG) pts->x)) * (((SLONG) (pts+1)->
                    _alpha = (FUBYTE) (_tmp / _tmp2);
                    break;
                }
    }
    return _alpha;
}
static FUBYTE _FLO_b_ploop (FLOAT var, int n, struct _FLO_b_point *pts);
static FUBYTE _FLO_b_ploop (FLOAT var, int n, struct _FLO_b_point *pts)
{
    register int i;
    FUBYTE _alpha;
    FLOAT _tmp;
    FLOAT _tmp2;
    if (var < pts->x)
        _alpha = ((FUBYTE) 0);
    else if (var == pts->x)
        _alpha = pts->y;
    else {
        _alpha = ((FUBYTE) 0);
        for (i = 0; i < n - 1; i++, pts++)
            if (var > pts->x && var <= (pts+1)->x) {
                _tmp2 =  (pts+1)->x - pts->x;
                _tmp =   ((double) pts->y) * _tmp2 +
                         (var - pts->x) * (((double) (pts+1)->y) - ((double) pts-
                _alpha = (FUBYTE) (_tmp / _tmp2);
                break;
            }
    }
    return _alpha;
}
FUBYTE _Area_Tiny_b_alpha;
FUBYTE _Area_Small_b_alpha;
FUBYTE _Area_Medium_b_alpha;
FUBYTE _Area_Large_b_alpha;
FUBYTE _Area_Huge_b_alpha;
FUBYTE _AR_Square_b_alpha;
FUBYTE _AR_Bar_b_alpha;
FUBYTE _P2A_Round_b_alpha;
FUBYTE _P2A_Oval_b_alpha;
FUBYTE _P2A_Odd_b_alpha;
FUBYTE _Red_D_Well_b_alpha;
FUBYTE _IR_D_Poor_b_alpha;
FUBYTE _IR_D_Low_b_alpha;
FUBYTE _IR_D_Well_b_alpha;
FUBYTE _FIR_D_Poor_b_alpha;
FUBYTE _FIR_D_Low_b_alpha;
FUBYTE _FIR_D_Medium_b_alpha;
FUBYTE _FIR_D_High_b_alpha;
FUBYTE _FIR_D_VeryHigh_b_alpha;
FUBYTE _Rule0000_alpha;
FUBYTE _Rule0050_alpha;
FUBYTE _Rule0048_alpha;
FUBYTE _Rule0047_alpha;
FUBYTE _Rule0046_alpha;
FUBYTE _Rule0044_alpha;
FUBYTE _Rule0042_alpha;
FUBYTE _Rule0041_alpha;
FUBYTE _Rule0036_alpha;
FUBYTE _Rule0039_alpha;
```

```
FUBYTE _Rule0037_alpha;
FUBYTE _Rule0032_alpha;
FUBYTE _Rule0029_alpha;
FUBYTE _Rule0034_alpha;
FUBYTE _Rule0030_alpha;
FUBYTE _Rule0027_alpha;
FUBYTE _Rule0028_alpha;
FUBYTE _Rule0022_alpha;
FUBYTE _Rule0023_alpha;
FUBYTE _Rule0017_alpha;
FUBYTE _Rule0018_alpha;
FUBYTE _Rule0015_alpha;
FUBYTE _Rule0025_alpha;
FUBYTE _Rule0016_alpha;
FUBYTE _Rule0010_alpha;
FUBYTE _Rule0011_alpha;
FUBYTE _Rule0013_alpha;
FUBYTE _Rule0007_alpha;
FUBYTE _Rule0008_alpha;
FUBYTE _Rule0005_alpha;
FUBYTE _Rule0004_alpha;
FUBYTE _Rule0001_alpha;
FUBYTE _Rule0003_alpha;
static struct _UWO_b_point _Area_Tiny_b_pts[] = {
    { 0x00, 255 },
    { 0x07, 255 },
    { 0x011, 2 }
};
static FUBYTE Area_Tiny_b (UWORD Area);
static FUBYTE Area_Tiny_b (UWORD Area)
{
    _Area_Tiny_b_alpha = _UWO_b_ploop (Area, 3, _Area_Tiny_b_pts);
    return _Area_Tiny_b_alpha;
}
static struct _UWO_b_point _Area_Small_b_pts[] = {
    { 0x07, 1 },
    { 0x015, 255 },
    { 0x01b, 255 },
    { 0x03a, 253 },
    { 0x065, 0 }
};
static FUBYTE Area_Small_b (UWORD Area);
static FUBYTE Area_Small_b (UWORD Area)
{
    _Area_Small_b_alpha = _UWO_b_ploop (Area, 5, _Area_Small_b_pts);
    return _Area_Small_b_alpha;
}
static struct _UWO_b_point _Area_Medium_b_pts[] = {
    { 0x027, 0 },
    { 0x067, 255 },
    { 0x09c, 255 },
    { 0x0e6, 0 }
};
static FUBYTE Area_Medium_b (UWORD Area);
static FUBYTE Area_Medium_b (UWORD Area)
{
    _Area_Medium_b_alpha = _UWO_b_ploop (Area, 4, _Area_Medium_b_pts);
    return _Area_Medium_b_alpha;
}
static struct _UWO_b_point _Area_Large_b_pts[] = {
    { 0x078, 0 },
    { 0x0fb, 253 },
    { 0x0129, 255 },
    { 0x0173, 5 }
```

```
;
static FUBYTE Area_Large_b (UWORD Area);
static FUBYTE Area_Large_b (UWORD Area)
{
    _Area_Large_b_alpha = _UWO_b_ploop (Area, 4, _Area_Large_b_pts);
    return _Area_Large_b_alpha;
}
static struct _UWO_b_point _Area_Huge_b_pts[] = {
    { 0x0118, 0 },
    { 0x0190, 252 },
    { 0x01f4, 255 }
};
static FUBYTE Area_Huge_b (UWORD Area);
static FUBYTE Area_Huge_b (UWORD Area)
{
    _Area_Huge_b_alpha = _UWO_b_ploop (Area, 3, _Area_Huge_b_pts);
    return _Area_Huge_b_alpha;
}
static struct _FLO_b_point _AR_Square_b_pts[] = {
    { 0.000000, 0 },
    { 0.400000, 255 },
    { 1.40000, 255 },
    { 2.20000, 0 }
};
static FUBYTE AR_Square_b (FLOAT AR);
static FUBYTE AR_Square_b (FLOAT AR)
{
    _AR_Square_b_alpha = _FLO_b_ploop (AR, 4, _AR_Square_b_pts);
    return _AR_Square_b_alpha;
}
static struct _FLO_b_point _AR_Bar_b_pts[] = {
    { 2.00000, 0 },
    { 2.40000, 255 },
    { 3.00000, 255 }
};
static FUBYTE AR_Bar_b (FLOAT AR);
static FUBYTE AR_Bar_b (FLOAT AR)
{
    _AR_Bar_b_alpha = _FLO_b_ploop (AR, 3, _AR_Bar_b_pts);
    return _AR_Bar_b_alpha;
}
static struct _til_hbinfo _Out_Stem_Calyx_hbinfo = { 24044L, 1717L };
static struct _til_hbinfo _Out_Rot_hbinfo = { 68699L, 1717L };
static struct _til_hbinfo _Out_LRot_hbinfo = { 171749L, 1717L };
static struct _til_hbinfo _Out_Bruise_hbinfo = { 274798L, 1717L };
static struct _til_hbinfo _Out_PIT_hbinfo = { 326323L, 1717L };
static struct _til_hbinfo _Out_PARLAT_hbinfo = { 377848L, 1717L };
static struct _til_hbinfo _Out_Nothing_hbinfo = { 417565L, 1717L };
static struct _FLO_b_point _P2A_Round_b_pts[] = {
    { 0.0114155, 255 },
    { 1.61644, 255 },
    { 2.33105, 0 }
};
static FUBYTE P2A_Round_b (FLOAT P2A);
static FUBYTE P2A_Round_b (FLOAT P2A)
{
    _P2A_Round_b_alpha = _FLO_b_ploop (P2A, 3, _P2A_Round_b_pts);
    return _P2A_Round_b_alpha;
}
static struct _FLO_b_point _P2A_Oval_b_pts[] = {
    { 1.68379, 0 },
    { 2.59132, 255 },
    { 4.00000, 255 },
    { 5.62671, 0 }
```

```
};
static FUBYTE P2A_Oval_b (FLOAT P2A);
static FUBYTE P2A_Oval_b (FLOAT P2A)
{
    _P2A_Oval_b_alpha = _FLO_b_ploop (P2A, 4, _P2A_Oval_b_pts);
    return _P2A_Oval_b_alpha;
}
static struct _FLO_b_point _P2A_Odd_b_pts[] = {
    { 3.68037, 1 },
    { 5.43721, 255 },
    { 11.9863, 255 }
};
static FUBYTE P2A_Odd_b (FLOAT P2A);
static FUBYTE P2A_Odd_b (FLOAT P2A)
{
    _P2A_Odd_b_alpha = _FLO_b_ploop (P2A, 3, _P2A_Odd_b_pts);
    return _P2A_Odd_b_alpha;
}
static struct _UBY_b_point _Red_D_Well_b_pts[] = {
    { 28, 0 },
    { 36, 255 },
    { 80, 255 }
};
static FUBYTE Red_D_Well_b (UBYTE Red_D);
static FUBYTE Red_D_Well_b (UBYTE Red_D)
{
    _Red_D_Well_b_alpha = _UBY_b_ploop (Red_D, 3, _Red_D_Well_b_pts);
    return _Red_D_Well_b_alpha;
}
static struct _UBY_b_point _IR_D_Poor_b_pts[] = {
    { 0, 255 },
    { 2, 255 },
    { 8, 0 }
};
static FUBYTE IR_D_Poor_b (UBYTE IR_D);
static FUBYTE IR_D_Poor_b (UBYTE IR_D)
{
    _IR_D_Poor_b_alpha = _UBY_b_ploop (IR_D, 3, _IR_D_Poor_b_pts);
    return _IR_D_Poor_b_alpha;
}
static struct _UBY_b_point _IR_D_Low_b_pts[] = {
    { 4, 0 },
    { 10, 255 },
    { 14, 255 },
    { 22, 0 }
};
static FUBYTE IR_D_Low_b (UBYTE IR_D);
static FUBYTE IR_D_Low_b (UBYTE IR_D)
{
    _IR_D_Low_b_alpha = _UBY_b_ploop (IR_D, 4, _IR_D_Low_b_pts);
    return _IR_D_Low_b_alpha;
}
static struct _UBY_b_point _IR_D_Well_b_pts[] = {
    { 12, 0 },
    { 24, 255 },
    { 80, 255 }
};
static FUBYTE IR_D_Well_b (UBYTE IR_D);
static FUBYTE IR_D_Well_b (UBYTE IR_D)
{
    _IR_D_Well_b_alpha = _UBY_b_ploop (IR_D, 3, _IR_D_Well_b_pts);
    return _IR_D_Well_b_alpha;
}
static struct _UBY_b_point _FIR_D_Poor_b_pts[] = {
```

```
    { 0, 255 },
    { 2, 255 },
    { 10, 0 }
};
static FUBYTE FIR_D_Poor_b (UBYTE FIR_D);
static FUBYTE FIR_D_Poor_b (UBYTE FIR_D)
{
    _FIR_D_Poor_b_alpha = _UBY_b_ploop (FIR_D, 3, _FIR_D_Poor_b_pts);
    return _FIR_D_Poor_b_alpha;
}
static struct _UBY_b_point _FIR_D_Low_b_pts[] = {
    { 4, 0 },
    { 10, 255 },
    { 18, 255 },
    { 24, 0 }
};
static FUBYTE FIR_D_Low_b (UBYTE FIR_D);
static FUBYTE FIR_D_Low_b (UBYTE FIR_D)
{
    _FIR_D_Low_b_alpha = _UBY_b_ploop (FIR_D, 4, _FIR_D_Low_b_pts);
    return _FIR_D_Low_b_alpha;
}
static struct _UBY_b_point _FIR_D_Medium_b_pts[] = {
    { 18, 0 },
    { 26, 255 },
    { 34, 255 },
    { 44, 0 }
};
static FUBYTE FIR_D_Medium_b (UBYTE FIR_D);
static FUBYTE FIR_D_Medium_b (UBYTE FIR_D)
{
    _FIR_D_Medium_b_alpha = _UBY_b_ploop (FIR_D, 4, _FIR_D_Medium_b_pts);
    return _FIR_D_Medium_b_alpha;
}
static struct _UBY_b_point _FIR_D_High_b_pts[] = {
    { 32, 0 },
    { 46, 255 },
    { 54, 255 },
    { 66, 0 }
};
static FUBYTE FIR_D_High_b (UBYTE FIR_D);
static FUBYTE FIR_D_High_b (UBYTE FIR_D)
{
    _FIR_D_High_b_alpha = _UBY_b_ploop (FIR_D, 4, _FIR_D_High_b_pts);
    return _FIR_D_High_b_alpha;
}
static struct _UBY_b_point _FIR_D_VeryHigh_b_pts[] = {
    { 50, 0 },
    { 60, 255 },
    { 80, 255 }
};
static FUBYTE FIR_D_VeryHigh_b (UBYTE FIR_D);
static FUBYTE FIR_D_VeryHigh_b (UBYTE FIR_D)
{
    _FIR_D_VeryHigh_b_alpha = _UBY_b_ploop (FIR_D, 3, _FIR_D_VeryHigh_b_pts);
    return _FIR_D_VeryHigh_b_alpha;
}
static void B_Classifier (FLOAT AR, UWORD Area, UBYTE FIR_D, UBYTE FIR_V, UBYTE G
static void B_Classifier (FLOAT AR, UWORD Area, UBYTE FIR_D, UBYTE FIR_V, UBYTE G
{
    FUBYTE _alpha;
    FUBYTE _AR_is_Square;
    FUBYTE _AR_is_Bar;
    FUBYTE _Area_is_Tiny;
```

```
FUBYTE _Area_is_Small;
FUBYTE _Area_is_Medium;
FUBYTE _Area_is_Large;
FUBYTE _Area_is_Huge;
FUBYTE _FIR_D_is_Poor;
FUBYTE _FIR_D_is_Low;
FUBYTE _FIR_D_is_Medium;
FUBYTE _FIR_D_is_High;
FUBYTE _FIR_D_is_VeryHigh;
FUBYTE _IR_D_is_Low;
FUBYTE _IR_D_is_Well;
FUBYTE _P2A_is_Round;
FUBYTE _P2A_is_Odd;
FUBYTE _Red_D_is_Well;
struct _til_hbinfo _Out_temp;
memset (&_Out_temp, 0, sizeof (_Out_temp));
_AR_is_Square = AR_Square_b (AR);
_AR_is_Bar = AR_Bar_b (AR);
_Area_is_Tiny = Area_Tiny_b (Area);
_Area_is_Small = Area_Small_b (Area);
_Area_is_Medium = Area_Medium_b (Area);
_Area_is_Large = Area_Large_b (Area);
_Area_is_Huge = Area_Huge_b (Area);
_FIR_D_is_Poor = FIR_D_Poor_b (FIR_D);
_FIR_D_is_Low = FIR_D_Low_b (FIR_D);
_FIR_D_is_Medium = FIR_D_Medium_b (FIR_D);
_FIR_D_is_High = FIR_D_High_b (FIR_D);
_FIR_D_is_VeryHigh = FIR_D_VeryHigh_b (FIR_D);
_IR_D_is_Low = IR_D_Low_b (IR_D);
_IR_D_is_Well = IR_D_Well_b (IR_D);
_P2A_is_Round = P2A_Round_b (P2A);
_P2A_is_Odd = P2A_Odd_b (P2A);
_Red_D_is_Well = Red_D_Well_b (Red_D);
_alpha = min(_Area_is_Tiny, _FIR_D_is_VeryHigh);
if (_alpha != ((FUBYTE) 0)) {
    /* Out = PIT */
    _Out_temp.hcentroid += _alpha * _Out_PIT_hbinfo.hcentroid;
    _Out_temp.height += _alpha * _Out_PIT_hbinfo.height;
}
_Rule0000_alpha = _alpha;
_alpha = min(min(min(_Area_is_Small, _FIR_D_is_Low), _AR_is_Bar), _IR_D_is_We
if (_alpha != ((FUBYTE) 0)) {
    _Out_temp.hcentroid += _alpha * _Out_Stem_Calyx_hbinfo.hcentroid;
    _Out_temp.height += _alpha * _Out_Stem_Calyx_hbinfo.height;
}
_Rule0050_alpha = _alpha;
_alpha = min(min(min(_Area_is_Small, _AR_is_Square), _FIR_D_is_Poor), _P2
if (_alpha != ((FUBYTE) 0)) {
    _Out_temp.hcentroid += _alpha * _Out_PARLAT_hbinfo.hcentroid;
    _Out_temp.height += _alpha * _Out_PARLAT_hbinfo.height;
}
_Rule0048_alpha = _alpha;
_alpha = min(min(min(min(_Area_is_Huge, _AR_is_Square), _FIR_D_is_Poor),
if (_alpha != ((FUBYTE) 0)) {
    _Out_temp.hcentroid += _alpha * _Out_Bruise_hbinfo.hcentroid;
    _Out_temp.height += _alpha * _Out_Bruise_hbinfo.height;
}
_Rule0047_alpha = _alpha;
_alpha = min(min(min(_Area_is_Large, _FIR_D_is_Poor), _AR_is_Square), _IR
if (_alpha != ((FUBYTE) 0)) {
    _Out_temp.hcentroid += _alpha * _Out_Bruise_hbinfo.hcentroid;
    _Out_temp.height += _alpha * _Out_Bruise_hbinfo.height;
}
_Rule0046_alpha = _alpha;
```

```
_alpha = min(min(min(_Area_is_Huge, _FIR_D_is_Poor), _AR_is_Square), _P2A_is_
if (_alpha != ((FUBYTE) 0)) {
    _Out_temp.hcentroid += _alpha * _Out_Bruise_hbinfo.hcentroid;
    _Out_temp.height += _alpha * _Out_Bruise_hbinfo.height;
}
_Rule0044_alpha = _alpha;
_alpha = min(min(min(_Area_is_Medium, _FIR_D_is_Low), _IR_D_is_Well), _P2A
if (_alpha != ((FUBYTE) 0)) {
    _Out_temp.hcentroid += _alpha * _Out_Rot_hbinfo.hcentroid;
    _Out_temp.height += _alpha * _Out_Rot_hbinfo.height;
}
_Rule0042_alpha = _alpha;
_alpha = min(min(min(_Area_is_Small, _FIR_D_is_Poor), _IR_D_is_Well), _P2
if (_alpha != ((FUBYTE) 0)) {
    _Out_temp.hcentroid += _alpha * _Out_Bruise_hbinfo.hcentroid;
    _Out_temp.height += _alpha * _Out_Bruise_hbinfo.height;
}
_Rule0041_alpha = _alpha;
_alpha = min(min(min(_Area_is_Medium, _AR_is_Square), _FIR_D_is_Poor), _I
if (_alpha != ((FUBYTE) 0)) {
    _Out_temp.hcentroid += _alpha * _Out_Bruise_hbinfo.hcentroid;
    _Out_temp.height += _alpha * _Out_Bruise_hbinfo.height;
}
_Rule0036_alpha = _alpha;
_alpha = min(_Area_is_Tiny, _FIR_D_is_Medium);
if (_alpha != ((FUBYTE) 0)) {
    _Out_temp.hcentroid += _alpha * _Out_PIT_hbinfo.hcentroid;
    _Out_temp.height += _alpha * _Out_PIT_hbinfo.height;
}
_Rule0039_alpha = _alpha;
_alpha = min(min(min(_Area_is_Medium, _AR_is_Square), _FIR_D_is_Low), _IR
if (_alpha != ((FUBYTE) 0)) {
    _Out_temp.hcentroid += _alpha * _Out_Bruise_hbinfo.hcentroid;
    _Out_temp.height += _alpha * _Out_Bruise_hbinfo.height;
}
_Rule0037_alpha = _alpha;
_alpha = min(min(min(_Area_is_Huge, _AR_is_Square), _FIR_D_is_Poor), _IR_
if (_alpha != ((FUBYTE) 0)) {
    _Out_temp.hcentroid += _alpha * _Out_Bruise_hbinfo.hcentroid;
    _Out_temp.height += _alpha * _Out_Bruise_hbinfo.height;
}
_Rule0032_alpha = _alpha;
_alpha = min(min(min(_Area_is_Large, _AR_is_Square), _FIR_D_is_Low), _IR_
if (_alpha != ((FUBYTE) 0)) {
    /* Out = Bruise */
    _Out_temp.hcentroid += _alpha * _Out_Bruise_hbinfo.hcentroid;
    _Out_temp.height += _alpha * _Out_Bruise_hbinfo.height;
}
_Rule0029_alpha = _alpha;
_alpha = min(min(min(_Area_is_Huge, _AR_is_Square), _FIR_D_is_Low), _IR_D_is_
if (_alpha != ((FUBYTE) 0)) {
    /* Out = Bruise */
    _Out_temp.hcentroid += _alpha * _Out_Bruise_hbinfo.hcentroid;
    _Out_temp.height += _alpha * _Out_Bruise_hbinfo.height;
}
_Rule0034_alpha = _alpha;
_alpha = min(min(min(_Area_is_Large, _AR_is_Square), _FIR_D_is_Poor), _IR
if (_alpha != ((FUBYTE) 0)) {
    /* Out = Bruise */
    _Out_temp.hcentroid += _alpha * _Out_Bruise_hbinfo.hcentroid;
    _Out_temp.height += _alpha * _Out_Bruise_hbinfo.height;
}
_Rule0030_alpha = _alpha;
_alpha = min(min(_Area_is_Medium, _FIR_D_is_High), ((FUBYTE) 255) - _AR_is_Ba
```

```
if (_alpha != ((FUBYTE) 0)) {
    _Out_temp.hcentroid += _alpha * _Out_Rot_hbinfo.hcentroid;
    _Out_temp.height += _alpha * _Out_Rot_hbinfo.height;
}
_Rule0027_alpha = _alpha;
_alpha = min(_Area_is_Medium, _FIR_D_is_VeryHigh);
if (_alpha != ((FUBYTE) 0)) {
    _Out_temp.hcentroid += _alpha * _Out_Rot_hbinfo.hcentroid;
    _Out_temp.height -= _alpha * _Out_Rot_hbinfo.height;
}
_Rule0028_alpha = _alpha;
_alpha = min(_Area_is_Small, _FIR_D_is_Poor);
if (_alpha != ((FUBYTE) 0)) {
    /* Out = Nothing */
    _Out_temp.hcentroid += _alpha * _Out_Nothing_hbinfo.hcentroid;
    _Out_temp.height += _alpha * _Out_Nothing_hbinfo.height;
}
_Rule0022_alpha = _alpha;
_alpha = min(min(min(_Area_is_Small, _FIR_D_is_Low), _IR_D_is_Well), _P2A_is_
if (_alpha != ((FUBYTE) 0)) {
    _Out_temp.hcentroid += _alpha * _Out_PIT_hbinfo.hcentroid;
    _Out_temp.height += _alpha * _Out_PIT_hbinfo.height;
}
_Rule0023_alpha = _alpha;
_alpha = min(_Area_is_Tiny, _FIR_D_is_Poor);
if (_alpha != ((FUBYTE) 0)) {
    _Out_temp.hcentroid += _alpha * _Out_Nothing_hbinfo.hcentroid;
    _Out_temp.height += _alpha * _Out_Nothing_hbinfo.height;
}
_Rule0017_alpha = _alpha;
_alpha = min(min(min(_Area_is_Tiny, _FIR_D_is_Low), _IR_D_is_Well), _P2A_is_R
if (_alpha != ((FUBYTE) 0)) {
    _Out_temp.hcentroid += _alpha * _Out_PIT_hbinfo.hcentroid;
    _Out_temp.height += _alpha * _Out_PIT_hbinfo.height;
}
_Rule0018_alpha = _alpha;
_alpha = min(min(_Area_is_Large, _FIR_D_is_Medium), ((FUBYTE) 255) - _P2A_is_
if (_alpha != ((FUBYTE) 0)) {
    _Out_temp.hcentroid += _alpha * _Out_LRot_hbinfo.hcentroid;
    _Out_temp.height += _alpha * _Out_LRot_hbinfo.height;
}
_Rule0015_alpha = _alpha;
_alpha = min(min(_Area_is_Tiny, _FIR_D_is_Low), ((FUBYTE) 255) - _P2A_is_Roun
if (_alpha != ((FUBYTE) 0)) {
    _Out_temp.hcentroid += _alpha * _Out_Nothing_hbinfo.hcentroid;
    _Out_temp.height += _alpha * _Out_Nothing_hbinfo.height;
}
_Rule0025_alpha = _alpha;
_alpha = min(min(_Area_is_Huge, _FIR_D_is_Medium), ((FUBYTE) 255) - _P2A_is_O
if (_alpha != ((FUBYTE) 0)) {
    _Out_temp.hcentroid += _alpha * _Out_LRot_hbinfo.hcentroid;
    _Out_temp.height += _alpha * _Out_LRot_hbinfo.height;
}
_Rule0016_alpha = _alpha;
_alpha = min(min(_Area_is_Large, _FIR_D_is_High), ((FUBYTE) 255) - _P2A_i
if (_alpha != ((FUBYTE) 0)) {
    _Out_temp.hcentroid += _alpha * _Out_LRot_hbinfo.hcentroid;
    _Out_temp.height += _alpha * _Out_LRot_hbinfo.height;
}
_Rule0010_alpha = _alpha;
_alpha = min(min(_Area_is_Large, _FIR_D_is_VeryHigh), ((FUBYTE) 255) - _P2A_i
if (_alpha != ((FUBYTE) 0)) {
    _Out_temp.hcentroid += _alpha * _Out_LRot_hbinfo.hcentroid;
    _Out_temp.height += _alpha * _Out_LRot_hbinfo.height;
}
```

```
    }
    _Rule0011_alpha = _alpha;
    _alpha = min(min(min(_Area_is_Huge, _FIR_D_is_High), ((FUBYTE) 255) - _P2A_is
    if (_alpha != ((FUBYTE) 0)) {
        _Out_temp.hcentroid += _alpha * _Out_LRot_hbinfo.hcentroid;
        _Out_temp.height += _alpha * _Out_LRot_hbinfo.height;
    }
    _Rule0013_alpha = _alpha;
    _alpha = min(_Area_is_Tiny, _FIR_D_is_High);
    if (_alpha != ((FUBYTE) 0)) {
        _Out_temp.hcentroid += _alpha * _Out_PIT_hbinfo.hcentroid;
        _Out_temp.height += _alpha * _Out_PIT_hbinfo.height;
    }
    _Rule0007_alpha = _alpha;
    _alpha = min(min(_Area_is_Small, _FIR_D_is_High), ((FUBYTE) 255) - _AR_is_Bar
    if (_alpha != ((FUBYTE) 0)) {
        _Out_temp.hcentroid += _alpha * _Out_PIT_hbinfo.hcentroid;
        _Out_temp.height += _alpha * _Out_PIT_hbinfo.height;
    }
    _Rule0008_alpha = _alpha;
    _alpha = min(min(min(_Area_is_Huge, _FIR_D_is_VeryHigh), ((FUBYTE) 255) - _P2
    if (_alpha != ((FUBYTE) 0)) {
        _Out_temp.hcentroid += _alpha * _Out_LRot_hbinfo.hcentroid;
        _Out_temp.height += _alpha * _Out_LRot_hbinfo.height;
    }
    _Rule0005_alpha = _alpha;
    _alpha = min(min(min(_Area_is_Medium, _AR_is_Square), _FIR_D_is_Medium), ((FU
    if (_alpha != ((FUBYTE) 0)) {
        _Out_temp.hcentroid += _alpha * _Out_LRot_hbinfo.hcentroid;
        _Out_temp.height += _alpha * _Out_LRot_hbinfo.height;
    }
    _Rule0004_alpha = _alpha;
    _alpha = min(_Area_is_Small, _FIR_D_is_VeryHigh);
    if (_alpha != ((FUBYTE) 0)) {
        _Out_temp.hcentroid += _alpha * _Out_PIT_hbinfo.hcentroid;
        _Out_temp.height += _alpha * _Out_PIT_hbinfo.height;
    }
    _Rule0001_alpha = _alpha;
    _alpha = min(min(min(_Area_is_Small, _FIR_D_is_Medium), ((FUBYTE) 255) -
    if (_alpha != ((FUBYTE) 0)) {
        _Out_temp.hcentroid += _alpha * _Out_PIT_hbinfo.hcentroid;
        _Out_temp.height += _alpha * _Out_PIT_hbinfo.height;
    }
    _Rule0003_alpha = _alpha;
    if (_Out_temp.height != 0L)
        *Out = ((UBYTE) (_Out_temp.hcentroid / _Out_temp.height));
}
void Blemish_Class (FLOAT AR, UWORD Area, UBYTE FIR_D, UBYTE FIR_V, UBYTE Green_D
{
    B_Classifier (AR, Area, FIR_D, FIR_V, Green_D, Green_V, IR_D, IR_V, P2A, Red_
}
```

APPENDIX I

```
/*
                                ID: 014
    File name: appl4.c
-----------------------------------------------------------------------
*/
int test_fl_decisions(unsigned char *, double *, int);
#include <fcntl.h>
#include <malloc.h>
#include <stdio.h>
#include <limits.h>
#include <conio.h>
#include <string.h>
#include <memory.h>
#include <math.h>
#include "adapter.h"
#define D_ST_CA      12
#define D_ROT        45
#define D_MOTH       65
#define D_LROT       101
#define D_RUSSET     131
#define D_BRUISE     161
#define D_PIT        191
#define D_PARLAT     220
#define D_NOTHING    241
#define BLEMISH_KINDS_N 9
int     combine_all_masks(PIXEL [FR_Y_SIZE][FR_X_SIZE],
                                                      PIXEL [FR_Y_SIZE][FR
int     cancel_color(PIXEL[FR_Y_SIZE][FR_X_SIZE],int );
int     combine_masks( PIXEL [FR_Y_SIZE][FR_X_SIZE],
                                          PIXEL *);
int     do_3dfile(char *,struct boundary_data *, struct boundary_data *,
                struct boundary_data *,PIXEL [FR_Y_SIZE][FR_X_SIZE],
                PIXEL [FR_Y_SIZE][FR_X_SIZE],PIXEL [FR_Y_SIZE][FR_X_SIZE],
                PIXEL [FR_Y_SIZE][FR_X_SIZE],double *);
int     smooth_bnd(struct boundary_data *);
int     make_draw_file(char *,struct boundary_data *, struct boundary_data *,
                struct boundary_data *,PIXEL [FR_Y_SIZE][FR_X_SIZE],
                                          PIXEL [FR_Y_SIZE][FR_X_SIZE],PIXE
                double *);
double  draw_all(struct boundary_data *, struct boundary_data *,
                struct boundary_data *,PIXEL [FR_X_SIZE][FR_Y_SIZE],
                PIXEL [FR_X_SIZE][FR_Y_SIZE],
                                PIXEL [FR_X_SIZE][FR_Y_SIZE],int *);
double  compute_line_all(int *, int *, int *,int *,int *,int *,int *);
double  compute_line_area(int *, int *, int *,int *,int *);
int     find_3d_location( int, int, int,float *,float *,float *,
                        struct boundary_data *, struct boundary_data *,
                        struct boundary_data *,int *);
double  calc_blemish_area(int ,int ,int ,int ,int ,
                        struct boundary_data *, struct boundary_data *,
                        struct boundary_data *,int *);
int     make_line_drawing(int *,int *,int *,int *,int *,PIXEL [FR_X_SIZE],
                        PIXEL [FR_X_SIZE],PIXEL [FR_X_SIZE],double);
void    imagin_stem_calix_coord(struct boundary_data *,struct boundary_data *,
                        struct boundary_data *,float *,float *,int *);
void    validate_in_pic(int *,int *,int *,int *,
        struct    boundary_data *,int);
double  calc_area_ratio(int ,int *,int *,int ,struct  boundary_data *,
                        struct boundary_data *,struct boundary_data *,
                        int *,int);
void insert_img(struct spot *, double, double, double);
double angle_between_n(double, double, double, double, double, double,double *);
#define CHAIN_SIZE 2048
#define CAM 1
```

```
#define DELTA 4
#define MIN_DIST 0.7
#define MIN_ANGLE 140
#define MIN_IR  160
#define MIN_FIR 170
#define MIN_ST_AREA 19
static int   _cam_number;
extern   int stem_index, calyx_index;
extern int debug_flag;
extern struct prog_settings prog_consts;
extern struct single_view_info  view_info[N_CAMERAS];
malv_fill_contour(contour, color, min_i, max_i, min_j, max_j)
      int min_i, max_i, min_j, max_j;
      PIXEL contour[FR_Y_SIZE][FR_X_SIZE];
      int color;

{
int i, j;
PIXEL string[FR_X_SIZE];
      for (i = min_i-1; i <= max_i+1; i++)
        {
          for (j = 0; j < FR_X_SIZE; j++)
             string[j] = 0;
          for (j = min_j-1 ;
                contour[i][j] != 85   && j <= max_j+1 ; ++j)
              {
                if ( (contour[i][j] ==76) || (contour[i][j] == 68) || (contour[i][
                   contour[i][j] = color;
                }
                if (j <= max_j)
                 {
                   contour[i][j] = color;
                   string_color (i,j, max_j, contour, string, color);
                 }
          for (j = 0; j < FR_X_SIZE; j++)
              {
                if ( string[j]  !=  0 )
                    contour[i][j] =  string[j];
              }
         }
         fill_string_black( contour, color,min_i, max_i, min_j, max_j);
    return(1);
}
string_color(i0, j0,max_j, contour, filled, color)
      Int i0, j0, max_j, color;
      PIXEL contour[FR_Y_SIZE][FR_X_SIZE];
      PIXEL filled[FR_X_SIZE];
{
int j, jbeg, j1;
      j= j0;
      jbeg = j;
         while ( (contour[i0][j] != 68) && ( j <= max_j))
            {
              if (contour[i0][j] == 85)    jbeg = j;
              if ( (contour[i0][j] ==76) || (contour[i0][j] == 68) || (contour[i
                 contour[i0][j] = color;
                 j++;
              }
         if (j > max_j)    return (-1);
         for (j1 = jbeg; j1 <= j ; j1++)
              filled[j1] = color;
         jbeg = j;
         while ( (contour[i0][j] != 85) && ( j <= max_j))
            {
              if ((contour[i0][j] == 68))
```

```
                {
                for (j1 = jbeg; j1 < j+1 ; j1++)
                   filled[j1] = color;
                }
                if(( (contour[i0][j] == 76)|| (contour[i0][j] == 82)))
                   {
                      filled[j] = color;
                      jbeg = j;
                   }
                j++;
             }
             if (j > max_j)   return (0);
       contour[i0][j] = color;
       string_color (i0,j, max_j, contour, filled, color);
       return(2);
}
fill_string_black ( filled, color, min_i, max_i, min_j, max_j)
       int min_i, max_i, min_j, max_j, color;
       PIXEL filled[FR_Y_SIZE][FR_X_SIZE];
{
int i,j ;
int color3 = 3*color;
int color2 = 2*color;
          for ( i = max_i-1; i > min_i; i--)
             {
                for ( j = max_j-1; j > min_j; j--)
                   {
                      if ( filled [i][j] == 0)
                      {
                      if ((( filled[i-1][j+1] + filled[i][j+1] + filled[i+1][j+1])
                                          == color3)       &&
                           ((filled[i-1][j] +filled[i+1][j])
                                          == color2))
                         filled[i][j] = (PIXEL)color;
                      }
                   }
             }
     return (1);
}
draw_contour_mem(mat, i, j, chain_buf, color)
             PIXEL mat[][FR_X_SIZE];
             int i,j;    char far *chain_buf;
{
char *p = &chain_buf[0];
    for ( ; *p ; ++p)
    {
       switch(*p)
         {
       case 'U':        --i ;    break;
       case 'D':         ++i ;   break;
       case 'L':        --j; break;
       case 'R':        ++j ; break;
       default:
           printf ("\n Illegal"); exit(0);
         }
       mat[i][j] =  *p;
    }
}
print_contour_data(spots, index, id)
      struct spot spots[];
{
double a1, b1;
    printf("\n contour ID %3d,  New ID: %3d",
                              id, spots[index].flag3);
```

```c
    printf ("\ngreen   %4d  %4d ",
        spots[index].green_cgl, spots[index].g_ar_mean);
    printf ("\nred     %4d  %4d ",
        spots[index].red_cgl, spots[index].r_ar_mean);
    printf ("\nir      %4d  %4d ",
        spots[index].ir_cgl, spots[index].i_ar_mean);
    printf ("\ngrid    %4d  %4d ",
        spots[index].grid_cgl, spots[index].grid_ar_mean);
    printf("\n\t\tarea   per    x    y     p2a    d1/d2    ar  occ_ar s_spot fl");
        a1 = (spots[index].a1 > spots[index].b1) ? spots[index].a1 : spots[index].b
        b1 = (spots[index].a1 < spots[index].b1) ? spots[index].a1 : spots[index].b
    printf("\n\t\t %4d  %4d %4d %4d  %5.2f  %5.2f  %5.2f %5.2f  %3d   %3d\n",
        spots[index].area,
        spots[index].per,
        spots[index].a1,
        spots[index].b1,
        spots[index].p2a,
        0.0,
        spots[index].ar,
        (double)(spots[index].area)/(double)(a1*b1),
        spots[index].flag1,
        spots[index].flag_g);
}
test_overlap(spot1, spot2)     struct spot *spot1, *spot2;
{
double f;
    if   ( (spot1->min_i <= spot2->min_i  &&  spot1->max_i >= spot2->max_i) &&
          (spot1->min_j <= spot2->min_j  &&  spot1->max_j >= spot2->max_j) )
        {
        f = (double)spot1->area / (double)spot2->area;
        if (f < 1.0) f = 1./f;
        if (f > 2.0) return(3);
        else return(1);
        }
    return(0);
}
display_all_selected(spots, spt_index, cam_number)
        struct spot spots[];
{
int i;
    printf("\n Findings:");
    for (i = 0 ; i < spt_index ; ++i)
        {
        if (spots[i].flag2 == 0) continue;
        if (debug_flag)
            draw_contour_file(&spots[i], i, 0, cam_number, 3, 0, 0);
        printf(" %2d)",i);
        switch(spots[i].flag2)
            {
            case D_ST_CA  : printf(" ST_CA");   break;
            case D_ROT    : printf(" ROT");     break;
            case D_MOTH   : printf(" MOTH");    break;
            case D_LROT   : printf(" LROT");    break;
            case D_RUSSET : printf(" RUSSET");  break;
            case D_BRUISE : printf(" BRUISE");  break;
            case D_PIT    : printf(" PIT");     break;
            case D_PARLAT : printf(" PARLAT");  break;
            case D_NOTHING: printf(" NOTHING"); break;
            }
        }
}
choose_defects_by_severity(spots, spt_index, cam_number)
    struct spot spots[];
{
```

```
int i, j;
    for (i = 0 ; i < spt_index ; ++i)
       {
           if (spots[i].cam_number != cam_number) continue;
           if (spots[i].flag1 == 0) continue;
           if (spots[i].flag2 == 0) continue;
           if (1 || spots[i].flag2 == D_ROT || spots[i].flag2 == D_LROT ||
              spots[i].flag2 == D_PIT)
                 {
                     cancel_occluding_contours_type(spots, i, D_ROT, D_LROT, D_PIT, D_S
                 }
       }
#ifdef AAA
    for (i = 0 ; i < spt_index ; ++i)
        {
            if (spots[i].flag1 == 0) continue;
            if (spots[i].flag2 == 0) continue;
            if (spots[i].flag2 == D_BRUISE)
                {
                    cancel_occluding_contours_type(spots, i, D_BRUISE, 0, 0, 0, spt_in
                }
        }
#endif
    for (i = 0 ; i < spt_index ; ++i)
        {
            if (spots[i].flag1 == 0) continue;
            if (spots[i].flag2 == 0) continue;
                cancel_remained(spots, i, 0, 0, 0, 0, spt_index);
        }
        display_all_selected(spots, spt_index, cam_number);
}
cancel_remained(spots, i, t1, t2, t3, t4, spt_index)
        struct spot spots[];
{
int j, ovlp;
 return(1);
        if (spots[i].flag1 == 0 || spots[i].flag1 >= 100) return(1);
        for (j = 0 ; j < i ; ++j)
            {
                if (spots[j].flag2 == 0) continue;
                if (spots[j].flag1 == 0 || spots[j].flag1 >= 100) continue;
                ovlp = test_overlap(&spots[j], &spots[i]);
                if (ovlp) (
                              spots[j].flag2 = 0 ;
                          }
            }
}
cancel_occluding_contours_type(spots, i, t1, t2, t3, t4, spt_index)
        struct spot spots[];
{
int j, ovlp;
        if (spots[i].flag1 == 0 || spots[i].flag1 >= 100) return(1);
        for (j = 0 ; j < i ; ++j)
            {
                if (spots[j].flag1 == 0 || spots[j].flag1 >= 100) continue;
                if (spots[j].flag2 == 0) continue;
                ovlp = test_overlap(&spots[j], &spots[i]);
                if (ovlp == 3) continue;
                if (ovlp) {
                              if (spots[i].mate > spots[j].mate) {
                                  spots[j].flag2 = 0 ;
                                  spots[j].flag3 = i;
                              }
                              else      {
```

```
                                        spots[i].flag2 = 0 ;
                                        spots[i].flag3 = j;
                                        break;
                    }
                }
        }
}
group_occluding(spots, spt_index)
        struct spot spots[];
{
int i, j;
    for (i = 0 ; i < spt_index ; ++i)
        {
            if (spots[i].flag1 == 0) continue;
            if (spots[i].flag2 == 0) continue;
            for (j = 0 ; j < spt_index ; ++j)
                {
                    if (spots[j].flag2 == 0) continue;
                    if (j == i) continue;
                    if (test_overlap(&spots[i], &spots[j]))
                                        spots[j].flag2 = 0;
                }
        }
}
draw_contour_file(spot, id, color, cam_number, magni, off_x, off_y)
            struct spot *spot;
{
int j, ret, per;
char c_name[80];
char chain[CHAIN_SIZE];
    sprintf(c_name, "%s%ld_%ld.cnt", TMP_DEVICE, cam_number, id);
    ret = undump_spots(c_name, chain, sizeof(chain), &per);
    if (ret == FAILURE) {
                printf("\nContour file %s not found", c_name); return(1);
                }
    draw_contour_nice(spot->start_i+off_y, spot->start_j+off_x,
                                    chain, magni, color );
}
undump_spots(name, buf, size, count)         unsigned int size; char *buf;
                                             int *count; char *name;
{
int in_file;
unsigned int br;
        in_file = open(name, (O_RDONLY | O_BINARY), 0 );
        if (in_file == -1) return(FAILURE);
        br = read(in_file, buf, size);
        if (br != size) {       close(in_file);    return(FAILURE);  }
        br = read(in_file, count, sizeof(int));
        if (br != sizeof(int)) {        close(in_file);    return(FAILURE);  }
        close(in_file);
      return(SUCCESS);
}
decide_about_contour(spots, index, draw_flag, cam_number)
            struct spot spots[]; int index;
{
double   AR, P2A, a1, b1, belief;
unsigned short Area;
PIXEL FIR_D, Green_D, IR_D, Red_D, Out;
PIXEL FIR_V, Green_V, IR_V, Red_V;
int d;
    a1 = (spots[index].a1 > spots[index].b1 ? spots[index].a1 : spots[index].b1)
    b1 = (spots[index].a1 < spots[index].b1 ? spots[index].a1 : spots[index].b1)
   AR = ( (b1 != 0) ? (double)(a1)/(double)(b1) : 0 );
   if (AR > 10.) {
```

```
        spots[index].flag2 = 0;
        return(D_NOTHING);
      }
   if (AR > 3.0) AR = 3.0;
   Area = spots[index].area;
   if (Area > 500) Area = 500;
#define MALUS 0
#define GRAD_FILL(v1, v2, res) d=v1-v2-MALUS;res=d;if (d<0) res=0;if (d>80) res=8
   GRAD_FILL(spots[index].grid_ar_mean, spots[index].grid_cgl,   FIR_D);
   GRAD_FILL(spots[index].r_ar_mean,    spots[index].red_cgl,    Red_D);
   GRAD_FILL(spots[index].g_ar_mean,    spots[index].green_cgl,  Green_D);
   GRAD_FILL(spots[index].i_ar_mean,    spots[index].ir_cgl,     IR_D);
   Green_V = spots[index].green_cgl;
   Red_V   = spots[index].red_cgl;
   IR_V    = spots[index].ir_cgl;
   FIR_V   = spots[index].grid_cgl;
   P2A     = spots[index].p2a;
   if (P2A > 11.0) P2A = 11.0;
   Blemish_Class  (AR, Area, FIR_D, FIR_V,
      Green_D, Green_V, IR_D, IR_V,  P2A,
      Red_D,Red_V, &Out);
   test_fl_decisions(&Out, &belief, index);
   spots[index].flag2 = Out;
   spots[index].dist = (float)belief;
   if (Out != D_NOTHING)    {
      if (draw_flag)    draw_contour_file(&spots[index], index, Out >> 1, cam_numb
   }
   if (Out == D_NOTHING) spots[index].flag2 = 0;
   return(Out);
}
dummy(a,b)
{
   printf("\n %d %d",a,b);
}
select_contour_1(spots, spt_ind, mark, mark1, cam_number)
      struct spot spots[];
      int spt_ind, mark, mark1;
{
int cc_i[MAX_SPOTS];
int cc_j[MAX_SPOTS];
int ar_ij[MAX_SPOTS];
int num[MAX_SPOTS];
int i, j, flag, ret, i1;
int dist_i, dist_j;
struct spot *spot1;
int diff_area, area_lim;
   i = 0;
   flag = 0;
#define BY_LARGEST_AREA
#ifdef BY_LARGEST_AREA
   ar_ij[0] = 0;
#else
   ar_ij[0] = 10000;
#endif
   for (ret = 0; ret < spt_ind; ret++)
      {
      spot1 = &spots[ret];
      if (spot1->cam_number != cam_number)  continue;
         if ( (spot1->area >= 0 &&  spot1->area < 3000) )
            {
            flag = 0;
            for (j = 0; j < 0 ; j++) {
               dist_i = ABS(cc_i[j] - spot1->ci);
               dist_j = ABS(cc_j[j] - spot1->cj);
```

```
                              diff_area = ABS(spot1->area - ar_ij[j]);
                              area_lim = (int)((double)spot1->area * 0.45);
                              if (dist_i < DELTA && dist_j < DELTA && diff_area < area_lim
                                  {
                                      flag = 1;
#ifdef BY_LARGEST_AREA
                                      if( spot1->area > ar_ij[j])
#else
                                      if( spot1->area < ar_ij[j])
#endif
                                          {
                                              i1 = num[j];
                                              ar_ij[j] = spot1->area ;
                                              cc_i[j] = spot1->ci;
                                              cc_j[j] = spot1->cj;
                                              num[j] = ret;
                                              spots[i1].flag1 = (unsigned char)mark1;
                                              spot1->flag1 = mark;
                                          }
                                          else { spot1->flag1 = (unsigned char)mark1; }
                                  }
                              if ( flag == 0)
                                  {
                                      cc_i[i] = spot1->ci;
                                      cc_j[i] = spot1->cj;
                                      ar_ij[i] = spot1->area;
                                      spot1->flag1 = (unsigned char)mark;
                                      num[i] = ret;
                                      i++;
                                  }
                          }
              }
}
convert_area(spt, bnd0, bnd1, bnd2, cam_number)
         struct boundary_data *bnd0, *bnd1, *bnd2;
         struct spot *spt;
{
double area_ratio, calc_area_ratio();
int new_cj, new_ci;
return(1);
         new_cj = spt -> cj;
         new_ci = spt -> ci;
         area_ratio = calc_area_ratio(cam_number, &new_cj, &new_ci,
                       spt->area,
                       bnd0, bnd1, bnd2,
                       prog_consts.camera_distance, 0);
}
convert_spots(spots, final_spots, count)
      struct spot spots[], final_spots[];
{
int i, f;
   f = 0;
   for (i = 0 ; i < count ; ++i)
      {
         if (f >= MAX_FINAL_SPOTS) {
            printf("\n*** Too many spots"); return(f);
         }
         if (spots[i].flag1 == 0) continue;
         if (spots[i].flag2 == 0) continue;
         memcpy(&final_spots[f], &spots[i], sizeof(struct spot));
         final_spots[f].flag3 = i;
         spots[i].flag3 = f;
         ++f;
```

```c
    }
    return(f);
}
display_found_contours(spots, spt_index, image)
            struct spot spots[];
            PIXEL image[FR_Y_SIZE][FR_X_SIZE];
{
int i;
    SWAP_IN_SIZE(image, 0,   normal_images.green, FR_Y_SIZE*FR_X_SIZE);
      display_image(430, 0, image,   FR_X_SIZE, FR_Y_SIZE, "cam 0");
    SWAP_IN_SIZE(image, 1,   normal_images.green, FR_Y_SIZE*FR_X_SIZE);
      display_image(430, FR_Y_SIZE, image,   FR_X_SIZE, FR_Y_SIZE, "cam 1");
    SWAP_IN_SIZE(image, 2, normal_images.green, FR_Y_SIZE*FR_X_SIZE);
      display_image(430, 2*FR_Y_SIZE, image,   FR_X_SIZE, FR_Y_SIZE, "cam 2");
   for (i = 0 ; i < spt_index ; ++i)
        {
        display_single(&spots[i], 253, i);
printf("\n%3d -> %3d  %3d",i,spots[i].flag2, spots[i].flag1);
        }
}
display_single(spot, color, ind)
    struct spot *spot;

{
int off_x, off_y;
char name[16];
      off_x = 430;
      switch (spot->cam_number)
         {
           case 0: off_y = 0; break;
           case 1: off_y = FR_Y_SIZE; break;
           case 2: off_y = 2*FR_Y_SIZE; break;
         }
        draw_contour_file(spot, spot->flag3, color, spot->cam_number,
                                                 1, off_x, off_y);
        sprintf(name,"%ld", ind);
        write_str(spot->cj+off_x, (spot->ci-1)+off_y, name, 1, 252);
}
void
insert_img(sp, x, y, z)
      struct spot *sp;
      double x, y, z;
{
   sp->x = (float)x;
   sp->y = (float)y;
   sp->z = (float)z;
   sp->ir_cgl = 33;
   sp->ir_cgl = 33;
   sp->ar = 99;
   sp->area = 66;
   sp->flag1 = IMG_ST_CA;
   sp->flag4 = IMG_ST_CA;
   sp->flag2 = D_ST_CA;
}
look_for_third(spots, spt_index, ca_index, mate_index)
            struct spot spots[];
{
int third_index, i;
int max_angle;
#define MIN_DIST 0.7
double angle_between_n(double, double, double, double, double, double,double *);
double angle_ca,angle_st,dist;
   max_angle = 0;
   third_index = -1;
   for (i = 0 ; i < spt_index ; ++i)
```

```
        {
            if (spots[i].flag4 != REAL_BLEMISH) continue;
            angle_st=angle_between_n(spots[i].x,spots[i].y,spots[i].z
                        ,spots[mate_index].x,spots[mate_index].y,spots[mate_index].
                        &dist);
            angle_ca=angle_between_n(spots[i].x,spots[i].y,spots[i].z
                        ,spots[ca_index].x,spots[ca_index].y,spots[ca_index].z,
                        &dist);
            angle_st = angle_st * 180. / 3.14159;
            angle_ca = angle_ca * 180. / 3.14159;
                if (spots[i].cam_number != spots[ca_index].cam_number &&
                    spots[i].cam_number != spots[mate_index].cam_number)
                {
printf("\n possible: %d %d  %d  %f  %f", i, ca_index, mate_index, angle_ca, angle
                    if (1 || spots[i].dist > MIN_DIST)  {
                        if (angle_st > max_angle || angle_ca > max_angle)
                        {   max_angle = (int)(angle_st > angle_ca ? angle_st : ang
                            printf("... Chosen (%d)", max_angle);
                            third_index = i;
                        }
                    }
                }
        }
    if (max_angle < MIN_ANGLE) third_index = -1;
    printf("\nthird: %d", third_index);
    return(third_index);
}
fill_3d_info(spots, spt_index, bnd0, bnd1, bnd2, display_flag)
            struct boundary_data *bnd0, *bnd1, *bnd2;
            struct spot spots[];
{
int i,j, new_ci, new_cj, cam_number, cam_dist;
double angle, angle_between_n(), v, max_angle, spot_max_angle;
char name[8];
#define FLOAT double
void st_ca_logic (FLOAT, FLOAT, FLOAT, FLOAT, FLOAT, FLOAT, FLOAT, FLOAT, PIXEL *
FLOAT   Angle, Darkness_1, Darkness_2, Distance,
        Roundness_1, Roundness_2, Spot_1_Size, Spot_2_Size;
PIXEL Which;
int top_cand, max_grade;
double distance, credibility;
#define FUBYTE unsigned char
#define FUBYTE_CONVERT(a) (((double) a) / 255.0)
extern FUBYTE _Rule0087_alpha;
float   North[3],South[3];
extern double dist;
    SWAP_IN_SIZE(bnd0,   CAM_1, bnd, sizeof(struct boundary_data));
    SWAP_IN_SIZE(bnd1,   CAM_2, bnd, sizeof(struct boundary_data));
    SWAP_IN_SIZE(bnd2,   CAM_3, bnd, sizeof(struct boundary_data));
printf("\n+++RADIUS: %f", dist);
    for (i = 0 ; i < spt_index ; ++i)
        {
        spots[i].flag4 = REAL_BLEMISH;
        if (debug_flag && display_flag) {
            draw_contour_file(&spots[i], spots[i].flag3, 254, spots[i].cam_number
            sprintf(name,"%1d",i);
            write_str(3*spots[i].cj, 3*(spots[i].ci-1), name, 1, 252);
            }
        cam_number = spots[i].cam_number;
        new_cj = spots[i].cj;
        new_ci = spots[i].ci;
        cam_dist = prog_consts.camera_distance[CAM_3];
        find_3d_location(cam_number, new_cj, new_ci,
                    &spots[i].x, &spots[i].y, &spots[i].z,
```

```
                               bnd0, bnd1, bnd2,
                               prog_consts.camera_distance);
=ifdef EY_OLD
        if (spots[i].cam_number == CAM_1) {
                cam_dist = prog_consts.camera_distance[CAM_1];
                compute_3d_1(&spots[i], bnd0, cam_dist);
        }
        if (spots[i].cam_number == CAM_2) {
                cam_dist = prog_consts.camera_distance[CAM_2];
                compute_3d_1(&spots[i], bnd1, cam_dist);
        }
        if (spots[i].cam_number == CAM_3) {
                cam_dist = prog_consts.camera_distance[CAM_3];
                compute_3d_1(&spots[i], bnd2, cam_dist);
        }
#endif
        }
printf("\n---STEP 1");
    imagin_stem_calix_coord(bnd0,bnd1,bnd2,North,South,prog_consts.camera_distance
printf("\n---STEP 2 North= %5.2f,%5.2f,%5.2f South= %5.2f,%5.2f,%5.2f ",
    North[0],North[1],North[2], South[0],South[1],South[2]);
    insert_img(&spots[spt_index], (double)North[0], (double)North[1], (double)Nort
    ++spt_index;
    insert_img(&spots[spt_index], (double)South[0], (double)South[1], (double)Sout
    ++spt_index;
    max_angle = 0;
    for (i = 0 ; i < spt_index ; ++i)
        {
            spots[i].angle = 0;
        spot_max_angle = 0;
        spots[i].flag_g = 0;
        max_grade = 0;
        top_cand = -1;
    if (debug_flag)
     printf("\n c1  c2) Angle Dist  [Darkness]    ( Size ) |Roundness|   credibilit
        for (j = 0 ; j < spt_index ; ++j)
            {
                Angle = (FLOAT)angle_between_n(spots[i].x, spots[i].y, spots[i].z,
                                               spots[j].x, spots[j].y, spots[j].z,
                                               &distance);
                Angle = Angle * 180. / 3.14159;
                if (Angle > 180) Angle = 180;
                Distance = distance / dist;
                if (Distance > 1.0) Distance = 1.0;
                v = (double)( (int)spots[i].red_cgl +
                              (int)spots[i].green_cgl + (int)spots[i].ir_cgl);
                Darkness_1 = (FLOAT)(v/3.);
                v = (double)((int)spots[j].red_cgl +
                              (int)spots[j].green_cgl + (int)spots[j].ir_cgl);
                Darkness_2 = (FLOAT)(v/3.);
                v = (FLOAT)spots[i].ar;
                Roundness_1 = 100.-v * 30.;     if (Roundness_1 < 1) Roundness_1 = 1
                v = (FLOAT)spots[j].ar;
                Roundness_2 = 100.-v * 30.;     if (Roundness_2 < 1) Roundness_2 = 1
                  if (Roundness_1 > 100) Roundness_1 = 100;
                  if (Roundness_2 > 100) Roundness_2 = 100;
                Spot_1_Size = (FLOAT)spots[i].area/3.50; if (Spot_1_Size > 120) Spo
                Spot_2_Size = (FLOAT)spots[j].area/3.50; if (Spot_2_Size > 120) Spo
                if (Spot_1_Size < 20)   Spot_1_Size = (FLOAT)spots[i].area;
                if (Spot_2_Size < 20)   Spot_2_Size = (FLOAT)spots[j].area;
=ifdef ST_FUZZY
                st_ca_logic (Angle,
                             Darkness_1, Darkness_2,
                             Distance,
```

```c
                                    Roundness_1, Roundness_2,
                                    Spot_1_Size, Spot_2_Size,
                                    &Which);
                    credibility = (double)FUBYTE_CONVERT(_Rule0087_alpha);
            if (debug_flag)
   printf("\n %3d %3d) %5.1f %5.3f  [%3.0f %3.0f]  [%3.0f %3.0f]  |%5.2f %5.2f|   %
                                    i, j, Angle, Distance, Darkness_1, Darkness_2,
                                    Spot_1_Size, Spot_2_Size, Roundness_1, Roundness_2,
                                    credibility, Which);
                    if (Which > 100 && credibility >= max_grade &&
                            Angle > max_angle) {
                        max_angle = Angle;
                        max_grade = credibility;
                        spots[i].flag_g = Which;
                        spots[i].mate = j;
                        spots[i].angle = Angle;
                        spots[i].dist = distance;
                        spots[i].flag1 = (unsigned char)(credibility*255.);
#endif
            credibility = 1.0;
            if (spots[i].flag4 == IMG_ST_CA || spots[j].flag4 == IMG_ST_CA)
                    Angle = Angle * 0.8;
            if (debug_flag)
   printf("\n %3d %3d) %5.1f %5.3f  [%3.0f %3.0f]  [%3.0f %3.0f]  |%5.2f %5.2f|   %
                                    i, j, Angle, Distance, Darkness_1, Darkness_2,
                                    Spot_1_Size, Spot_2_Size, Roundness_1, Roundness_2,
                                    credibility, Which);
                    if (Angle > spot_max_angle && distance > MIN_DIST &&
                            Spot_1_Size > MIN_ST_AREA  && Spot_2_Size > MIN_ST_AREA &
                            spots[i].ir_cgl < MIN_IR && spots[j].ir_cgl < MIN_IR &&
                            spots[i].grid_cgl < MIN_FIR && spots[j].grid_cgl < MIN_IR
                        spot_max_angle= (int)Angle;
                        spots[i].angle= (int)Angle;
                        spots[i].mate = j;
                        spots[i].dist = Distance;
                        )
                    if (Angle > max_angle && distance > MIN_DIST &&
                            Spot_1_Size > MIN_ST_AREA  && Spot_2_Size > MIN_ST_AREA &
                            spots[i].ir_cgl < MIN_IR && spots[j].ir_cgl < MIN_IR &&
                            spots[i].grid_cgl < MIN_FIR && spots[j].grid_cgl < MIN_IR
                        max_angle = (int)Angle;
                        max_grade = 1.00;
                        spots[i].flag_g = 200;
                        spots[i].mate = j;
                        spots[i].angle = (int)Angle;
                        spots[i].dist = Distance;
                        spots[i].flag1 = 255;
                    )
            }
            if (debug_flag) printf("\n");
            }
    return(spt_index);
}
#ifdef USE_FUZZY
choose_stem_calyx(spots, spt_index, display_flag)
            struct spot spots[];
{
int i, max_i, max_cred, max_angle, max_dist, mate;
    max_cred = 0;
    max_angle = 0;
    max_dist = 0;
    for (i = 0 ; i < spt_index ; ++i)
        {
            if (spots[i].flag2 == D_PARLAT) {
```

```
                                                                continue; }
            if (spots[i].flag1 >= max_cred) {
                max_cred = spots[i].flag1;
                max_i = i;
            }
        }
        printf("\nmax cred is: %d", max_i);
        for (i = 0 ; i < spt_index ; ++i)
        {
            if (spots[i].flag2 == D_PARLAT) continue;
            if (spots[i].flag1 < max_cred) continue;
            if (spots[i].angle >= max_angle) {
                max_angle = spots[i].angle;
                max_i = i;
            }
        }
        printf("\nmax angle is: %d", max_i);
        for (i = 0 ; i < spt_index ; ++i)
        {
            if (spots[i].flag1 < max_cred) continue;
            if (spots[i].angle < max_angle) continue;
            if (spots[i].dist >= max_dist) {
                max_dist = spots[i].dist;
                max_i = i;
            }
        }
        printf("\nmax dist is: %d", max_i);
    mate = spots[max_i].mate;
    printf("\nChosen for Stem/Calyx:  %3d  %3d", max_i, mate);
    return(max_i);
}
#endif
choose_stem_calyx(spots, spt_index, display_flag)
            struct spot spots[];
{
int i, max_i, max_angle, max_dist, mate;
    max_angle = 0;
    max_dist = 0;
        for (i = 0 ; i < spt_index ; ++i)
        {
        printf("\n angle : %d , i : %d",spots[i].angle,i);
        if (spots[i].flag4 == IMG_ST_CA && spots[spots[i].mate].flag4 == IMG_ST_CA)
        if (spots[i].angle >= max_angle && spots[i].dist > MIN_DIST) {
                max_angle = spots[i].angle;
                max_i = i;
            }
        }
        printf("\nmax angle is: %d", max_angle);
    if (max_angle < MIN_ANGLE) {
        mate = -1;
        max_i = -1;
        }
    mate = spots[max_i].mate;
    printf("\nChosen for Stem/Calyx:  %3d  %3d", max_i, mate);
    return(max_i);
}
cancel_no_zone_litter(spots, spt_index, image)
            struct spot spots[];
            PIXEL image[FR_Y_SIZE][FR_X_SIZE];
{
int i, cam_in;
#define MIN_NO_ZONE_SPOT       35
#define MIN_NO_ZONE_CONTRAST   20
        cam_in = -1;
```

```
                for (i = 0 ; i < spt_index ; ++i)
                {
                    if (spots[i].area > MIN_NO_ZONE_SPOT) continue;
                    if (spots[i].flag2 == D_ST_CA) continue;
                    if (spots[i].ir_cgl - spots[i].i_ar_mean > MIN_NO_ZONE_CONTRAST) conti
                    if (cam_in != spots[i].cam_number){
                            cam_in = spots[i].cam_number;
                                SWAP_IN_SIZE(image, cam_in, spots_3, FR_Y_SIZE*FR_X_SIZE);
                    }
                    if (image[spots[i].ci][spots[i].cj] < 5) {
                        spots[i].flag2 = D_NOTHING;
                        printf("\nNO_ZONE: %d  %d %d",i, spots[i].cj, spots[i].ci);
                    }
                }
}
fill_color_mask(spots, spt_index, mask)
    struct spot spots[];
    PIXEL mask[FR_Y_SIZE][FR_X_SIZE];
{
int i,j, ret, per, color,index,cam;
char c_name[32];
char chain[CHAIN_SIZE];
    index=0;
    for (cam=0 ; cam < N_CAMERAS ; cam++) {
        for (i=0 ; i<FR_Y_SIZE ; i++)
        for (j=0 ; j<FR_X_SIZE ; j++)      mask[i][j]=100;
        for (index=0 ; index < spt_index ; index++)
            {
            if (spots[i].flag4 == REAL_BLEMISH) continue;
                if (spots[index].cam_number!=cam   ) continue;
                sprintf(c_name, "%s%1d_%1d.cnt", TMP_DEVICE, cam,spots[index].flag3);
                ret = undump_spots(c_name, chain, CHAIN_SIZE, &per);
                if (ret == FAILURE) {
                    printf("\nContour file %s not found", c_name); return(1);
                }
                if   (spots[index].flag2==D_LROT  && index!=stem_index &&   index!=ca
                    continue;
                if ((color=spin_color_blemish(spots[index].flag2)) > 0)
                    {
                    draw_contour_mem(mask, (int)spots[index].start_i,
                                        (int)spots[index].start_j, chain, 0);
                    malv_fill_contour(mask, color, (int)spots[index].min_i,
                                (int)spots[index].max_i,   (int)spots[index].min_j,
                    }
            }
        printf("\n at . SWAP_OUT ... combi_map index=%d",index);
        SWAP_OUT_SIZE(mask, cam, combi_map, FR_Y_SIZE*FR_X_SIZE);
        }
}
spin_color_blemish(blemish)
int blemish;
{
    switch (blemish)
        {
        case D_ST_CA :
                        return(1);
        case D_ROT   :
        case D_LROT  :
                        return(5);
        case D_MOTH  :
                        return(10);
        case D_RUSSET:
                        return(7);
        case D_BRUISE:
```

```
                                return(14);
        case D_PIT    :
                                return(3);
        case D_PARLAT:
                                return(4);
        case D_NOTHING:
                                printf("\n WARNING : final contour fuond with flag2=D_NOTHI
                                return(0);
        default    :
                                printf("\n WARNING : final contour fuond with flag2 not kno
                                return(0);
        )
}
do_try_single_st_ca(spots, spt_index)
                    struct spot spots[];
{
int i;
    for (i = 0 ; i < spt_index ; ++i)
        {
          if (spots[i].green_cgl < 50   &&
              spots[i].red_cgl   < 50   &&
              spots[i].ir_cgl    < 100  &&
              spots[i].area > 10
              )
            return(i);
        }
    return(-1);
}
pre_re_classify(spots, spt_index, ca_indexp, mate_indexp, third_indexp)
                    struct spot spots[];
                    int *ca_indexp, *mate_indexp, *third_indexp;
{
int i, j, ci, cj, area_diff;
int ca_index, mate_index, third_index;
float Angle;
double distance;
#define SET_LABELS(ind, xmate) if (ind>=0){spots[ind].flag2 = D_ST_CA; if (xmate>
    ca_index    = *ca_indexp;
    mate_index  = *mate_indexp;
    third_index = *third_indexp;
    SET_LABELS(third_index, ca_index);
    SET_LABELS(ca_index, mate_index);
    SET_LABELS(mate_index, ca_index);
    for (i = 0 ; i < spt_index ; ++i)
        {
          if (i == ca_index || i == mate_index || i == third_index) continue;
          if (spots[i].flag2 != D_ST_CA) continue;
          printf("\nChanged : ca_index= %d  i= %d",ca_index,i);
          spots[i].flag2 = D_ROT;
        }
    correct_mate(spots, spt_index, ca_indexp,   mate_indexp);
    correct_mate(spots, spt_index, mate_indexp, ca_indexp);
    ca_index    = *ca_indexp;
    mate_index  = *mate_indexp;
    third_index = *third_indexp;
    SET_LABELS(third_index, ca_index);
    SET_LABELS(ca_index, mate_index);
    SET_LABELS(mate_index, ca_index);
    for (i = 0 ; i < spt_index ; ++i)
        {
          if (i == ca_index || i == mate_index || i == third_index) continue;
          if (spots[i].flag2 != D_ST_CA) continue;
          printf("\nChanged : ca_index= %d  i= %d",ca_index,i);
          spots[i].flag2 = D_ROT;
```

```
    }
correct_mate(spots, spt_index, ca_indexp, mate_indexp)
                struct spot spots[];
                int *ca_indexp, *mate_indexp;
{
int i, j, ci, cj, area_diff;
    i = *ca_indexp;
    ci = spots[i].ci; cj = spots[i].cj;
    for (j = 0 ; j < spt_index ; ++j)
        {
        if (i == j) continue;
        if (!(spots[j].flag2 == D_LROT || spots[j].flag2 == D_ROT)) continue;
            if (spots[i].cam_number != spots[j].cam_number) continue;
            if (!(spots[j].min_i <= ci && spots[j].max_i >= ci &&
                    spots[j].min_j <= cj && spots[j].max_j >= cj)) continue;
            area_diff = spots[j].area - spots[i].area;
printf("\nMMM: %d %d   %d %d %d",i, j, area_diff,spots[j].area, spots[i].area);
            if (area_diff < 0) continue;
            if (area_diff > 250) continue;
            printf("\nCa corrected: %d -> %d", *ca_indexp, j);
            *ca_indexp = j;
        }
}
re_classify(spots, spt_index, ca_index, mate_index, third_index)
                struct spot spots[];
{
int i, j, ci, cj, cgl_i, cgl_j;
#ifdef AAA
    for (i = 0 ; i < spt_index ; ++i)
        {
        if (i == ca_index || i == mate_index || i == third_index)
            {
            ci = spots[i].ci; cj = spots[i].cj;
            for (j = 0 ; j < spt_index ; ++j)
                {
                if (j == i) continue;
                if (spots[i].cam_number != spots[j].cam_number) continue;
                if (spots[j].flag2 == D_ST_CA) continue;
                cgl_i = spots[j].ci;
                cgl_j = spots[j].cj;
                if (cgl_i >= spots[i].min_i && cgl_i <= spots[i].max_i &&
                    cgl_j <= spots[i].max_j && cgl_j <= spots[i].max_j )
                spots[j].flag2=D_NOTHING;
                if (ci >= spots[j].max_i && cj >= spots[j].max_j &&
                    ci <= spots[j].min_i && cj <= spots[j].min_j)
                spots[j].flag2=D_NOTHING;
                }
            }
        }
#endif
    for (i = 0 ; i < spt_index ; ++i)
        {
        if (spots[i].flag2 == D_ST_CA)
            {
            ci = spots[i].ci; cj = spots[i].cj;
            for (j = 0 ; j < spt_index ; ++j)
                {
                if (spots[j].flag2 == D_ST_CA) continue;
                if (j == i) continue;
                if (spots[j].cam_number != spots[i].cam_number) continue;
                if (spots[j].flag2 != D_ROT && spots[j].flag2 != D_LROT) con
                if (ci <= spots[j].max_i && cj <= spots[j].max_j &&
                    ci >= spots[j].min_i && cj >= spots[j].min_j)
```

```c
                        spots[j].flag2=D_NOTHING;
                }
        }
    for (i = 0 ; i < spt_index ; ++i)
    {
        if (spots[i].flag2 == D_PIT)
        {
            ci = spots[i].ci; cj = spots[i].cj;
            if (spots[i].flag2 != D_PIT) continue;
            for (j = 0 ; j < spt_index ; ++j)
            {
                if (j == i) continue;
                if (spots[j].cam_number != spots[i].cam_number) continue;
                if (spots[j].flag2 == D_NOTHING) continue;
                if (ci <= spots[j].max_i && cj <= spots[j].max_j &&
                    ci >= spots[j].min_i && cj >= spots[j].min_j)
                    spots[i].flag2=D_NOTHING;
            }
        }
    }
    for (i = 0 ; i < spt_index ; ++i)
    {
        if (spots[i].flag2 == D_ROT || spots[i].flag2 == D_LROT)
        {
            ci = spots[i].ci; cj = spots[i].cj;
            if (spots[i].flag2 == D_ST_CA) continue;
            for (j = 0 ; j < spt_index ; ++j)
            {
                if (j == i) continue;
                if (spots[j].cam_number != spots[i].cam_number) continue;
                if (spots[j].flag2 == D_NOTHING) continue;
                if (ci <= spots[j].max_i && cj <= spots[j].max_j &&
                    ci >= spots[j].min_i && cj >= spots[j].min_j)
                    spots[i].flag2=D_NOTHING;
            }
        }
    }
    for (i = 0 ; i < spt_index ; ++i)
    {
        if (spots[i].flag2 == D_BRUISE)
        {
            ci = spots[i].ci; cj = spots[i].cj;
            for (j = 0 ; j < spt_index ; ++j)
            {
                if (j == i) continue;
                if (spots[j].cam_number != spots[i].cam_number) continue;
                if (spots[j].flag2 == D_NOTHING) continue;
                if (ci <= spots[j].max_i && cj <= spots[j].max_j &&
                    ci >= spots[j].min_i && cj >= spots[j].min_j)
                    spots[i].flag2=D_NOTHING;
            }
        }
    }
}
#define FUBYTE unsigned char
#define FUBYTE_CONVERT(a) (((double) a) / 255.0)
extern FUBYTE _Area_Tiny_b_alpha;
extern FUBYTE _Area_Small_b_alpha;
extern FUBYTE _Area_Medium_b_alpha;
extern FUBYTE _Area_Large_b_alpha;
extern FUBYTE _Area_Huge_b_alpha;
extern FUBYTE _AR_Square_b_alpha;
extern FUBYTE _AR_Bar_b_alpha;
```

```
extern FUBYTE _FIR_D_Poor_b_alpha;
extern FUBYTE _FIR_D_Low_b_alpha;
extern FUBYTE _FIR_D_Medium_b_alpha;
extern FUBYTE _FIR_D_High_b_alpha;
extern FUBYTE _FIR_D_VeryHigh_b_alpha;
extern FUBYTE _IR_D_Poor_b_alpha;
extern FUBYTE _IR_D_Low_b_alpha;
extern FUBYTE _IR_D_Medium_b_alpha;
extern FUBYTE _IR_D_High_b_alpha;
extern FUBYTE _IR_D_VeryHigh_b_alpha;
extern FUBYTE _IR_D_Well_b_alpha;
extern FUBYTE _P2A_Round_b_alpha;
extern FUBYTE _P2A_Oval_b_alpha;
extern FUBYTE _P2A_Odd_b_alpha;
FUBYTE _Red_D_Well_b_alpha;
extern FUBYTE _Rule0000_alpha;
extern FUBYTE _Rule0017_alpha;
extern FUBYTE _Rule0018_alpha;
extern FUBYTE _Rule0015_alpha;
extern FUBYTE _Rule0016_alpha;
extern FUBYTE _Rule0010_alpha;
extern FUBYTE _Rule0011_alpha;
extern FUBYTE _Rule0013_alpha;
extern FUBYTE _Rule0007_alpha;
extern FUBYTE _Rule0008_alpha;
extern FUBYTE _Rule0005_alpha;
extern FUBYTE _Rule0004_alpha;
extern FUBYTE _Rule0001_alpha;
extern FUBYTE _Rule0003_alpha;
extern FUBYTE _Rule0022_alpha;
extern FUBYTE _Rule0023_alpha;
extern FUBYTE _Rule0025_alpha;
extern FUBYTE _Rule0027_alpha;
extern FUBYTE _Rule0028_alpha;
extern FUBYTE _Rule0029_alpha;
extern FUBYTE _Rule0030_alpha;
extern FUBYTE _Rule0032_alpha;
extern FUBYTE _Rule0034_alpha;
extern FUBYTE _Rule0036_alpha;
extern FUBYTE _Rule0037_alpha;
extern FUBYTE _Rule0039_alpha;
extern FUBYTE _Rule0041_alpha;
extern FUBYTE _Rule0042_alpha;
extern FUBYTE _Rule0044_alpha;
extern FUBYTE _Rule0046_alpha;
extern FUBYTE _Rule0047_alpha;
extern FUBYTE _Rule0048_alpha;
extern FUBYTE _Rule0050_alpha;
test_fl_decisions(Out, belief, ind)     PIXEL *Out; double *belief; int ind;
{
double credibility, fmax, f;
   credibility = 0.0;
   credibility += (double)FUBYTE_CONVERT(_Rule0000_alpha);
   credibility += (double)FUBYTE_CONVERT(_Rule0018_alpha);
   credibility += (double)FUBYTE_CONVERT(_Rule0015_alpha);
   credibility += (double)FUBYTE_CONVERT(_Rule0016_alpha);
   credibility += (double)FUBYTE_CONVERT(_Rule0010_alpha);
   credibility += (double)FUBYTE_CONVERT(_Rule0011_alpha);
   credibility += (double)FUBYTE_CONVERT(_Rule0013_alpha);
   credibility += (double)FUBYTE_CONVERT(_Rule0007_alpha);
   credibility += (double)FUBYTE_CONVERT(_Rule0008_alpha);
   credibility += (double)FUBYTE_CONVERT(_Rule0005_alpha);
   credibility += (double)FUBYTE_CONVERT(_Rule0004_alpha);
   credibility += (double)FUBYTE_CONVERT(_Rule0001_alpha);
```

```
    credibility += (double)FUBYTE_CONVERT(_Rule0003_alpha);
    credibility += (double)FUBYTE_CONVERT(_Rule0023_alpha);
    credibility += (double)FUBYTE_CONVERT(_Rule0027_alpha);
    credibility += (double)FUBYTE_CONVERT(_Rule0028_alpha);
    credibility += (double)FUBYTE_CONVERT(_Rule0029_alpha);
    credibility += (double)FUBYTE_CONVERT(_Rule0030_alpha);
    credibility += (double)FUBYTE_CONVERT(_Rule0032_alpha);
    credibility += (double)FUBYTE_CONVERT(_Rule0034_alpha);
    credibility += (double)FUBYTE_CONVERT(_Rule0036_alpha);
    credibility += (double)FUBYTE_CONVERT(_Rule0037_alpha);
    credibility += (double)FUBYTE_CONVERT(_Rule0039_alpha);
    credibility += (double)FUBYTE_CONVERT(_Rule0041_alpha);
    credibility += (double)FUBYTE_CONVERT(_Rule0042_alpha);
    credibility += (double)FUBYTE_CONVERT(_Rule0044_alpha);
    credibility += (double)FUBYTE_CONVERT(_Rule0046_alpha);
    credibility += (double)FUBYTE_CONVERT(_Rule0047_alpha);
    credibility += (double)FUBYTE_CONVERT(_Rule0048_alpha);
    credibility += (double)FUBYTE_CONVERT(_Rule0050_alpha);
        if (credibility  < 0.4) {
            *Out = D_NOTHING;
            *belief = 0.0;
            return(1);
        }
#define DECIDE(a,n) f = ((double)FUBYTE_CONVERT(a)); if (f > 0.34 && \
        f >= fmax)     { fmax = f; *Out = n; }
    fmax = 0.0;
    *Out = D_NOTHING;
    DECIDE(_Rule0017_alpha, D_NOTHING);
    DECIDE(_Rule0022_alpha, D_NOTHING);
    DECIDE(_Rule0025_alpha, D_NOTHING);
    DECIDE(_Rule0000_alpha, D_PIT);
    DECIDE(_Rule0001_alpha, D_PIT);
    DECIDE(_Rule0003_alpha, D_PIT);
    DECIDE(_Rule0004_alpha, D_LROT);
    DECIDE(_Rule0005_alpha, D_LROT);
    DECIDE(_Rule0007_alpha, D_PIT);
    DECIDE(_Rule0008_alpha, D_PIT);
    DECIDE(_Rule0010_alpha, D_LROT);
    DECIDE(_Rule0011_alpha, D_LROT);
    DECIDE(_Rule0013_alpha, D_LROT);
    DECIDE(_Rule0015_alpha, D_LROT);
    DECIDE(_Rule0016_alpha, D_LROT);
    DECIDE(_Rule0018_alpha, D_PIT);
    DECIDE(_Rule0023_alpha, D_PIT);
    DECIDE(_Rule0027_alpha, D_ROT);
    DECIDE(_Rule0028_alpha, D_ROT);
    DECIDE(_Rule0029_alpha, D_BRUISE);
    DECIDE(_Rule0030_alpha, D_BRUISE);
    DECIDE(_Rule0032_alpha, D_BRUISE);
    DECIDE(_Rule0034_alpha, D_BRUISE);
    DECIDE(_Rule0036_alpha, D_BRUISE);
    DECIDE(_Rule0037_alpha, D_BRUISE);
    DECIDE(_Rule0039_alpha, D_PIT);
    DECIDE(_Rule0041_alpha, D_BRUISE);
    DECIDE(_Rule0042_alpha, D_ROT);
    DECIDE(_Rule0044_alpha, D_BRUISE);
    DECIDE(_Rule0046_alpha, D_BRUISE);
    DECIDE(_Rule0047_alpha, D_BRUISE);
    DECIDE(_Rule0048_alpha, D_PARLAT);
    DECIDE(_Rule0050_alpha, D_PIT);
    if (ind == 80)   printf("\nDeci 80: %d", *Out);
    *belief = (float)fmax;
}
FL_debug(Out)    PIXEL Out;
```

```c
{
#define TIL_WRITE     fprintf
#define TIL_DATAFILE  stdout
int count;
char form[32];
      TIL_WRITE (TIL_DATAFILE, "\nArea:\tTiny\tSmall\tMedium\tLarge\tHuge\n");
      TIL_WRITE (TIL_DATAFILE, "\t%5.3f", FUBYTE_CONVERT(_Area_Tiny_b_alpha));
      TIL_WRITE (TIL_DATAFILE, "\t%5.3f", FUBYTE_CONVERT(_Area_Small_b_alpha));
      TIL_WRITE (TIL_DATAFILE, "\t%5.3f", FUBYTE_CONVERT(_Area_Medium_b_alpha))
      TIL_WRITE (TIL_DATAFILE, "\t%5.3f", FUBYTE_CONVERT(_Area_Large_b_alpha));
      TIL_WRITE (TIL_DATAFILE, "\t%5.3f", FUBYTE_CONVERT(_Area_Huge_b_alpha));
      TIL_WRITE (TIL_DATAFILE, "\nAR:\tSquar\tBar\n");
      TIL_WRITE (TIL_DATAFILE, "\t%5.3f", FUBYTE_CONVERT(_AR_Square_b_alpha));
      TIL_WRITE (TIL_DATAFILE, "\t%5.3f", FUBYTE_CONVERT(_AR_Bar_b_alpha));
      TIL_WRITE (TIL_DATAFILE, "\nP2A:\tRound\tOval\tOdd\n");
      TIL_WRITE (TIL_DATAFILE, "\t%5.3f", FUBYTE_CONVERT(_P2A_Round_b_alpha));
      TIL_WRITE (TIL_DATAFILE, "\t%5.3f", FUBYTE_CONVERT(_P2A_Oval_b_alpha));
      TIL_WRITE (TIL_DATAFILE, "\t%5.3f", FUBYTE_CONVERT(_P2A_Odd_b_alpha));
      TIL_WRITE (TIL_DATAFILE, "\nFIR_D:\tPoor\tLow\tMedium\tHigh\tVeryHigh\n")
      TIL_WRITE (TIL_DATAFILE, "\t%5.3f", FUBYTE_CONVERT(_FIR_D_Poor_b_alpha));
      TIL_WRITE (TIL_DATAFILE, "\t%5.3f", FUBYTE_CONVERT(_FIR_D_Low_b_alpha));
      TIL_WRITE (TIL_DATAFILE, "\t%5.3f", FUBYTE_CONVERT(_FIR_D_Medium_b_alpha)
      TIL_WRITE (TIL_DATAFILE, "\t%5.3f", FUBYTE_CONVERT(_FIR_D_High_b_alpha));
      TIL_WRITE (TIL_DATAFILE, "\t%5.3f", FUBYTE_CONVERT(_FIR_D_VeryHigh_b_alph
      TIL_WRITE (TIL_DATAFILE, "\nIR_D:\tPoor\tLow\tMedium\tHigh\tVeryHigh\tWel
      TIL_WRITE (TIL_DATAFILE, "\t%5.3f", FUBYTE_CONVERT(_IR_D_Poor_b_alpha));
      TIL_WRITE (TIL_DATAFILE, "\t%5.3f", FUBYTE_CONVERT(_IR_D_Low_b_alpha));
      TIL_WRITE (TIL_DATAFILE, "\t?");
      TIL_WRITE (TIL_DATAFILE, "\t?");
      TIL_WRITE (TIL_DATAFILE, "\t?            ");
      TIL_WRITE (TIL_DATAFILE, "\t%5.3f", FUBYTE_CONVERT(_IR_D_Well_b_alpha));
      TIL_WRITE (TIL_DATAFILE, "\nRed_D:\tPoor\tLow\tMedium\tHigh\tVeryHigh\tWe
      TIL_WRITE (TIL_DATAFILE, "\t?");
      TIL_WRITE (TIL_DATAFILE, "\t?");
      TIL_WRITE (TIL_DATAFILE, "\t?");
      TIL_WRITE (TIL_DATAFILE, "\t?");
      TIL_WRITE (TIL_DATAFILE, "\t?            ");
      TIL_WRITE (TIL_DATAFILE, "\t%5.3f", FUBYTE_CONVERT(_Red_D_Well_b_alpha));
   TIL_WRITE (TIL_DATAFILE, "\nLevel of belief:\n");
   count = 0;
#define TIL_WRITE_C(f,s1,d,d1)  if((d1) > 0.0)  ( \
      if (count > 0) sprintf(form, "\t%s",s1); else strcpy(form, s1); \
      TIL_WRITE(f,form,d,d1); ++count; ) \
      if(count>4) { count = 0; TIL_WRITE(f, "\n"); )
      TIL_WRITE_C (TIL_DATAFILE, "%3d.. %6.4f", 0, FUBYTE_CONVERT(_Rule0000_alpha
      TIL_WRITE_C (TIL_DATAFILE, "%3d.. %6.4f",17, FUBYTE_CONVERT(_Rule0017_alpha
      TIL_WRITE_C (TIL_DATAFILE, "%3d.. %6.4f",18, FUBYTE_CONVERT(_Rule0018_alpha
      TIL_WRITE_C (TIL_DATAFILE, "%3d.. %6.4f",15, FUBYTE_CONVERT(_Rule0015_alpha
      TIL_WRITE_C (TIL_DATAFILE, "%3d.. %6.4f",16, FUBYTE_CONVERT(_Rule0016_alpha
      TIL_WRITE_C (TIL_DATAFILE, "%3d.. %6.4f",10, FUBYTE_CONVERT(_Rule0010_alpha
      TIL_WRITE_C (TIL_DATAFILE, "%3d.. %6.4f",11, FUBYTE_CONVERT(_Rule0011_alpha
      TIL_WRITE_C (TIL_DATAFILE, "%3d.. %6.4f",13, FUBYTE_CONVERT(_Rule0013_alpha
      TIL_WRITE_C (TIL_DATAFILE, "%3d.. %6.4f", 7, FUBYTE_CONVERT(_Rule0007_alpha
      TIL_WRITE_C (TIL_DATAFILE, "%3d.. %6.4f", 8, FUBYTE_CONVERT(_Rule0008_alpha
      TIL_WRITE_C (TIL_DATAFILE, "%3d.. %6.4f", 5, FUBYTE_CONVERT(_Rule0005_alpha
      TIL_WRITE_C (TIL_DATAFILE, "%3d.. %6.4f", 4, FUBYTE_CONVERT(_Rule0004_alpha
      TIL_WRITE_C (TIL_DATAFILE, "%3d.. %6.4f", 1, FUBYTE_CONVERT(_Rule0001_alpha
      TIL_WRITE_C (TIL_DATAFILE, "%3d.. %6.4f", 3, FUBYTE_CONVERT(_Rule0003_alpha
      TIL_WRITE_C (TIL_DATAFILE, "%3d.. %6.4f",22, FUBYTE_CONVERT(_Rule0022_alpha
      TIL_WRITE_C (TIL_DATAFILE, "%3d.. %6.4f",23, FUBYTE_CONVERT(_Rule0023_alpha
      TIL_WRITE_C (TIL_DATAFILE, "%3d.. %6.4f",25, FUBYTE_CONVERT(_Rule0025_alpha
      TIL_WRITE_C (TIL_DATAFILE, "%3d.. %6.4f",27, FUBYTE_CONVERT(_Rule0027_alpha
      TIL_WRITE_C (TIL_DATAFILE, "%3d.. %6.4f",28, FUBYTE_CONVERT(_Rule0028_alpha
      TIL_WRITE_C (TIL_DATAFILE, "%3d.. %6.4f",29, FUBYTE_CONVERT(_Rule0029_alpha
```

```
        TIL_WRITE_C (TIL_DATAFILE, "%3d.. %6.4f",30, FUBYTE_CONVERT(_Rule0030_alpha
        TIL_WRITE_C (TIL_DATAFILE, "%3d.. %6.4f",32, FUBYTE_CONVERT(_Rule0032_alpha
        TIL_WRITE_C (TIL_DATAFILE, "%3d.. %6.4f",34, FUBYTE_CONVERT(_Rule0034_alpha
        TIL_WRITE_C (TIL_DATAFILE, "%3d.. %6.4f",36, FUBYTE_CONVERT(_Rule0036_alpha
        TIL_WRITE_C (TIL_DATAFILE, "%3d.. %6.4f",37, FUBYTE_CONVERT(_Rule0037_alpha
        TIL_WRITE_C (TIL_DATAFILE, "%3d.. %6.4f",39, FUBYTE_CONVERT(_Rule0039_alpha
        TIL_WRITE_C (TIL_DATAFILE, "%3d.. %6.4f",41, FUBYTE_CONVERT(_Rule0041_alpha
        TIL_WRITE_C (TIL_DATAFILE, "%3d.. %6.4f",42, FUBYTE_CONVERT(_Rule0042_alpha
        TIL_WRITE_C (TIL_DATAFILE, "%3d.. %6.4f",44, FUBYTE_CONVERT(_Rule0044_alpha
        TIL_WRITE_C (TIL_DATAFILE, "%3d.. %6.4f",46, FUBYTE_CONVERT(_Rule0046_alpha
        TIL_WRITE_C (TIL_DATAFILE, "%3d.. %6.4f",47, FUBYTE_CONVERT(_Rule0047_alpha
        TIL_WRITE_C (TIL_DATAFILE, "%3d.. %6.4f",48, FUBYTE_CONVERT(_Rule0048_alpha
        TIL_WRITE_C (TIL_DATAFILE, "%3d.. %6.4f",50, FUBYTE_CONVERT(_Rule0050_alpha
        TIL_WRITE  (TIL_DATAFILE, "\n");
#define DECISION(a, l1, l2, str) if (a >= l1 && a < l2) printf("%s", str);
    printf("\nDecision: %3d ... ",Out);
    DECISION(Out,   0,  25, "St/Ca");
    DECISION(Out,  25,  55, "Rot");
    DECISION(Out,  55,  85, "Moth");
    DECISION(Out,  85, 115, "Large Rot");
    DECISION(Out, 115, 145, "Russet");
    DECISION(Out, 145, 175, "Bruise");
    DECISION(Out, 175, 205, "Pit");
    DECISION(Out, 205, 235, "Parlat");
    DECISION(Out, 235, 255, "Nothing");
    printf("\n---------------------+");
}
```

APPENDIX J

```c
/*                      ID: 017
   File name is: app17.h
----------------------------------------------------------------
*/
#include "\cfg\include\itexvsp.h"
#include "\cfg\include\gaoi.h"
#include "adapter.h"
#include <time.h>
#include <conio.h>
#include <process.h>
#include <stdio.h>
#include <ctype.h>
#include <fcntl.h>
#include <malloc.h>
#include <stdlib.h>
#include <limits.h>
#include <signal.h>
#include <math.h>
#include <setjmp.h>
#include <float.h>
#include <memory.h>
#include <string.h>
extern int debug_flag;
#define  POSITIVE_REF_STEP   (31.25/1000.)
#define  NEGATIVE_REF_STEP   (23.05/1000.)
#define  NEGATIVE_REF   0x1
#define  POSITIVE_REF   0x2
#define BASE 0x340
#define RED_ADC          (BASE + 0xE)
#define RED_ADC_LUT      (BASE + 0xC)
#define GREEN_ADC        (BASE + 0x12)
#define GREEN_ADC_LUT    (BASE + 0x10)
#define BLUE_ADC         (BASE + 0x16)
#define BLUE_ADC_LUT     (BASE + 0x14)
static int __pen_x, __pen_y;
static int __aoi;
static int init_count = 0;
static char modify_flag = 0;
init_cfg()
{
int finit_cfg(), ret;
   if (init_count <= 0)
   {
     ret = inquire_sys(CFG);
     if (ret <= 0 || init_count < 0) {
        load_cnf("c:\\eyal\\cfg\\elop.cnf");
     }
     err_level(SEVERE);
     __aoi = cfg_gaoi_fbcreate(CURRENT_F, 0, 0, 1023, 1023);
     restore_setup_data();
      cfg_sync(PLL);
     cfg_videosync(EXTSYNC);
      atexit(finit_cfg);
     ++init_count;
   }
     __pen_x = __pen_y = 0;
}
reinit_cfg()
{
    __aoi = cfg_gaoi_fbcreate(CURRENT_F, 0, 0, 1023, 1023);
}
first_time_init_cfg()
{
```

```
    init_count = -1;
    initsys();
    cfg_init();
    cfg_initluts();
    cfg_camera(VIDEO0);
    init_cfg();
    write_setup_data();
    set_color_channel_cfg(_GREEN);
    zoom_cfg(0);
    pan_cfg(0,0);
    init_count = 1;
}
restore_setup_data()
{
int in_file;
    in_file = open("c:\\ey_cfg.dat",(O_RDONLY | O_BINARY));
    if (in_file == -1) return(0);
    read(in_file, &_cfg_settings, sizeof(struct _cfg_data));
    close(in_file);
    cfg_setframe(_cfg_settings.color_plane);
    cfg_pan(_cfg_settings.pan);
    cfg_scroll(_cfg_settings.scroll);
    cfg_zoom(_cfg_settings.zoom);
}
write_setup_data()
{
int out_file;
    out_file = open("c:\\ey_cfg.dat",(O_WRONLY | O_CREAT |
                  O_TRUNC | O_BINARY), (0200 | 0400) );
    if (out_file == -1) return(0);
    write(out_file, &_cfg_settings, sizeof(struct _cfg_data));
    close(out_file);
}
move_abs_cfg(x,y)
{
    _pen_x = x;  _pen_y = y;
}
draw_abs_cfg(x1,y1,color)
{
    dline(_pen_x, _pen_y, x1, y1, color);
    _pen_x = x1;  _pen_y = y1;
}
finit_cfg()
{
    if (init_count)
    {
        --init_count;
        if (modify_flag)
            write_setup_data();
    }
    gaoi_delete(_aoi);
    gaoi_delall(GAOI_USER);
}
init_grab_cfg()
{
    cfg_videosync(EXTSYNC);
    set_dac_limits(1, 45);
}
grab_cfg(camera)
{
    cfg_grab(camera, _aoi);
}
stopgrab_cfg()
{
```

```
   int field;
      field = cfg_field();
      if (field == EVEN)
      {   cfg_waitvb();      cfg_enqvb();  }
      cfg_waitvb();
      cfg_freeze();
}
snap_cfg(camera)
{
     cfg_snap(CAMERA, __aoi);
}
shadow_snap_cfg(camera)
{
     cfg_snap(__aoi, __aoi);
}
null_cfg()
{
}
clear_screen_cfg(color)
{
       cfg_clf(__aoi, color);
}
pan_cfg(x,y)
{
   cfg_pan(x);
   cfg_scroll(y);
   __cfg_settings.pan = x; modify_flag = 1;
   __cfg_settings.scroll = y;
}
zoom_cfg(factor)
{
   if (factor <= 1) factor = 0.
   __cfg_settings.zoom = factor; modify_flag = 1
     cfg_zoom(factor);
}
wpixel_rgb_cfg(x,y,r,g,b)
{
   cfg_setframe(R);
   cfg_wpixel(__aoi, x,y,r);
   cfg_setframe(G);
   cfg_wpixel(__aoi, x,y,g);
   cfg_setframe(B);
   cfg_wpixel(__aoi, x,y,b);
}
rpixel_rgb_cfg(x,y,r,g,b)          int *r, *g, *b;
{
   cfg_setframe(R);
   *r = cfg_rpixel(__aoi, x,y);
   cfg_setframe(G);
   *g = cfg_rpixel(__aoi, x,y);
   cfg_setframe(B);
   *b = cfg_rpixel(__aoi, x,y);
}
set_color_channel_cfg(chan)
{
int f;
   switch(chan)
      {
        case __RED:     chan = R; break;
        case __GREEN:   chan = G; break;
        case __BLUE: chan = B; break;
        case __FILLER: chan = O; break;
        case __ENTIRE_DEPTH: chan = RGB; break;
        default: ;
```

```
    }
    cfg_setframe(chan);
    __cfg_settings.color_plane = chan; modify_flag = 1;
}
get_color_channel_cfg()
{
int f;
    f = cfg_setframe(INQUIRE);
    switch (f)
    {
        case R: f = __RED; break;
        case G: f = __GREEN; break;
        case B: f = __BLUE; break;
        case RGB: f = __ENTIRE_DEPTH; break;
        case O:  f = __FILLER; break;
    }
    return(f);
}
wpixel_cfg(x,y,v)
{
    cfg_wpixel(__aoi, x,y,v);
}
rpixel_cfg(x,y)
{
    cfg_rpixel(__aoi, x,y);
}
set_plane_cfg(n)
{
    if (n == 1) cfg_setframe(R);
    else if (n == 2) cfg_setframe(G);
    else if (n == 3) cfg_setframe(B);
}
whline_cfg(x, y, size, buf)      char *buf;
{
    cfg_bwhline(__aoi, x, y, size, buf);
}
rhline_cfg(x, y, size, buf)      char *buf;
{
    cfg_brhline(__aoi, x, y, size, buf);
}
cfg_2_ram(array,x1,y1,x2,y2,xdst,ydst)           PIXEL *array;
{
    x2 = x2-x1;
    y2 -= y1;
    y2 += ydst;
    for (y1 = ydst ; y1 < y2 ; ++y1)
    {
        cfg_brhline(__aoi, xdst, y1, x2, array);
        array += x2;
    }
}
get_dfield(array,x1,y1,x2,y2,xdst,ydst,field)    PIXEL *array;
{
int diff;
    x2 = x2-x1;
    diff = ydst & 0x1;
    diff += field;
    ydst -= diff;
    y2 -= y1;
    y2 += ydst;
printf("\n diff: %d (%d %d)",diff, ydst, y2);
    for (y1 = ydst ; y1 < y2 ; y1 += 2)
    {
        cfg_brhline(__aoi, xdst, y1, x2, array);
```

```
        array += x2;
        cfg_brhline(__aoi, xdst, y1, x2, array);
        array += x2;
    }
}
get_block_field1(array,x1,y1,x2,y2,xdst,ydst)           PIXEL *array;
{
int diff;
    x2 = x2-x1;
    diff = y1 - (y1 & 0xFFFE);
    if (diff == 0) { diff = 1;
                     y1 -= diff;
                     y2 -= diff;
                   }
    y2 -= y1;
    y2 += ydst;
    for (y1 = ydst ; y1 < y2 ; y1 += 2)
    {
        cfg_brhline(__aoi, xdst, y1, x2, array);
        array += x2;
        cfg_brhline(__aoi, xdst, y1, x2, array);
        array += x2;
    }
}
get_block_field0(array,x1,y1,x2,y2,xdst,ydst)           PIXEL *array;
{
int diff;
    x2 = x2-x1;
    diff = ydst & 0x1;
    ydst -= diff;
    y2 -= y1;
    y2 += ydst;
printf("\n diff: %d (%d %d)",diff, ydst, y2);
    for (y1 = ydst ; y1 < y2 ; y1 += 2)
    {
        cfg_brhline(__aoi, xdst, y1, x2, array);
        array += x2;
        cfg_brhline(__aoi, xdst, y1, x2, array);
        array += x2;
    }
}
ram_2_cfg(array,x1,y1,x2,y2,xdst,ydst)                  PIXEL *array;
{
    x2 = x2-x1;
    y2 -= y1;
    y2 += ydst;
    for (y1 = ydst ; y1 < y2 ; ++y1)
    {
        cfg_bwhline(__aoi, xdst, y1, x2, array);
        array += x2;
    }
}
dline_cfg(x1,y1,x2,y2, color)
{
    cfg_cline(__aoi, x1, y1, x2, y2, color);
}
filled_rectangle_cfg(x1,y1,x2,y2,color)
{
    cfg_block(__aoi, x1, y1, x2-x1, y2-y1, color);
}
rectangle_cfg(x1,y1,x2,y2,color)
{
    cfg_rectangle(__aoi, x1, y1, x2-x1-1, y2-y1-1, color);
}
```

```
filled_circle_cfg(x,y,radius, color)
{
    filled_rectangle_cfg(x-radius,y-radius,x+radius,y+radius,color);
}
circle_cfg(x,y,radius,color)
{
    cfg_circle(__aoi, x,y,radius, 1, 1, color);
}
text_cfg(x,y,stri,size,color)   char *stri;
{
    cfg_text(__aoi, x,y+10, 0 ,size, color, stri);
}
set_dac_limits_all(l1, h1, l2, h2, l3, h3)
{
int v;
#define P_LUT_REF(l, h, adc_lut, adc)       \
    outp(adc_lut, _NEGATIVE_REF);           \
    v = (int)((double)l * 2. / (NEGATIVE_REF_STEP * 1000.) +.5); \
    outp(adc, (v << 2) & 0xFC);             \
    outp(adc_lut, _POSITIVE_REF);           \
    v = (int)((double)h * 2. / (POSITIVE_REF_STEP * 1000.) +.5); \
    outp(adc, (v << 2) & 0xFC);
    P_LUT_REF(l1, h1, RED_ADC_LUT,   RED_ADC);
    P_LUT_REF(l2, h2, GREEN_ADC_LUT, GREEN_ADC);
    P_LUT_REF(l3, h3, BLUE_ADC_LUT,  BLUE_ADC);
}
set_dac_limits(n_ref, p_ref)
{
    outp(BLUE_ADC_LUT, _NEGATIVE_REF);
    outp(BLUE_ADC, (n_ref << 2) & 0xFC);
    outp(BLUE_ADC_LUT, _POSITIVE_REF);
    outp(BLUE_ADC, (p_ref << 2) & 0xFC);
    outp(RED_ADC_LUT, _NEGATIVE_REF);
    outp(RED_ADC, (n_ref << 2) & 0xFC);
    outp(RED_ADC_LUT, _POSITIVE_REF);
    outp(RED_ADC, (p_ref << 2) & 0xFC);
    outp(GREEN_ADC_LUT, _NEGATIVE_REF);
    outp(GREEN_ADC, (n_ref << 2) & 0xFC);
    outp(GREEN_ADC_LUT, _POSITIVE_REF);
    outp(GREEN_ADC, (p_ref << 2) & 0xFC);
}
get_dac_limits(n_ref, p_ref)
        int *n_ref, *p_ref;
{
   outp(RED_ADC_LUT, _NEGATIVE_REF);
   *n_ref = ((inp(RED_ADC) >> 2) & 0x3F);
   outp(RED_ADC_LUT, _POSITIVE_REF);
   *p_ref = ((inp(RED_ADC) >> 2) & 0x3F);
}
jmp_buf jmp_mark;
#define STAT_PORT      0x2fd
#define OUT_PORT       0x2f8
#define IN_PORT        0x2f8
#define INT_DIVISOR    0x2f9
#define INT_ID         0x2fa
#define LINE_CONTROL   0x2fb
#define MODEM_CONTROL  0x2fc
#define LINE_STATUS    0x2fd
#define MODEM_STATUS   0x3fe
#define etext_image    write_str
#define direct_line    dline
p_ctl_c_handler()
{
char c;
```

```c
   signal(SIGINT, SIG_IGN);
#ifdef AAA
   printf("\n Terminate Processing? [y|n] ");
   c = getch();
   if (c == 'Y' || c == 'y') { printf(" Yes, please terminate!\n");
                               escape("OK, good Bye"); }
   else printf(" Not yet, Man. Maby next time.");
   signal(SIGINT, ctl_c_handler);
#endif
     exit(1);
}
void
p_float_handler(int sig, int num )
{
extern int p_errno;
    _fpreset();
    p_errno = FLOAT_ERROR;
    longjmp(jmp_mark, -1 );
}
init_exception_handlers()
{
   if (signal(SIGINT, p_ctl_c_handler) == (int(*)())-1) { printf("Can't set signa
}
display_datum_line(x,y,val,header)   char *header;
{
char s[32];
    sprintf(s, "%s: %4d", header, val);
    write_str(x, y, s, 1, 255);
}
draw_boundary(boundary, boundary_index, out_rect, off_x, off_y, b_color, rect_col
     struct line_pair boundary[];
     struct rect out_rect;
{
int i,x1,x2,y;
    for (i = 0 ; i < boundary_index ; ++i)
    {
      y = boundary[i].y + off_y;
      x1 = boundary[i].x1 + off_x;
      x2 = boundary[i].x2 + off_x;
      wpixel(x1,y,b_color);
      wpixel(x2,y,b_color);
    }
    if (rect_color >= 0) {
    dline(out_rect.x1+off_x, out_rect.y1+off_y, out_rect.x2+off_x, out_rect.y1+o
    dline(out_rect.x2+off_x, out_rect.y1+off_y, out_rect.x2+off_x, out_rect.y2+o
    dline(out_rect.x2+off_x, out_rect.y2+off_y, out_rect.x1+off_x, out_rect.y2+o
    dline(out_rect.x1+off_x, out_rect.y2+off_y, out_rect.x1+off_x, out_rect.y1+o
    }
}
display_fr_256(image, x1, y1, x2, y2, xs, ys)
             PIXEL8 _far image[FR_Y_SIZE][FR_X_SIZE];
{
   copy_block(image,xs,ys,x2-x1,y2-y1,xs,ys);
}
read_fr_pic(file_name,mat,size_x,size_y, magic, header)
          PIXEL _far *mat; char file_name[];
          char *header;
          int *size_x, *size_y, *magic;
{
long btbr, bytes_read;
#define PACKET_SIZE (INT_MAX & 0xfffc)
int in_file,pz;
long l[4];
#define L_SIZE 3
```

```
    in_file = open(file_name, (O_RDONLY | O_BINARY) , 0) ;
    if (in_file == -1) return(0);
    if ( read(in_file, 1, 4*L_SIZE) != 4*L_SIZE) { printf ("\n error in read #1")
            close(in_file);   return(FAILURE);  }
    *size_x = (int)l[1];
    *size_y = (int)l[2];
    btbr = (long)(*size_y);
    btbr = btbr * (*size_x);
    while ( btbr > 0 )
      {
       if (btbr > PACKET_SIZE) pz = PACKET_SIZE;
       else            pz = (int) btbr;
       bytes_read = read(in_file, mat, pz);
       btbr -= pz;
       mat += pz;
      }
    close(in_file);
    return(SUCCESS);
}
read_fr_pic_extended(file_name,mat,size_x,size_y, magic, header)
            PIXEL _far *mat; char file_name[];
            char *header;
            int *size_x, *size_y, *magic;
{
long btbr, bytes_read;
#define PACKET_SIZE (INT_MAX & 0xfffc)
int in_file,pz;
long l[4];
#define L_SIZE 3
    in_file = open(file_name, (O_RDONLY | O_BINARY) , 0) ;
    if (in_file == -1) return(0);
    if ( read(in_file, 1, 4*L_SIZE) != 4*L_SIZE) { printf ("\n error in read #1")
            close(in_file);   return(FAILURE);  }
    *size_x = (int)l[1];
    *size_y = (int)l[2];
    btbr = (long)(*size_y);
    btbr = btbr * (*size_x);
    while ( btbr > 0 )
      {
       if (btbr > PACKET_SIZE) pz = PACKET_SIZE;
       else            pz = (int) btbr;
       bytes_read = read(in_file, mat, pz);
       btbr -= pz;
       mat += pz;
      }
    bytes_read = read(in_file, header, FR_HEADER_SIZE);
    if (bytes_read != FR_HEADER_SIZE) { close(in_file);  return(10); }
    close(in_file);
    return(SUCCESS);
}
read_mtrx_pic(file_name,mat,x,y)
            PIXEL _far *mat; char file_name[];
{
int in_file, pz;
long btbr, bytes_read;
    in_file = open(file_name, (O_RDONLY | O_BINARY) , 0) ;
    if (in_file == -1) return(0);
    btbr = (long)(y);
    btbr *= (x);
    while ( btbr > 0 )
      {
       if (btbr > PACKET_SIZE) pz = PACKET_SIZE;
       else            pz = (int) btbr;
       bytes_read = read(in_file, mat, pz);
```

```c
        if (bytes_read != pz)
            {   fprintf(stderr,"err 2"); close(in_file); return(FAILURE); }
        btbr -= pz;
        mat += pz;
      }
    close(in_file);
return(SUCCESS);
}
write_fr_pic(file_name,mat,size_x,size_y,header)
        PIXEL _far *mat; char file_name[];
           int size_x, size_y;
           char *header;
{
int out_file, pz;
long bytes_written, btbr;
long l[4];
    out_file = open(file_name,(O_WRONLY | O_CREAT |
        O_TRUNC | O_BINARY), (0200 | 0400) );
    if (out_file == -1) return(0);
    l[0] = (long)100;
    l[1] = (long)size_x;
    l[2] = (long)size_y;
    l[3] = (long)0;
    if ( write(out_file, l, L_SIZE*4) != L_SIZE*4) { printf ("\n error in write ≠
                close(out_file);  return(FAILURE);  }
    btbr = (long)(size_y);
    btbr *= (size_x);
    while ( btbr > 0 )
    {
      if (btbr > PACKET_SIZE) pz = PACKET_SIZE;
      else           pz = (int) btbr;
       bytes_written = write(out_file, mat, pz);
      if (bytes_written != pz)
          {   fprintf(stderr,"err 2"); close(out_file); return(FAILURE); }
      btbr -= pz;
      mat += pz;
    }
    bytes_written = write(out_file, header, FR_HEADER_SIZE);
    if (bytes_written != FR_HEADER_SIZE)  { close(out_file); return(FAILURE); }
      close(out_file);
return(SUCCESS);
}
compute_his_fr(image, margins, his)
        PIXEL8 _far image[FR_Y_SIZE][FR_X_SIZE];
           unsigned int his[256];
{
int line, i,j;
unsigned int pix;
   for (i = 0 ; i < 256 ; ++i)  his[i] = 0;
   for (i = 0+margins ; i < FR_Y_SIZE-margins ; ++i)
      for (j = 0+margins ; j < FR_X_SIZE-margins ; ++j)
         {
           pix = (unsigned int) image[i][j];
           if (pix <= 2) continue;
           ++his[pix];
         }
      return(SUCCESS);
}
smooth_his(his, his1)
           unsigned int his[256];
           unsigned int his1[256];
{
int line, i,j;
unsigned int pix;
```

```
    for (i = 1 ; i < 256-1 ; ++i)
        his1[i] = (his[i-1]+his[i]+his[i]+his[i+1]) >> 2;
    his1[0] = his1[1];
    his1[255] = his1[255-1];
    return(SUCCESS);
}
display_histogram_fr(his, low_thresh, up_thresh, color)
        unsigned int his[256];
{
int i, max_i,x , y1, y2;
unsigned int min,max;
double  factor;
char string[10];
#define XDELTA 64
    etext_image(160+XDELTA, 120, "MAGNITUDE DISTRIBUTION", 1,255,1);
    min = UINT_MAX ;
    max = 0;
    max_i = -1;
#define X_START low_thresh
#define X_END  up_thresh
    for (i = X_START ; i < X_END ; ++i) {
        if (his[i] > max) { max = his[i]; max_i = i; }
        if (his[i] < min) min = his[i];
    }
    if (max_i == -1) return(FAILURE);
    if (max == min) max = min+1;
    factor = 255. / (float)(max - min);
    x = (X_START + 1) * 2;
    y1 = 480 - (int)((his[X_START] - min) * factor + .5) - 1 - 50;
    for (i = X_START + 1 ; i < X_END ; ++i) {
            y2 = 480 - (int)((his[i] - min) * factor + .5) - 1 - 50;
            direct_line(x+XDELTA,y1,x+2+XDELTA,y2,color);
            direct_line(x+XDELTA,y1-1,x+2+XDELTA,y2-1,color);
            x += 2;
            y1 = y2;
            }
    y1 = 480 - 50  + 15;
    x = 0;
    direct_line(0+XDELTA, y1, 512+XDELTA, y1, 254);
    direct_line(0+XDELTA, 175, 512+XDELTA, 175, 254);
    for (i = 1 ; i <= (512+1) ; i += 64)
        {
        direct_line(i+XDELTA,   y1, i+XDELTA,   y1 + 10, 254);
        direct_line(i-1+XDELTA, y1, i-1+XDELTA, y1 + 10, 254);
        direct_line(i+1+XDELTA, y1, i+1+XDELTA, y1 + 10, 254);
        direct_line(i+2+XDELTA, y1, i+2+XDELTA, y1 + 10, 254);
        sprintf (string,"%4d",x);
        etext_image(i - 10+XDELTA ,y1 + 15, string, 1, 254, 2);
        x += 32;
        }
    i = 480 - 0 - 1 - 50;
    direct_line(0+XDELTA, 445, 0+XDELTA, 175, 254);
    direct_line(512+XDELTA, 445, 512+XDELTA, 175, 254);
    for (y1 = 100 ; y1 >= 0 ; y1 -= 40)
    {
      y2 = i - (int)((float)y1 * 2.55);
      direct_line(0 + XDELTA, y2, 6 + XDELTA, y2, 254);
      direct_line(0 + XDELTA, y2+1, 6 + XDELTA, y2+1, 254);
      direct_line(512 + XDELTA, y2, 512-6 + XDELTA, y2, 254);
      direct_line(512 + XDELTA, y2+1, 512-6 + XDELTA, y2+1, 254);
      sprintf(string,"%1d%%",y1);
      if (y1 > 0) etext_image(12 + XDELTA, y2 - 10, string, 1,254,2);
    }
    y1 = 480 - his[max_i] - 1 - 50;
```

```
        sprintf(string, "%ld",max_i);
        return(SUCCESS);
}
compute_accumulated(his, hisl, low_thresh, high_thresh)
                            unsigned int his[256];
                            unsigned int hisl[256];
{
int i;
    if (low_thresh <= 0) low_thresh = 1;
    hisl[low_thresh-1] = 0;
    for (i = low_thresh ; i < high_thresh ; ++i)
                            hisl[i] = hisl[i-1]+his[i];
}
get_per_data(file_name, boundary, boundary_index, out_rect)
        struct line_pair boundary[MAX_BOUNDARY];
        int *boundary_index;
        struct rect *out_rect;
        char *file_name;
{
int in_file, bytes_read, by;
    in_file = open(file_name,(O_RDONLY |   O_BINARY), 0);
    if (in_file == -1) {printf("\n BND file %s not found", file_name);
            return(FAILURE); }
#define read_it(a,b,c,d)     by = sizeof(a) * d;   \
            bytes_read = read(in_file, b, by); \
            if (bytes_read != by)   \
            {   fprintf(stderr,"DR-err %ld",c); close(in_file); return(FAILURE); }
    read_it(int, boundary_index, 1, 1);
    read_it(struct rect, out_rect, 2, 1);
    read_it(struct line_pair, boundary, 3, *boundary_index);
    close(in_file);
    return(SUCCESS);
}
dump_per_data(file_name, boundary, boundary_index, out_rect)
        struct line_pair boundary[MAX_BOUNDARY];
        int boundary_index;
        struct rect *out_rect;
        char *file_name;
{
int out_file, bytes_written, by;
    out_file = open(file_name,(O_WRONLY | O_CREAT |
        O_TRUNC | O_BINARY), (0200 | 0400) );
    if (out_file == -1) {printf("\n Unable to open dump"); return(FAILURE); }
#define write_it(a,b,c,d)    by = sizeof(a) * d;   \
            bytes_written = write(out_file, b, by); \
            if (bytes_written != by)   \
            {   fprintf(stderr,"D-err %ld",c); close(out_file); return(FAILURE); }
    write_it(int, &boundary_index, 1, 1);
    write_it(struct rect, out_rect, 2, 1);
    write_it(struct line_pair, boundary, 3, boundary_index);
    close(out_file);
    return(SUCCESS);
}
#ifdef DEMO_1
grid_light()
{
unsigned char c;
      c = inp(MODEM_CONTROL);
      c = 1;
      outp(MODEM_CONTROL,c);
}
diffuse_light(v)
{
unsigned char c;
```

```
        c = inp(MODEM_CONTROL);
        c = 2;
        outp(MODEM_CONTROL,c);
}
no_light(v)
{
unsigned char c;
        c = inp(MODEM_CONTROL);
        c = 3;
        outp(MODEM_CONTROL,c);
}
#endif
speaker_beep(freq, dur1, dur2, count)
{
int clk1, clk2;
unsigned char p;
union {
   unsigned short divisor;
   unsigned char c[2];
   } cn;
    cn.divisor = (unsigned short)(1193180. / (double)freq);
    outp(67, 182);
    outp(66, cn.c[0]);
    outp(66, cn.c[1]);
    p = inp(97);
    for ( ; count ; --count)
      {
        clk1 = clock();
        outp(97, p | 3);
        do {
            clk2 = clock() - clk1;
        } while (clk2 < dur1);
        clk1 = clock();
        outp(97, p & 253);
        do {
            clk2 = clock() - clk1;
        } while (clk2 < dur2);
      }
    outp(97, p & 253);
}
extern struct single_view_info  view_info[N_CAMERAS];
#ifdef  EYAL_OLD
#pragma optimize("", off)
correct_wires_presence(image, wireless_image, bnd)
      PIXEL image[FR_Y_SIZE][FR_X_SIZE];
      PIXEL wireless_image[FR_Y_SIZE][FR_X_SIZE];
      struct boundary_data *bnd;
{
#define DO_CANCEL_WIRES
#ifdef DO_CANCEL_WIRES
#define ENV 1
#define N_PART 7
int i,j, k, l, w, z;
double x[N_PART], y[N_PART];
      for (i = 0 ; i < FR_Y_SIZE ; ++i)
      {
         for (j = 0 ; j < FR_X_SIZE ; ++j)
           {
             if (image[i][j] == WIRE_MARK)
               {
                 for (k = j+1 ; k < FR_X_SIZE && image[i][k] == WIRE_MARK ; ++k) ;
                 y[0]   = (double)image[i][j-ENV-2]; x[0] = (double)(j-ENV-2);
                 y[1]   = (double)image[i][j-ENV-1]; x[1] = (double)(j-ENV-1);
                 y[2]   = (double)image[i][j-ENV];   x[2] = (double)(j-ENV);
```

```
                    y[3]    = (double)image[i][k+ENV];    x[3] = (double)(k+ENV);
                    y[4]    = (double)image[i][k+ENV+1];  x[4] = (double)(k+ENV+1);
                    y[5]    = (double)image[i][k+ENV+2];  x[5] = (double)(k+ENV+2);
                    y[6]    = (double)image[i][k+ENV+3];  x[6] = (double)(k+ENV+3);
#ifdef AAA
                    if (y[0] > 253 || y[6] > 253)   {
                                    wireless_image[i][j] = image[i][j];
                                    continue;
                                    }
#endif
                    for (l = j-ENV-2 ; l <= k+ENV+2 ; ++l)
                    {
                        w = lin_interp(l, x ,y ,N_PART);
                        w = (w + wireless_image[i-1][l]) >> 1;
                        wireless_image[i][l] = w;
                    }
                        j = l-1;
                }
            else
                wireless_image[i][j] = image[i][j];
            }
        }
        clear_outside(wireless_image, bnd->boundary, bnd->boundary_index, 255);
#else
        memcpy(wireless_image, image, FR_Y_SIZE * FR_X_SIZE);
#endif
}
lin_interp(x0, x ,y ,nn)
            int x0;    double x[], y[]; unsigned nn;
{
double m, n, y1, y2, x1, x2, y0;
int i;
    x1 = x[0];      y1 = y[0];
    x2 = x[nn-1];   y2 = y[nn-1];
    y1 = 255.;
    for (i = 0 ; i < nn ; ++i)
            if (y[i] < 253) { y1 = y[i]; break; }
    if (y1 == 255.) return((int)y[0]);
    y2 = 255.;
    for (i = nn-1 ; i ; --i)
            if (y[i] < 253) { y2 = y[i]; break; }
    if (y1 == y2) return((int)y1);
    if (x1 == x2) { printf("\n Err"); return(0); }
    m = (y2-y1) / (x2-x1);
    n = y2 - m*x2;
    y0 = (double)x0 * m + n;
    return((int)(y0 + 0.5));
}
#pragma optimize("", on)
#endif
cancel_wires_n(l_image, l_image_1, bnd, cam_number,pic_n,x_offset)
            PIXEL  l_image[L_FR_Y_SIZE][L_FR_X_SIZE];
            PIXEL  l_image_1[L_FR_Y_SIZE][L_FR_X_SIZE];
            struct boundary_data *bnd;
            int    pic_n,x_offset;
{
    int     complete_shape();
    int     i,j,l;
    int cam_0_wire_locations[4][3][2]={29, 38, 51, 59,  0, 0,
                                       32, 41, 53, 61,  0, 0,
                                       30, 39, 51, 58,  0, 0,
                                       30, 39, 51, 58,  0, 0 };
    int cam_2_wire_locations[4][3][2]={52, 62, 104, 114, 137, 145,
                                       52, 62, 104, 114, 137, 145,
```

```
                                                      50, 64, 103 ,115 ,133 ,145,
                                                      '0, 64, 103 ,115 ,133 ,145 };
    for (i=0;i<4;i++)
        for (j=0;j<3;j++)
            for (l=0;l<2;l++)
                {
                cam_2_wire_locations[i][j][l]-= x_offset;
                if( cam_0_wire_locations[i][j][l] )
                    cam_0_wire_locations[i][j][l]-= x_offset;
                }
    if (cam_number==CAM_1)
        {
        if (pic_n==0)
            {
            correct_cam_0_bnd(l_image,bnd ,cam_number,cam_0_wire_locations[0][pic_n]
            SWAP_OUT_SIZE(bnd,cam_number ,bnd,sizeof(struct boundary_data));
            }
        if (pic_n == 0 || pic_n == 1) paint_wires_black(l_image,bnd ,cam_number,cam
        complete_shape(l_image,bnd,cam_0_wire_locations[pic_n][1]);
        printf("\n");
        dilate_mean(l_image, l_image_1, bnd,cam_number ,cam_0_wire_locations,pic_n)
        }
    else   if   (cam_number==CAM_3)
        {
        if (pic_n == 0 || pic_n == 1) paint_wires_black(l_image,bnd ,cam_number,cam
        complete_shape(l_image,bnd,cam_2_wire_locations[pic_n][0]);
        printf("\n");
        complete_shape(l_image,bnd,cam_2_wire_locations[pic_n][1]);
        printf("\n");
        complete_shape(l_image,bnd,cam_2_wire_locations[pic_n][2]);
        dilate_mean(l_image, l_image_1, bnd, cam_number,cam_2_wire_locations,pic_n)
        }
    else   dilate_mean(l_image, l_image_1, bnd, cam_number,cam_0_wire_locations,pi
    printf("\n\n");
    return(SUCCESS);
}
int     correct_cam_0_bnd(image,bnd ,cam_num,wire_locat)
    struct boundary_data *bnd;
    PIXEL  image[FR_Y_SIZE][FR_X_SIZE];
        int    cam_num,wire_locat[2];
{
        int i,j,min=255;
        if (cam_num != 0)
                {
                printf("\n  ERROR : wrong Camera ");
                return(0);
                }
    for (i=2 ; i<bnd->boundary_index-2; i++)
        {
        if ( bnd->boundary[i].x1 <= wire_locat[1])
            bnd->boundary[i].x1+=0.8*(wire_locat[1] - bnd->boundary[i].x1 + 1) + 0.6
        }
}
dilate_mean(scr, dst, bnd, cam_number,wire_locat,pic)
struct boundary_data *bnd;
PIXEL  scr[FR_Y_SIZE][FR_X_SIZE];
PIXEL  dst[FR_Y_SIZE][FR_X_SIZE];
int    wire_locat[4][3][2],cam_number,pic;
{
#define N_MAX  5
#define N_MEAN 3
    int    l,m,r,i,j,wire,y;
    PIXEL  *S,*D,*tmp;
    for (i=0; i<FR_Y_SIZE; i++)
```

```
        for (j=0; j<FR_X_SIZE; j++)    dst[i][j]=scr[i][j];
    if (cam_number ==CAM_2)      return(0);
    S=&dst[0][0];    D=&scr[0][0];    m=1;
    for (l=0; l<N_MAX; l++)
    {
       tmp=D;     D=S;   S=tmp;
        for (i=0 ; i<bnd->boundary_index; i++)
        for (   y=bnd->boundary[i].y,j=bnd->boundary[i].x1-1; j<bnd->boundary[i].x
        {
            r=y*FR_Y_SIZE + j;
            if (cam_number == CAM_1)
            {
                if (j <= wire_locat[pic][1][1]-m && j >= wire_locat[pic][1][0]+m)
                {
                    (*(D+r))=MAX(*(S + r),MAX(*(S + r+1),*(S + r-1)));
                    if (*(D+r) > 245)    *(D+r)=(*(S+r));
                }
                else *(D+r)=(*(S+r));
            }
            else
            {
                if ((j <= wire_locat[pic][0][1]-m && j >= wire_locat[pic][0][0]+m)  ||
                    (j <= wire_locat[pic][1][1]-m && j >= wire_locat[pic][1][0]+m)  ||
                    (j <= wire_locat[pic][2][1]-m && j >= wire_locat[pic][2][0]+m)   )
                {
                    (*(D+r))=MAX(*(S + r),MAX(*(S + r+1),*(S + r-1)));
                    if (*(D+r) > 245)    *(D+r)=(*(S+r));
                }
                else (*(D+r))=(*(S+r));
            }
        }
        m++;
    }
    m=1;
    for (l=0; l<N_MEAN; l++)
    {
       tmp=D;       D=S;   S=tmp;
        for (i=0 ; i<bnd->boundary_index; i++)
        for (   y=bnd->boundary[i].y,j=bnd->boundary[i].x1-1; j<bnd->boundary[i].x
        {
            r=y*FR_Y_SIZE + j;
            if (cam_number == CAM_1)
            {
                if (j < wire_locat[pic][1][1] && j > wire_locat[pic][1][0])
                {
                    m = (int) (((*(S+r)) + (*(S+r+1)) + (*(S+r-1))) / 3. + 0.5);
                    (*(D+r)) = m;
                }
                else (*(D+r))=(*(S+r));
            }
            else
            {
                if ((j <= wire_locat[pic][0][1] && j >= wire_locat[pic][0][0])  ||
                    (j <= wire_locat[pic][1][1] && j >= wire_locat[pic][1][0])  ||
                    (j <= wire_locat[pic][2][1] && j >= wire_locat[pic][2][0])   )
                {
                    if (*(S+r+1) > 245 || *(S+r-1) > 245) (*(D+r))=(*(S+r));
                    else
                    {
                        m = (int) (((*(S+r)) + (*(S+r+1)) + (*(S+r-1))) / 3. + 0.5);
                        (*(D+r)) = m;
                    }
                }
                else (*(D+r))=(*(S+r));
```

```
                    }
                }
            }
        if (D != &dst[0][0])
            for (i=0; i<FR_Y_SIZE; i++)
            for (j=0; j<FR_X_SIZE; j++)   dst[i][j]=scr[i][j];
}
complete_shape(image,bnd,wire_locat)
struct boundary_data *bnd;
PIXEL   image[FR_Y_SIZE][FR_X_SIZE];
int     wire_locat[2];
{
    int  i,j,y,r,old_x1,old_x2,old_i1,old_i2,Xr,Xl;
    int  x1,x2;
    int  interp_and_paint(PIXEL [FR_Y_SIZE][FR_X_SIZE],int,int,int,int,int);
        old_x1=bnd->boundary[0].x1;
        old_x2=bnd->boundary[0].x2;
        old_i1=0;
        old_i2=0;
        Xl=wire_locat[0];
        Xr=wire_locat[1];
        for (i=1 ; i<bnd->boundary_index; i++)
        {
            x1= bnd->boundary[i].x1;
            x2= bnd->boundary[i].x2;
            if (old_x1 >  Xl)
            {
                if ( x1 >= Xr)   { old_x1=x1; old_i1=i;  }
                if (x1 < Xl)
                {
                    printf("\n befor interp_1...xr=%d xl=%d old_x1=%d  x1=%d",Xr,Xl,ol
                    interp_and_paint(image,Xl,Xr,bnd->boundary[i].y,bnd->boundary[old_
                    old_x1=x1; old_i1=i;
                }
            }
            else
            {
                if (x1 <= Xl) { old_x1=x1; old_i1=i;  }
                if (x1 >= Xr)
                {
                    printf("\n befor interp_2...xr=%d xl=%d ",Xr,Xl);
                    interp_and_paint(image,Xr,Xl,bnd->boundary[i].y,bnd->boundary[old_
                    old_x1=x1; old_i1=i;
                }
            }
            if (old_x2 <  Xr)
            {
                if ( x2 <= Xl)   { old_x2=x2; old_i2=i;  }
                if (x2 > Xr)
                {
                    printf("\n befor interp_3...xr=%d xl=%d ",Xr,Xl);
                    interp_and_paint(image,Xr,Xl,bnd->boundary[i].y,bnd->boundary[old_
                    old_x2=x2;   old_i2=i;
                }
            }
            else
            {
                if (x2 >= Xr) { old_x2=x2; old_i2=i;  }
                if (x2 <= Xl)
                {
                    printf("\n befor interp_4...xr=%d xl=%d ",Xr,Xl);
                    interp_and_paint(image,Xl,Xr,bnd->boundary[i].y,bnd->boundary[old_
                    old_x2=x2;   old_i2=i;
                }
```

```c
            }
        }
}
int  interp_and_paint(img,x1,x2,y1,y2,flag)
    int    x1,x2,y1,y2,flag;
    PIXEL  img[FR_Y_SIZE][FR_X_SIZE];
{
    int    d,i,j,l,begin;
    double diff_x,diff_m;
        printf("\n In interp_...x1=%d x2=%d y1=%d y2=%d  ",x1,x2,y1,y2);
    if (y1 <= y2)
        {
        printf("\n ERROR : in complete_shape(); ");
        return(0);
        }
    if ((flag == 0 && x1 > x2) || (flag==1 && x1 < x2)) d=-1;
    else d=1;
    diff_x= (x1-x2)/(double)(y1-y2);
    begin=img[y2+3*d][x2];
    diff_m= (img[y1+3*d][x1] - begin )/(double)(y1-y2);
    for (i=y2 -1; i <= y1 + 1; i++)
        {
        j=x2 + (int) ((i-y2-d)*diff_x + 0.5);
        if (flag)
            {
            for (l=j+1 ; l<= MAX(x1,x2)+3; l++) img[i][l]=252;
            for (l=MIN(x1+1,x2+1) ; l< j ; l++) img[i][l]=3;
            }
        else
            {
            for (l=j-1 ; l>= MIN(x1,x2)-3; l--) img[i][l]=252;
            for (l=MAX(x1-1,x2-1) ; l> j; l--) img[i][l]=3;
            }
        img[i][j]=(PIXEL) (begin + (int)((i-y2-d)*diff_m + 0.5));
        printf("\n INTERP : %d , y=%d   x=%d beg=%d diff=%f",img[i][j],i,j,begin,di
        }
}
paint_wires_black(image,bnd ,cam_number,wire_locat,pic)
struct boundary_data *bnd;
PIXEL  image[FR_Y_SIZE][FR_X_SIZE];
int    wire_locat[4][3][2],cam_number,pic;
{
    int   i,j,R1,R2,R3,L1,L2,L3,mid,diff;
    if (cam_number ==CAM_2)  return(0);
    mid =  (wire_locat[pic][1][1] + wire_locat[pic][1][0]) >> 1;
    diff =  (wire_locat[pic][1][1] - wire_locat[pic][1][0]) >> 1;
    R1=MAX(wire_locat[pic][1][0] +1,mid-N_MAX+1);
    L1=MIN(wire_locat[pic][1][1] -1,mid+N_MAX);
    printf("\n PR=%d    PL=%d",R1,L1);
    for (i=0; i<FR_Y_SIZE; i++)
    for (j=R1; j<= L1; j++)
        {
        image[i][j]=1;
        }
    if (cam_number ==CAM_3)
        {
        mid =  (wire_locat[pic][0][1] + wire_locat[pic][0][0]) >> 1;
        R2=MAX(wire_locat[pic][0][0] +1,mid-N_MAX+1);
        L2=MIN(wire_locat[pic][0][1] -1,mid+N_MAX);
        mid =  (wire_locat[pic][2][1] + wire_locat[pic][2][0]) >> 1;
        R3=MAX(wire_locat[pic][2][0] +1,mid-N_MAX+1);
        L3=MIN(wire_locat[pic][2][1] -1,mid+N_MAX);
        for (i=0; i<FR_Y_SIZE; i++)
        for (j=R2; j<= L2; j++)
```

```
                {
                image[i][j]=1;
                }
            for (i=0; i<FR_Y_SIZE; i++)
        for (j=R3; j<= L3; j++)
                {
                image[i][j]=1;
                }
        }
}
clear_x_sel(image,boundary,boundary_index)
    PIXEL image[][FR_X_SIZE];
    struct line_pair boundary[];
{
int i,j,y,x1,x2;
        for (y = 0 ; y < boundary[0].y ; ++y)
            for (j = 0 ; j < FR_X_SIZE ; ++j)    image[y][j] = 0;
        for (i = 0 ; i < boundary_index ; ++i)
        {
            y = boundary[i].y;
            x1 = boundary[i].x1;
            x2 = boundary[i].x2;
            for (j = 0 ; j < x1 ; ++j)          image[y][j] = 0.;
            for (j = x2 ; j < FR_X_SIZE ; ++j)  image[y][j] = 0;
        }
        for (y = boundary[boundary_index-1].y+1 ; y < FR_Y_SIZE ; ++y)
            for (j = 0 ; j < FR_X_SIZE ; ++j)   image[y][j] = 0;
}
clear_x_sel_color(image,boundary,boundary_index, color)
    PIXEL image[][FR_X_SIZE];
    struct line_pair boundary[];
{
int i,j,y,x1,x2;
        for (y = 0 ; y < boundary[0].y ; ++y)
            for (j = 0 ; j < FR_X_SIZE ; ++j)   image[y][j] = color;
        for (i = 0 ; i < boundary_index ; ++i)
        {
            y = boundary[i].y;
            x1 = boundary[i].x1;
            x2 = boundary[i].x2;
            for (j = 0 ; j < x1 ; ++j)          image[y][j] = color;
            for (j = x2 ; j < FR_X_SIZE ; ++j)  image[y][j] = color;
        }
        for (y = boundary[boundary_index-1].y+1 ; y < FR_Y_SIZE ; ++y)
            for (j = 0 ; j < FR_X_SIZE ; ++j)   image[y][j] = color;
}
correct_pip_hole_n(image, boundary, boundary_index, off_x, off_y)
        PIXEL   image[L_FR_Y_SIZE][L_FR_X_SIZE];
        struct line_pair boundary[];
{
int i, y, x1, y1, j, x2;
#define MARGIN 4
    for (i = 0 ; i < boundary_index ; ++i)
    {
        y = boundary[i].y - off_y;
        if (y < 0 || y >= L_FR_Y_SIZE) continue;
        x1 = boundary[i].x1 - off_x + MARGIN; if (x1 < 0) x1 = 0;
        x2 = boundary[i].x2 - off_x - MARGIN; if (x2 > L_FR_X_SIZE) x2 = L_FR_X_SIZ
        if (x1 == 0 && x2 == L_FR_X_SIZE)
            for (j = 0 ; j < x2 ; ++j) image[y][j] = 255;
        else {
            for (j = 0 ; j < x1 ; ++j)          image[y][j] = 255;
            for (j = x2 ; j < L_FR_X_SIZE ; ++j) image[y][j] = 255;
        }
```

```c
    }
    for (y = 0 ; y < boundary[0].y - off_y ; ++y)
        for (j = 0 ; j < L_FR_X_SIZE ; ++j)
                        image[y][j] = 255;
    for (y = boundary[boundary_index-1].y - off_y ; y < L_FR_Y_SIZE ; ++y)
        for (j = 0 ; j < L_FR_X_SIZE ; ++j)
                        image[y][j] = 255;
#undef MARGIN
}
clear_outside(image, boundary, boundary_index, color)
        PIXEL   image[FR_Y_SIZE][FR_X_SIZE];
        struct line_pair boundary[];
{
int i, y, x1, y1, j, x2;
#define MARGIN 0
    for (i = 0 ; i < boundary_index ; ++i)
    {
        y = boundary[i].y;
        if (y < 0 || y >= L_FR_Y_SIZE) continue;
        x1 = boundary[i].x1 + MARGIN; if (x1 < 0) x1 = 0;
        x2 = boundary[i].x2 - MARGIN; if (x2 > FR_X_SIZE) x2 = FR_X_SIZE;
        if (x1 == 0 && x2 == FR_X_SIZE)
            for (j = 0 ; j < x2 ; ++j) image[y][j] = color;
        else {
           for (j = 0 ; j < x1 ; ++j)         image[y][j] = color;
           for (j = x2 ; j < FR_X_SIZE ; ++j) image[y][j] = color;
        }
    }
    for (y = 0 ; y < boundary[0].y  ; ++y)
        for (j = 0 ; j < FR_X_SIZE ; ++j)
                        image[y][j] = color;
    for (y = boundary[boundary_index-1].y ; y < FR_Y_SIZE ; ++y)
        for (j = 0 ; j < FR_X_SIZE ; ++j)
                        image[y][j] = color;
#undef MARGIN
}
do_smooth_masked(src,dst)
        PIXEL src[][FR_X_SIZE];
        PIXEL dst[][FR_X_SIZE];
{
int i,j, cnt;
unsigned int n, p;
    for (i = 1 ; i < FR_Y_SIZE-1 ; ++i)
       for (j = 1 ; j < FR_X_SIZE-1 ; ++j)
       {
          p = src[i][j];
          if (p < 253)  { n = p << 2; cnt = 4; }
          else (  dst[i][j] = (PIXEL)p; continue;    }
#define ADD_COND4(a,b) p = src[a][b]; if (p < 253) {n += (p << 1); cnt += 2;}
#define ADD_COND8(a,b) p = src[a][b]; if (p < 253) {n += p;        cnt += 1;}
          ADD_COND4(i,j-1);
          ADD_COND4(i-1,j);
          ADD_COND4(i+1,j);
          ADD_COND4(i,j+1);
          ADD_COND8(i-1,j-1);
          ADD_COND8(i-1,j+1);
          ADD_COND8(i+1,j-1);
          ADD_COND8(i+1,j+1);
          n = (int)((double)n / (double)cnt + 0.5);
          dst[i][j] = (PIXEL)n;
      }
  return(1);
}
static
```

```
fill_margins(im2)
          PIXEL im2[][FR_X_SIZE];
{
int i,j;
   for (i = 0 ; i < FR_Y_SIZE ; ++i)
       {
         im2[i][0] = im2[i][1];
         im2[i][FR_X_SIZE-1] = im2[i][FR_X_SIZE-2];
       }
   for (j = 1 ; j < FR_X_SIZE-1 ; ++j)
       {
         im2[0][j] = im2[1][j];
         im2[FR_Y_SIZE-1][j] = im2[FR_Y_SIZE-2][j];
       }
}
do_sobel(im1,im2)              PIXEL im1[][FR_X_SIZE];
          PIXEL im2[][FR_X_SIZE];
{
int i,j,g1,g2,h,v,n;
   for (i = 1 ; i < FR_Y_SIZE-1 ; ++i)
      for (j = 1 ; j < FR_X_SIZE-1 ; ++j)
        {
          g1 = im1[i-1][j-1] + im1[i-1][j+1]; g1 += (im1[i-1][j] << 1);
          g2 = im1[i+1][j-1] + im1[i+1][j+1]; g2 += (im1[i+1][j] << 1);
          h = g1 - g2;
          if (h < 0) h = -h;
          g1 = im1[i-1][j-1] + im1[i+1][j-1]; g1 += (im1[i][j-1] << 1);
          g2 = im1[i-1][j+1] + im1[i+1][j+1]; g2 += (im1[i][j+1] << 1);
          v = g1 - g2;
          if (v < 0) v = -v;
          n = (v + h);
          n = n >> 2;
          if (n > 255) n = 255;
          im2[i][j] = (PIXEL)n;
        }
   fill_margins(im2);
  return(1);
}
do_stretch(im1,im2,delta)        PIXEL im1[][FR_X_SIZE];
          PIXEL im2[][FR_X_SIZE];
{
int i,j;
int min = 256, max = -1, pix;
double factor;
   for (i = delta ; i < FR_Y_SIZE-delta ; ++i)
      for (j = delta ; j < FR_X_SIZE-delta ; ++j)
        {
        pix = (int) im1[i][j];
        if (pix > max) max = pix;
        if (pix < min) min = pix;
        }
   factor = 255./(double)(max - min);
   for (i = delta ; i < FR_Y_SIZE-delta ; ++i)
      for (j = delta ; j < FR_X_SIZE-delta ; ++j)
        {
          pix = (int) im1[i][j];
          pix = (int) ((double) (pix - min) * factor + 0.5) ;
          im2[i][j] = (PIXEL) pix;
        }
}
do_sharpening(im1,im2)       PIXEL im1[][FR_X_SIZE];
          PIXEL im2[][FR_X_SIZE];
{
int i,j,n;
```

```c
int min,max;
   for (i = 1 ; i < FR_Y_SIZE-1 ; ++i)
     for (j = 1 ; j < FR_X_SIZE-1 ; ++j)
       {
         n = im1[i][j];
         n = n << 4;
         n = n - (im1[i-1][j] + im1[i][j-1] + im1[i+1][j] + im1[i][j+1]);
         n = n >> 4;
         if (n > 255) n = 255;
         else if (n < 0) n = 0;
         im2[i][j] = n;
       }
   fill_margins(im2);
      do_stretch(im2,im2,5);
}
do_smooth(im1,im2)          PIXEL im1[][FR_X_SIZE];
         PIXEL im2[][FR_X_SIZE];
{
int i,j;
unsigned int n;
   for (i = 1 ; i < FR_Y_SIZE-1 ; ++i)
     for (j = 1 ; j < FR_X_SIZE-1 ; ++j)
       {
         n = im1[i][j] << 2;
         n +=
            ((im1[i][j-1] + im1[i-1][j] + im1[i+1][j] + im1[i][j+1]) << 1);
         n +=
            im1[i-1][j-1] + im1[i-1][j+1] + im1[i+1][j-1] + im1[i+1][j+1];
         n = n >> 4;
         im2[i][j] = (PIXEL)n;
       }
   fill_margins(im2);
   return(1);
}
do_erosion_0(im1,im2,color)     PIXEL im1[][FR_X_SIZE];
         PIXEL im2[][FR_X_SIZE];
{
int i,j,n, l, c4 = color << 2, fr;
   l = 0;
   for (i = 1 ; i < FR_Y_SIZE-1 ; ++i)
     for (j = 1 ; j < FR_X_SIZE-1 ; ++j)
       {
         fr = 0;
         if (im1[i][j] == color)
         {
         n = im1[i-1][j] + im1[i+1][j] +
             im1[i][j+1] + im1[i][j-1]   ;
         if (n == c4) { fr = color; l = 1; }
         }
         im2[i][j] = fr;
       }
   return(l);
}
do_dialation_0(im1,im2,color)     PIXEL im1[][FR_X_SIZE];
             PIXEL im2[][FR_X_SIZE];
{
int i,j,n, l;
   l = 0;
   for (i = 1 ; i < FR_Y_SIZE-1 ; ++i)
     for (j = 1 ; j < FR_X_SIZE-1 ; ++j)
       {
         im2[i][j] = im1[i][j];
         if (im1[i][j] != color)
         {
```

```
            n = im1[i-1][j] + im1[i+1][j] +
                im1[i][j+1] + im1[i][j-1]   ;
            if (n) { im2[i][j] = color; l = 1; }
           }
         }
      fill_margins(im2);
    return(l);
}
do_dialation(im1,im2,color)      PIXEL im1[][FR_X_SIZE];
                 PIXEL im2[][FR_X_SIZE];
{
int i,j,n, l;
    l = 0;
    for (i = 1 ; i < FR_Y_SIZE-1 ; ++i)
      for (j = 1 ; j < FR_X_SIZE-1 ; ++j)
        {
          im2[i][j] = im1[i][j];
          if (im1[i][j] != color)
          {
          if (im1[i-1][j] == color)  goto cont;
          if (im1[i+1][j] == color)  goto cont;
          if (im1[i][j+1] == color)  goto cont;
          if (im1[i][j-1] == color)  goto cont;
          im2[i][j] = im1[i][j];
          continue;
           cont:
          im2[i][j] = color; l = 1;
          }
        }
      fill_margins(im2);
    return(l);
}
do_erosion(im1,im2,color)      PIXEL im1[][FR_X_SIZE];
              PIXEL im2[][FR_X_SIZE];
{
int i,j,n, l;
    l = 0;
    for (i = 1 ; i < FR_Y_SIZE-1 ; ++i)
      for (j = 1 ; j < FR_X_SIZE-1 ; ++j)
        {
          if (im1[i][j] != color)  im2[i][j] = im1[i][j] ;
          else {
          n = 0;
          if (im1[i-1][j] == color) ++n;
          if (im1[i+1][j] == color) ++n;
          if (im1[i][j+1] == color) ++n;
          if (im1[i][j-1] == color) ++n;
          if (n < 4) im2[i][j] = 0 ; else { im2[i][j] = color; l = 1; }
          }
        }
      fill_margins(im2);
    return(l);
}
static
order_it(vec)                    int vec[9];
{
int i,j ;
int order_flag ;
    do
       {
       order_flag = 0 ;
       for (i=1 ; i < 9 ; ++i)
          if (vec[i-1] > vec[i])
              {
```

```
                    j = vec[i-1] ;
                    vec[i-1] = vec[i] ;
                    vec[i] = j ;
                    order_flag = 1 ;
                    }
        } while ( order_flag ) ;
}
do_median(im1,im2)
            PIXEL im1[][FR_X_SIZE];
            PIXEL im2[][FR_X_SIZE];

{
int i,j,k;
int mm[9];
    for (i = 1 ; i < FR_Y_SIZE-1 ; ++i)
      for (j = 1 ; j < FR_X_SIZE-1 ; ++j)
         {
         mm[0] = im1[i][j];      mm[1] = im1[i-1][j];
         mm[2] = im1[i+1][j];    mm[3] = im1[i][j-1];
         mm[4] = im1[i][j+1];    mm[5] = im1[i-1][j-1];
         mm[6] = im1[i-1][j+1];  mm[7] = im1[i+1][j-1];
         mm[8] = im1[i+1][j+1];
         order_it(mm);
         k = mm[4];
        im2[i][j] = k;
            }
    fill_margins(im2);
}
smooth_screen(x1,y1,x2,y2,x_off_1, y_off_1, x_off_2, y_off_2)
{
int x,y,i,j,l = x2-x1, n;
unsigned char *ar;
    ar = malloc(l*3);
    if (ar == 0) { printf ("\n No MEM"); exit(1); }
    for (i = y1 ; i < y2 ; ++i)
        {
        get_block(ar, 0, 0, 3, l, x1 + x_off_1, i+1+ y_off_1);
        for (j = l+2 ; j < l+l ; ++j)
            {
            n  = (*(ar + j - 1)) ;
            n += (*(ar + j + 1)) ;
            n += (*(ar + j - 1)) ;
            n += (*(ar + j + 1)) ;
            n = n << 1;
            x = ((*(ar + j)) << 2);
            n += x;
            n += (*(ar + j - l - 1));
            n += (*(ar + j - l + 1));
            n += (*(ar + j + l - 1));
            n += (*(ar + j + l + 1));
            n = n >> 4;
            *(ar+j-2) = n;
            }
        copy_block(ar+1,0,0,1,l,x1+2+x_off_2,i+1+y_off_2);
        }
        free(ar);
}
image_max(image)              PIXEL image[][FR_X_SIZE];
{
int i,j, max;
    max = 0;
    for (i = 0 ; i < FR_Y_SIZE ; ++i)
        for (j = 0 ; j < FR_X_SIZE ; ++j)
            if (image[i][j] > max) max = image[i][j];
     printf ("\n max = %d",max);
```

```
      return(max);
}
dialate_color(mat, mat1,color)
   PIXEL mat[][FR_X_SIZE];
   PIXEL mat1[][FR_X_SIZE];
{
int i,j, count = 0;
   for (i = 1 ; i < FR_Y_SIZE-1 ; ++i)
      for (j = 1 ; j < FR_X_SIZE-1 ; ++j)
            if (mat[i-1][j] == color || mat[i][j-1] == color ||
               mat[i+1][j] == color || mat[i][j+1] == color)
                        { mat1[i][j] = color; ++count; }
                     else mat1[i][j] = mat[i][j];
   return(count);
}
erode_color(mat, mat1,color)
   PIXEL mat[][FR_X_SIZE];
   PIXEL mat1[][FR_X_SIZE];
{
int i,j, count = 0;
   for (i = 1 ; i < FR_Y_SIZE-1 ; ++i)
      for (j = 1 ; j < FR_X_SIZE-1 ; ++j)
            if (mat[i-1][j] != color || mat[i][j-1] != color ||
               mat[i+1][j] != color || mat[i][j+1] != color)
                     { mat1[i][j] = 0; }
                     else { mat1[i][j] = mat[i][j]; ++count; }
   return(count);
}
static int x_resolution, y_resolution;
static int x_pos, y_pos, init_status;
vga_null() {}
vga_clear_screen(color)
{
int y;
unsigned char c;
   vga_filled_rectangle(0,0,x_resolution,y_resolution,color);
#ifdef BIOS_CLS
   c = color;
_asm \
   {
      mov      ah, 0bh
      mov      bh, 00
      mov      bl, c
      int      10h
      nop
   }
#endif
}
init_vga_display(mode)
{
int i;
unsigned short lut[256][4];
   switch(mode)
   {
      case 5:
         bios_vga_mode(0x5d);
         x_resolution = 640;
         y_resolution = 480;
         break;
   }
      for (i = 0 ; i < 256 ; ++i)
      {
         lut[i][0] = i;
         lut[i][1] = i;
```

```c
        lut[i][2] = i;
        lut[i][3] = 255;
    }
    vga_set_pallate(lut);
    init_status = 1;
}
reinit_vga()
{
        x_resolution = 640;
        y_resolution = 480;
        init_status = 2;
}
vga_filled_rectangle(x1,y1,x2,y2,color)
{
    for ( ; y1 <= y2 ; ++y1)
        vga_hline(x1, y1, (x2-x1+1), color);
}
vga_rectangle(x1,y1,x2,y2,color)
{
    vga_hline(x1, y1, (x2-x1+1), color);
    vga_hline(x1, y2, (x2-x1+1), color);
    vga_vline(x1, y1, (y2-y1+1), color);
    vga_vline(x2, y1, (y2-y1+1), color);
}
vga_vline(xdst, ydst, len, color)
{
int i,j;
unsigned short a_h, a_l;
unsigned long address;
    address = (unsigned long)ydst * x_resolution + (unsigned long)xdst;
    for (i = 0 ; i < len ; ++i)
    {
        a_l = address & 0xFFFF;
        a_h = (address >> 16) & 0xF;
        address += x_resolution;
    _asm {
        mov     bh, a_h
        mov     di, a_l
        mov     ax, 0A000h
        mov     es, ax
        mov     ah, bh
        xor     ah, 2
        mov     dx, 3c4h
        mov     al, 0Eh
        out     dx, ax
        mov     al, color
        stosb
        }
    }
}
vga_hline(xdst, ydst, len, color)
{
int i,j;
unsigned short a_h, a_l;
unsigned long address;
    address = (unsigned long)ydst * x_resolution + (unsigned long)xdst;
    for (i = 0 ; i < len ; ++i)
    {
        a_l = address & 0xFFFF;
        a_h = (address >> 16) & 0xF;
        address += 1;
    _asm {
        mov     bh, a_h
        mov     di, a_l
```

```
            mov     ax, 0A000h
            mov     es, ax
            mov     ah, bh
            xor     ah, 2
            mov     dx, 3c4h
            mov     al, 0Eh
            out     dx, ax
            mov     al, color
            stosb
            }
        }
    }
}
vga_put_image(image, ximage, yimage, xdst, ydst)
                    unsigned char *image;
{
int i,j;
unsigned short a_h, a_l;
unsigned long address;
unsigned char color;
    address = (unsigned long)ydst * x_resolution + (unsigned long)xdst;
    for (i = 0 ; i < yimage ; ++i)
    {
        for (j = 0 ; j < ximage ; ++j)
        {
          a_l = address & 0xFFFF;
          a_h = (address >> 16) & 0xF;
          color = *image++;
          address += 1;
    _asm {
            mov     bh, a_h
            mov     di, a_l
            mov     ax, 0A000h
            mov     es, ax
            mov     ah, bh
            xor     ah, 2
            mov     dx, 3c4h
            mov     al, 0Eh
            out     dx, ax
            mov     al, color
            stosb
            }
        }
        address += (x_resolution - ximage);
    }
}
vga_get_image(image, ximage, yimage, xdst, ydst)
                    unsigned char *image;
{
int i,j;
unsigned short a_h, a_l;
unsigned long address;
unsigned char color;
    address = (unsigned long)ydst * x_resolution + (unsigned long)xdst;
    for (i = 0 ; i < yimage ; ++i)
    {
        for (j = 0 ; j < ximage ; ++j)
        {
          a_l = address & 0xFFFF;
          a_h = (address >> 16) & 0xF;
    _asm {
            push    ds
            push    si
            mov     bh, a_h
            mov     si, a_l
```

```
            mov     ah, bh
            xor     ah, 2
            mov     dx, 3c4h
            mov     al, 0Eh
            out     dx, ax
            mov     ax, 0A000h
            mov     ds, ax
            lodsb
            pop     si
            pop     ds
            mov     color, al
         }
            *image++ = color;
            address += 1;
      }
         address += (x_resolution - ximage);
   }
}
vga_set_pallate(lut)        unsigned short *lut;
{
unsigned short a_l, a_h;
unsigned long v;
int i;
unsigned char *p = (unsigned char *)lut;
   for (i = 0 ; i < 256*4 ; i += 4)
      {
         *p++   = lut[i] >> 2;
         *p++ = lut[i+1] >> 2;
         *p++ = lut[i+2] >> 2;
      }
      v = (unsigned long)lut;
      a_l = v & 0xFFFF;
      v = v >> 16;
      a_h = v & 0xFFFF;
   _asm \
      {
         mov         es, a_h
         mov         dx, a_l
         mov         ah, 10h
         mov         al, 12h
         mov         bx, 0
         mov         cx, 256
         int         10h
         nop
      }
}
vga_set_1_cval(value, r,g,b)
{
_asm \
   {
      mov         ah, 10h
      mov         al, 10h
      mov         bx, value
      mov         dh, r
      mov         ch, g
      mov         cl, b
      int         10h
      nop
   }
}
vga_direct_rpixel(x,y)
{
unsigned char color;
unsigned long address;
```

```c
unsigned short a_h, a_l;
    address = (unsigned long)y * x_resolution + (unsigned long)x;
    a_l = address & 0xFFFF;
    address = address >> 16;
    a_h = address & 0xF;
  _asm {
      push   ds
      push   si
      mov    bh, a_h
      mov    si, a_l
      mov    ah, bh
      xor    ah, 2
      mov    dx, 3c4h
      mov    al, 0Eh
      out    dx, ax
      mov    ax, 0A000h
      mov    ds, ax
      lodsb
      pop    si
      pop    ds
      mov    color, al
      }
 return(color);
}
vga_direct_wpixel(x,y,color)
{
unsigned short a_h, a_l;
unsigned long address;
    address = (unsigned long)y * x_resolution + (unsigned long)x;
    a_l = address & 0xFFFF;
    address = address >> 16;
    a_h = address & 0xF;
  _asm {
      mov    bh, a_h
      mov    di, a_l
      mov    bl, color
      mov    ax, 0A000h
      mov    es, ax
      mov    ah, bh
      xor    ah, 2
      mov    dx, 3c4h
      mov    al, 0Eh
      out    dx, ax
      mov    al, bl
      stosb
      }
}
bios_vga_mode(mode)
{
unsigned char ml = mode & 0xff;
_asm \
    {
       mov         ah, 00h
       mov         al, ml
       int         10h
       nop
                   ;SELECT 64K mode
       mov    dx, 3C4h
       mov    al, 0Bh
       out    dx, al
       inc    dx
       in     al, dx
       mov    dx, 3CEh
       mov    ax, 506h
```

```c
        out     dx, ax
    }
}
restore_vga()
{
unsigned char m1 = 0x3;
    if (init_status == 1)
    {
_asm \
    {
        mov         ah, 00h
        mov         al, m1
        int         10h
        nop
    }
    }
}
bios_vga_stat()
{
unsigned char disp_mode;
unsigned char chars_in_line;
unsigned char err;
_asm \
    {
        mov         ah, 0Fh
        int         10h
        mov         disp_mode, al
        mov         chars_in_line, ah
    }
    printf("\n %d %d", disp_mode, chars_in_line);
}
etext_vga(x,y,string,hvflag,color,magnification)
        int x,y,hvflag,magnification,color;
        char string[];
{
int index, size;
    size = magnification * 8;
    for (index = 0 ; string[index] ; ++index)
    {
        vga_single_char_1(string[index],x,y,magnification,color);
        if (hvflag) x += size;
        else        y += size;
    }
}
vga_single_char_1(ascii,x,y,magnification,color)
{
int table_index = ascii - 040;
int row, col, bits, old_x = x;
int row_1, col_1;
    if (table_index < 0 || table_index > 200) return(0);
    for (row = 0 ; row < 9 ; ++row)
    {
    bits = demi(table_index,row);
    x = old_x;
    for (col = 0 ; col < 8 ; ++col)
    {
        if (bits & 0x80) {
          for (row_1 = y ; row_1 < y + magnification; ++row_1)
           for (col_1 = x ; col_1 < x + magnification; ++col_1)
                vga_direct_wpixel( col_1, row_1, color);
        }
        else {
        }
        bits = bits << 1;
```

```c
                x += magnification ;
            }
        y -= magnification ;
        }
}
#include <math.h>
#define RASTER_SIZE_X   x_resolution
#define RASTER_SIZE_Y   y_resolution
#define putpix_v        vga_direct_wpixel
static
put_dot(x,y,color)
int x,y ;
{
    if (x > RASTER_SIZE_X || y > RASTER_SIZE_Y || x < 0 || y < 0 )
        {
        return (0) ;
        }
    else
        {
        putpix_v(x,y,color);
        return(1);
        }
}
unsigned char char_table[][10] = {
    { 0000, 0000, 0000, 0000, 0000, 0000, 0000, 0000, 0000, 0000 },
    { 0020, 0020, 0020, 0020, 0020, 0000, 0020, 0000, 0000, 0000 },
    { 0120, 0120, 0120, 0000, 0000, 0000, 0000, 0000, 0000, 0000 },
    { 0120, 0120, 0370, 0120, 0370, 0120, 0120, 0000, 0000, 0000 },
    { 0040, 0170, 0240, 0160, 0050, 0360, 0040, 0000, 0000, 0000 },
    { 0300, 0310, 0020, 0040, 0100, 0230, 0030, 0000, 0000, 0000 },
    { 0100, 0240, 0240, 0100, 0250, 0220, 0150, 0000, 0000, 0000 },
    { 0040, 0040, 0040, 0000, 0000, 0000, 0000, 0000, 0000, 0000 },
    { 0040, 0100, 0200, 0200, 0200, 0100, 0040, 0000, 0000, 0000 },
    { 0040, 0020, 0010, 0010, 0010, 0020, 0040, 0000, 0000, 0000 },
    { 0040, 0250, 0160, 0040, 0160, 0250, 0040, 0000, 0000, 0000 },
    { 0000, 0040, 0040, 0370, 0040, 0040, 0000, 0000, 0000, 0000 },
    { 0000, 0000, 0000, 0000, 0040, 0040, 0100, 0000, 0000, 0000 },
    { 0000, 0000, 0000, 0370, 0000, 0000, 0000, 0000, 0000, 0000 },
    { 0000, 0000, 0000, 0000, 0000, 0040, 0000, 0000, 0000, 0000 },
    { 0000, 0010, 0020, 0040, 0100, 0200, 0000, 0000, 0000, 0000 },
    { 0160, 0210, 0230, 0250, 0310, 0210, 0160, 0000, 0000, 0000 },
    { 0040, 0140, 0040, 0040, 0040, 0040, 0160, 0000, 0000, 0000 },
    { 0160, 0210, 0010, 0060, 0100, 0200, 0370, 0000, 0000, 0000 },
    { 0370, 0010, 0020, 0060, 0010, 0210, 0160, 0000, 0000, 0000 },
    { 0020, 0060, 0120, 0220, 0370, 0020, 0020, 0000, 0000, 0000 },
    { 0370, 0200, 0360, 0010, 0010, 0010, 0360, 0000, 0000, 0000 },
    { 0160, 0200, 0200, 0360, 0210, 0210, 0160, 0000, 0000, 0000 },
    { 0370, 0010, 0020, 0040, 0100, 0100, 0100, 0000, 0000, 0000 },
    { 0160, 0210, 0210, 0160, 0210, 0210, 0160, 0000, 0000, 0000 },
    { 0160, 0210, 0210, 0170, 0010, 0010, 0160, 0000, 0000, 0000 },
    { 0000, 0000, 0040, 0000, 0040, 0000, 0000, 0000, 0000, 0000 },
    { 0000, 0000, 0040, 0000, 0040, 0040, 0100, 0000, 0000, 0000 },
    { 0020, 0040, 0100, 0200, 0100, 0040, 0020, 0000, 0000, 0000 },
    { 0000, 0000, 0370, 0000, 0370, 0000, 0000, 0000, 0000, 0000 },
    { 0200, 0100, 0040, 0020, 0040, 0100, 0200, 0000, 0000, 0000 },
    { 0160, 0210, 0020, 0040, 0040, 0000, 0040, 0000, 0000, 0000 },
    { 0160, 0210, 0250, 0270, 0260, 0200, 0170, 0000, 0000, 0000 },
    { 0040, 0120, 0210, 0210, 0370, 0210, 0210, 0000, 0000, 0000 },
    { 0360, 0210, 0210, 0360, 0210, 0210, 0360, 0000, 0000, 0000 },
    { 0160, 0210, 0200, 0200, 0200, 0210, 0160, 0000, 0000, 0000 },
    { 0360, 0210, 0210, 0210, 0210, 0210, 0360, 0000, 0000, 0000 },
    { 0370, 0200, 0200, 0360, 0200, 0200, 0370, 0000, 0000, 0000 },
    { 0370, 0200, 0200, 0360, 0200, 0200, 0200, 0000, 0000, 0000 },
    { 0170, 0200, 0200, 0200, 0230, 0210, 0170, 0000, 0000, 0000 },
```

```
    { 0210, 0210, 0210, 0370, 0210, 0210, 0210, 0000, 0000, 0000 },
    { 0160, 0040, 0040, 0040, 0040, 0040, 0160, 0000, 0000, 0000 },
    { 0010, 0010, 0010, 0010, 0010, 0210, 0160, 0000, 0000, 0000 },
    { 0210, 0220, 0240, 0300, 0240, 0220, 0210, 0000, 0000, 0000 },
    { 0200, 0200, 0200, 0200, 0200, 0200, 0370, 0000, 0000, 0000 },
    { 0210, 0330, 0250, 0210, 0210, 0210, 0210, 0000, 0000, 0000 },
    { 0210, 0210, 0310, 0250, 0230, 0210, 0210, 0000, 0000, 0000 },
    { 0160, 0210, 0210, 0210, 0210, 0210, 0160, 0000, 0000, 0000 },
    { 0360, 0210, 0210, 0360, 0200, 0200, 0200, 0000, 0000, 0000 },
    { 0160, 0210, 0210, 0210, 0250, 0220, 0150, 0000, 0000, 0000 },
    { 0360, 0210, 0210, 0360, 0240, 0220, 0210, 0000, 0000, 0000 },
    { 0160, 0210, 0200, 0160, 0010, 0210, 0160, 0000, 0000, 0000 },
    { 0370, 0040, 0040, 0040, 0040, 0040, 0040, 0000, 0000, 0000 },
    { 0210, 0210, 0210, 0210, 0210, 0210, 0160, 0000, 0000, 0000 },
    { 0210, 0210, 0210, 0210, 0210, 0120, 0040, 0000, 0000, 0000 },
    { 0210, 0210, 0210, 0250, 0250, 0330, 0210, 0000, 0000, 0000 },
    { 0210, 0210, 0120, 0040, 0120, 0210, 0210, 0000, 0000, 0000 },
    { 0210, 0210, 0120, 0040, 0040, 0040, 0040, 0000, 0000, 0000 },
    { 0370, 0010, 0020, 0040, 0100, 0200, 0370, 0000, 0000, 0000 },
    { 0370, 0300, 0300, 0300, 0300, 0300, 0370, 0000, 0000, 0000 },
    { 0000, 0200, 0100, 0040, 0020, 0010, 0000, 0000, 0000, 0000 },
    { 0370, 0030, 0030, 0030, 0030, 0030, 0370, 0000, 0000, 0000 },
    { 0000, 0000, 0040, 0120, 0210, 0000, 0000, 0000, 0000, 0000 },
    { 0000, 0000, 0000, 0000, 0000, 0000, 0370, 0000, 0000, 0000 },
    { 0100, 0040, 0020, 0000, 0000, 0000, 0000, 0000, 0000, 0000 },
    { 0000, 0000, 0150, 0230, 0210, 0230, 0150, 0000, 0000, 0000 },
    { 0200, 0200, 0260, 0310, 0210, 0310, 0260, 0000, 0000, 0000 },
    { 0000, 0000, 0170, 0200, 0200, 0200, 0170, 0000, 0000, 0000 },
    { 0010, 0010, 0150, 0230, 0210, 0230, 0150, 0000, 0000, 0000 },
    { 0000, 0000, 0160, 0210, 0370, 0200, 0160, 0000, 0000, 0000 },
    { 0020, 0040, 0040, 0160, 0040, 0040, 0040, 0000, 0000, 0000 },
    { 0000, 0000, 0150, 0230, 0210, 0230, 0150, 0010, 0010, 0160 },
    { 0200, 0200, 0260, 0310, 0210, 0210, 0210, 0000, 0000, 0000 },
    { 0040, 0000, 0140, 0040, 0040, 0040, 0160, 0000, 0000, 0000 },
    { 0020, 0000, 0020, 0020, 0020, 0020, 0020, 0020, 0020, 0140 },
    { 0200, 0210, 0220, 0240, 0340, 0220, 0210, 0000, 0000, 0000 },
    { 0140, 0040, 0040, 0040, 0040, 0040, 0160, 0000, 0000, 0000 },
    { 0000, 0000, 0320, 0250, 0250, 0250, 0250, 0000, 0000, 0000 },
    { 0000, 0000, 0360, 0210, 0210, 0210, 0210, 0000, 0000, 0000 },
    { 0000, 0000, 0160, 0210, 0210, 0210, 0160, 0000, 0000, 0000 },
    { 0000, 0000, 0260, 0310, 0210, 0310, 0260, 0200, 0200, 0200 },
    { 0000, 0000, 0150, 0230, 0210, 0230, 0150, 0010, 0010, 0010 },
    { 0000, 0000, 0270, 0300, 0200, 0200, 0200, 0000, 0000, 0000 },
    { 0000, 0000, 0170, 0200, 0160, 0010, 0360, 0000, 0000, 0000 },
    { 0040, 0040, 0160, 0040, 0040, 0040, 0020, 0000, 0000, 0000 },
    { 0000, 0000, 0210, 0210, 0210, 0210, 0170, 0000, 0000, 0000 },
    { 0000, 0000, 0210, 0210, 0120, 0120, 0040, 0000, 0000, 0000 },
    { 0000, 0000, 0210, 0210, 0210, 0250, 0120, 0000, 0000, 0000 },
    { 0000, 0000, 0210, 0120, 0040, 0120, 0210, 0000, 0000, 0000 },
    { 0000, 0000, 0210, 0210, 0210, 0210, 0170, 0010, 0010, 0160 },
    { 0000, 0000, 0370, 0020, 0040, 0100, 0370, 0000, 0000, 0000 },
    { 0040, 0100, 0100, 0200, 0100, 0100, 0040, 0000, 0000, 0000 },
    { 0040, 0040, 0040, 0000, 0040, 0040, 0040, 0000, 0000, 0000 },
    { 0040, 0020, 0020, 0010, 0020, 0020, 0040, 0000, 0000, 0000 },
    { 0000, 0000, 0010, 0160, 0200, 0000, 0000, 0000, 0000, 0000 },
    { 0370, 0370, 0370, 0370, 0370, 0370, 0370, 0370, 0370, 0370 },
};
demi(d1,d2)
{
  return(char_table[d1][d2]);
}
#define N_SPLITTER 4
struct single_view_info   view_info[N_CAMERAS];
struct prog_settings prog_consts;
```

```
load_splitter_locations()
{
int cam, ret, j;
char tmp_name[16];
struct boundary_data bnd;
    for (cam = 0 ; cam < N_CAMERAS ; ++cam) {
            for (j = 0 ; j < N_SPLITTER ; ++j) {
                sprintf(tmp_name,"%s.%1d", prog_consts.SPLITTER_LOCATIONS[cam], j
                ret = get_per_data(tmp_name, bnd.boundary, &(bnd.boundary_index),
                                                                     &(bnd.out
                if (ret != SUCCESS) exit(1);
                swap_out(&bnd, view_info[cam].xms_handle, (long)sizeof(struct bou
                                        view_info[cam].splitter[j]);
                }
        return(SUCCESS);
}
load_no_zone_images(image)     char *image;
{
int cam, ret, j, x, y, m;
char tmp_name[16], header[FR_HEADER_SIZE];
    for (cam = 0 ; cam < N_CAMERAS ; ++cam) {
                sprintf(tmp_name,"%s.%1d", "NO_ZONE", cam);
        ret =  read_fr_pic(tmp_name, image, &x, &y, &m, header);
                if (ret != SUCCESS) { printf("\nNO_ZONE images notfound"); exit(1
                SWAP_OUT_SIZE(image, cam, spots_3, FR_Y_SIZE*FR_X_SIZE);
                }
        return(SUCCESS);
}
reinit_storage()
{
int r;
        init_xms();
        init_storage(1);
        r = undump_from_file(STORAGE_FILE);
        if (r != SUCCESS)     {
                fprintf(stderr, "Can't restore %s", STORAGE_FILE);
                exit(0);
                }
        return(SUCCESS);
}
init_xms()
{
  if (is_xms(0)) ;
    else { printf ("\n NO XMS!!"); exit(1); }
}
undump_from_file(name)       char *name;
{
int in_file, handles[N_CAMERAS], i, br;
                in_file = open(name,(O_RDONLY | O_BINARY), 0 );
            if (in_file == -1) return(FAILURE);
                i = sizeof(handles);
                br = read(in_file, handles, i);
                close(in_file);
                if (br != i)   return(FAILURE);
                for ( i = 0 ; i < N_CAMERAS ; ++i)
                                view_info[i].xms_handle = handles[i];
                return(SUCCESS);
}
dump_into_file(name)          char *name;
{
int out_file, handles[N_CAMERAS], i, bw;
        for ( i = 0 ; i < N_CAMERAS ; ++i)
                                handles[i] = view_info[i].xms_handle;
```

```
    out_file = open(name,(O_WRONLY | O_CREAT |
                                    O_TRUNC | O_BINARY), (0200 | 0400) );
        if (out_file == -1) return(FAILURE);
        i = sizeof(handles);
        bw = write(out_file, handles, i);
        close(out_file);
        if (bw != i) return(FAILURE);
        return(SUCCESS);
}
init_storage(flag)
{
int cam, handle, kb, j;
unsigned long offset;
#define SET_OFFSET(a,s) a = offset; offset += s;  /* printf("\n%ld",offset); */
#define LARGE_BUFFER  (unsigned long)((long)L_FR_X_SIZE * (long)L_FR_Y_SIZE)
#define MEDIUM_BUFFER (unsigned long)((long)L_FR_X_SIZE * (long)L_FR_Y_SIZE)
#define BOUNDARY_DATA (unsigned long)(sizeof(struct boundary_data))
int largest;
        for (cam = 0 ; cam < N_CAMERAS ; ++cam) {
        offset = 0;
                SET_OFFSET(view_info[cam].w_images.green, LARGE_BUFFER);
                SET_OFFSET(view_info[cam].w_images.red,   LARGE_BUFFER);
                SET_OFFSET(view_info[cam].w_images.ir,    LARGE_BUFFER);
                SET_OFFSET(view_info[cam].w_images.grid,  LARGE_BUFFER);
                SET_OFFSET(view_info[cam].r_images.green, LARGE_BUFFER);
                SET_OFFSET(view_info[cam].r_images.red,   LARGE_BUFFER);
                SET_OFFSET(view_info[cam].r_images.ir,    LARGE_BUFFER);
                SET_OFFSET(view_info[cam].r_images.grid,  LARGE_BUFFER);
                SET_OFFSET(view_info[cam].raw_images.green, MEDIUM_BUFFER);
                SET_OFFSET(view_info[cam].raw_images.red,   MEDIUM_BUFFER);
                SET_OFFSET(view_info[cam].raw_images.ir,    MEDIUM_BUFFER);
                SET_OFFSET(view_info[cam].raw_images.grid,  MEDIUM_BUFFER);
                SET_OFFSET(view_info[cam].enhanced_images.green, MEDIUM_BUFFER)
                SET_OFFSET(view_info[cam].enhanced_images.red,   MEDIUM_BUFFER)
                SET_OFFSET(view_info[cam].enhanced_images.ir,    MEDIUM_BUFFER)
                SET_OFFSET(view_info[cam].enhanced_images.grid,  MEDIUM_BUFFER)
                SET_OFFSET(view_info[cam].normal_images.green, MEDIUM_BUFFER);
                SET_OFFSET(view_info[cam].normal_images.red,   MEDIUM_BUFFER);
                SET_OFFSET(view_info[cam].normal_images.ir,    MEDIUM_BUFFER);
                SET_OFFSET(view_info[cam].normal_images.grid,  MEDIUM_BUFFER);
                SET_OFFSET(view_info[cam].stem_mask, MEDIUM_BUFFER);
                SET_OFFSET(view_info[cam].spots_1,   MEDIUM_BUFFER);
                SET_OFFSET(view_info[cam].spots_2,   MEDIUM_BUFFER);
                SET_OFFSET(view_info[cam].spots_3,   MEDIUM_BUFFER);
                SET_OFFSET(view_info[cam].combi_map, MEDIUM_BUFFER);
                for (j = 0 ; j < N_SPLITTER ; ++j) {   /* splitter pip holes
                        SET_OFFSET(view_info[cam].splitter[j], BOUNDARY_DATA);
                        }
                SET_OFFSET(view_info[cam].bnd,    BOUNDARY_DATA);
                SET_OFFSET(view_info[cam].bnd_z,  BOUNDARY_DATA);
                SET_OFFSET(view_info[cam].ref_bnd, BOUNDARY_DATA);
        if (flag == 0)     {    /* init XMS as well */
                kb = (offset >> 10) + 1;
                handle = malloc_extended(kb);
                if (handle == 0) { printf("\n no handles"); exit(0); }
                view_info[cam].xms_handle = handle;
            }
        }
        return(SUCCESS);
}
swap_out(buf, xms_handle, size, offset)
                                PIXEL *buf; int xms_handle; unsigned long offset,
{
int ret, handle;
```

```
        ret = xms_mem_move(xms_handle, (void _far *)offset, (unsigned long)size,
              0, (void _far *)buf);
        if (ret)       return(SUCCESS);
        return(FAILURE);

swap_in(buf, xms_handle, size, offset)
                                PIXEL *buf; int xms_handle; unsigned long offset,
{
int ret, handle;
        ret = xms_mem_move(0, (void _far *)buf, (unsigned long)size,
              xms_handle, (void _far *)offset);
        if (ret)       return(SUCCESS);
        return(FAILURE);
}
read_rul_pic(file_name,mat,size_x,size_y,magic_nu)
                                PIXEL *mat; char file_name[];
                                int *size_x, *size_y, *magic_nu;
{
int in_file, bytes_read, btbr;
long l[3];
#undef L_SIZE
#define L_SIZE 4
    in_file = open(file_name,  (O_RDONLY | O_BINARY) , 0) ;
    if (in_file == -1) return(0);
    if ( read(in_file, l, 3*L_SIZE) != 3*L_SIZE) { printf ("\n error in read #1")
                                    return(FAILURE); }
    *magic_nu = (int)l[0];
    *size_x = (int)l[1];
    *size_y = (int)l[2];
    btbr = (*size_x) * (*size_y);
    bytes_read = read(in_file, mat, btbr);
        if (bytes_read != btbr)
                        {  return(FAILURE); }
        close(in_file);
return(SUCCESS);
}
read_rul_pic_extended(file_name,mat,size_x,size_y,magic_nu,header)
                                PIXEL *mat; char file_name[];
                                char *header;
                                int *size_x, *size_y, *magic_nu;
{
int in_file, bytes_read, btbr;
long l[3];
#define L_SIZE 4
    in_file = open(file_name,  (O_RDONLY | O_BINARY) , 0) ;
    if (in_file == -1) return(0);
    if ( read(in_file, l, 3*L_SIZE) != 3*L_SIZE) { printf ("\n error in read #1")
                                    return(FAILURE); }
    *magic_nu = (int)l[0];
    *size_x = (int)l[1];
    *size_y = (int)l[2];
    btbr = (*size_x) * (*size_y);
    bytes_read = read(in_file, mat, btbr);
        if (bytes_read != btbr)  return(FAILURE);
        bytes_read = read(in_file, header, FR_HEADER_SIZE);
        if (bytes_read != FR_HEADER_SIZE)  return(NO_HEADER);
        close(in_file);
return(SUCCESS);
}
write_ru_pic_extended(file_name,mat,size_x,size_y,magic_nu,header)
                                PIXEL *mat; char file_name[];
                                int size_x, size_y, magic_nu;
                                char *header;
{
```

```c
int out_file;
long bytes_written, btbr;
long l[3];
    out_file = open(file_name,(O_WRONLY | O_CREAT |
                     O_TRUNC | O_BINARY), (0200 | 0400) );
    if (out_file == -1) return(0);
    l[0] = (long)magic_nu;
    l[1] = (long)size_x;
    l[2] = (long)size_y;
    if ( write(out_file, l, L_SIZE*3) != L_SIZE*3) { printf ("\n error in write #
                                                    return(FAILURE);   }
        btbr = (size_x) * (size_y);
        bytes_written = write(out_file, mat, btbr);
            if (bytes_written != btbr)  return(FAILURE);
        bytes_written = write(out_file, header, FR_HEADER_SIZE);
            if (bytes_written != FR_HEADER_SIZE)  return(FAILURE);
                close(out_file);
return(SUCCESS);
}
write_ru_pic(file_name,mat,size_x,size_y,magic_nu)
                            PIXEL *mat; char file_name[];
                            int size_x, size_y, magic_nu;

{
int out_file;
long bytes_written, btbr;
long l[3];
    out_file = open(file_name,(O_WRONLY | O_CREAT |
                     O_TRUNC | O_BINARY), (0200 | 0400) );
    if (out_file == -1) return(0);
    l[0] = (long)magic_nu;
    l[1] = (long)size_x;
    l[2] = (long)size_y;
    if ( write(out_file, l, L_SIZE*3) != L_SIZE*3) { printf ("\n error in write #
                                                    return(FAILURE);   }
        btbr = (size_x) * (size_y);
        bytes_written = write(out_file, mat, btbr);
            if (bytes_written != btbr)
                          {  return(FAILURE);  }
        close(out_file);
return(SUCCESS);
}
eliminate_reserved_numbers_1(image)
            PIXEL   image[FR_Y_SIZE][FR_X_SIZE];
{
int i,j;
        return(1);
        for (i = 0 ; i < FR_Y_SIZE ; ++i)
          for (j = 0 ; j < FR_X_SIZE ; ++j)
                {
                if (image[i][j] >= 253) image[i][j] = 253;
                else if(image[i][j] == 0) image[i][j] = 1;
                }
}
display_eliminate(xorg,yorg,image,x_size,y_size,name)    char *name, *image;
{
        eliminate_reserved_numbers_1(image);
        copy_block(image,0,0,y_size,x_size,xorg,yorg);
        rectangle(xorg,yorg,xorg+x_size, yorg+y_size,255);
        rectangle(xorg-1,yorg-1,xorg+x_size+1, yorg+y_size+1,255);
        rectangle(xorg-2,yorg-2,xorg+x_size+2, yorg+y_size+2,255);
        filled_rectangle_1(xorg+x_size+2, yorg+12, xorg+x_size+2+10, yorg+y_size+
        filled_rectangle_1(xorg+14, yorg+y_size+2, xorg+x_size+2+10, yorg+y_size+
        write_str(xorg+20,yorg+y_size-6,name,1,254);
}
```

```
display_plain_image(xorg,yorg,image,x_size,y_size)     char   *image;
{
        copy_block(image,0,0,y_size,x_size,xorg,yorg);
}
display_plain_magnified_3(xorg,yorg,image,x_size,y_size)
                                PIXEL    *image;
{
PIXEL *tmp_buf, *b1, *b2, *b3;
PIXEL p;
int i,j,s_line, n_size;
        n_size = x_size * 3 ;
        tmp_buf = malloc(n_size * 3);
        if (tmp_buf == 0) { printf ("\n Not enough memory (display-magni)");
                                return(0); }
        for (i = 0 ; i < y_size ; ++i)
        {
                b1 = tmp_buf;
                b2 = b1 + n_size;
                b3 = b2 + n_size;
                for (j = 0 ; j < x_size ; ++j)
                {
                        p = *image++;
                        *b1++ = p; *b2++ = p; *b3++ = p;
                        *b1++ = p; *b2++ = p; *b3++ = p;
                        *b1++ = p; *b2++ = p; *b3++ = p;
                }
                copy_block(tmp_buf, 0, 0, 3 , n_size, xorg, i*3+yorg);
        }
        free(tmp_buf);
        x_size *= 3;
        y_size *= 3;
}
display_eliminate_magnified_3(xorg,yorg,image,x_size,y_size,name)
                                char *name;
                                PIXEL   image[][FR_X_SIZE];
{
PIXEL *tmp_buf, *b1, *b2, *b3;
PIXEL p;
int i,j,s_line, n_size;
        n_size = x_size * 3 ;
        tmp_buf = malloc(n_size * 3);
        if (tmp_buf == 0) { printf ("\n Not enough memory (display-magni)");
                                return(0); }
        eliminate_reserved_numbers_1(image);
        for (i = 0 ; i < y_size ; ++i)
        {
                b1 = tmp_buf;
                b2 = b1 + n_size;
                b3 = b2 + n_size;
                for (j = 0 ; j < x_size ; ++j)
                {
                        p = image[i][j];
                        *b1++ = p; *b2++ = p; *b3++ = p;
                        *b1++ = p; *b2++ = p; *b3++ = p;
                        *b1++ = p; *b2++ = p; *b3++ = p;
                }
                copy_block(tmp_buf, 0, 0, 3 , n_size, xorg, i*3+yorg);
        }
        free(tmp_buf);
        x_size *= 3;
        y_size *= 3;
        rectangle(xorg,yorg,xorg+x_size, yorg+y_size,255);
        rectangle(xorg-1,yorg-1,xorg+x_size+1, yorg+y_size+1,255);
        rectangle(xorg-2,yorg-2,xorg+x_size+2, yorg+y_size+2,255);
```

```c
                write_str(xorg+10,yorg+y_size-4,name,1,254);
}
display_magnified_3(xorg,yorg,image,x_size,y_size,name)
                                char *name;
                                PIXEL   image[][FR_X_SIZE];
{
PIXEL *tmp_buf, *b1, *b2, *b3;
PIXEL p;
int i,j,s_line, n_size;
        n_size = x_size * 3 ;
        tmp_buf = malloc(n_size * 3);
        if (tmp_buf == 0) { printf ("\n Not enough memory (display-magni)");
                                return(0); }
        for (i = 0 ; i < y_size ; ++i)
        {
                b1 = tmp_buf;
                b2 = b1 + n_size;
                b3 = b2 + n_size;
                for (j = 0 ; j < x_size ; ++j)
                {
                        p = image[i][j];
                        *b1++ = p; *b2++ = p; *b3++ = p;
                        *b1++ = p; *b2++ = p; *b3++ = p;
                        *b1++ = p; *b2++ = p; *b3++ = p;
                }
                copy_block(tmp_buf, 0, 0, 3 , n_size, xorg, i*3+yorg);
        }
        free(tmp_buf);
        x_size *= 3;
        y_size *= 3;
        rectangle(xorg,yorg,xorg+x_size, yorg+y_size,255);
        rectangle(xorg-1,yorg-1,xorg+x_size+1, yorg+y_size+1,255);
        rectangle(xorg-2,yorg-2,xorg+x_size+2, yorg+y_size+2,255);
        write_str(xorg+10,yorg+y_size-4,name,1,254);
}
sleep_ms(mseconds)
{
time_t  tm1, tm2;
double dt, dtr;
clock_t t1, t2;
        t1 = clock();
        do {
        t2 = clock() - t1;
        if (kbhit()) { getch(); return(0); }
        } while(t2 < (clock_t)(mseconds));
        return(1);
}
load_color_map(char *name)
{
FILE *map_file;
int r,g,b, i, ret;
short lut[256][4];
char *t_env, namex[80];
        map_file = fopen(name,"r");
        if (map_file == NULL)
            {
            t_env = getenv("C_LUTS");
            strcpy(namex,t_env);
            strcat(namex,name);
            t_env = strchr(name,'.');
            if (t_env == NULL) strcat(namex,".lut");
                map_file = fopen(namex,"r");
            }
        if (map_file == NULL) { printf ("\n File %s Not exists",name);
```

```
                                    return(0); }
               for (i =  0 ; i < 256 ; ++i)
               {
                   ret = fscanf(map_file,"%d %d %d%*[^\n]",&r,&g,&b);
                   if (ret == EOF) break;
                   lut[i][__RED] = r; lut[i][__GREEN] = g;
                   lut[i][__BLUE] = b;
                   lut[i][__FILLER] = 0;
               }
        fclose(map_file);
        return(1);
}
read_map_file(name,lut)
                        char *name;
                        short lut[256][4];
{
char n[32], *t_env;
int ret, i;
FILE *map_file;
int r,g,b;
        map_file = fopen(name,"r");
        if (map_file == NULL)
        {
            t_env = getenv("C_LUTS");
            strcpy(n,t_env);
            strcat(n,name);
            t_env = strchr(n,'.');
            if (t_env == NULL) strcat(n,".lut");
                map_file = fopen(n,"r");
        }
    if (map_file == NULL)         return(FAILURE);
        else
        {
                for (i =  0 ; i < 256 ; ++i)
                {
                    ret = fscanf(map_file,"%d %d %d%*[^\n]",&r,&g,&b);
                    if (ret == EOF) break;
                    lut[i][__RED] = r; lut[i][__GREEN] = g; lut[i][__BLUE] = b;
                    lut[i][__FILLER] = 0;
                }
        }
        fclose(map_file);
        return(SUCCESS);
}
output_header(h)            char *h;
{
#define LINE_LEN 72
int len = strlen(h);
int i, l;
char c;
        for (i = 0 ; i < len ; i += LINE_LEN)
        {
                l = i + LINE_LEN;
                if (l >= FR_HEADER_SIZE) l = FR_HEADER_SIZE-1;
                c = h[l];  h[l] = 0;
                printf("%s",&h[i]);
                h[l] = c;
        }
}
pic_invert_x(p,x,y)                                         char *p;
{
char *c1, *c2, c;
int i,j;
        for (j = 0 ; j < (x >> 1) ; ++j)
```

```
            {
                c1 = p+j;
                c2 = p+(x-j-1);
                for (i = 0 ; i < y ; ++i)
                {
                  c    = *c1; *c1 = *c2; *c2 = c; c1 += x; c2 += x;
                }
            }
    }
pic_invert_y(p,x,y)                                                   char *p;
{
char *l1, *l2, c;
int i,j;
        for (i = 0 ; i < (y >> 1) ; ++i)
        {
                l1 = p+i*x;
                l2 = p+(y-i-1)*x;
                for (j = 0 ; j < x ; ++j)
                {
                  c   = *l1; *l1 = *l2; *l2 = c; ++l1; ++l2;
                }
        }
}
write_byte_stream(file_name, image, x, y)
                        char *file_name, *image; int x,y;
{
int out_file;
long bytes_written, btbr;
        out_file = open(file_name,(O_WRONLY | O_CREAT | if (out_file == -1) return(0);
    btbr = x * y;
    bytes_written = write(out_file, image, btbr);
        if (bytes_written != btbr)  return(FAILURE);
        close(out_file);
        return(SUCCESS);
}
read_byte_stream(file_name, image, x, y)
                        char *file_name, *image; int x,y;
{
int in_file;
long bytes_read, btbr;
    in_file = open(file_name,  (O_RDONLY | O_BINARY) , 0) ;
    if (in_file == -1) return(0);
    btbr = x * y;
    bytes_read = read(in_file, image, btbr);
        if (bytes_read != btbr)  return(FAILURE);
        close(in_file);
        return(SUCCESS);
}
z_transform_f(dst, src, mean_p, mad_p, min_p, max_p)
                        PIXEL dst[FR_Y_SIZE][FR_X_SIZE];
                        PIXEL src[FR_Y_SIZE][FR_X_SIZE];
                        int *mean_p, *mad_p, *min_p, *max_p;
{
int i,j, mean, k, mad, ignore_flag;
        ignore_flag = 0;
        mean = f_mean(src,min_p, max_p,8, ignore_flag);
        mad = c_mad(src, mean, 8, ignore_flag);
                                        /* make mad fixed */
        mad = 18;
        do_s_transform_image(dst, src, mean, mad);
        if (debug_flag)
                printf("\n min: %d max: %d mean: %d  mad: %d",*min_p, *max_p, mea
```

```
                return(SUCCESS);
}
z_transform(dst, src, mean_p, mad_p, min_p, max_p)
                        PIXEL dst[FR_Y_SIZE][FR_X_SIZE];
                        PIXEL src[FR_Y_SIZE][FR_X_SIZE];
                        int *mean_p, *mad_p, *min_p, *max_p;

{
int ret, x, y,  mad, mean, ignore_flag;
        ignore_flag = 0;
        mean = f_mean(src,min_p, max_p,8, ignore_flag);
        mad = c_mad(src, mean, 8, ignore_flag);
        do_s_transform_image(dst, src, mean, mad);
        if (debug_flag)
                printf("\n min: %d max: %d mean: %d  mad: %d",*min_p, *max_p, mea
        *mean_p = mean;
        *mad_p = mad;
        return(SUCCESS);
}
f_mean_env(buf,pmin,pmax,shoulders, ignore_flag, i0, j0, env )
                        PIXEL  buf[][FR_X_SIZE];
                        int *pmin, *pmax;

{
int i,j, imx, jmx;
unsigned int n;
double mean, f;
int min = 255, max = 0;
                                        /* find mean */
        mean = 0.0;
        n = 0;
        for (i = i0-env ; i < i0+env ; ++i)
          {
          f = 0.0;
          for (j = j0-env ; j < j0+env ; ++j)
                {
                        if (buf[i][j] > 253) continue;
                        if (ignore_flag && buf[i][j] < 64) continue;
                        f += (double)buf[i][j];
                        if (buf[i][j] < min) min = buf[i][j];
                        if (buf[i][j] > max) { max = buf[i][j]; imx = i; jmx = j; }
                        ++n;
                }
            mean += f;
          }
        if (n < 2) return(255);
        mean /= (double)n;
  *pmin = min;
  *pmax = max;
  return((int)(mean+0.5));
}
f_mean(buf,pmin,pmax,shoulders, ignore_flag)        PIXEL   buf[][FR_X_SIZE];
                        int *pmin, *pmax;
{
int i,j, imx, jmx;
unsigned int n;
double mean, f;
int min = 255, max = 0;
        mean = 0.0;
        n = 0;
        for (i = shoulders ; i < FR_Y_SIZE - shoulders ; ++i)
          {
          f = 0.0;
          for (j = shoulders ; j < FR_X_SIZE - shoulders; ++j)
                {
                        if (buf[i][j] > 253) continue;
```

```
                                        if (ignore_flag && buf[i][j] < 64) continue;
                if (buf[i+8][j] > 253 || buf[i-8][j] > 253 || buf[i][j-8] > 253 ||
                                        buf[i][j+8] > 253) continue;
                        f += (double)buf[i][j];
                        if (buf[i][j] < min) min = buf[i][j];
                        if (buf[i][j] > max) { max = buf[i][j]; imx = i; jmx = j; }
                        ++n;
                        }
                mean += f;
                }
        if (n < 2) return(255);
        mean /= (double)n;
  *pmin = min;
  *pmax = max;
  return((int)(mean+0.5));
}
do_float_image(buf,mean, shoulders)
                                PIXEL buf[][FR_X_SIZE];
                                        int mean;
{
int i,j, n;
        for (i = shoulders ; i < FR_Y_SIZE - shoulders; ++i)
                for (j = shoulders ; j < FR_X_SIZE - shoulders ; ++j)
                        {
                                if (buf[i][j] > 253) continue;
                                n = buf[i][j] - mean + 128;
                                if (n < 0) n = 0;
                                if (n > 250) n = 250;
                                buf[i][j] = n;
                        }
}
do_float_single(value, mean)
                                        int mean, value;
{
int n;
  if (value > 253 || mean > 253) n = 255;
        else {
                n = value - mean + 128;
                if (n < 0) n = 0;
                if (n > 250) n = 250;
                }
  return(n);
}
do_s_transform_image(dst, src, mean, mad)
        PIXEL  dst[][FR_X_SIZE];
        PIXEL  src[][FR_X_SIZE];
{
int i,j, k;
double f, fmad = (double)mad;
        for (i = 0 ; i < FR_Y_SIZE ; ++i)
                for (j = 0 ; j < FR_X_SIZE ; ++j)
                        {
                        if (src[i][j] > 253) { dst[i][j] = src[i][j] ; continue; }
                        k = src[i][j] - mean;
                        f = (double)k / fmad;
                                /* scale to 100 is 3*/
                        f = f * 100. / 3.;
                        k = 128 + (int)(f+0.5);
                        if (k < 0) k = 0;
                        if (k > 255) k = 255;
                        dst[i][j] = (PIXEL)k;
                        }
}
c_mad(buf,mean, shoulders, ignore_flag)
```

```
                                        PIXEL buf[][FR_X_SIZE];
                                            int mean;
{
int i,j, n;
double mad,f;
        mad = 0.0;
        n = 0;
        for (i = shoulders ; i < FR_Y_SIZE - shoulders; ++i)
            {
            f = 0.0;
            for (j = shoulders ; j < FR_X_SIZE - shoulders ; ++j)
                {
                                    if (buf[i][j] > 253) continue;
                                        if (ignore_flag && buf[i][j] < 64
                                        f += ABS((buf[i][j] - mean));
                                        ++n;
                }
                mad += f;
            }
        if (n < 2) return(255);
        mad /= (double)n;
    return((int)(mad + 0.5));
}
f_mean_mask(buf,pmin,pmax,shoulders, mask)
                    PIXEL   buf[][FR_X_SIZE];
                    PIXEL   mask[][FR_X_SIZE];
                    int *pmin, *pmax;
{
int i,j, imx, jmx;
unsigned int n;
double mean, f;
int min = 255, max = 0;
        mean = 0.0;
        n = 0;
        for (i = shoulders ; i < FR_Y_SIZE - shoulders ; ++i)
            {
            f = 0.0;
            for (j = shoulders ; j < FR_X_SIZE - shoulders; ++j)
                {
                            if (buf[i][j] > 253) continue;
                            if (mask[i][j] > 10) continue;
                    if (buf[i+8][j] > 253 || buf[i-8][j] > 253 || buf[i][j-8] > 2
                                    buf[i][j+8] > 253) continue;
                    f += (double)buf[i][j];
                    if (buf[i][j] < min) min = buf[i][j];
                    if (buf[i][j] > max) { max = buf[i][j]; imx = i; jmx = j; }
                        ++n;
                }
            mean += f;
            }
        mean /= (double)n;
    *pmin = min;
    *pmax = max;
    return((int)(mean+0.5));
}
c_mad_mask(buf,mean, shoulders, mask)
                    PIXEL buf[][FR_X_SIZE];
                    PIXEL mask[][FR_X_SIZE];
                        int mean;
{
int i,j, n;
double mad,f;
        mad = 0.0;
        n = 0;
```

```
                for (i = shoulders ; i < FR_Y_SIZE - shoulders; ++i)
                {
                f = 0.0;
                for (j = shoulders ; j < FR_X_SIZE - shoulders ; ++j)
                    {
                                if (mask[i][j] > 10) continue;
                                if (buf[i][j] > 253) continue;
                                if (buf[i+8][j] > 253 || buf[i-8][j] > 253 || buf[i][j
                                        buf[i][j+8] > 253) continue;
                                f += ABS((buf[i][j] - mean));
                                ++n;
                    }
                    mad += f;
                }
        mad /= (double)n;
    return((int)(mad + 0.5));
}
static struct ( unsigned int min_area;
                                        int min_angle;
                                        int cx, cy;
                                        int.x1, x2, y1, y2;
                                } caliber_data;
enclosing_rectangle_chain(chain, start_i, start_j, xybuf, x1p, y1p, x2p, y2p, ang
                char chain[];
                struct point xybuf[];
                int *x1p, *y1p, *x2p, *y2p, *anglep;
{
struct point xybuf_r[MAX_LENGTH];
int min_i, min_j, max_i, max_j, d1, d2, len;
        caliber_data.min_area = 160*180;
        len = chain_to_raster(start_i, start_j, chain,
                                                                                x
        get_centroid(len, &caliber_data.cy, &caliber_data.cx, xybuf);
        do_rot_caliber(len, &d1, &d2, xybuf, xybuf_r, caliber_data.cx, caliber_da
        *x1p     = caliber_data.x1; /* + caliber_data.cx; */
        *y1p     = caliber_data.y1; /* + caliber_data.cy; */
        *x2p     = caliber_data.x2; /* + caliber_data.cx; */
        *y2p     = caliber_data.y2; /* + caliber_data.cy; */
        *anglep = caliber_data.min_angle;
}
do_rot_caliber(len, d1p, d2p, xybuf, xybuf_r, cx, cy)
                                int *d1p, *d2p;
                        struct point xybuf[], xybuf_r[];
{
int angle, l2, l1;
struct rect occ_rect;
                *d1p = INT_MIN; *d2p = INT_MAX;
                                        /* last iteration should be angle == 0 */
                for (angle = 90 ; angle > 0 ; angle -= 5)
                    {
                                        /* first, rotate it */
                        rotate_xy(angle ,cx, cy, len, xybuf, xybuf_r);
                                        /* now check for occluding rectangle */
                        occluding_xy(&occ_rect, len, &l1, &l2, xybuf_r);
                        set_caliber_data(occ_rect, angle, l1, l2, d1p, d2p);
                    }
}
set_caliber_data(occ_rect, angle, l1, l2, d1, d2)
                int *d1, *d2;
                struct rect occ_rect;
{
unsigned int area;
                area = (occ_rect.x2 - occ_rect.x1) *
                                (occ_rect.y2 - occ_rect.y1);
```

```c
                      if (area < caliber_data.min_area) {
                                      caliber_data.min_area   = area;
                                      caliber_data.min_angle  = angle;
                                      caliber_data.x1         = occ_rect
                                      caliber_data.x2         = occ_rect
                                      caliber_data.y1         = occ_rect
                                      caliber_data.y2         = occ_rect
                      }
}
occluding_xy(occ_rect, len, l1p, l2p, xybuf_r)
                struct point xybuf_r[];
                struct rect *occ_rect;
                int *l1p, *l2p;
{
int     i, x, y, max_x_i, min_x_i, max_y_i, min_y_i;
int     min_x = INT_MAX, min_y = INT_MAX, max_x = INT_MIN, max_y = INT_MIN;
                for (i = 0 ; i < len ; ++i)
                {
                        x = xybuf_r[i].x;
                        y = xybuf_r[i].y;
                        if (x < min_x)      { min_x = x; min_x_i = i; }
                        else if (x > max_x) { max_x = x; max_x_i = i; }
                        if (y < min_y)      { min_y = y; min_y_i = i; }
                        else if (y > max_y) { max_y = y; max_y_i = i; }
                }
        occ_rect->x1 = min_x;
        occ_rect->x2 = max_x;
        occ_rect->y1 = min_y;
        occ_rect->y2 = max_y;
        *l1p = max_x - min_x;
        *l2p = max_y - min_y;
}
rotate_xy(angle_deg, cx, cy, len, xybuf, xybuf_r)
                                struct point xybuf[], xybuf_r[];
{
double angle = 3.14159*(double)angle_deg/180.;
double sin_a = sin(angle), cos_a = cos(angle);
double f_x, f_y;
int x,y, i;
static color = 10;
                for (i = 0 ; i < len ; ++i)
                {
                        y = xybuf[i].x;
                        x = xybuf[i].y;
                        f_x = -(double)(y - cy)*sin_a + (double)(x- cx)*cos_a;
                        f_y = (double)(y - cy)*cos_a + (double)(x- cx)*sin_a;
                        y = (int) (f_y + cy + 0.5);
                        x = (int) (f_x + cx + 0.5);
                        xybuf_r[i].x = x;
                        xybuf_r[i].y = y;
                }
        color += 5;
}
rotate_point(x, y, angle_deg, cx, cy)           int *x, *y;
{
double angle = 3.14159*(double)angle_deg/180.;
double sin_a = sin(angle), cos_a = cos(angle);
double f_x, f_y;
                        f_x = -(double)(*y - cy)*sin_a + (double)(*x- cx)*cos_a;
                        f_y = (double)(*y - cy)*cos_a + (double)(*x- cx)*sin_a;
                        *y = (int) (f_y + cy + 0.5);
                        *x = (int) (f_x + cx + 0.5);
}
get_centroid(len, cxp, cyp, xybuf)              int *cxp, *cyp;
```

```c
                                struct point xybuf[];
{
int i;
long sum_x, sum_y;
                sum_x = sum_y = 0;
                for (i = 0 ; i < len ; ++i)
                {
                        sum_x += xybuf[i].x;
                        sum_y += xybuf[i].y;
                }
        *cxp = (int)((double)sum_x / (double)len);
        *cyp = (int)((double)sum_y / (double)len);
}
#define DISPLAY_RESOLUTION 1
#undef  __RED
#undef  __GREEN
#undef  __BLUE
#define __WHITE         7
#define __RED           4
#define __GREEN         2
#define __BLUE          1
#define __YELLOW        14
#define __CYAN                          3
#define __MAGENTA                       5
#define __GRAY                          8
#define __BROWN         6
#define __LIGHT_RED             12
#define __LIGHT_GREEN   10
#define __LIGHT_BLUE    9
#define __LIGHT_YELLOW  14
#define __LIGHT_CYAN            11
#define __LIGHT_MAGENTA 13
#define __INTENSIFIED_WHITE 15
#define __BLACK         0
static FILE    *out_file;
static float   FACTOR=0.6;
double  calc_blemish_area();
extern struct prog_settings prog_consts;  /* process setup file */
extern int debug_flag;
extern int n_stems, stem_index, calyx_index;
extern struct c_dat candidates[MAX_CANDIDATES];
extern int global_color_grade, apple_size;
static unsigned long p_count = 0;
int     combine_masks(mask,blemish)
                        PIXEL   mask[FR_Y_SIZE][FR_X_SIZE];
                        PIXEL   *blemish;
{
        int i,j,r,defult_color;
        extern int apple_brand;
#ifndef DISTRIB_COLOR
          switch (apple_brand)
                {
                        case SMITH_TYPE:        defult_color=__GREEN ;

case ANA_TYPE:
                        case HERMON_TYPE:
                        case ORLEANS_TYPE: defult_color=__RED ;

}
#endif
                for (i=0, r=0 ; i < FR_Y_SIZE ; i++ ,r+=FR_Y_SIZE)
                for (j=0 ; j < FR_Y_SIZE ; j++)
                {
                        if (*(blemish + r + j) > 50 && mask[i][j] > 0)
```

```
                                                    /* set base color with random */
                                {                   p_count = rand();
                                                    if (p_count < (RAND_MAX >> (15-9)
#ifdef  DISTRIB_COLOR
                                                        switch (mask[i][j])
                                                        {
                                                        case SIMPLE_RED_C
                                                            *(blemish
                                                            break;
                                                        case DARK_RED_COL
                                                            *(blemish
                                                            break;
                                                        case ORANGE_COLOR
                                                            *(blemish
                                                            break;
                                                        case  GREEN_COLOR
                                                            *(blemish
                                                            break;
                                                        case YELLOW_COLOR
                                                            *(blemish
                                                            break;
                                                        }
else
                                                        *(blemish + r + j)=deful
#endif
                                    }
                                }
}
do_3dfile(name, bnd0, bnd1, bnd2, image0, image1, image2,color_mask,t_volume)
                                                    char *name;
                                                    PIXEL image0[FR_Y_SIZE]
                                                    PIXEL image1[FR_Y_SIZE]
                                                    PIXEL image2[FR_Y_SIZE]
                                                    PIXEL color_mask[FR_Y_S
                                                    struct boundary_data *b
                                                    struct boundary_data *b
                                                    struct boundary_data *b
                        double *t_volume;
{
        int i;
        PIXEL   *point[N_CAMERAS];
                /* get data from XMS */
            SWAP_IN_SIZE(bnd0,   CAM_1, bnd, sizeof(struct boundary_data));
            SWAP_IN_SIZE(bnd1,   CAM_2, bnd, sizeof(struct boundary_data));
            SWAP_IN_SIZE(bnd2,   CAM_3, bnd, sizeof(struct boundary_data));
                SWAP_IN_SIZE(image0, CAM_1, combi_map, FR_Y_SIZE*FR_X_SIZE);
                SWAP_IN_SIZE(image1, CAM_2, combi_map, FR_Y_SIZE*FR_X_SIZE);
                SWAP_IN_SIZE(image2, CAM_3, combi_map, FR_Y_SIZE*FR_X_SIZE);
                smooth_bnd(bnd0);                   /* this is to ensure smoo
                smooth_bnd(bnd1);
                smooth_bnd(bnd2);
        point[0]=image0[0];
        point[1]=image1[0];
        point[2]=image2[0];
                                        /*   Combine the color mask with
        for (i=0 ; i<N_CAMERAS ; i++)
                {
                SWAP_IN_SIZE(color_mask, i, spots_1, FR_Y_SIZE*FR_X_SIZE);
                combine_masks(color_mask,point[i]);
                }
                make_draw_file(name, bnd0, bnd1, bnd2, image0,
#ifdef MAKE_XMS_BND_Z
                SWAP_OUT_SIZE(bnd0,   CAM_1,bnd_z,sizeof(struct boundary_data));
```

```
                    SWAP_OUT_SIZE(bnd1,  CAM_2,bnd_z,sizeof(struct boundary_data));
                    SWAP_OUT_SIZE(bnd2,  CAM_3,bnd_z,sizeof(struct boundary_data));
=endif
          printf("\n Volume : %4d cc\n",(int)(*t_volume /1000.));
              return(SUCCESS);
}
smooth_bnd(bnd)
                                                    struct boundary_data *bnd;

{
int i,j, y_1, x1_1, x2_1, y_2, x1_2, x2_2, y_3, x1_3, x2_3;
          for (i = 1; i < bnd -> boundary_index-1 ; ++i)
           {
                         y_1  = bnd -> boundary[i-1].y;
                         x1_1 = bnd -> boundary[i-1].x1;
                         x2_1 = bnd -> boundary[i-1].x2;
              if (i > 1) {
                           bnd->boundary[i-1].y  = y_2;
                           bnd->boundary[i-1].x1 = x1_2;
                           bnd->boundary[i-1].x2 = x2_2;
                     }
                     y_2  = bnd -> boundary[i].y;
                     x1_2 = bnd -> boundary[i].x1;
                     x2_2 = bnd -> boundary[i].x2;
                     y_3  = bnd -> boundary[i+1].y;
                     x1_3 = bnd -> boundary[i+1].x1;
                     x2_3 = bnd -> boundary[i+1].x2;
                     y_2  = (y_2  + y_2  + y_1  + y_3) >> 2;
                     x1_2 = (x1_2 + x1_2 + x1_1 + x1_3) >> 2;
                     x2_2 = (x2_2 + x2_2 + x2_1 + x2_3) >> 2;
              }
}
make_draw_file(name, bnd0, bnd1, bnd2,  mask0, mask1, mask2, volp)
                                                    char *name;
                                                    PIXEL mask0[FR_Y_SIZE][
                                                    PIXEL mask1[FR_Y_SIZE][
                                                    PIXEL mask2[FR_Y_SIZE][
                                                    struct boundary_data *b
                                                    struct boundary_data *b
                                                    struct boundary_data *b
                                                    double *volp;
{
double t_volume;
double draw_all();
float  so[3],no[3];
void   imagin_stem_calix_coord();
char name1[64];
         strcpy(name1, "E:\\");
         strcat(name1, name);
    out_file = fopen(name1, "w");
       if (out_file == NULL) {
              printf("\n Can't open %s", name);
              return(FAILURE);
              }
       printf("\n %s opened", name);
       t_volume = draw_all( bnd0,bnd1,bnd2, mask0,mask1,mask2, prog_consts.camer
       fprintf(out_file, "   -40.0  -40.0  -40.0  1  4 \n");
       fprintf(out_file, "    40.0   40.0   40.0  1  4 \n");
   imagin_stem_calix_coord(bnd0,bnd1,bnd2,no,so,prog_consts.camera_distance);
       fprintf(out_file, "    %7.2f %7.2f %7.2f  %2d  %1d\n",so[0],so[1],so[2],
       fprintf(out_file, "    %7.2f %7.2f %7.2f  %2d  %1d\n",no[0],no[1],no[2],
       fclose(out_file);
       *volp = t_volume;
       return(SUCCESS);
}
```

```
double draw_all(bnd0,bnd1,bnd2, mask0, mask1, mask2, camera_distance)
                    int     *camera_distance;
                    struct  boundary_data *bnd0,*bnd1,*bnd2;
                    PIXEL   mask0[FR_X_SIZE][FR_Y_SIZE], mask1[FR_Y_SIZE][FR_
                    PIXEL   mask2[FR_X_SIZE][FR_Y_SIZE];
{
    int   x1[N_CAMERAS], x2[N_CAMERAS], y[N_CAMERAS], x, i, xz1[N_CAMERAS],xz2[N_CA
          size[3], diff[3],xl1[N_CAMERAS],xl2[N_CAMERAS],min_y,begin_val=1,j;
    double volume, area;
    float  y_height,min_height,z_3d[3];
    double compute_line_all();
          fprintf(out_file, "Set Color %2d\n",10+0 /* cam_number */);
          /* Set the boundary sizes of all the cameras to be the same size
          if ((size[0]=bnd0->boundary_index) > (size[1]=bnd1->boundary_inde
                   min_y=1;
          else min_y=0;
      if ((size[2]=bnd2->boundary_index) < size[min_y])
                   min_y=2;
          diff[(min_y+2)%3]=size[(min_y+2)%3]-size[min_y];
          if ((diff[(min_y+1)%3]=size[(min_y+1)%3]-size[min_y]) > SIZE_BND_
                   diff[(min_y+2)%3] > SIZE_BND_DIFF_LIMIT)  {
                   if (debug_flag) printf("\n  WARNING : Boundary structurs
          }
          diff[min_y]=0;
          for (i=0 ; i < N_CAMERAS ; i++) {
                   if (size[i]==0) continue;
                       diff[i]/=2;
                   }
          y_height=(*camera_distance+(*(camera_distance+1))+
                    (*(camera_distance+2)))*CCD_SIZE_Y/((float) CCD_RESOLU
          min_height=y_height*size[min_y]/2.;
          fprintf(out_file,"PointList X Y Z Color Layer\n");
#ifdef MAKE_XMS_BND_Z
          bnd0->out_rect.y1=bnd0 -> boundary[begin_val+diff[0]].y;
          bnd1->out_rect.y1=bnd1 -> boundary[begin_val+diff[1]].y;
          bnd2->out_rect.y1=bnd2 -> boundary[begin_val+diff[2]].y;
#endif
          volume = 0.;
          /* Line loop exeqution & bnd_z structur  setting  */
          for (i = begin_val; i < size[min_y]-begin_val ; ++i)
          {
                    y[0]  = bnd0 -> boundary[i+diff[0]].y;
                    x1[0] = bnd0 -> boundary[i+diff[0]].x1;
                    x2[0] = bnd0 -> boundary[i+diff[0]].x2;
                    y[1]  = bnd1 -> boundary[i+diff[1]].y;
                    x1[1] = bnd1 -> boundary[i+diff[1]].x1;
                    x2[1] = bnd1 -> boundary[i+diff[1]].x2;
                    y[2]  = bnd2 -> boundary[i+diff[2]].y;
                    x1[2] = bnd2 -> boundary[i+diff[2]].x1;
                    x2[2] = bnd2 -> boundary[i+diff[2]].x2;
               area=compute_line_all(x1, x2, camera_distance,xz1,xz2,xl1,xl2)
                   make_line_drawing( xz1, xz2,xl1,xl2, camera_distance,mask
                                       mask1[y[1]],mask2[y[2]],min_height);
#ifdef MAKE_XMS_BND_Z
          bnd0 -> boundary[i-begin_val].y  = y[0];
                   bnd0 -> boundary[i-begin_val].x1 = xz1[0];
                   bnd0 -> boundary[i-begin_val].x2 = xz2[0];
                   bnd1 -> boundary[i-begin_val].y  = y[1];
                   bnd1 -> boundary[i-begin_val].x1 = xz1[1];
                   bnd1 -> boundary[i-begin_val].x2 = xz2[1];
                   bnd2 -> boundary[i-begin_val].y  = y[2];
                   bnd2 -> boundary[i-begin_val].x1 = xz1[2];
                   bnd2 -> boundary[i-begin_val].x2 = xz2[2];
#endif
```

```
                                min_height-=y_height;
                        volume += area * y_height;
            } /* of single line loop */
#ifdef MAKE_XMS_BND_Z
            bnd0->out_rect.y2=bnd0 -> boundary[(--i)+diff[0]].y;
            bnd1->out_rect.y2=bnd1 -> boundary[(--i)+diff[1]].y;
            bnd2->out_rect.y2=bnd2 -> boundary[(--i)+diff[2]].y;
            bnd0->boundary_index=bnd1->boundary_index=bnd2->boundary_index=size[min
#endif
            return(volume);
}
double  compute_line_all(x1, x2, cam_dist,XZ1,XZ2,XL1,XL2)
        int     *x1,*x2,*cam_dist,XZ1[N_CAMERAS],XZ2[N_CAMERAS],XL1[N_CAMERAS],XL2[N
{
        int     i,center;
        int     zX1[N_CAMERAS], zX2[N_CAMERAS];
        double  Curve_Area;
        center=FR_X_SIZE/2;
        for (i=0 ; i < N_CAMERAS ; i++) {
                zX1[i]=center-(*(x1+i));
                zX2[i]=(*(x2+i))-center;
        }
        calc_line(zX1[0],zX2[0],zX1[1],zX2[1],zX1[2],zX2[2],cam_dist);
        do_bezier_interp(FACTOR);
        calc_area(&Curve_Area);
    calc_curves_projections(cam_dist,XL1,XL2);
        calc_sight_limits(cam_dist,XZ1,XZ2);
                for (i=0 ; i < N_CAMERAS ; i++) {
                    XZ1[i]=center-XZ1[i];
                    XZ2[i]=XZ2[i]+center;
        }
    return(Curve_Area);
}
#undef X1
#undef X2
double  compute_line_area(x1, x2, cam_dist,XZ1,XZ2)
        int     *x1,*x2,*cam_dist,XZ1[N_CAMERAS],XZ2[N_CAMERAS];
{
        int     i,center;
        int     X1[N_CAMERAS],X2[N_CAMERAS];
        double  Curve_Area;
        center=FR_X_SIZE/2;
        for (i=0 ; i < N_CAMERAS ; i++) {
                X1[i]=center-(*(x1+i));
                X2[i]=(*(x2+i))-center;
        }
        calc_line(X1[0],X2[0],X1[1],X2[1],X1[2],X2[2],cam_dist);
        do_bezier_interp(FACTOR);
        calc_area(&Curve_Area);
        calc_sight_limits(cam_dist,XZ1,XZ2);
        for (i=0 ; i < N_CAMERAS ; i++)
        {
                XZ1[i]=center-XZ1[i];
                XZ2[i]=XZ2[i]+center;
        }
        return(Curve_Area);
}
int  find_3d_location(cam_n,X_2d,Y_2d,x_3d,y_3d,z_3d,bnd0,bnd1,bnd2,cam_dist)
   float   *x_3d,*y_3d,*z_3d;
   struct boundary_data *bnd0,*bnd1,*bnd2;
   int     cam_n,*cam_dist,X_2d,Y_2d;
{
   int x1[N_CAMERAS], x2[N_CAMERAS], y[N_CAMERAS], x, i, XZ1[N_CAMERAS],XZ2[N_CAM
        XL1[N_CAMERAS],XL2[N_CAMERAS];
```

```
        struct boundary_data *bnd;
        int    j,center,index[N_CAMERAS],cv_num,min_size;
        float  y_height,height,A;
        switch (cam_n)
                {
                case 0: bnd=bnd0;
                        break;
                case 1: bnd=bnd1;
                        break;
                case 2: bnd=bnd2;
                        break;
                }
        if ((i=bnd->out_rect.y1)>Y_2d || Y_2d > bnd->out_rect.y2 )
                {
                if (debug_flag) printf("\n  WARNING 1: requested coordinats are out of sight f
                }
        min_size=find_index(index,Y_2d,bnd0,bnd1,bnd2,cam_n,bnd);
    x1[0] = bnd0 -> boundary[index[0]].x1;
        x2[0] = bnd0 -> boundary[index[0]].x2;
        x1[1] = bnd1 -> boundary[index[1]].x1;
        x2[1] = bnd1 -> boundary[index[1]].x2;
        x1[2] = bnd2 -> boundary[index[2]].x1;
        x2[2] = bnd2 -> boundary[index[2]].x2;
        for (i=0 ;i<N_CAMERAS ; i++)
                {
                if (index[i]<=1)
                        {
                        index[i]==2;
                        if (debug_flag) printf("\n WARNING 2: activate Y coordinate correcting");
                        }
                }
        if (index[0]>=bnd0->boundary_index-2) index[0]==bnd0->boundary_index-2;
        if (index[1]>=bnd1->boundary_index-2) index[1]==bnd1->boundary_index-2;
        if (index[2]>=bnd2->boundary_index-2) index[2]==bnd2->boundary_index-2;
        if (X_2d <= x1[cam_n] || X_2d >= x2[cam_n])
                {
                if (debug_flag) printf("\n WARNING 3: activate X coordinate correcting");
                X_2d = (X_2d <= x1[cam_n]) ? x1[cam_n]+2 : x2[cam_n]-2;
                }
    A=compute_line_all(x1, x2, cam_dist,XZ1,XZ2,XL1,XL2);
        cv_num=X_2d < XL1[cam_n] ? 0: X_2d < XL2[cam_n] ? 1 : 2;
        calc_xz_coord(cam_n,X_2d,cv_num,x_3d,z_3d,cam_dist);
        y_height=(*cam_dist+(*(cam_dist+1))+
                        (*(cam_dist+2)))*CCD_SIZE_Y/((float) CCD_RESOLUTION_Y*CAM_FOCAL_LENGTH
        /*     Coordinate  Adjusting       */
        *x_3d= -(*x_3d);
        *y_3d=-y_height*(-min_size/2. + index[cam_n]-((bnd->boundary_index-min_size)/2));
        if (XZ1[cam_n] > X_2d || XZ2[cam_n] < X_2d )
                {
                if (debug_flag) printf("\n WARNING 4: out of sight limits (bnd_z)");
                }
        return(0);
}
double calc_blemish_area(cam_n,Xs_h,Ys_h,Xs_l,Ys_l,bnd0,bnd1,bnd2,cam_dist)
    struct boundary_data *bnd0,*bnd1,*bnd2;
    int    cam_n,*cam_dist,Xs_h,Ys_h,Xs_l,Ys_l;
{
        float  crd[4][3],a,b,c,d,f,p,Ar;
        float  calc_sphr_dist();
        double DD;
    if (find_3d_location(cam_n,Xs_h,Ys_h,&crd[0][0],&crd[0][1],&crd[0][2],bnd0,bnd1,bnd2,cam_di
                < 0 ) return(-1.);
    if (find_3d_location(cam_n,Xs_h,Ys_l,&crd[1][0],&crd[1][1],&crd[1][2],bnd0,bnd1,bnd2,cam_di
                < 0 ) return(-1.);
```

```
        if (find_3d_location(cam_n,Xs_l,Ys_h,&crd[2][0],&crd[2][1],&crd[2][2],bnd0,bnd1,bnd2,cam_di
                < 0 ) return(-1.);
        if (find_3d_location(cam_n,Xs_l,Ys_l,&crd[3][0],&crd[3][1],&crd[3][2],bnd0,bnd1,bnd2,cam_di
                < 0 ) return(-1.);
            a=calc_sphr_dist(crd[0],crd[1]);
            b=calc_sphr_dist(crd[1],crd[3]);
            c=calc_sphr_dist(crd[2],crd[3]);
            d=calc_sphr_dist(crd[0],crd[2]);
            f=calc_sphr_dist(crd[0],crd[3]);
            p=(a+b+f)/2.;
            Ar=sqrt(p*(p-a)*(p-b)*(p-f));
            if (errno==EDOM) printf("\n SQRT ERROR : at calc blemish area");
            p=(d+c+f)/2.;
            Ar+=sqrt(p*(p-d)*(p-c)*(p-f));
            if (errno==EDOM) printf("\n SQRT ERROR : at calc blemish area 2");
            DD=(double)Ar;
            return(DD);
}
make_line_drawing(x1, x2,x11,x12, cam_dist, mask0, mask1, mask2,view_heig)
                                        double     view_heig;
                                        int        *x1,*x2,*x11,*x12,*cam_dist;
                                        PIXEL      mask0[FR_X_SIZE],mask1[FR_X_SIZE],mask2[FR_X_S
{
        PIXEL   *Ptr[N_CAMERAS];
                int     i,cam,color,curve_num;
int             base_color;
                float   x,z;
                Ptr[0]=mask0; Ptr[1]=mask1; Ptr[2]=mask2;
                for (cam=0 ; cam<N_CAMERAS ; cam++) {
                                for (i = *(x1+cam) ; i<*(x2+cam) ; i+= DISPLAY_RESOLUTION)
                                {
                                        color=(*(Ptr[cam]+i));
                                    if (color < 50 && color > 0)
                                        {
                                                curve_num=i < *(x11+cam) ? 0: i < *(x12+cam)
                                                calc_xz_coord(cam,i,curve_num,&x,&z,cam_dist);
                                                fprintf(out_file, "  %7.2f %7.2f %7.2f %2d %ld\n
                                        }
                                }
                }
        return(SUCCESS);
}
void    imagin_stem_calix_coord(bnd0,bnd1,bnd2,North,South,camera_dist)
        struct boundary_data *bnd0,*bnd1,*bnd2;
    float   North[3],South[3];
        int     *camera_dist;
{
                int                     i,j,center,X1[N_CAMERAS],X2[N_CAMERAS];
                float                   x,y,z,y_height,max_height;
                int                     size[N_CAMERAS],diff[N_CAMERAS],min_y;
                if ((size[0]=bnd0->boundary_index) > (size[1]=bnd1->boundary_index))
                        min_y=1;
                else min_y=0;
        if ((size[2]=bnd2->boundary_index) < size[min_y])
                        min_y=2;
                diff[(min_y+2)%3]=size[(min_y+2)%3]-size[min_y];
                if ((diff[(min_y+1)%3]=size[(min_y+1)%3]-size[min_y]) > SIZE_BND_DIFF_LIMIT
                        diff[(min_y+2)%3] > SIZE_BND_DIFF_LIMIT)  {
                            if (debug_flag) printf("\n  WARNING 5: Boundary structurs sizes are no
                }
                diff[min_y]=0;
                for (i=0 ; i < N_CAMERAS ; i++) {
                        if (size[i]==0) continue;
                        diff[i]/=2;
```

```
                y_height=(*camera_dist-(*(camera_dist+1))+
                        (*(camera_dist+2)))*CCD_SIZE_Y/((float) CCD_RESOLUTION_Y*CAM_FOCAL
        max_height=y_height*size[min_y]/2.+y_height;
                center=FR_X_SIZE/2;
                X1[0]=center-bnd0->boundary[diff[0]].x1;
                X2[0]=bnd0->boundary[diff[0]].x2-center;
                X1[1]=center-bnd1->boundary[diff[1]].x1;
                X2[1]=bnd1->boundary[diff[1]].x2-center;
                X1[2]=center-bnd2->boundary[diff[2]].x1;
                X2[2]=bnd2->boundary[diff[2]].x2-center;
        calc_line(X1[0],X2[0],X1[1],X2[1],X1[2],X2[2],camera_dist);
        find_poligon_mean(South);
        South[1]=max_height;
                X1[0]=center-bnd0->boundary[size[min_y]+diff[0]-1].x1;
                X2[0]=bnd0->boundary[size[min_y]+diff[0]-1].x2-center;
                X1[1]=center-bnd1->boundary[size[min_y]+diff[1]-1].x1;
                X2[1]=bnd1->boundary[size[min_y]+diff[1]-1].x2-center;
                X1[2]=center-bnd2->boundary[size[min_y]+diff[2]-1].x1;
                X2[2]=bnd2->boundary[size[min_y]+diff[2]-1].x2-center;
        calc_line(X1[0],X2[0],X1[1],X2[1],X1[2],X2[2],camera_dist);
        find_poligon_mean(North);
        North[1]=-max_height +3.*y_height;
}
void    validate_in_pic(cx,cy,dcx,dcy,bnd,index)
    int    *cx,*cy,*dcx,*dcy,index;
    struct    boundary_data    *bnd;
{
        int    j,i,d,dx,dy;
        dx=*dcx; dy=*dcy;
        /* Adjust the central pixel so all the squar will be inside the bnd line frame */
        while (*cy-dy <= bnd->boundary[0].y+2) (*cy)++;
        while (*cy+dy >= bnd->boundary[bnd->boundary_index-1].y-2) (*cy)--;
        while ((bnd->boundary[(*cy)-dy].x2-bnd->boundary[(*cy)-dy].x1 < 2*dx-2) ||
                        (bnd->boundary[(*cy)+dy].x2-bnd->boundary[(*cy)+dy].x1 < 2*dx-2) )
                {
                if (dx>9)  dx--;
                else *cy=(*cy > FR_Y_SIZE/2)?(*cy)-1:(*cy)+1;
                }
        for (i=0;i<MAX_BOUNDARY;i++)
                if (bnd->boundary[i].y==*cy) break;
        if (i==MAX_BOUNDARY)        {
                printf("\n ERROR : Cant find line");
                exit(0);
                }
                        /* for apper left corner */
        d = (*cx)-dx - (bnd->boundary[i-dy].x1+2);
        if (d < 0)
                {
                if (debug_flag) printf("\n Count=%4d Apper left cor",index);
                for (j=i-dy+1;j<i+2*dy+2;j++)
                        if ((*cx)-dx - (bnd->boundary[j].x1+2) > 0) break;
                if (d > i-dy-j) *cx-=d;
                else *cy-=i-dy-j;
                }
                        /* for lower left corner */
        d = (*cx)-dx - (bnd->boundary[i+dy].x1+2);
        if (d < 0)
                {
                if (debug_flag) printf("\n Count=%4d Lower left cor",index);
                for (j=i+dy-1;j<i-2*dy-2;j--)
                        if ((*cx)-dx - (bnd->boundary[j].x1+2) > 0) break;
                if (d > j-i-dy) *cx-=d;
                else *cy-=j-i-dy;
```

```c
                }
        d = (*cx)+dx - (bnd->boundary[i-dy].x2-2);
        if (d > 0)
                {
                if (debug_flag) printf("\n Count=%4d Apper write cor",index);
                for (j=i-dy+1;j<i+2*dy+2;j++)
                        if ((*cx)+dx - (bnd->boundary[j].x2-2) < 0) break;
                if (d < j-i+dy) *cx-=d;
                else *cy-=i-dy-j;
                }
                        /* for lower write corner */
        d = (*cx)+dx - (bnd->boundary[i+dy].x2-2);
        if (d > 0)
                {
                if (debug_flag) printf("\n Cuont=%4d Lower write cor",index);
                for (j=i+dy-1;j<i-2*dy-2;j--)
                        if ((*cx)+dx - (bnd->boundary[j].x2-2) < 0) break;
                if (d < i+dy-j) *cx-=d;
                else *cy-=j-i-dy;
                }
   *dcy=dy;
   *dcx=dx;
}
double  calc_area_ratio(cam,x,y,pix_area,bnd0,bnd1,bnd2,cam_dist,index)
   int     *x,*y,cam,*cam_dist,index,pix_area;
   struct  boundary_data  *bnd0,*bnd1,*bnd2;
{
        int   dx,dy;
        double ar;
        ar=(double)pix_area;
        ar=sqrt(ar);
        if (errno==EDOM) printf("\n SQRT ERROR : at calc_area_ratio ");
        if((dy=dx=(int) ar/2. - 0.5)<=0) {
                dx=1;
                dy=1;
                }
        if (cam==0) validate_in_pic(x,y,&dx,&dy,bnd0,index);
        if (cam==1) validate_in_pic(x,y,&dx,&dy,bnd1,index);
        if (cam==2) validate_in_pic(x,y,&dx,&dy,bnd2,index);
        ar=calc_blemish_area(cam,*x-dx,*y-dy,*x+dx,*y+dy,bnd0,bnd1,bnd2,cam_dist);
   if (debug_flag)  printf("\n 5)  AR=%7.2f",ar);
        ar/=(double)(2*dx)*(double)(2*dy);
        if (debug_flag)  printf("\n  Area_Ratio=%7.2f",ar);
        return(ar);
}
#define  Cam_dist       800.
#define  Eps            1e-10
#define  NUM_STEPS      16
#define  pi             3.14159265359
#define  TAN60                  1.7320508
#define  TAN180         0.
#define  TAN300         -1.7320508
#undef FALSE
#undef TRUE
enum  boolean { FALSE,TRUE };
float   calc_distance();
float   Tg();
float   calc_projection();
static struct  lines{
                float       tg[6];
                                                float    offset[6];
}Cam_lines;
static struct  points{
                                                float    F_K_x[6],F_K_y[6];
```

```
                                                    float    mid_x[6],mid_y[6];
} Poligon_pts;
static float     recons_pts[6][NUM_STEPS][2];
float    AREA;
float    Are;
static float Cam_Angels[N_CAMERAS]= { 3.*pi/2. , 5.*pi/6.      , pi/6. };
static float pixel_size;
do_bezier_interp(fact)
   float  fact;
{
   int   i;
       for (i=0; i<6 ;i++ )
          calc_bezier_curve(fact,Poligon_pts.mid_x[i],Poligon_pts.mid_y[i],
                           Poligon_pts.F_K_x[(i+1)%6],Poligon_pts.F_K_y[(i+1)%6],
                           Poligon_pts.F_K_x[(i+1)%6],Poligon_pts.F_K_y[(i+1)%6],
                           Poligon_pts.mid_x[(i+1)%6],Poligon_pts.mid_y[(i+1)%6],&recons_pts[i][0
}
calc_bezier_curve(factor,P1_x,P1_y,P2_x,P2_y,P3_x,P3_y,P4_x,P4_y,Pts)
   float  factor,P1_x,P1_y,P2_x,P2_y,P3_x,P3_y,P4_x,P4_y,*Pts;
{
       float  t,delta,mult=1.;
       int    index;
       t=delta=1./(mult*NUM_STEPS);
       P2_x=factor*(P2_x-P1_x)+P1_x;
       P2_y=factor*(P2_y-P1_y)+P1_y;
       P3_x=factor*(P3_x-P4_x)+P4_x;
       P3_y=factor*(P3_y-P4_y)+P4_y;
       *Pts=P1_x;
       *(Pts+1)=P1_y;
       for (index=1;index < mult*NUM_STEPS; index++) {
               *(Pts+(index<<1))=P1_x*pow(1-t,3.)+3.*P2_x*t*pow(1-t,2)+3.*P3_x*t*t*(1-t)+P4_x
               *(Pts+1+(index<<1))=P1_y*pow(1-t,3.)+3.*P2_y*t*pow(1-t,2)+3.*P3_y*t*t*(1-t)+P4
               t+=delta;
       }
}
void  calc_points()
{
   int   i;
   float    calc_point_y(int i,int j);
   float    calc_point_x(int i,int j);
   Poligon_pts.F_K_x[0]=calc_point_x(2,5);
       Poligon_pts.F_K_y[0]=calc_point_y(2,5);
   Poligon_pts.F_K_x[1]=calc_point_x(1,2);
       Poligon_pts.F_K_y[1]=calc_point_y(1,2);
   Poligon_pts.F_K_x[2]=calc_point_x(4,1);
       Poligon_pts.F_K_y[2]=calc_point_y(4,1);
   Poligon_pts.F_K_x[3]=calc_point_x(3,4);
       Poligon_pts.F_K_y[3]=calc_point_y(3,4);
   Poligon_pts.F_K_x[4]=calc_point_x(0,3);
       Poligon_pts.F_K_y[4]=calc_point_y(0,3);
   Poligon_pts.F_K_x[5]=calc_point_x(5,0);
       Poligon_pts.F_K_y[5]=calc_point_y(5,0);
       for (i=0;i<6;i++) {
       Poligon_pts.mid_x[i]=(Poligon_pts.F_K_x[i]+Poligon_pts.F_K_x[(i+1)%6])/2.;
               Poligon_pts.mid_y[i]=(Poligon_pts.F_K_y[i]+Poligon_pts.F_K_y[(i+1)%6])/2.;
       }
}
float    calc_point_x(i,j)
   int i,j;
{
   return((Cam_lines.offset[i]-Cam_lines.offset[j])/(Cam_lines.tg[j]-Cam_lines.tg[i]));
}
float    calc_point_y(i,j)
   int  i,j;
```

```c
        {
            return((Cam_lines.tg[i]*Cam_lines.offset[j]-Cam_lines.tg[j]*Cam_lines.offset[i])/(Cam_lines
        }
float   calc_distance(x1,y1,x2,y2)
        float   x1,y1,x2,y2;
{
            if (fabs(x1-x2)<Eps) return(fabs(y1-y2));
            if (fabs(y1-y2)<Eps) return(fabs(x1-x2));
        return(sqrt(pow(x1-x2,2.)+pow(y1-y2,2.)));
            if (errno==EDOM) printf("\n SQRT ERROR : calc distance");
}
float   calc_sphr_dist(crd1,crd2)
        float   *crd1,*crd2;
{
        float tmp;
        tmp=pow(*crd1-(*crd2),2.);
        tmp+=pow(*(crd1+1)-(*(crd2+1)),2.);
        tmp+=pow(*(crd1+2)-(*(crd2+2)),2.);
        tmp=(float)sqrt(tmp);
        if (errno==EDOM) printf("\n SQRT ERROR : at calc_sphr_dist");
        return(tmp);
}
calc_line(xa1,xa2,xb1,xb2,xc1,xc2,cam_dist)
        int     xa1,xa2,xb1,xb2,xc1,xc2;
        int     *cam_dist;
{
        float   alpha_a,beta_a,alpha_b,beta_b,alpha_c,beta_c;
        static int flag=FALSE;
        int     i;
        if (flag==FALSE) {
                flag=TRUE;
                pixel_size=CCD_SIZE_X/(float) CCD_RESOLUTION_X;
        }
        Cam_lines.tg[0]= (xa1 != 0)?CAM_FOCAL_LENGTH/(pixel_size*xa1):FLT_MAX;
        Cam_lines.tg[1]=-((xa2 != 0)?CAM_FOCAL_LENGTH/(pixel_size*xa2):FLT_MAX);
        alpha_a=atan( pixel_size*xa1/(float) CAM_FOCAL_LENGTH);
        beta_a =atan( pixel_size*xa2/(float) CAM_FOCAL_LENGTH);
        alpha_b=atan( pixel_size*xb1/(float) CAM_FOCAL_LENGTH);
        beta_b =atan( pixel_size*xb2/(float) CAM_FOCAL_LENGTH);
        alpha_c=atan( pixel_size*xc1/(float) CAM_FOCAL_LENGTH);
        beta_c =atan( pixel_size*xc2/(float) CAM_FOCAL_LENGTH);
        Cam_lines.tg[2]=tan(5.*pi/6.-alpha_b);
        Cam_lines.tg[3]=tan(5*pi/6.+beta_b);
        Cam_lines.tg[4]=tan(pi/6.-alpha_c);
        Cam_lines.tg[5]=tan(pi/6.+beta_c);
        Cam_lines.offset[0]=-(float) *cam_dist;
        Cam_lines.offset[1]=-(float) *cam_dist;
            Cam_lines.offset[2]=-(*(cam_dist+1))*sin(alpha_b)/sin(pi/3.-alpha_b);
            Cam_lines.offset[3]= (*(cam_dist+1))*sin(beta_b)/sin(2*pi/3.-beta_b);
            Cam_lines.offset[4]= (*(cam_dist+2))*sin(alpha_c)/sin(2*pi/3.-alpha_c);
            Cam_lines.offset[5]=-(*(cam_dist+2))*sin(beta_c)/sin(pi/3.-beta_c);
            calc_points();
}
#undef A
#undef B
calc_perpendicular(A,B,Ix,Iy,Ox,Oy)
        float   A,B,Ix,Iy,*Ox,*Oy;
{
        float   Ap,Bp;
    Ap=(fabs(A)>Eps)?(-1/A):FLT_MAX;
        Bp=Iy-Ix*Ap;
        *Ox=(Bp-B)/(A-Ap);
        *Oy=(A*Bp-Ap*B)/(A-Ap);
}
```

```
calc_curves_projections(cam_dist,xl1,xl2)
    int  *xl1,*xl2,*cam_dist;
{
    float  l1,l2;
    int    i,cam,center;
    center=FR_X_SIZE/2;
    for (cam=0 ; cam<N_CAMERAS*2 ; cam+=2) {
            l2=calc_projection(Poligon_pts.mid_x[cam],Poligon_pts.mid_y[cam],
                               cam/2,*(cam_dist+cam/2));
            l1=-calc_projection(Poligon_pts.mid_x[(cam+5)%6],Poligon_pts.mid_y[(ca
                               cam/2,*(cam_dist+cam/2));
            l2=l2/pixel_size;
            l1=l1/pixel_size;
            *(xl2+cam/2)=center+(int) (l2+SGN(l2)*0.5);
            *(xl1+cam/2)=center-(int) (l1+SGN(l1)*0.5);
    }
}
calc_xz_coord(cam,line_pix,curve,x,z,cam_dist)
    int    cam,curve,line_pix,*cam_dist;
    float  *x,*z;
{
    int    index,p,k,center,jump_size,l;
    float  p_x,p_y,k_x,k_y,*P,tmp;
    jump_size=NUM_STEPS;
    l=0,index;
    center=FR_X_SIZE/2;
    P=recons_pts[0][0];
    curve=((cam<<1)+4+curve)%6;
    while (abs(jump_size)>1) {
        jump_size=jump_size/2;
            l=l+jump_size;
            index=curve*NUM_STEPS+l;
            p_x=*(P+(index<<1));
        p_y=*(P+1+(index<<1));
            tmp=calc_projection(p_x,p_y,cam,*(cam_dist+cam));
            p=center + (int) (tmp/pixel_size +SGN(tmp)*0.5);
        jump_size=SGN_0(line_pix-p)*abs(jump_size);
    }
    if (jump_size!=0) {
            index=(curve*NUM_STEPS+l+jump_size)%(NUM_STEPS*6);
            k_x=*(P+(index<<1));
            k_y=*(P+1+(index<<1));
            tmp=calc_projection(k_x,k_y,cam,*(cam_dist+cam));
            k=center + (int) (tmp/pixel_size + SGN(tmp)*0.5);
    *x=-((p_x-k_x)*(line_pix-k)/((float) (p-k)) +k_x);
        *z=-((p_y-k_y)*(line_pix-k)/((float) (p-k)) +k_y);
            return(0);
    }
    *x=-p_x;
    *z=-p_y;
}
calc_sight_limits(cam_dist,xz1,xz2)
    int  *cam_dist,xz1[N_CAMERAS],xz2[N_CAMERAS];
{
    void  cam_sight_limits();
    int   i;
    cam_sight_limits(&xz2[0],&xz1[1],TAN300,0,cam_dist);   /* 0 for curve FG-GH */
    cam_sight_limits(&xz2[1],&xz1[2],TAN180,2,cam_dist);   /* 2 for curve HI-IJ */
    cam_sight_limits(&xz2[2],&xz1[0],TAN60,4,cam_dist);         /* 4 for curve JK-KF *
}
void  cam_sight_limits(xz2,xz1,angle,num,cam_dist)
    int    *xz2,*xz1,num,*cam_dist;
    float  angle;
{
```

```c
    float  *P,z1,z2;
        int   i,cam;
        P=recons_pts[0][0];
        i=num*NUM_STEPS - (NUM_STEPS>>1);
        if (Tg(i,P) > angle)
                while(Tg(++i,P)>angle && i<6*NUM_STEPS);
        else
                while(Tg(--i,P)<angle && i>-1);
        if (abs(i-num*NUM_STEPS-(NUM_STEPS>>1)) > (NUM_STEPS>>1)) {
          i=num*NUM_STEPS + (NUM_STEPS>>1);
                printf("\n WARNING : not a normal curve ");
        }
        cam=num/2;
        z2= calc_projection(*(P+(i<<1)),*(P+1+(i<<1)),cam,*(cam_dist+cam));
        z1=-calc_projection(*(P+(i<<1)),*(P+1+(i<<1)),(cam+1)%3,*(cam_dist+(cam+1)%3));
        *xz2=z2/pixel_size+SGN(z2)*0.5;
        *xz1=z1/pixel_size+SGN(z1)*0.5;
}
float           calc_projection(X,Y,cam_no,dist)
    float   X,Y;
    int     dist,cam_no;
{
        int     center;
        float   Ox,Oy,length,xz;
        rotation(3*pi/2-Cam_Angels[cam_no],X,Y,&Ox,&Oy);
        xz=-Ox*CAM_FOCAL_LENGTH/(dist+Oy);
        return(xz);
}
float   Tg(i,P)
    int     i;
        float  *P;
{
        return(((*(P+((i+1)<<1)+1))-(*(P+(i<<1)+1)))/((*(P+((i+1)<<1)))-(*(P+(i<<1)))));
}
calc_area(AREA)
    double  *AREA;
{
        int     i;
        int     mult=6;
        float   temp=0,*pts;
        pts=recons_pts[0][0];
        Are=0.;
        for (i=0;i<6*NUM_STEPS-1;i++) {
     temp+=(*(pts+((i+1)<<1)))*(*(pts+1+(i<<1)))-(*(pts+(i<<1)))*(*(pts+1+((i+1)<<1)));
        }
        temp+=(*pts)*(*(pts+1+(i<<1)))-(*(pts+(i<<1)))*(*(pts+1));
        *AREA=temp/2.;
}
rotation(alpha,X,Y,new_x,new_y)
    float   alpha,X,Y,*new_x,*new_y;
{
    static  float  aph=0.,mx_trn[2][2];
        if (fabs(alpha-aph)>Eps) {
                aph=alpha;
                mx_trn[0][0]=cos(aph);
                mx_trn[0][1]=(aph>pi)?sqrt(1-mx_trn[0][0]*mx_trn[0][0]):-sqrt(1-mx_trn[0][0]*m
          if (errno==EDOM) printf("\n SQRT ERROR : rotation");
                mx_trn[0][2]=0.;
                mx_trn[1][0]=-mx_trn[0][1];
                mx_trn[1][1]=mx_trn[0][0];
                mx_trn[1][2]=0.;
        }
        *new_x=mx_trn[0][0]*X + mx_trn[0][1]*Y ;
        *new_y=mx_trn[1][0]*X + mx_trn[1][1]*Y ;
```

```
        return(0);
}
int  find_index(i,y,bnd0,bnd1,bnd2,cam,bnd)
    int *i,y,cam;
        struct boundary_data *bnd0,*bnd1,*bnd2,*bnd;
{
        int size[3],diff[3],count,min,j;
        size[0]=bnd0->boundary_index;
        size[1]=bnd1->boundary_index;
    size[2]=bnd2->boundary_index;
        diff[(cam+2)%3]=(size[(cam+2)%3]-size[cam])/2;
        diff[(cam+1)%3]=(size[(cam+1)%3]-size[cam])/2;
        diff[cam]=0;
        min=bnd->boundary[0].y;
        count=0;
        do
                {
                if ((j=y-bnd->boundary[y-min].y) > 0) min++;
                else if (j<0) min--;
                count++;
                }
        while (j!=0 && count<100 );
        if (count>=100)
                {
                printf("\n ERROR : cannot find y line in boundary struct ");
                exit(0);
                }
        for (j=0;j<N_CAMERAS;j++)
                *(i+j)=y-min+diff[j];
        return(MIN(MIN(size[0],size[1]),size[2]));
}
double  angle_between_n(x1,y1,z1,x2,y2,z2,length)
                        double x1,y1,z1,x2,y2,z2,*length;
{
double   p1,p2,p3,p4,p5,p6,p7,cosg,g;
        p1 = x1 * x2;
        p2 = y1 * y2;
        p3 = z1 * z2;
        p4 = x1*x1 + y1*y1 + z1*z1;
        p5 = x2*x2 + y2*y2 + z2*z2;
        p6 = p1+p2+p3;
        p7 = sqrt(p4) * sqrt(p5);
        if (errno==EDOM)
                {
                printf("\n SQRT ERROR : at angle between 1");
                errno=0;
                }
        cosg = p6 / p7;
        if (cosg >  0.999) cosg =  0.999;
        if (cosg < -0.999999) cosg = -0.999999;
        g = acos(cosg);
        *length=sqrt(p4+p5-2*p7*cosg);
        if (errno==EDOM)
                {
                printf("\n SQRT ERROR : at angle between 2");
                printf("\n x1=%7.3f  y1=%7.3f  z1=%7.3f x2=%7.3f  y2=%7.3f  z2=%7.3f ",x1,y1,
                printf("\n p1=%7.3f  p4=%7.3f p5=%7.3f  p7=%7.3f cosg=%7.3f",p1,p4,p5,p7,cosg)
                errno=0;
                }
        return(g);
}
find_poligon_mean(Pole)
    float   *Pole;
{
```

```c
        int     i;
        *Pole=0.;
        *(Pole+2)=0.;
        for (i=0 ; i<6 ; i++)
                {
                        *Pole+=Poligon_pts.F_K_x[i];
                        *(Pole+2)+=Poligon_pts.F_K_y[i];
                }
        *Pole/=6.;
        *(Pole+2)/=6.;
}
float   calc_diameter(vol)
        double  vol;
{
        float factor=1.;
        return(2.*pow(factor*vol*3./(4.*pi),0.33333));
}
static unsigned long api_address = 0;
static unsigned char quiet;
static
report_error(int err,int where)
{
char str[80];
        if (quiet) return(1);
    strcpy(str,"*** Extended memory (XMS) error: ");
        switch (err)
        {
          case 0x80: strcat(str,"Function not implemented"); break;
          case 0x81: strcat(str,"Vdisk was detected"); break;
          case 0x82: strcat(str,"A20 Error"); break;
          case 0xA0: strcat(str,"No room in extended memory"); break;
          case 0xA1: strcat(str,"Out of extended memory HANDLES"); break;
          case 0xA2: strcat(str,"Attenpt to free invalid handle"); break;
          case 0xAB: strcat(str,"HANDLE is locked"); break;
          case 0xA3: strcat(str,"Source Handle is invalid"); break;
          case 0xA4: strcat(str,"Source Offset is invalid"); break;
          case 0xA5: strcat(str,"Dest Handle is invalid"); break;
          case 0xA6: strcat(str,"Dest Offest is invalid"); break;
          case 0xA7: strcat(str,"Length is invalid"); break;
          case 0xA8: strcat(str,"Move has invalid overlap"); break;
          case 0xA9: strcat(str,"Parity error has occured"); break;
          default:   strcat(str,"Unrecognized XMS error"); break;
        }
        printf("\n%s",str);
        strcpy(str,"    Error detected by: ");
        switch (where)
        {
           case 1: strcat(str,"malloc_extended"); break;
           case 2: strcat(str,"free_extended"); break;
           case 3: strcat(str,"xms_mem_move");
           default:strcat(str,"Anonymos routine"); break;
        }
        printf ("\n%s",str);
        exit(1);
}
free_extended(unsigned int handle)
{
unsigned int r;
unsigned char err;
_asm \
   {
      mov       ah, 0Ah
      mov       dx, handle
      call      [api_address]
```

```c
        mov     r, ax
        mov     err, bl
    }
    if (r == 0x0001) return(1);
    else {
        report_error(err,2);
        return(0);
    }
}
malloc_extended(unsigned int Kbyte_size)
{
unsigned int kbytes = Kbyte_size;
unsigned int r, handle;
unsigned char err;
_asm \
    {
        mov     ah, 09h
        mov     dx, kbytes
        call    [api_address]
        mov     r, ax
        mov     handle, dx
        mov     err, bl
    }
    if (r == 0x0001) return(handle);
    else {
        report_error(err,1);
        return(0);
    }
}
xms_get_free(int *largest)
{
int r,rl;
_asm \
    {
        mov     ah, 08h
        call    [api_address]          ;get XMS Number
        mov     r, dx
        mov     rl, ax
    }
    *largest = rl;
    return(r);
}
xms_version()
{
int r;
_asm \
    {
        mov     ah, 00h
        call    [api_address]          ;get XMS Number
        mov     r, ax
    }
    return(r);
}
is_xms(quiet_mode)
{
unsigned char r;
    quiet = (char) quiet_mode;
_asm \
    {
        mov     ax,4300h
        int     2Fh
        mov     r,al
    }
        if (r == 0x80)
```

```
            _asm \
            {
            mov     ax,4310h
            int     2Fh
            mov     word ptr [api_address],bx
            mov     word ptr [api_address+2],es
            }
        return(1);
        }
    else return(0);
}
xms_mem_move(unsigned int dst_handle, void _far *dst, unsigned long bytes,
             unsigned int src_handle, void _far *src)
{
int r;
unsigned char err;
struct {
        unsigned long bytes_count;
        unsigned int  src_handle;
        void _far *src_offset;
        unsigned int  dst_handle;
        void _far *dst_offset;
    } emms, *addr;
    addr = &emms;
    emms.bytes_count = bytes;
    emms.src_handle = src_handle;
    emms.src_offset = src;
    emms.dst_handle = dst_handle;
    emms.dst_offset = dst;
_asm \
    {
        push    si
        push    ds
        lds     si, addr
        mov     ah, 0Bh
        call    [api_address]
        pop     ds
        pop     si
        mov     r, ax
        mov     err, bl
    }
    if (r == 0x001) return(1);
    else { report_error(err,3);
           return(0);
         }
}
copy_to_xms(buf,length,handle)
                        void _far *buf; unsigned long length; int handle;
{
unsigned int kbytes = (length >> 10) + 1;
int ret;
        if (handle == 0)    {
                handle = malloc_extended(kbytes);
                                if (handle == 0) return(0);
                            }
    ret = xms_mem_move(handle, 0L, length, 0, buf);
        if (ret) return(handle);
        else return(0);
}
copy_from_xms(buf,length,handle)
                        void _far *buf; unsigned long length; int handle;
{
int ret;
```

```c
        ret = xms_mem_move(0, buf, length, handle, 01);
        if (ret) return(handle);
        else return(0);
}
#define DELAY_16ms_BY_COUNTER
#define DIO_CLOCK_PERIOD 10
#define DIO_BASE_ADDRESS          0x2A0
#define DIO_COUNTER0    (DIO_BASE_ADDRESS+4)
#define DIO_COUNTER1    (DIO_BASE_ADDRESS+5)
#define DIO_CONTROL     (DIO_BASE_ADDRESS+7)
grab_moving_apple(time1, time2, sensor)
                                                        unsigned short time1, time2;
{
int ret;
#ifdef _CFG
        if (sensor)
                time1 = get_delay_from_sensor();
        cfg_xtrigger(OFF);
        init_dio_trigger(time1, time2);         /* time in ms */
        init_triggered_grab();
        wait_trig();
                        ret = wait_trig();
                        if (ret == 0) return(0);
                        cfg_xtrigger(OFF);
#endif
                        speaker_beep(400, 200, 100, 1);
                        speaker_beep(300, 200, 0, 1);
                        return(1);
}
init_triggered_grab()
{
#ifdef _CFG
int field;
        cfg_sync(PLL);
        cfg_videosync(EXTSYNC);
        cfg_trigpl(HIGH);
                do      {
                                field = cfg_field();
                }       while (field != 0);
                cfg_xtrigger(ON);
                shadow_snap_cfg(0);
#endif
                }
wait_trig()
{
#ifdef _CFG
char status;
        cfg_waitvb();
        while (((status = inp(0x340 + 4)) & 0x08))
                if (kbhit()) return(0);
        return(1);
#endif
}
test_trigger()
{
}
init_dio_trigger(time1, time2)
        unsigned int time1, time2;
{
unsigned port;
unsigned char itim10, itim20;
unsigned short int tim1;
unsigned int divider = 1000 / DIO_CLOCK_PERIOD;
        port = DIO_BASE_ADDRESS;                        /* I/O board base address */
```

```c
        tim1  = time1 * divider;            /* ms in umits of 100 micro-seconds (10us clock
        itim10 = (unsigned char)(tim1 >> 8);   /* counter #0 high byte */
        itim20 = (unsigned char)(tim1 & 0xFF);  /* counter #0 low byte  */
        outp (DIO_CONTROL, 0x3A);        /* load control byte 0 0 1 1 1 0 1 0 - mode 5  */
        outp (DIO_COUNTER0, itim20);        /*load counter0 */
        outp (DIO_COUNTER0, itim10);
        tim1  = time2 * divider;
        itim10 = (unsigned char)(tim1 >> 8);          /* counter #1 high byte */
        itim20 = (unsigned char)(tim1 & 0xFF);        /* counter #1 low byte  */
        outp(DIO_CONTROL, 0x7A);        /* load control byte 0 1 1 1 1 0 1 0 - mode 5  */
        outp (DIO_COUNTER1, itim20);        /*load counter1 */
        outp (DIO_COUNTER1, itim10);
        return(SUCCESS);
}
get_delay_from_sensor()
{
unsigned char c;
double speed, t;
#define DIST 0.045
        c = (inp(DIO_BYTE0) & 0xFF);
        speed = 82./(double)c;
        t = 1000. * DIST / speed;
        return((int)(t+0.5));
}
#define MAX_ARGS         4
#define NAME_MAX   32
#define R_LOW_DAC_LIM            1788
#define R_HIGH_DAC_LIM           1834
#define G_LOW_DAC_LIM            1777
#define G_HIGH_DAC_LIM           1823
#define B_LOW_DAC_LIM            1772
#define B_HIGH_DAC_LIM           1818
#define APPLE_TRAVEL_INTERVAL    1635
#define FRAME_TIME_INTERVAL      1469
#define OPTICAL_DISTANCE_CAMERA_1 1870
#define OPTICAL_DISTANCE_CAMERA_2 1871
#define OPTICAL_DISTANCE_CAMERA_3 1872
#define SYSTEM_COMMAND_3D_FILE   1688
process_command_file(file_name, prog_consts, settings)    char file_name[];
                                struct prog_settings *prog_consts;
                                struct setup_data    *settings;

{
char    new_line;
int     line_counter = 0, ret;                  /* input line counter */
int     i, sum, index, arg_c;
FILE *in_fp;
char command[80];
char arg_v[MAX_ARGS][NAME_MAX];
        init_program(prog_consts);
        if ((in_fp = fopen(file_name,"r")) == 0) {
                                fprintf(stderr,"Can't find input file");
                                exit(1);
                                }
        while (fscanf (in_fp,"%[^\n]%*[\n]",command) != EOF)
        {
        sum = compute_index(command,&i);
        arg_c = separate_args(command,arg_v);
         switch(sum)
             {
             case        SYSTEM_COMMAND_3D_FILE:
                                if (strchr(arg_v[1]+1, '"') != NULL)
                                        *strchr(arg_v[1]+1, '"') = '\0
                                settings->demo_file_command = strdup(arg_v[1]+
                                break;
```

```
        case    FRAME_TIME_INTERVAL:
                                    prog_consts->frame_time_interval = atoi(arg_v[
                                    settings->frame_time_interval = atoi(arg_v[1])
                                    break;
        case    R_LOW_DAC_LIM:
                                    prog_consts->dac_low_lim[CAM_1] = atoi(arg_v[1
                                    settings->dac_low_lim[CAM_1] = atoi(arg_v[1]);
                                    break;
        case    R_HIGH_DAC_LIM:
                                    prog_consts->dac_high_lim[CAM_1] = atoi(arg_v[
                                    settings->dac_high_lim[CAM_1] = atoi(arg_v[1])
                                    break;
        case    G_LOW_DAC_LIM:
                                    prog_consts->dac_low_lim[CAM_2] = atoi(arg_v[1
                                    settings->dac_low_lim[CAM_2] = atoi(arg_v[1]);
                                    break;
        case    G_HIGH_DAC_LIM:
                                    prog_consts->dac_high_lim[CAM_2] = atoi(arg_v[
                                    settings->dac_high_lim[CAM_2] = atoi(arg_v[1])
                                            break;
        case    B_LOW_DAC_LIM:
                                    prog_consts->dac_low_lim[CAM_3] = atoi(arg_v[1
                                    settings->dac_low_lim[CAM_3] = atoi(arg_v[1]);
                                    break;
        case    B_HIGH_DAC_LIM:
                                    prog_consts->dac_high_lim[CAM_3] = atoi(arg_v[
                                    settings->dac_high_lim[CAM_3] = atoi(arg_v[1])
                                    break;
        case    APPLE_TRAVEL_INTERVAL:
                                    prog_consts->apple_travel_time_interval = atoi
                                    settings->apple_travel_time_interval = atoi(ar
                                    break;
        case    OPTICAL_DISTANCE_CAMERA_1:
                                    prog_consts->camera_distance[CAM_1] = atoi(arg
                                    settings->camera_distance[CAM_1] = atoi(arg_v[
                                    break;
        case    OPTICAL_DISTANCE_CAMERA_2:
                                    prog_consts->camera_distance[CAM_2] = atoi(arg
                                    settings->camera_distance[CAM_2] = atoi(arg_v[
                                    break;
        case    OPTICAL_DISTANCE_CAMERA_3:
                                    prog_consts->camera_distance[CAM_3] = atoi(arg
                                    settings->camera_distance[CAM_3] = atoi(arg_v[
                                    break;
        default:
                                    printf("\n%s == %d",arg_v[0], sum);
                                    break;
        } /* of switch */
    } /* of while */
    fclose(in_fp);
    return(1);
}
show_setup(settings)
    struct setup_data *settings;
{
    printf("\n R_Low dac  lim:       %3d",settings->dac_low_lim[CAM_1]);
    printf("\n R High dac lim:       %3d",settings->dac_high_lim[CAM_1]);
    printf("\n G Low dac  lim:       %3d",settings->dac_low_lim[CAM_2]);
    printf("\n G High dac lim:       %3d",settings->dac_high_lim[CAM_2]);
    printf("\n B Low dac  lim:       %3d",settings->dac_low_lim[CAM_3]);
    printf("\n B High dac lim:       %3d",settings->dac_high_lim[CAM_3]);
    printf("\n Cam 1 Optical distance: %3d",settings->camera_distance[CAM_1]);
    printf("\n Cam 2 Optical distance: %3d",settings->camera_distance[CAM_2]);
    printf("\n Cam 3 Optical distance: %3d",settings->camera_distance[CAM_3]);
```

```c
                printf("\n Apple Travel Interval:     %3d",settings->apple_travel_time_interval);
                printf("\n Frame Time Interval:    %3d",settings->frame_time_interval);
                printf("\n 3D-demo command:           %s", settings->demo_file_command);
}
compute_index(st, end_pos)              char *st; int *end_pos;
{
int sum;
        for ( ; *st == ' ' || *st == '\t' ; ++st);
        for (*end_pos = 0, sum = 0 ;
        *st && *st != ' ' && *st != ':' && *st != '\t' ; ++st, ++*end_pos)
                                sum += toupper(*st);
        if (*st == ':') ++*end_pos;
        return(sum);
}
separate_args(st,arg_v)         char *st;
                                char arg_v[MAX_ARGS][NAME_MAX];
{
int argc, i, sum;
char c_delimit;
        for (i = 0 ; i < MAX_ARGS ; ++i) arg_v[i][0] = 0;
        argc = 0;
        do {
   start:
        for ( ; isspace(*st) || (*st) == ':' || *st == 0 ; ++st) {
                                if (!(*st)) return(argc); } /* skip blanks */
                                /* check for comment */
        if (*st == '/' && (*(st+1)) == '*')   /* scan for end of comment */
                { do {
                    ++st;
                    } while(!(*st == '*' && (*(st+1)) == '/') && (*(st+1)));
                ++st; if (*st == '/') ++st;
                goto start;}
        if (*st == '/' && *(st+1) == '/')  break;    /* C++ comment */
                while(isspace(*st)) ++st;
                c_delimit = 0;
                if (*st == '"') c_delimit = '"';
                if (*st == '\'') c_delimit = '\'';
                if (*st == '\`') c_delimit = '\`';
                if (c_delimit != 0) { arg_v[argc][0] = *st; ++st;
                for (i=1 ; *st && i < NAME_MAX && *st != c_delimit; ++st )
                                                                                { arg_v[argc][i] = *st
                        arg_v[argc][i] = c_delimit; ++i;
                }
                else {
                for (i=0 ; (!isspace(*st)) && *st && i < NAME_MAX; ++st )
                                                                                { arg_v[argc][i] = *st
                }
         while ( !isspace(*st) && *st ) ++st;
         arg_v[argc][i] = 0;
         ++argc;
         if (argc == MAX_ARGS) { fprintf(stderr, "Too Many Argumants");
                                return(argc); }
         } while(*st);
      return(argc);
}
init_program(prog_consts)
                        struct prog_settings *prog_consts;
{
char tmp[32];
int i;
#define GREEN_NAME  "green"                                          /* for final images
#define RED_NAME    "red"
#define IR_NAME     "ir"
#define GRID_NAME   "grid"
```

```c
#define W_GREEN_NAME        "w_green"                           /* for image aquired f
#define W_GRID_NAME         "w_grid"
#define W_RED_NAME          "w_red"
#define W_IR_NAME           "w_ir"
#define HUE_NAME            "hue"                               /* for hsv data */
#define SATUR_NAME          "satur"
#define VALUE_NAME          "value"
#define BND_NAME            "bnd"
#define BND_Z_NAME          "bndz"
#define NORM_FILE           "norm"
#define COLORS_FILE         "colors"
#define SPOTS_FILE          "spots"
#define BRUIS_FILE          "bruis"
#define STEM_FILE           "stem"
#define PIP_H_FILE          "pip_h.bnd"
#define SPLITTER_LOCATIONS_MASTER_NAME "split"
                            /* display coordinates for the images */
#ifdef DISPLAY_640
        prog_consts->T_WIN_X_OFF[0] = "52";  prog_consts->T_WIN_Y_OFF[0] = "30";
        prog_consts->T_WIN_X_OFF[1] = "248"; prog_consts->T_WIN_Y_OFF[1] = "30";
        prog_consts->T_WIN_X_OFF[2] = "444"; prog_consts->T_WIN_Y_OFF[2] = "30";
#else
        prog_consts->T_WIN_X_OFF[0] = "10";   prog_consts->T_WIN_Y_OFF[0] = "10";
        prog_consts->T_WIN_X_OFF[1] = "10";   prog_consts->T_WIN_Y_OFF[1] = "10";
        prog_consts->T_WIN_X_OFF[2] = "10";   prog_consts->T_WIN_Y_OFF[2] = "10";
#endif
        prog_consts->stem_disp_x[0] = "30";         prog_consts->stem_disp_y[0] = "300";
        prog_consts->stem_disp_x[1] = "30";         prog_consts->stem_disp_y[1] = "300";
        prog_consts->stem_disp_x[2] = "30";         prog_consts->stem_disp_y[2] = "300";
        prog_consts->color_disp_x[0] = "42";    prog_consts->color_disp_y[0] = "230";
        prog_consts->color_disp_x[1] = "238";   prog_consts->color_disp_y[1] = "230";
        prog_consts->color_disp_x[2] = "434";   prog_consts->color_disp_y[2] = "230";
        for (i = 0 ; i < NUMBER_OF_CAMERAS ; ++i)
        {
                sprintf(tmp,"%s.%ld", GREEN_NAME, i);   prog_consts->GREEN_name[i] = strdup(tm
                sprintf(tmp,"%s.%ld", RED_NAME, i);     prog_consts->RED_name[i] = strdup(t
                sprintf(tmp,"%s.%ld", IR_NAME, i);      prog_consts->IR_name[i] = strd
                sprintf(tmp,"%s.%ld", GRID_NAME, i);    prog_consts->GRID_name[i] = strdup(tmp
                sprintf(tmp,"%s.%ld", W_GRID_NAME, i);  prog_consts->GRID_W_name[i] =
                sprintf(tmp,"%s.%ld", W_GREEN_NAME, i); prog_consts->GREEN_W_name[i] = strdup(
                sprintf(tmp,"%s.%ld", W_RED_NAME, i);   prog_consts->RED_W_name[i] = s
                sprintf(tmp,"%s.%ld", W_IR_NAME, i);    prog_consts->IR_W_name[i] = st
                sprintf(tmp,"%s.%ld", HUE_NAME, i);         prog_consts->HUE_name[
                sprintf(tmp,"%s.%ld", SATUR_NAME, i);   prog_consts->SATUR_name[i] = s
                sprintf(tmp,"%s.%ld", VALUE_NAME, i);      prog_consts->VALUE_name[i] = s
                sprintf(tmp,"%s.%ld", BND_NAME, i);     prog_consts->BND_name[i] = strdup(t
                sprintf(tmp,"%s.%ld", BND_Z_NAME, i);    prog_consts->BND_Z_name[i] = strdup(
                sprintf(tmp,"%s.%ld", COLORS_FILE, i);  prog_consts->COLORS_file[i] = strdup(t
                sprintf(tmp,"%s.%ld", SPOTS_FILE, i);       prog_consts->SPOTS_file[i] = s
                sprintf(tmp,"%s.%ld", BRUIS_FILE , i);  prog_consts->BRUISE_file[i] = strdup(t
                sprintf(tmp,"%s.%ld", STEM_FILE  , i);  prog_consts->STEM_file[i] = strdup(tmp
                sprintf(tmp,"%s.%ld", PIP_H_FILE , i);  prog_consts->PIP_H_file[i] = strdup(tm
                sprintf(tmp,"%s%ld",  SPLITTER_LOCATIONS_MASTER_NAME, i);
                                prog_consts->SPLITTER_LOCATIONS[i] = strdup(tmp);
        }
}
static FILE *out_file;
double compute_volume(bnd0,bnd1,bnd2,camera_distance)
                        int     *camera_distance;
                        struct  boundary_data *bnd0,*bnd1,*bnd2;
{
    int x1[N_CAMERAS], x2[N_CAMERAS], y[N_CAMERAS], x, i, xz1[N_CAMERAS],xz2[N_CAMERAS],
        size[3], diff[3],xl1[N_CAMERAS],xl2[N_CAMERAS],min_y,begin_val=1;
    double  volume, area;
```

```c
        float    y_height,min_height,z_3d[3];
        double   compute_line_area();
                if ((size[0]=bnd0->boundary_index) > (size[1]=bnd1->boundary_index))
                        min_y=1;
                else min_y=0;
        if ((size[2]=bnd2->boundary_index) < size[min_y])
                        min_y=2;
                diff[(min_y+2)%3]=size[(min_y+2)%3]-size[min_y];
                if ((diff[(min_y+1)%3]=size[(min_y+1)%3]-size[min_y]) > SIZE_BND_DIFF_LIMIT
                        diff[(min_y+2)%3] > SIZE_BND_DIFF_LIMIT  {
                        printf("\n WARNING : Boundary structurs sizes are not similar ");
                }
                diff[min_y]=0;
                for (i=0 ; i < N_CAMERAS ; i++) {
                        if (size[i]==0) continue;
                                diff[i]/=2;
                }
                y_height=(*camera_distance+(*(camera_distance+1))+
                        (*(camera_distance+2)))*CCD_SIZE_Y/((float) CCD_RESOLUTION_Y*CAM_FO
                min_height=-y_height*size[min_y]/2.;
                printf("\n y_h=%5.3f  min_h=%5.3f cam_d_0=%d cam_d_2=%d",y_height,min_height,
            bnd0->out_rect.y1=bnd0 -> boundary[begin_val+diff[0]].y;
            bnd1->out_rect.y1=bnd1 -> boundary[begin_val+diff[1]].y;
            bnd2->out_rect.y1=bnd2 -> boundary[begin_val+diff[2]].y;
                volume = 0.;
                /* Line loop exeqution & bnd_z structur setting */
                for (i = begin_val; i < size[min_y]-begin_val ; ++i)
        {
                        y[0]  = bnd0 -> boundary[i+diff[0]].y;
                        x1[0] = bnd0 -> boundary[i+diff[0]].x1;
                        x2[0] = bnd0 -> boundary[i+diff[0]].x2;
                        y[1]  = bnd1 -> boundary[i+diff[1]].y;
                        x1[1] = bnd1 -> boundary[i+diff[1]].x1;
                        x2[1] = bnd1 -> boundary[i+diff[1]].x2;
                        y[2]  = bnd2 -> boundary[i+diff[2]].y;
                        x1[2] = bnd2 -> boundary[i+diff[2]].x1;
                        x2[2] = bnd2 -> boundary[i+diff[2]].x2;
                        area=compute_line_area(x1, x2, camera_distance,xz1,xz2,x11,x12);
                bnd0 -> boundary[i-begin_val].y  = y[0];
                        bnd0 -> boundary[i-begin_val].x1 = xz1[0];
                        bnd0 -> boundary[i-begin_val].x2 = xz2[0];
                        bnd1 -> boundary[i-begin_val].y  = y[1];
                        bnd1 -> boundary[i-begin_val].x1 = xz1[1];
                        bnd1 -> boundary[i-begin_val].x2 = xz2[1];
                        bnd2 -> boundary[i-begin_val].y  = y[2];
                        bnd2 -> boundary[i-begin_val].x1 = xz1[2];
                        bnd2 -> boundary[i-begin_val].x2 = xz2[2];
                        min_height+=y_height;
                volume += (double)area * (double)y_height;
        }
            bnd0->out_rect.y2=bnd0 -> boundary[(--i)+diff[0]].y;
            bnd1->out_rect.y2=bnd1 -> boundary[(--i)+diff[1]].y;
            bnd2->out_rect.y2=bnd2 -> boundary[(--i)+diff[2]].y;
            bnd0->boundary_index=bnd1->boundary_index=bnd2->boundary_index=size[min_y]-2*begin_v
                printf("\n glb_all Volume:", "%4d","cc", (int)(volume / 1000.));
                        return(volume);
}
int  do_simple_grade(spots,spt_index,Dark_Red,Simple_red,Yellow,Green,Orange,apple_size)
        struct spot  spots[];
        int          apple_size;
        long         Dark_Red,Simple_red,Yellow,Green,Orange;
{
                return(1);
}
```

APPENDIX K

```
/*
        ID: 009.
   File name: app09.h
---------------------------------------------------------------
*/
#define _CFG
define VGA define wait sleep define finit_display   finit_cfg
define init_display    init_cfg
#define INIT_DISPLAY    init_cfg()
define reinit_display  reinit_cfg define copy_block(p,a,b,c,d,e,f)   ram_2_cfg(p, 0,0,(d)-(b),(c)-(a),e,f)
define get_block(p,a,b,c,d,e,f)    cfg_2_ram(p, 0,0,(d)-(b),(c)-(a),e,f)

#define clear_screen    clear_screen_cfg
define pan_window      pan_cfg define set_lut_active  load_output_lut_cfg
define get_lut_values  read_output_lut_cfg define set_channel     set_color_channel_cfg
define get_channel     get_color_channel_cfg define write_str       text_cfg
define rpixel          rpixel_cfg
#define wpixel          wpixel_cfg
#define zoom_window     zoom_cfg
#define rectangle       rectangle_cfg
#define filled_rectangle   filled_rectangle_cfg
#define filled_rectangle_1 filled_rectangle_cfg
#define dline           dline_cfg
#define init_grab       init_grab_cfg
#define cont_grab       grab_cfg
#define freese          stopgrab_cfg
#define snap            snap_cfg
#define set_line_writing_mode null_cfg
#define move_abs        move_abs_cfg
define draw_abs        draw_abs_cfg define circle          circle_cfg
define filled_circle   filled_circle_cfg define DRAW_ABS(a,b,c)   draw_abs((b),(a),(c))
define MOVE_ABS(a,b)     move_abs((b),(a));

#define MODE_SRC    1
define ARROW       1 define __RED       0
define __GREEN     1
```

```
#define __BLUE           2
#define __FILLER         3
define __ENTIRE_DEPTH   1000 ifndef PIXEL
define PIXEL unsigned char
endif struct __cfg_data {
        int color_plane;
        int pan;
        int scroll;
        int zoom;
     } __cfg_settings;

#ifdef VGA
#define DISPLAY_640
endif define MAX_SPOTS 512
define MAX_FINAL_SPOTS 96
#define IMG_ST_CA    10
define REAL_BLEMISH 11 enum apple_brands        { SMITH_TYPE = 0, HERMON_TYPE, ANA_TYPE, ORLEANS_TYPE };

define S_CALYX_GREEN_LOW       0
#define S_CALYX_GREEN_HIGH      85
#define S_CALYX_RED_LOW         0
#define S_CALYX_RED_HIGH        85
#define S_CALYX_IR_LOW          0
define S_CALYX_IR_HIGH         85 define H_CALYX_GREEN_LOW       0
define H_CALYX_GREEN_HIGH      150
#define H_CALYX_RED_LOW         0
#define H_CALYX_RED_HIGH        100
#define H_CALYX_IR_LOW          0
define H_CALYX_IR_HIGH         65 define O_CALYX_GREEN_LOW       0
define O_CALYX_GREEN_HIGH      150
#define O_CALYX_RED_LOW         0
#define O_CALYX_RED_HIGH        100
#define O_CALYX_IR_LOW          0
define O_CALYX_IR_HIGH         65 define RUSSET_GREEN_LOW        0
define RUSSET_GREEN_HIGH       90
#define RUSSET_RED_LOW          0
#define RUSSET_RED_HIGH         170
#define RUSSET_IR_LOW           0
#define RUSSET_IR_HIGH          145
```

```
#define BRUISE_GREEN_LOW      60
#define BRUISE_GREEN_HIGH    110
#define BRUISE_RED_LOW        80
#define BRUISE_RED_HIGH      120
#define BRUISE_IR_LOW        120
define BRUISE_IR_HIGH       170 define GREEN_GREEN_LOW       85
define GREEN_GREEN_HIGH     130
#define GREEN_RED_LOW         70
#define GREEN_RED_HIGH       120
#define GREEN_IR_LOW         140
define GREEN_IR_HIGH        200 define RED_GREEN_LOW         50
define RED_GREEN_HIGH        90
#define RED_RED_LOW           85
#define RED_RED_HIGH         110
#define RED_IR_LOW           140
define RED_IR_HIGH          180 define TOP_VAL 200 define display_eliminate display_image define    FILE_3D_NAME      "glob.out"

define HEIGHT                165
#define CALYX_MARK            200
#define STEM_MARK             CALYX_MARK
#define CALYX_RUSSET_MARK     240
#define RUSSET_MARK           150
#define BRUSE_MARK            100
#define WIRE_MARK             254
#define GREEN_MARK             50
define RED_MARK              230 define STACK_CHECK    if (stackavail() < 512) { printf("\n OOPSS"); return(0); } define FLOAT_ERROR 1
define NO_PER      2 define MAX_EDGE_LEN (FR_X_SIZE * FR_Y_SIZE / sizeof(struct point))

define LOW_MARK  100
define HIGH_MARK 200 define MIN(a,b) ((a) < (b) ? (a) : (b))
```

```c
#define MAX(a,b) ((a) > (b) ? (a) : (b))
#define SGN(a) ((a) > 0 ? 1 : -1)
#define SGN_0(a) ((a) > 0 ? 1 : ((a) == 0 ? 0 : -1))

#define L_ON    1
define L_OFF   0 define WIRE_WIDTH 4
define EXTERNAL_COLOR 255 define L_FR_X_SIZE 192
define L_FR_Y_SIZE 192
#define FR_X_SIZE 144
define FR_Y_SIZE 144 define FR_HEADER_SIZE 512
define PIXEL8 unsigned char
#define PIXEL  unsigned char
#define SUCCESS 1
#define FAILURE 0
define NO_HEADER 10 define N_CAMERAS 3
define CAM_1   0
#define CAM_2   1
define CAM_3   2 define CCD_RESOLUTION_X   640
define CCD_RESOLUTION_Y   480 define CAMERA_DISTANCE    camera_distance
define CCD_SIZE_X         6.4
#define CCD_SIZE_Y         4.8
define CAM_FOCAL_LENGTH   12 define MAX_BOUNDARY 512
struct line_pair { int y, x1, x2; };
struct rect { int x1, y1, x2, y2; };
struct point { int x,y; };
struct cam_data {
            struct line_pair boundary[MAX_BOUNDARY];
            int boundary_index;
            struct rect out_rect;
            int camera_distance;
    };

struct two_d_data {
    signed char green_off_x, green_off_y;
    signed char red_off_x,   red_off_y;
```

```
        signed char ir_off_x,   ir_off_y;
        signed char grid_off_x, grid_off_y;
        } ;

#define CAM_1_GREEN_OFF_X    0
#define CAM_1_GREEN_OFF_Y    0
#define CAM_1_RED_OFF_X      0
#define CAM_1_RED_OFF_Y         0
#define CAM_1_IR_OFF_X       0
#define CAM_1_IR_OFF_Y       0
#define CAM_1_GRID_OFF_X     0
define CAM_1_GRID_OFF_Y     0 define MAX_LENGTH 2048
typedef struct consts_t {
      int min_area;
      int max_area;
      int min_per;
      int max_per;
      int min_p2a;
      int max_p2a;
      int min_aspect_ratio;
      int max_aspect_ratio;
      int min_fract;
      int max_fract;
      int magnification;
      int smooth;
      int step;
      int start_level;
      int end_level;
      int min_pile_depth;
      int max_pile_depth;
      float gaus_parameter_1;
      char screening_only;
      char use_area_absolute_val;
          } contour_prog_globals;

#define gtext_vga(x,y,s,sz,c,n)    etext_vga(x,(y+15),s,1,c,(sz))
#define gtext_demo           etext_vga
#define init_display_demo    reinit_vga
#define dline_demo           vga_direct_line
#define display_image_demo(x,y,im,sx,sy,str)   vga_put_image(im,sx,sy,x,y,str)
#define finit_vga            restore_vga
#define finit_display_demo   finit_vga
#define wpixel_demo          vga_direct_wpixel
#define rectangle_demo       vga_rectangle
#define filled_rectangle_demo   vga_filled_rectangle
#define move_abs_demo        vga_move_abs
#define draw_abs_demo        vga_draw_abs
```

```
#define VISITED    1
#define NO_SPOT    200
#define STEM_CALYX 10
#define RUSSETING  100
define BRUISE     170 define NUMBER_OF_CAMERAS   3 define SETUP_FILE "screen3d.set"

struct setup_data {
        int camera_distance[NUMBER_OF_CAMERAS];
        int dac_low_lim[NUMBER_OF_CAMERAS];
        int dac_high_lim[NUMBER_OF_CAMERAS];

int apple_travel_time_interval;
        int frame_time_interval;

char *demo_file_command;
    };

struct prog_settings {
        char *GREEN_name[NUMBER_OF_CAMERAS];
        char *RED_name[NUMBER_OF_CAMERAS];
        char *IR_name[NUMBER_OF_CAMERAS];
        char *GRID_name[NUMBER_OF_CAMERAS];

char *GRID_W_name[NUMBER_OF_CAMERAS];
        char *GREEN_W_name[NUMBER_OF_CAMERAS];
        char *IR_W_name[NUMBER_OF_CAMERAS];
        char *RED_W_name[NUMBER_OF_CAMERAS];

char *GREEN_WIRES_name[NUMBER_OF_CAMERAS];
        char *IR_WIRES_name[NUMBER_OF_CAMERAS];
        char *RED_WIRES_name[NUMBER_OF_CAMERAS];

char *BND_name[NUMBER_OF_CAMERAS];
        char *BND_Z_name[NUMBER_OF_CAMERAS];
        char *COLORS_file[NUMBER_OF_CAMERAS];
        char *SPOTS_file[NUMBER_OF_CAMERAS];
        char *BRUISE_file[NUMBER_OF_CAMERAS];
        char *STEM_file[NUMBER_OF_CAMERAS];
        char *PIP_H_file[NUMBER_OF_CAMERAS];

char *HUE_name[NUMBER_OF_CAMERAS];
        char *SATUR_name[NUMBER_OF_CAMERAS];
        char *VALUE_name[NUMBER_OF_CAMERAS];

char *T_WIN_X_OFF[NUMBER_OF_CAMERAS];
        char *T_WIN_Y_OFF[NUMBER_OF_CAMERAS];
        char *SPLITTER_LOCATIONS[NUMBER_OF_CAMERAS];

char *stem_disp_x[NUMBER_OF_CAMERAS];
```

```
        char *stem_disp_y[NUMBER_OF_CAMERAS];
        char *color_disp_x[NUMBER_OF_CAMERAS];
        char *color_disp_y[NUMBER_OF_CAMERAS];

int camera_distance[NUMBER_OF_CAMERAS];
        int dac_low_lim[NUMBER_OF_CAMERAS];
        int dac_high_lim[NUMBER_OF_CAMERAS];

int apple_travel_time_interval;
        int frame_time_interval;
};

#define AUTO_MODE 1
define MANUAL_MODE 2 define DIO_CLOCK_PERIOD 10
define DIO_BASE_ADDRESS   0x2A0
#define DIO_BYTE0       (DIO_BASE_ADDRESS+0)
#define DIO_COUNTER0    (DIO_BASE_ADDRESS+4)
#define DIO_COUNTER1    (DIO_BASE_ADDRESS+5)
#define DIO_CONTROL     (DIO_BASE_ADDRESS+7)

define  SIZE_BND_DIFF_LIMIT  2 define   ORLEANS_RED_THRESH          50
define   ORLEANS_R_G_RATIO_THRESH_A  2.22
#define   ORLEANS_R_G_RATIO_THRESH_B  1.81
define   ORLEANS_R_G_RATIO_THRESH_C  1.54 define   SMITH_RED_THRESH            60
define   SMITH_R_G_RATIO_THRESH_A    2.22
#define   SMITH_R_G_RATIO_THRESH_B    1.71
define   SMITH_R_G_RATIO_THRESH_C    1.3 grab_moving_apple(unsigned short, unsigned short, int);
double angle_between(double, double, double, double, double, double, double *);

#define STORAGE_FILE "c:\\storage.xms"
#define SWAP_OUT(buf,cam,item) swap_out(buf,view_info[cam].xms_handle, \
          (unsigned long)sizeof(buf), view_info[cam].item)
#define SWAP_OUT_SIZE(buf,cam,item,size) swap_out(buf,view_info[cam].xms_handle, \
          (unsigned long)size, view_info[cam].item)

#define SWAP_IN(buf,cam,item)   swap_in(buf, view_info[cam].xms_handle, \
          (unsigned long)sizeof(buf),view_info[cam].item)
#define SWAP_IN_SIZE(buf,cam,item,size)  swap_in(buf, view_info[cam].xms_handle, \
          (unsigned long)size,view_info[cam].item)

#define MAX_CANDIDATES 96
struct c_dat {
        int si, sj, ci, cj, area, cam_number;
```

```
               double a_r, x, y, z, dist;
               int angle;
               int type;
               int mate;
     };

struct images_offsets {
               unsigned long green;
               unsigned long red;
               unsigned long ir;
               unsigned long grid;
     };

struct boundary_data {
               struct line_pair boundary[MAX_BOUNDARY];
               int boundary_index;
               struct rect out_rect;
          };

struct single_view_info  {
               int dim_1;
               int dim_2;
               int angle;
               double volume;

unsigned int xms_handle;

unsigned long splitter[4];

struct images_offsets w_images;
               struct images_offsets r_images;
               struct images_offsets raw_images;
               struct images_offsets enhanced_images;
               struct images_offsets normal_images;

unsigned long bnd;
               unsigned long bnd_z;
               unsigned long ref_bnd;

unsigned long stem_mask;
               unsigned long spots_1;
               unsigned long spots_2;
               unsigned long spots_3;
               unsigned long combi_map;
               };

#define   ORLEANS_GRID_THRESH                    40
#define   ORLEANS_RED_THRESH_LOW         0.40
#define   ORLEANS_RED_THRESH_MEDIUM      0.5
define   ORLEANS_RED_THRESH_HIGH              0.7 define   ORLEANS_GREEN_THRESH_LOW       0.30
```

```
#define  ORLEANS_GREEN_THRESH_MEDIUM    0.3
define  ORLEANS_GREEN_THRESH_HIGH      0.4 define  SMITH_GRID_THRESH                        40
define  SMITH_RED_THRESH_LOW          0.40
#define  SMITH_RED_THRESH_MEDIUM            0.5
define  SMITH_RED_THRESH_HIGH                 0.7 define  SMITH_GREEN_THRESH_LOW        0.30
define  SMITH_GREEN_THRESH_MEDIUM     0.3
define  SMITH_GREEN_THRESH_HIGH            0.4 define  SIMPLE_RED_COLOR     1
define  DARK_RED_COLOR       2
#define  ORANGE_COLOR         3
#define  GREEN_COLOR          4
define  YELLOW_COLOR         5 define TMP_DEVICE "d:"

define LENGTH(x,y)     ( x * x + y * y)
define PI 3.14159265358 define FR_HEADER_SIZE 512
define CONTOUR_COL    255
define BRUISE_COLOR   254 struct spot{
        unsigned char start_i, start_j, ci, cj;
        unsigned char  min_i, max_i, min_j, max_j;
        int area, per;
        float  ar, p2a;
        unsigned char a1, b1;
        unsigned char  green_cgl, red_cgl, ir_cgl, grid_cgl;
        unsigned char  g_ar_mean, r_ar_mean, i_ar_mean, grid_ar_mean;
        unsigned char flag1, flag2, flag3, flag4, flag_g;
        unsigned char cam_number;
        float x,y,z;
        float dist;
        int angle;
        int mate;
        } ;

do_bruse_1(int cam, struct boundary_data *bnd,PIXEL im0[FR_Y_SIZE][FR_X_SIZE],
                    PIXEL im1[FR_Y_SIZE][FR_X_SIZE],PIXEL im2[FR_Y_SIZE][FR_X
                    PIXEL im3[FR_Y_SIZE][FR_X_SIZE],PIXEL im4[FR_Y_SIZE][FR_X
                    PIXEL im5[FR_Y_SIZE][FR_X_SIZE],
                    struct spot spots[1]);

int cntr(PIXEL im0[FR_Y_SIZE][FR_X_SIZE], PIXEL im1[FR_Y_SIZE][FR_X_SIZE],
                PIXEL im2[FR_Y_SIZE][FR_X_SIZE],      PIXEL im3[FR_Y_SIZE][FR_X_
               int cam, PIXEL im4[FR_Y_SIZE][FR_X_SIZE],
```

```
struct spot spots[.,
PIXEL im6[FR_Y_SIZE][FR_X_SIZE]);
```

APPENDIX L

```
rem ID: 011
rem File name: build.bat
rem also, create the file screen3d.set, in this appendix
rem to run: at DOS prompt, type 'build' rem -----------------------------  --  ---------------  -------------
del *.lib
copy app08.h adapter.h
cl /AL   /G2   /c /nologo /Zi app01.c
cl /AL   /G2   /c /nologo /Zi app03.c
cl /AL   /G2   /c /nologo /Zi app09.c
cl /AL   /G2   /c /nologo /Zi app10.c
cl /AL   /G2   /c /nologo /Zi app12.c
cl /AL   /G2   /c /nologo /Zi app13.c
cl /AL   /G2   /c /nologo /Zi app14.c
cl /AL   /G2   /c /nologo /Zi app15.c
cl /AL   /G2   /c /nologo /Zi app16.c
cl /AL   /G2   /c /nologo /Zi app17.c lib /nologo all + app01;
lib /nologo all + app03;
lib /nologo all + app09;
lib /nologo all + app10;
lib /nologo all + app12;
lib /nologo all + app14;
lib /nologo all + app13;
lib /nologo all + app16;
lib /nologo all + app17;

:next
link /ST:5000 /nologo app15,,,all+itxcfgml+itxvspml+itxstbml; > 1.1 rem run the program
app15 Orleans 0 1 > nul:

rem---------------Autoexec.bat-----------------------------------
set lib=c:\c600\lib
set include=c:\c600\include
PATH C:\C600\BINB;C:\C600\BIN;%path%
SET HELPFILES=C:\C600\HELP\*.HLP
SET INIT=C:\C600\INIT rem---------------Config.sys-------------------------------------
DEVICE=HIMEM.SYS /numhandles=16
device=RAMDRIVE.SYS 7168 512 1024 /e
SHELL=C:\DOS\COMMAND.COM C:\ /P /E:2048
BREAK=ON
FILES=40
BUFFERS=30 rem---------------Screen3d.set-----------------------------------
grabber_low_dac_limit_R            65
grabber_high_dac_limit_R           700
grabber_low_dac_limit_G      65
grabber_high_dac_limit_G           700
grabber_low_dac_limit_B            70
grabber_high_dac_limit_B           700
apple_travel_interval              17
frame_time_interval                66
optical_distance_camera_1          720
optical_distance_camera_2          720
```

```
optical_distance_camera_3      720
system_command_3d_file         ""
```

We claim:

1. Apparatus for inspecting agricultural produce having a stem and/or a calyx, the apparatus comprising:
   an imager operative to provide an image of generally the entire surface of the agricultural produce including at least one of its stem location and its calyx location;
   a stem/calyx identifier operative to determine the location of at least one of the stem and the calyx in said image of the agricultural produce; and
   a blemish detector, cooperative with said stem/calyx identifier including logic apparatus operative to detect blemishes on said image and to avoid false detection of the stem location as a blemish and/or the calyx location as a blemish.

2. Apparatus according to claim 1 and wherein said logic apparatus is also operative to ignore color variations in the vicinity of the stem location and/or the calyx location.

3. Apparatus according to claim 1 wherein the agricultural produce comprises an apple.

4. Apparatus according to claim 1 and further comprising:
   an automatic agricultural produce grading unit including an image processor receiving the image generated by the imager and the output of the blemish detector and providing an output indication of a grade for the individual agricultural produce.

5. Apparatus according to claim 4 wherein the grading unit is user-tunable such that criteria employed by the grading unit may be modified by the user.

6. Apparatus according to claim 1 and wherein said logic apparatus is operative to provide an output indication of at least one blemish characteristic other than the size thereof.

7. Apparatus according to claim 1 wherein said logic apparatus is operative to detect at least one blemish candidate and to reclassify at least one blemish candidate corresponding to a stem location and/or to a calyx location as a non-blemish.

8. Apparatus according to claim 1 wherein said logic apparatus is operative to detect at least one blemish candidate and to record at least one feature for each blemish candidate.

9. Apparatus according to claim 8 wherein said at least one feature includes an area of the blemish candidate.

10. Apparatus according to claim 8 wherein said at least one feature includes an indication of darkness of the area of the blemish candidate.

11. Apparatus according to claim 8 wherein said at least one feature includes an indication of darkness outside the area of the blemish candidate.

12. Apparatus according to claim 8 wherein said at least one feature includes a ratio between horizontal and vertical dimensions of the area of the blemish candidate.

13. Apparatus according to claim 1 wherein said logic apparatus is operative to reclassify only stem and calyx locations which are located along a central axis of the fruit, as non-blemishes.

14. Apparatus according to claim 1 wherein said imager is operative to inspect generally all exposed surfaces of the agricultural produce generally simultaneously.

15. Apparatus according to claim 1 wherein said imager is operative to provide an image of generally the entire surface of the agricultural produce regardless of the extent of rotation of the agricultural produce during imaging.

16. Apparatus according to claim 1 wherein said stem/calyx identifier is operative to determine said location of at least one of the stem and the calyx in said image of generally the entire surface of the agricultural produce provided by said imager.

17. Apparatus for inspecting agricultural produce having a stem and/or a calyx, the apparatus comprising:
   an imager operative to provide an image of generally the entire surface of the agricultural produce including at least one of its stem location and its calyx location;
   a stem/calyx identifier operative to determine the location of at least one of the stem and the calyx in the image of the agricultural produce; and
   a blemish detector, cooperative with said stem/calyx identifier, including logic apparatus operative to detect blemishes and to avoid false detection of the stem location as a blemish and/or the calyx location as a blemish,
   wherein the stem/calyx identifier comprises a valley contour detector.

18. Apparatus according to claim 17 wherein said stem/calyx identifier also comprises apparatus operative to inspect a putative location of the stem and of the calyx relative to the shape of the produce and to reject putative locations which are not located generally one opposite the other.

19. Apparatus for inspecting agricultural produce having a stem and/or a calyx, the apparatus comprising:
   an imager operative to provide an image of generally the entire surface of the agricultural produce including at least one of its stem location and its calyx location;
   a stem/calyx identifier operative to determine the location of at least one of the stem and the calyx in the image of the agricultural produce;
   a blemish detector, operative with said stem/calyx identifier, including logic apparatus operative to detect blemishes and to avoid false detection of the stem location as a blemish and/or the calyx location as a blemish; and
   a produce supporting cable assembly including a plurality of cables arranged to support the agricultural produce.

20. Apparatus according to claim 19 and also comprising an additional cable assembly interlaced with the produce supporting cable assembly.

21. Apparatus according to claim 19 and also comprising:
   a kicker element; and
   a kicker element activator operative to slide the kicker element between the produce supported by the cable assembly so as to allow the kicker element to engage the produce and to remove the produce from the plurality of cables.

22. Apparatus for inspecting agricultural produce having a stem and/or a calyx, the apparatus comprising:
   an imager operative to provide an image of generally the entire surface of the agricultural produce including at least one of its stem location and its calyx location;
   a stem/calyx identifier operative to determine the location of at least one of the stem and the calyx in the image of the agricultural produce;
   a blemish detector, cooperative with said stem/calyx identifier, including logic apparatus operative to detect blemishes and to avoid false detection of the stem location as a blemish and/or the calyx location as a blemish;
   an automatic agricultural produce grading unit including an image processor receiving the image generated by the imager and the output of the blemish detector and providing an output indication of a grade for the individual agricultural produce,
   wherein the grading unit is user-tunable such that criteria employed by the grading unit may be modified by the user, and
   wherein the grading unit comprises a user-tunable fuzzy logic unit.

23. Apparatus for inspecting agricultural produce having a stem and/or a calyx, the apparatus comprising:
   an imager operative to provide an image of generally the entire surface of the agricultural produce including at least one of its stem location and its calyx location;

a stem/calyx identifier operative to determine the location of at least one of the stem and the calyx in the image of the agricultural produce;

a blemish detector, cooperative with said stem/calyx identifier, including logic apparatus operative to detect blemishes and to avoid false detection of the stem location as a blemish and/or the calyx location as a blemish; and a fuzzy logic image entity classifier operative to employ fuzzy logic criteria in order to inspect a representation of an entity forming at least a portion of the agricultural produce and to classify the entity according to a predetermined classification scheme, wherein said fuzzy logic image entity classifier is cooperative with said stem/calyx identifier and said blemish detector.

24. Apparatus according to claim 23 wherein the agricultural produce is expected to have at least one discolored area on its surface and wherein the entity comprises a discolored portion of the agricultural produce and wherein the predetermined classification scheme includes two classes:

expected discoloration; and unexpected discoloration.

25. Apparatus according to claim 24 wherein the entity comprises a pair of discolored areas and the predetermined classification scheme comprises a binary classification scheme including a first class of stem location/calyx location and a second class of not stem location/not calyx location.

26. Apparatus according to claim 23 wherein the predetermined classification scheme includes a plurality of classes corresponding to a plurality of types of blemishes.

27. Apparatus according to claim 23 wherein the entity comprises the agricultural produce and wherein the predetermined classification scheme includes a plurality of classes corresponding to a plurality of grades of agricultural produce.

28. Apparatus according to claim 23 wherein the representation of the entity is derived by employing fuzzy logic criteria in order to inspect a representation of at least one subentity forming a portion of the entity.

29. Apparatus according to claim 23 wherein a plurality of classification rules are employed, each rule corresponding to an individual class and having associated therewith, for each entity to be classified, a degree of belief, wherein said fuzzy logic image entity classifier is operative to identify, for each entity, a classification rule having a maximal degree of belief and to associate the entity with the class corresponding to the classification rule having the maximal degree of belief.

30. A method for inspecting agricultural produce having a stem and/or a calyx, the method comprising:

providing an image of generally the entire surface of the agricultural produce including its stem location and/or its calyx location;

determining the location of the stem and/or the calyx in the image of the agricultural produce; and detecting blemishes and avoiding false detections of the stem location and/or the calyx location as a blemish.

31. A method according to claim 30 and also comprising providing an output indication of at least one blemish characteristic other than the size thereof.

32. Apparatus for inspecting agricultural produce having a stem and/or a calyx, the apparatus comprising:

an imager operative to provide an image of generally the entire surface of the agricultural produce including at least one of its stem location and its calyx location;

a stem/calyx identifier operative to determine the location of at least one of the stem and the calyx in the image of the agricultural produce; and a blemish detector, cooperative with said stem/calyx identifier, including logic apparatus operative to detect blemishes and to avoid false detection of the stem location as a blemish and/or the calyx location as a blemish, wherein said imager comprises:

a camera; and a spectral filler defining a plurality of light paths from the agricultural produce to the camera, said plurality of light paths having different spectral characteristics, wherein said spectral filler comprises a prism operative to provide a plurality of images of the agricultural produce having different spectral characteristics and being disposed in generally non-overlapping positions on an image plane of the camera.

33. A method for inspecting agricultural produce having a stem and/or a calyx, the method comprising:

providing an image of generally the entire surface of the agricultural produce including its stem location and/or its calyx location;

determining the location of the stem and/or the calyx in the image of the agricultural produce; and detecting blemishes and avoiding false detections of the stem location and/or the calyx location as a blemish, wherein providing an image comprises:

providing a spectral filter defining a plurality of light paths from the agricultural produce to a camera, said plurality of light paths having different spectral characteristics, and wherein said spectral filler comprises a prism operative to provide a plurality of images of the agricultural produce having different spectral characteristics and being disposed in generally non-overlapping positions on an image plane of the camera.

34. Apparatus for inspecting agricultural produce having a stem and/or a calyx, the apparatus comprising:

an imager operative to provide an image of generally the entire surface of the agricultural produce including at least one of its stem location and its calyx location;

a stem/calyx identifier operative to determine the location of at least one of the stem and the calyx in the image of the agricultural comprising; and a blemish detector, cooperative with said stem/calyx identifier, including logic apparatus operative to detect blemishes and to avoid false detection of the stem location as a blemish and/or the calyx location as a blemish, wherein said imager comprises an IR imager operative to generate an IR image of the produce and a color imager operative to generate a color image of the produce.

35. A method for inspecting agricultural produce having a stem and/or a calyx, the method comprising:

providing an image of generally the entire surface of the agricultural produce including its stem location and/or its calyx location;

determining the location of the stem and/or the calyx in the image of the agricultural produce; and detecting blemishes and avoiding false detections of the stem location and/or the calyx location as a blemish, wherein said step of providing an image comprises providing an IR image of the produce and providing a color image of the produce.

* * * * *